United States Patent
Klein et al.

(10) Patent No.: US 10,806,776 B2
(45) Date of Patent: Oct. 20, 2020

(54) METHOD OF TREATING FUNGAL INFECTION

(71) Applicant: Wisconsin Alumni Research Foundation, Madison, WI (US)

(72) Inventors: Bruce Steven Klein, Madison, WI (US); Theodore Tristan Brandhorst, Madison, WI (US); Thomas Sullivan, Madison, WI (US); Marcel Wuethrich, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 15/969,169

(22) Filed: May 2, 2018

(65) Prior Publication Data

US 2019/0000942 A1 Jan. 3, 2019

Related U.S. Application Data

(63) Continuation of application No. 14/203,898, filed on Mar. 11, 2014, now Pat. No. 9,993,534.

(60) Provisional application No. 61/777,842, filed on Mar. 12, 2013.

(51) Int. Cl.
*A61K 38/00* (2006.01)
*A61K 39/00* (2006.01)
*C07K 14/37* (2006.01)
*C07K 16/14* (2006.01)

(52) U.S. Cl.
CPC .......... *A61K 39/0002* (2013.01); *C07K 14/37* (2013.01); *C07K 16/14* (2013.01); *A61K 2039/545* (2013.01); *A61K 2039/55566* (2013.01)

(58) Field of Classification Search
CPC .................................................. A61K 39/002
See application file for complete search history.

(56) References Cited

U.S. PATENT DOCUMENTS

| | | | |
|---|---|---|---|
| 5,691,306 A | 11/1997 | Bergeron et al. | |
| 5,888,722 A | 3/1999 | Costa De Beauregard et al. | |
| 6,171,864 B1 | 1/2001 | Coughlan et al. | |
| 6,476,194 B1 | 11/2002 | Tessier et al. | |
| 6,524,825 B1 | 2/2003 | Mizzen et al. | |
| 7,157,089 B1 | 1/2007 | Mizzen et al. | |
| 7,504,490 B1 | 3/2009 | Weinstock et al. | |
| 7,858,343 B2 | 12/2010 | Gellissen et al. | |
| 8,546,126 B2 | 10/2013 | Goedegebuur et al. | |
| 9,993,534 B2 * | 6/2018 | Klein .................. | A61K 39/0002 |
| 2002/0155436 A1 | 10/2002 | Classen | |
| 2002/0160408 A1 | 10/2002 | Pelletier et al. | |
| 2003/0082195 A1 | 5/2003 | Jefferies et al. | |
| 2005/0054820 A1 | 3/2005 | Wu et al. | |
| 2005/0130125 A1 | 6/2005 | Zagyansky | |
| 2005/0202044 A1 | 9/2005 | Mizzen et al. | |
| 2007/0207161 A1 | 9/2007 | Ralph | |
| 2008/0118950 A1 | 5/2008 | Gellissen et al. | |
| 2009/0203605 A1 | 8/2009 | Segatori et al. | |
| 2009/0221030 A1* | 9/2009 | Bao ....................... | C12N 9/0061 |
| | | | 435/69.1 |
| 2010/0158930 A1 | 6/2010 | Zhu et al. | |
| 2010/0291683 A1 | 11/2010 | Chang et al. | |
| 2011/0070154 A1 | 3/2011 | Hyde et al. | |
| 2012/0020938 A1 | 1/2012 | Hyde et al. | |
| 2013/0150285 A1 | 6/2013 | Gold et al. | |
| 2013/0259905 A1 | 10/2013 | Han-Min et al. | |

FOREIGN PATENT DOCUMENTS

| | | |
|---|---|---|
| EP | 0705842 | 4/1996 |
| WO | 01/28583 | 4/2001 |
| WO | 02/012281 | 2/2002 |
| WO | 2005/037293 | 4/2005 |
| WO | 2008028963 | 3/2008 |
| WO | 2008/049329 | 5/2008 |
| WO | 2008049329 | 5/2008 |
| WO | 2008049329 A1 | 5/2008 |
| WO | 2008/119024 | 10/2008 |
| WO | 2009/058956 | 5/2009 |

OTHER PUBLICATIONS

Brandhorst, et al., Targeted Gene Disruption Reveals an Adhesin Indispensable for Pathogenicity of Blastomyces Dermatitidis, J. Exp. Med., 1999, 189(8):1207-1216.
Dos Santos Feitosa, et al., Cloning, Characterization and Expression of a Calnexin Homologue from the Pathogenic Fungus Paracoccidioides Brasiliensis, Yeast, 2007, 24:79-87.
Ellgaard, et al., Quality Control in the Endoplasmic Reticulum, Nature Reviews Molecular Cell Biology, 2003, 4:181-191.
Fisher, et al., Biostatistics, A Methodology for Health Sciences, A Wiley-Interscience Publication, Copyright 1993 by John Wiley & Sons, Inc., pp. 611-613.
Harvey, et al., Mouse Model of Pulmonary Blastomycosis: Utility, Simplicity, and Quantitative Parameters, The American Review of Respiratory Disease, 1978, 117(4):695-703.
Leibundgut-Landmann, et al., Syk- and CARD9-dependent Coupling of Innate Immunity to the Induction of T Helper Cells that Produce Interleukin 17, Nature Immunology, 2007, 8:630-638.
Levine, et al., Division of Microbiology: Immunity to Coccidioidomycosis Induced in Mice by Purified Spherule, Arthrospore, and Mycelial Vaccines, Transactions of the New York Academy of Sciences, 1960, 22(6):436-449.
Levine, et al., Immunization of Mice to Coccidioides Immitis: Dose, Regimen and Spherulation Stage of Killed Spherule Vaccines, Journal of Immunology, 1965, 94(1):132-142.
Myhill, et al., The Subcellular Distribution of Calnexin is Mediated by PACS-2, Molecular Biology of the Cell, 2008, 19:2777-2788.

(Continued)

*Primary Examiner* — Albert M Navarro
(74) *Attorney, Agent, or Firm* — Quarles & Brady LLP

(57) ABSTRACT

A vaccine comprising Calnexin fragment and a method of using the vaccine to immunize a patient against fungi are disclosed. The Calnexin fragment may be either a full-length native version or a functionally equivalent version of full-length Calnexin.

15 Claims, 19 Drawing Sheets
(4 of 19 Drawing Sheet(s) Filed in Color)
Specification includes a Sequence Listing.

(56) References Cited

OTHER PUBLICATIONS

Nemecek, et al., Global Control of Dimorphism and Virulence in Fungi, Science, 2006, 312:583-588.
Nesvizhskii, et al., A Statistical Model for Identifying Proteins by Tandem Mass Spectrometry, Anal. Chem., 2003, 75:4646-4658.
Thompson, et al., CLUSTAL W: Improving the Sensitivity of Progressive Multiple Sequence Alignment Through Sequence Weighting, Position-Specific Gap Penalties and Weight Matrix Choice, Nucleic Acids Research, 1994, 22 (22):4673-4680.
Wang, et al., Lentiviral Calnexin-Modified Dendritic Cells Promote Expansion of High-Avidity Effector T Cells with Central Memory Phenotype, Immunology, 2009, 128:43-57.
Williams, Beyond Lectins: The Calnexin/Calreticulin Chaperone System of the Endoplasmic Reticulum, Journal of Cell Science, 2006, 119:615-623.
Wisniewski, et al., Universal Sample Preparation Method for Proteome Analysis, Nature Methods, 2009, 6 (5):359-362.
Wuthrich, et al., Mutation of the WI-1 Gene Yields an Attenuated Blastomyces Dermatitidis Strain That Induces Host Resistance, Journal of Clinical Investigation, 2000, 106(11):1381-1389.
Wuthrich, et al., VB1+ JB1.1+ Na2+ Ja49+ CD4+ T Cells Mediate Resistance Against Infection with Blastomyces Dermatitidis, Infection and Immunity, 2007, 75(1):193-200.
Wuthrich, et al., Vaccine-Induced Protection Against 3 Systemic Mycoses Endemic to North America Requires Th17 Cells in Mice, Journal of Clinical Investigation, 2011, 121(2):554-568.
Wuthrich, et al., A TCR Transgenic Mouse Reactive with Multiple Systemic Dimorphic Fungi, Journal of Immunology, 2011, 187:1421-1431.
Wuthrich, et al., Fungi Subvert Vaccine T Cell Priming at the Respiratory Mucosa by Preventing Chemokine-Induced Influx of Inflammatory Monocytes, Immunity, 2012, 36:680-692.
PCT International Search Report and Written Opinion, PCT/US2014/023340, dated Sep. 2, 2014.
Boslego, Chapter 17, Gonorrhea Vaccines, pp. 211-223, Vaccines and Immunotherapy, 1991.
Conesa, Ana et al, Applied and Environmental Microbiology, Feb. 2002, pp. 846-851, vol. 68(2), Calnexin Overexpression increases Manganese Peroxidase Production in Aspergillus niger.
Ellis, Vaccines 1988, Chapter 29, pp. 568-575, New Technologies for making Vaccines.
FEBS Letters vol. 581, 2007, pp. 3641-3651.
Feitosa, L.d.S et al, Yeast, 2007, vol. 24, pp. 79-87, Cloning, charaterization and expression of a calnexin homologue from the pathogenic fungus Paracoccidioides brasiliensis.
Hajjar, F et al, Yeast, 2007, vol. 24, pp. 89-103, The 160 N-terminal residues of calnexin define a novel region supporting viability in Schizosaccharomyes pombe.
Leach, Michael R. et al, The Journal of Biological Chemistry, vol. 277(33), Aug. 16, 2002, pp. 29696-29697 Localization of the Lectin, ERp57 binding and Polypeptide Binding sites of Calnexin and Calreticulin.
Ou et al, Journal of Biological Chemistry, vol. 270, 1995, pp. 18051-18059.
Schrag, Joseph D. et al, Molecular Cell, vol. 8, pp. 633-644, Sep. 2001, The Structure of Calnexin, an ER Chaperone Involved in Quality Control of Protein Folding.
The Journal of Biological Chemistry, vol. 275(17), Apr. 28, 2000, pp. 13089-13097.
Thompson, et al., Clustal W: Improving the Sensitivity of Progressive Multiple Sequence Alignment Through Sequence Neighting, Position-Specific Gap Penalties and Weight Matrix Choice, Nucleic Acids Research, 1994, 22 (22):4673-4680.
Wang, W et al, Journal of Celluar Biochemistry, vol. 111, pp. 343-349, 2010, Calnexin inhibits thermal aggregation and neurotoxicity of Prion Protein.
Wier et al, Immunology—Laboratory manuals, Immunochemistry, pp. 1-4, Edited by D. M. Weir, Handbook of experimental immunology, pp. 8.14-8.15, 1986.
Xu, Y et al, Cell Press, Chemistry and Biology, vol. 15, pp. 898-907, Sep. 22, 2008,Biosynthesis of the Cyclooligomer Depsipeptide Beauvericin, a Virulence Factor of the Entomopathogenic Fungus Beauveria bassiana.
Yeast, 2007, vol. 24, pp. 79-87.

* cited by examiner

Fig. 3A  *In vitro* activation of 1807 cells by Calnexin peptide#1
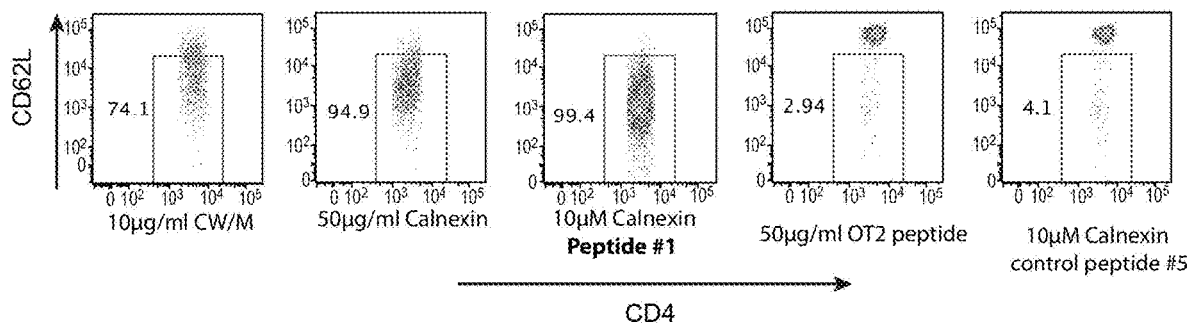
Fig. 3B  *In vitro* IFN-γ by 1807 cells
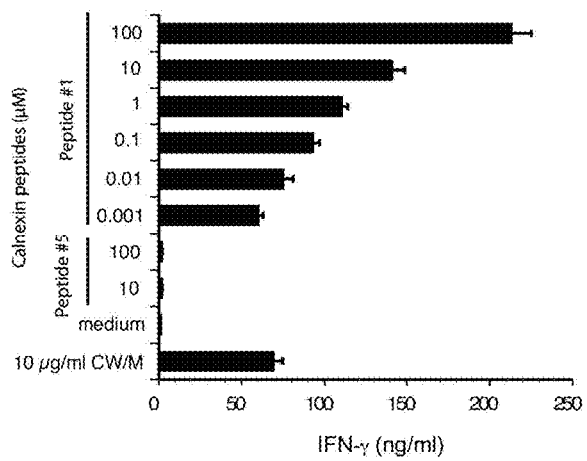
Fig. 3C  *In vivo* activation of 1807 cells by Calnexin peptide#1
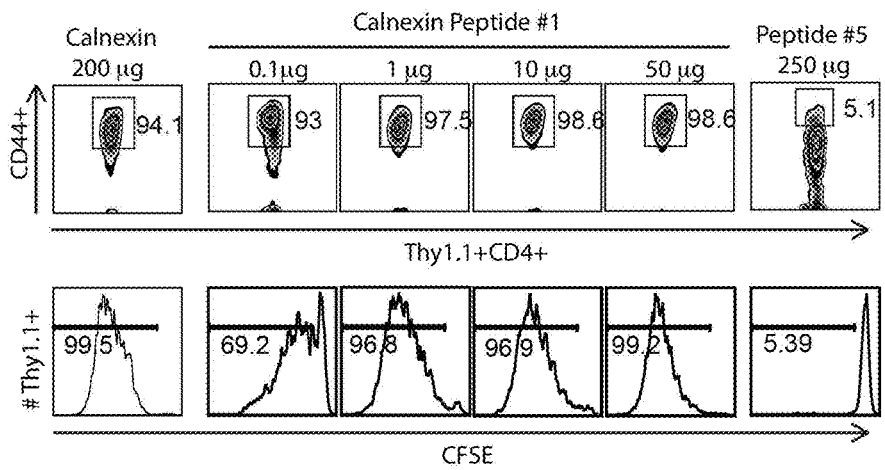

Expression of Calnexin in *B. dermatitidis* vaccine yeast #55

Fig. 4B anti-Calnexin serum          non-immune serum

Fig. 4C

Expression of Calnexin in *A. fumigatus* hyphae and spores

Calnexin Alignment

| | | | |
|---|---|---|---|
| B.d. 26199 | 1 | MRLNASLASLILSSIALIGNVHAEDEVKEDATSTSSVIEKPTFTPTTLKAPFLEQFTDGWETRWT | 65 |
| H.c. G217B | 1 | MRLNASLASLILSSVALIGNVRAEEEVKGDAPSPSSAIEKPTFTPTTLKAPFLEQFTDDWETRWT | 65 |
| C.p. C735 | 1 | MRLNARTASLILSYIALLGQVHABSEATKEEP-TATSISRPTFTPTTLKAPFLEQFTDDWQTRWT | 64 |
| P.b. Pb01 | 1 | MRLNASLASLILTSIALIGNVHAEDEVEGKPSSTSSVIEKPLFTPTTLKAPFLEQFTDDWETRWT | 65 |

| | | | |
|---|---|---|---|
| B.d. 26199 | 66 | PSHAKKEDSKSEEDWAYVGTWAVEEPHVFNGMVGDKGLVVKNPAAHHAISAKFPKKIDNKGKTLV | 130 |
| H.c. G217B | 66 | PSHAKKEDSSDEDWAYIGTWAVEEPHVLNGMVGDKGLVVKNPAAHHAISAKFPKKIDNKGKTLV | 130 |
| C.p. C735 | 65 | PSHAKKEDSKSEEEWAYVGEWAVEEPTVFKGIDGDKGLVVKNAAAHHAISAKFPKKIDNKGKTLV | 129 |
| P.b. Pb01 | 66 | PSHAKKQDSSSEEDWAYVGTWAVEEPHVFNGMKGDKGLVTKNAAAHHAISAKFPKKIDNKGNTLV | 130 |

| | | | |
|---|---|---|---|
| B.d. 26199 | 131 | VQYEVKLQNSLNCGGAYMKLLQDNKKLHAEEFSNTSPYVIMFGPDKCGVTNKVHFIHKHKNPKTG | 195 |
| H.c. G217B | 131 | VQYEVKLQDSLVCGGAYMKLLQDNKKLHAEEFSNASPYVIMFGPDKCGVTNKVHFIRHKNPKTG | 195 |
| C.p. C735 | 130 | VQYEVKLQNSLVCGGAYMKLLQDNKKLHAEEFSNASPYVIMFGPDKCGATNKVHFIHKHKNPKTG | 194 |
| P.b. Pb01 | 131 | VQYEVKLQNGLNCGGAYMKLLQDNKKLHAEEFSNASPYVIMFGPDKCGVTNKVHFIRHKNPKTG | 195 |

| | | | |
|---|---|---|---|
| B.d. 26199 | 196 | EYEEKHMKLPPAVRVSKLSTLYTLIVNPDQSFQIRIDGAAVKNGTLLEDFSPAVNPEKEIDDPED | 260 |
| H.c. G217B | 196 | EYEEKHMNAAPAAKINKLSTLYTLIVKPDQSFQIRIDGKAVKNGTLLEDFSPAVNPPKEIDDPED | 260 |
| C.p. C735 | 195 | EYEEKHLNNAPTARVSKLSTLYTLIVKPDQTFQIQINGEAVKNGTLLEDHQPPVNPPKEIDDPND | 259 |
| P.b. Pb01 | 196 | EYEEKHLKNPPAARVSKLSTLYTLIVKPDQSFQILIDGHAVKNGTLLEDFSPAVNPQKEIDDPED | 260 |

| | | | |
|---|---|---|---|
| B.d. 26199 | 261 | KKPEDWVDEAHIPDPEATKPEDWDEDAPYEIVDTDATQPEDWLVDEPTSIPDPEAQKPEDWDDEE | 325 |
| H.c. G217B | 261 | KKPEDWVDEARIADPDATKPEDWDEDAPYEIVDTDAVQPEDWLVDEPTSIPDPEAEKPEDWDDEE | 325 |
| C.p. C735 | 260 | KKPADWVDEAKIPDPEAKKPEDWDEDAPFEIVDTEAKKPDDWLDDEPSSIPDPEAQKPEDWDDEE | 324 |
| P.b. Pb01 | 261 | KKPKDWVDETRIPDPTATKPDDWDEDAPYEIIDTEATKPDDWLDSEPDSIPDPEAQKPEDWDDEE | 325 |

| | | | |
|---|---|---|---|
| B.d. 26199 | 326 | DGDWPPTIPNPKCSEVSGCGMWEPPMKKNPEYKGKWTAPMIDNPAYKGPWAPRKIANPNYFEDK | 390 |
| H.c. G217B | 326 | DGDWTPPTIPNPKCSEVSGCGKWQQPMKKNPDYKGKWVAPMIDNPAYKGPWAPRKIPNPDYFEDK | 390 |
| C.p. C735 | 325 | DGDWFAPTVPNPKCEEASGCGKWEPPMKRNPDYKGKWTAPLIDNPAYKGPWSPRKIANPDFFEDK | 389 |
| P.b. Pb01 | 326 | DGDWAAPTIPNPKCSEVSGCGKWBAPMKKNPDYKGKWTPPMIDNPAYKGPWTPRKIPNPNYFEDK | 390 |

| | | | |
|---|---|---|---|
| B.d. 26199 | 391 | TPSNFEPMGAIGFEIWTMQNDILRDNIYIGHSVEDAEKLKAETWDLKHPVEVAEEEAARPKDEEK | 455 |
| H.c. G217B | 391 | TPSNFEPMGAIGFEIWTMQSDILRDNIYIGHSIEDAEKLKAETWDLKHPVEVAEEEASRPKDEEK | 455 |
| C.p. C735 | 390 | KPANFEPMGAIGFEIWTMQNDILRDNIYIGHSIEDAKKLKAETFDIKQPIEVAEEEAAKPKDEPS | 454 |
| P.b. Pb01 | 391 | TPANFEPMGAIGFEIWTMQNDILRNNIYIGHSIEDAQKLKSETWDIKHPIEVAEEEATRPKDDEK | 455 |

| | | | |
|---|---|---|---|
| B.d. 26199 | 456 | KEGTLSFKEAPVKYIRGKIELFISLALENPVEAVKAVPEVAGGLALVTLVLIIVGAMGLGSPS | 520 |
| H.c. G217B | 456 | EAGT-SFKEDPVQYIRKKIDLFISLALENPVEAVKAVPEVAGGLCALLVTLIILIIVSGLSLGSSS | 519 |
| C.p. C735 | 455 | TDSGLNFKDPVKYIRSKVDQFILMAKDNPVEAVKTVPEVAGGLAALLITLILVVHGAIGLSSPA | 519 |
| P.b. Pb01 | 456 | DSSFVSFKEAPVQFVREKINLFISIARKDPVQAAKSVPEVAGGLGALVITLALIIVGAIGLSSPA | 520 |

| | | | |
|---|---|---|---|
| B.d. 26199 | 521 | PAPAAKKQAEKGKEK------TAEAVSTAADNVKGEAKKRSGKAGE- | 560 |
| H.c. G217B | 520 | -SPAPKKQAEKGKEKEKAS---ASEAVSTGADNVKGGAKKRSTKTSE- | 562 |
| C.p. C735 | 520 | PAPAKKDAGK-GKEKAKEK---AAEAVSTGAENIKAGATKRS-KSSE- | 561 |
| P.b. Pb01 | 521 | PAPAVAKKVD-GKEKDGASKEKAAEAVSTADNVKGAATRRSGKANNE | 567 |

Figure 6

```
               ----10--------20--------30--------40--------50--------60--------70--------80----
DRB1_0101: MRLNASLASLILSSIALIGNVHAEDEVKEDATSTSSVIEKPTFTPTTLKAPFLEQFTDGWETRWTPSHAKKEDSKSEED
DRB1_0102: MRLNASLASLILSSIALIGNVHAEDEVKEDATSTSSVIEKPTFTPTTLKAPFLEQFTDGWETRWTPSHAKKEDSKSEED
DRB1_0301: MRLNASLASLILSSIALIGNVHAEDEVKEDATSTSSVIEKPTFTPTTLKAPFLEQFTDGWETRWTPSHAKKEDSKSE
DRB1_0305: MRLNASLASLILSSIALIGNVHAEDEVKEDATSTSSVIEKPTFTPTTLKAPFLEQFTDGWETRWTPSHAKKEDSKSI
DRB1_0306: MRLNASLASLILSSIALIGNVHAEDEVKEDATSTSSVIEKPTFTPTTLKAPFLEQFTDGWETRWTPSHAKKEDSKSI
DRB1_0307: MRLNASLASLILSSIALIGNVHAEDEVKEDATSTSSVIEKPTFTPTTLKAPFLEQFTDGWETRWTPSHAKKEDSKSI
DRB1_0308: MRLNASLASLILSSIALIGNVHAEDEVKEDATSTSSVIEKPTFTPTTLKAPFLEQFTDGWETRWTPSHAKKEDSKSI
DRB1_0309: MRLNASLASLILSSIALIGNVHAEDEVKEDATSTSSVIEKPTFTPTTLKAPFLEQFTDGWETRWTPSHAKKEDSKSI
DRB1_0311: MRLNASLASLILSSIALIGNVHAEDEVKEDATSTSSVIEKPTFTPTTLKAPFLEQFTDGWETRWTPSHAKKEDSKSE
DRB1_0401: MRLNASLASLILSSIALIGNVHAEDEVKEDATSTSSVIEKPTFTPTTLKAPFLEQFTDGWETRWTPSHAKKEDSKSE
DRB1_0402: MRLNASLASLILSSIALIGNVHAEDEVKEDATSTSSVIEKPTFTPTTLKAPFLEQFTDGWETRWTPSHAKKEDSKSEE
DRB1_0404: MRLNASLASLILSSIALIGNVHAEDEVKEDATSTSSVIEKPTFTPTTLKAPFLEQFTDGWETRWTPSHAKKEDSKSEE
DRB1_0405: MRLNASLASLILSSIALIGNVHAEDEVKEDATSTSSVIEKPTFTPTTLKAPFLEQFTDGWETRWTPSHAKKEDSKSEED
DRB1_0408: MRLNASLASLILSSIALIGNVHAEDEVKEDATSTSSVIEKPTFTPTTLKAPFLEQFTDGWETRWTPSHAKKEDSKSEE
DRB1_0410: MRLNASLASLILSSIALIGNVHAEDEVKEDATSTSSVIEKPTFTPTTLKAPFLEQFTDGWETRWTPSHAKKEDSKSEE
DRB1_0421: MRLNASLASLILSSIALIGNVHAEDEVKEDATSTSSVIEKPTFTPTTLKAPFLEQFTDGWETRWTPSHAKKEDSKSEE
DRB1_0423: MRLNASLASLILSSIALIGNVHAEDEVKEDATSTSSVIEKPTFTPTTLKAPFLEQFTDGWETRWTPSHAKKEDSKSEE
DRB1_0426: MRLNASLASLILSSIALIGNVHAEDEVKEDATSTSSVIEKPTFTPTTLKAPFLEQFTDGWETRWTPSHAKKEDSKSI
DRB1_0701: MRLNASLASLILSSIALIGNVHAEDEVKEDATSTSSVIEKPTFTPTTLKAPFLEQFTDGWETRWTPSHAKKEDSKSEE
DRB1_0703: MRLNASLASLILSSIALIGNVHAEDEVKEDATSTSSVIEKPTFTPTTLKAPFLEQFTDGWETRWTPSHAKKEDSKSEE
DRB1_0801: MRLNASLASLILSSIALIGNVHAEDEVKEDATSTSSVIEKPTFTPTTLKAPFLEQFTDGWETRWTPSHAKKEDSKSEE
DRB1_0802: MRLNASLASLILSSIALIGNVHAEDEVKEDATSTSSVIEKPTFTPTTLKAPFLEQFTDGWETRWTPSHAKKEDSKSEE
DRB1_0804: MRLNASLASLILSSIALIGNVHAEDEVKEDATSTSSVIEKPTFTPTTLKAPFLEQFTDGWETRWTPSHAKKEDSKSEED
DRB1_0806: MRLNASLASLILSSIALIGNVHAEDEVKEDATSTSSVIEKPTFTPTTLKAPFLEQFTDGWETRWTPSHAKKEDSKSEED
DRB1_0813: MRLNASLASLILSSIALIGNVHAEDEVKEDATSTSSVIEKPTFTPTTLKAPFLEQFTDGWETRWTPSHAKKEDSKSEED
DRB1_0817: MRLNASLASLILSSIALIGNVHAEDEVKEDATSTSSVIEKPTFTPTTLKAPFLEQFTDGWETRWTPSHAKKEDSKSEE
DRB1_1101: MRLNASLASLILSSIALIGNVHAEDEVKEDATSTSSVIEKPTFTPTTLKAPFLEQFTDGWETRWTPSHAKKEDSKSEED
DRB1_1102: MRLNASLASLILSSIALIGNVHAEDEVKEDATSTSSVIEKPTFTPTTLKAPFLEQFTDGWETRWTPSHAKKEDSKSEED
DRB1_1104: MRLNASLASLILSSIALIGNVHAEDEVKEDATSTSSVIEKPTFTPTTLKAPFLEQFTDGWETRWTPSHAKKEDSKSEED
DRB1_1106: MRLNASLASLILSSIALIGNVHAEDEVKEDATSTSSVIEKPTFTPTTLKAPFLEQFTDGWETRWTPSHAKKEDSKSEED
DRB1_1107: MRLNASLASLILSSIALIGNVHAEDEVKEDATSTSSVIEKPTFTPTTLKAPFLEQFTDGWETRWTPSHAKKEDSKSE
DRB1_1114: MRLNASLASLILSSIALIGNVHAEDEVKEDATSTSSVIEKPTFTPTTLKAPFLEQFTDGWETRWTPSHAKKEDSKSEED
DRB1_1120: MRLNASLASLILSSIALIGNVHAEDEVKEDATSTSSVIEKPTFTPTTLKAPFLEQFTDGWETRWTPSHAKKEDSKSEED
DRB1_1121: MRLNASLASLILSSIALIGNVHAEDEVKEDATSTSSVIEKPTFTPTTLKAPFLEQFTDGWETRWTPSHAKKEDSKSEED
DRB1_1128: MRLNASLASLILSSIALIGNVHAEDEVKEDATSTSSVIEKPTFTPTTLKAPFLEQFTDGWETRWTPSHAKKEDSKSEED
DRB1_1301: MRLNASLASLILSSIALIGNVHAEDEVKEDATSTSSVIEKPTFTPTTLKAPFLEQFTDGWETRWTPSHAKKEDSKSEED
DRB1_1302: MRLNASLASLILSSIALIGNVHAEDEVKEDATSTSSVIEKPTFTPTTLKAPFLEQFTDGWETRWTPSHAKKEDSKSEED
DRB1_1304: MRLNASLASLILSSIALIGNVHAEDEVKEDATSTSSVIEKPTFTPTTLKAPFLEQFTDGWETRWTPSHAKKEDSKSEED
DRB1_1305: MRLNASLASLILSSIALIGNVHAEDEVKEDATSTSSVIEKPTFTPTTLKAPFLEQFTDGWETRWTPSHAKKEDSKSEED
DRB1_1307: MRLNASLASLILSSIALIGNVHAEDEVKEDATSTSSVIEKPTFTPTTLKAPFLEQFTDGWETRWTPSHAKKEDSKSEED
DRB1_1311: MRLNASLASLILSSIALIGNVHAEDEVKEDATSTSSVIEKPTFTPTTLKAPFLEQFTDGWETRWTPSHAKKEDSKSEED
DRB1_1321: MRLNASLASLILSSIALIGNVHAEDEVKEDATSTSSVIEKPTFTPTTLKAPFLEQFTDGWETRWTPSHAKKEDSKSEED
DRB1_1322: MRLNASLASLILSSIALIGNVHAEDEVKEDATSTSSVIEKPTFTPTTLKAPFLEQFTDGWETRWTPSHAKKEDSKSEED
DRB1_1323: MRLNASLASLILSSIALIGNVHAEDEVKEDATSTSSVIEKPTFTPTTLKAPFLEQFTDGWETRWTPSHAKKEDSKSEED
DRB1_1327: MRLNASLASLILSSIALIGNVHAEDEVKEDATSTSSVIEKPTFTPTTLKAPFLEQFTDGWETRWTPSHAKKEDSKSEED
DRB1_1328: MRLNASLASLILSSIALIGNVHAEDEVKEDATSTSSVIEKPTFTPTTLKAPFLEQFTDGWETRWTPSHAKKEDSKSEED
DRB1_1501: MRLNASLASLILSSIALIGNVHAEDEVKEDATSTSSVIEKPTFTPTTLKAPFLEQFTDGWETRWTPSHAKKEDSKSEED
DRB1_1502: MRLNASLASLILSSIALIGNVHAEDEVKEDATSTSSVIEKPTFTPTTLKAPFLEQFTDGWETRWTPSHAKKEDSKSEED
DRB1_1506: MRLNASLASLILSSIALIGNVHAEDEVKEDATSTSSVIEKPTFTPTTLKAPFLEQFTDGWETRWTPSHAKKEDSKSEED
DRB5_0101: MRLNASLASLILSSIALIGNVHAEDEVKEDATSTSSVIEKPTFTPTTLKAPFLEQFTDGWETRWTPSHAKKEDSKSEEDW
DRB5_0105: MRLNASLASLILSSIALIGNVHAEDEVKEDATSTSSVIEKPTFTPTTLKAPFLEQFTDGWETRWTPSHAKKEDSKSEEDW
```

FIGURE 7 (SEQ ID NOs: 37-87)

FIGURE 7 (CONTINUED) (SEQ ID NOs: 37-87)

```
          180         190         200         210         220         230
NTSPYVIMFGPDKCGVTNKVHFIFKHKNPKTGEYEEKHMKLPPAVRVSKLSTLYTLIVN
SNTSPYVIMFGPDKCGVTNKVHFIFKHKNPKTGEYEEKHMKLPPAVRVSKLSTLYTL
EFSNTSPYVIMFGPDKCGVTNKVHFIFKHKNPKTGEYEEKHMKLPPAVRVSKLSTLYTL
EEFSNTSPYVIMFGPDKCGVTNKVHFIFKHKNPKTGEYEEKHMKLPPAVRVSKLSTLY
AEEFSNTSPYVIMFGPDKCGVTNKVHFIFKHKNPKTGEYEEKHMKLPPAVRVSKLSTLYT
HAEEFSNTSPYVIMFGPDKCGVTNKVHFIFKHKNPKTGEYEEKHMKLPPAVRVSKLSTL
HAEEFSNTSPYVIMFGPDKCGVTNKVHFIFKHKNPKTGEYEEKHMKLPPAVRVSKLSTL
EFSNTSPYVIMFGPDKCGVTNKVHFIFKHKNPKTGEYEEKHMKLPPAVRVSKLSTLYT
IAEEFSNTSPYVIMFGPDKCGVTNKVHFIFKHKNPKTGEYEEKHMKLPPAVRVSKLSTLY
EEFSNTSPYVIMFGPDKCGVTNKVHFIFKHKNPKTGEYEEKHMKLPPAVRVSKLSTLY
FSNTSPYVIMFGPDKCGVTNKVHFIFKHKNPKTGEYEEKHMKLPPAVRVSKLSTLYTLIV
EFSNTSPYVIMFGPDKCGVTNKVHFIFKHKNPKTGEYEEKHMKLPPAVRVSKLSTLYTI
NTSPYVIMFGPDKCGVTNKVHFIFKHKNPKTGEYEEKHMKLPPAVRVSKLSTLYTLIVN
EFSNTSPYVIMFGPDKCGVTNKVHFIFKHKNPKTGEYEEKHMKLPPAVRVSKLSTLYT
SNTSPYVIMFGPDKCGVTNKVHFIFKHKNPKTGEYEEKHMKLPPAVRVSKLSTLYTLIV
EFSNTSPYVIMFGPDKCGVTNKVHFIFKHKNPKTGEYEEKHMKLPPAVRVSKLSTLYTL
EFSNTSPYVIMFGPDKCGVTNKVHFIFKHKNPKTGEYEEKHMKLPPAVRVSKLSTLYT
EFSNTSPYVIMFGPDKCGVTNKVHFIFKHKNPKTGEYEEKHMKLPPAVRVSKLSTLYTLI
SNTSPYVIMFGPDKCGVTNKVHFIFKHKNPKTGEYEEKHMKLPPAVRVSKLSTLYTL
SNTSPYVIMFGPDKCGVTNKVHFIFKHKNPKTGEYEEKHMKLPPAVRVSKLSTLYTL
EFSNTSPYVIMFGPDKCGVTNKVHFIFKHKNPKTGEYEEKHMKLPPAVRVSKLSTLYT
EFSNTSPYVIMFGPDKCGVTNKVHFIFKHKNPKTGEYEEKHMKLPPAVRVSKLSTLY
FSNTSPYVIMFGPDKCGVTNKVHFIFKHKNPKTGEYEEKHMKLPPAVRVSKLSTLYTLI
FSNTSPYVIMFGPDKCGVTNKVHFIFKHKNPKTGEYEEKHMKLPPAVRVSKLSTLYTLI
SNTSPYVIMFGPDKCGVTNKVHFIFKHKNPKTGEYEEKHMKLPPAVRVSKLSTLYTL
EFSNTSPYVIMFGPDKCGVTNKVHFIFKHKNPKTGEYEEKHMKLPPAVRVSKLSTLYT
EFSNTSPYVIMFGPDKCGVTNKVHFIFKHKNPKTGEYEEKHMKLPPAVRVSKLSTLYT
FSNTSPYVIMFGPDKCGVTNKVHFIFKHKNPKTGEYEEKHMKLPPAVRVSKLSTLYT
EFSNTSPYVIMFGPDKCGVTNKVHFIFKHKNPKTGEYEEKHMKLPPAVRVSKLSTLY
EFSNTSPYVIMFGPDKCGVTNKVHFIFKHKNPKTGEYEEKHMKLPPAVRVSKLSTLY
EEFSNTSPYVIMFGPDKCGVTNKVHFIFKHKNPKTGEYEEKHMKLPPAVRVSKLSTLY
SNTSPYVIMFGPDKCGVTNKVHFIFKHKNPKTGEYEEKHMKLPPAVRVSKLSTLYTL
NTSPYVIMFGPDKCGVTNKVHFIFKHKNPKTGEYEEKHMKLPPAVRVSKLSTLYTLI
SNTSPYVIMFGPDKCGVTNKVHFIFKHKNPKTGEYEEKHMKLPPAVRVSKLSTLYTL
TSPYVIMFGPDKCGVTNKVHFIFKHKNPKTGEYEEKHMKLPPAVRVSKLSTLYTLIVNP
FSNTSPYVIMFGPDKCGVTNKVHFIFKHKNPKTGEYEEKHMKLPPAVRVSKLSTLYTLIV
NTSPYVIMFGPDKCGVTNKVHFIFKHKNPKTGEYEEKHMKLPPAVRVSKLSTLYTLI
FSNTSPYVIMFGPDKCGVTNKVHFIFKHKNPKTGEYEEKHMKLPPAVRVSKLSTLYTL
TSPYVIMFGPDKCGVTNKVHFIFKHKNPKTGEYEEKHMKLPPAVRVSKLSTLYTLIVNP
FSNTSPYVIMFGPDKCGVTNKVHFIFKHKNPKTGEYEEKHMKLPPAVRVSKLSTLYT
EFSNTSPYVIMFGPDKCGVTNKVHFIFKHKNPKTGEYEEKHMKLPPAVRVSKLSTLYT
SNTSPYVIMFGPDKCGVTNKVHFIFKHKNPKTGEYEEKHMKLPPAVRVSKLSTLYTL
FSNTSPYVIMFGPDKCGVTNKVHFIFKHKNPKTGEYEEKHMKLPPAVRVSKLSTLYT
FSNTSPYVIMFGPDKCGVTNKVHFIFKHKNPKTGEYEEKHMKLPPAVRVSKLSTLYT
EFSNTSPYVIMFGPDKCGVTNKVHFIFKHKNPKTGEYEEKHMKLPPAVRVSKLSTLYTLI
FSNTSPYVIMFGPDKCGVTNKVHFIFKHKNPKTGEYEEKHMKLPPAVRVSKLSTLYTLIV
SNTSPYVIMFGPDKCGVTNKVHFIFKHKNPKTGEYEEKHMKLPPAVRVSKLSTLYTLI
TSPYVIMFGPDKCGVTNKVHFIFKHKNPKTGEYEEKHMKLPPAVRVSKLSTLYTLIVNPD
SNTSPYVIMFGPDKCGVTNKVHFIFKHKNPKTGEYEEKHMKLPPAVRVSKLSTLYTLI
TSPYVIMFGPDKCGVTNKVHFIFKHKNPKTGEYEEKHMKLPPAVRVSKLSTLYTLIVN
TSPYVIMFGPDKCGVTNKVHFIFKHKNPKTGEYEEKHMKLPPAVRVSKLSTLYTLIVN
```

FIGURE 7 (CONTINUED) (SEQ ID NOs:37-87)

```
      ---240---------250---------260---------270---------280---------290---------300---
     JPDQSFQIRIDGAAVKNGTLLEDFSPAVNPEKEIDDPEDKKPEDWVDEAHIPDPEATKPEDWDEDAPYEI
     IVNPDQSFQIRIDGAAVKNGTLLEDFSPAVNPEKEIDDPEDKKPEDWVDEAHIPDPEATKPEDWDEDAP
    .IVNPDQSFQIRIDGAAVKNGTLLEDFSPAVNPEKEIDDPEDKKPEDWVDEAHIPDPEATKPEDWDEC
    TLIVNPDQSFQIRIDGAAVKNGTLLEDFSPAVNPEKEIDDPEDKKPEDWVDEAHIPDPEATKPEDWC
    TLIVNPDQSFQIRIDGAAVKNGTLLEDFSPAVNPEKEIDDPEDKKPEDWVDEAHIPDPEATKPEDWDEC
    YTLIVNPDQSFQIRIDGAAVKNGTLLEDFSPAVNPEKEIDDPEDKKPEDWVDEAHIPDPEATKPEDWDE
    YTLIVNPDQSFQIRIDGAAVKNGTLLEDFSPAVNPEKEIDDPEDKKPEDWVDEAHIPDPEATKPEDWDE
    LIVNPDQSFQIRIDGAAVKNGTLLEDFSPAVNPEKEIDDPEDKKPEDWVDEAHIPDPEATKPEDWDEI
    TLIVNPDQSFQIRIDGAAVKNGTLLEDFSPAVNPEKEIDDPEDKKPEDWVDEAHIPDPEATKPEDWDE
    TLIVNPDQSFQIRIDGAAVKNGTLLEDFSPAVNPEKEIDDPEDKKPEDWVDEAHIPDPEATKPEDWD
    /NPDQSFQIRIDGAAVKNGTLLEDFSPAVNPEKEIDDPEDKKPEDWVDEAHIPDPEATKPEDWDEDAPYI
    LIVNPDQSFQIRIDGAAVKNGTLLEDFSPAVNPEKEIDDPEDKKPEDWVDEAHIPDPEATKPEDWDED.
    JPDQSFQIRIDGAAVKNGTLLEDFSPAVNPEKEIDDPEDKKPEDWVDEAHIPDPEATKPEDWDEDAPYE
    LIVNPDQSFQIRIDGAAVKNGTLLEDFSPAVNPEKEIDDPEDKKPEDWVDEAHIPDPEATKPEDWDED.
    NPDQSFQIRIDGAAVKNGTLLEDFSPAVNPEKEIDDPEDKKPEDWVDEAHIPDPEATKPEDWDEDAPY
    VNPDQSFQIRIDGAAVKNGTLLEDFSPAVNPEKEIDDPEDKKPEDWVDEAHIPDPEATKPEDWDEDAF
    TLIVNPDQSFQIRIDGAAVKNGTLLEDFSPAVNPEKEIDDPEDKKPEDWVDEAHIPDPEATKPEDWDE
    IVNPDQSFQIRIDGAAVKNGTLLEDFSPAVNPEKEIDDPEDKKPEDWVDEAHIPDPEATKPEDWDED.
    .IVNPDQSFQIRIDGAAVKNGTLLEDFSPAVNPEKEIDDPEDKKPEDWVDEAHIPDPEATKPEDWDEDAF
    LIVNPDQSFQIRIDGAAVKNGTLLEDFSPAVNPEKEIDDPEDKKPEDWVDEAHIPDPEATKPEDWDED.
    LIVNPDQSFQIRIDGAAVKNGTLLEDFSPAVNPEKEIDDPEDKKPEDWVDEAHIPDPEATKPEDWDEDAI
    YTLIVNPDQSFQIRIDGAAVKNGTLLEDFSPAVNPEKEIDDPEDKKPEDWVDEAHIPDPEATKPEDWDE
    VNPDQSFQIRIDGAAVKNGTLLEDFSPAVNPEKEIDDPEDKKPEDWVDEAHIPDPEATKPEDWDEDAF
    IVNPDQSFQIRIDGAAVKNGTLLEDFSPAVNPEKEIDDPEDKKPEDWVDEAHIPDPEATKPEDWDEDAP
    LIVNPDQSFQIRIDGAAVKNGTLLEDFSPAVNPEKEIDDPEDKKPEDWVDEAHIPDPEATKPEDWDEDAF
    LIVNPDQSFQIRIDGAAVKNGTLLEDFSPAVNPEKEIDDPEDKKPEDWVDEAHIPDPEATKPEDWDEDAI
    LIVNPDQSFQIRIDGAAVKNGTLLEDFSPAVNPEKEIDDPEDKKPEDWVDEAHIPDPEATKPEDWDED.
    LIVNPDQSFQIRIDGAAVKNGTLLEDFSPAVNPEKEIDDPEDKKPEDWVDEAHIPDPEATKPEDWDEDAI
    TLIVNPDQSFQIRIDGAAVKNGTLLEDFSPAVNPEKEIDDPEDKKPEDWVDEAHIPDPEATKPEDWDED
    TLIVNPDQSFQIRIDGAAVKNGTLLEDFSPAVNPEKEIDDPEDKKPEDWVDEAHIPDPEATKPEDWDED
    TLIVNPDQSFQIRIDGAAVKNGTLLEDFSPAVNPEKEIDDPEDKKPEDWVDEAHIPDPEATKPEDWD
    LIVNPDQSFQIRIDGAAVKNGTLLEDFSPAVNPEKEIDDPEDKKPEDWVDEAHIPDPEATKPEDWDEDAF
    VNPDQSFQIRIDGAAVKNGTLLEDFSPAVNPEKEIDDPEDKKPEDWVDEAHIPDPEATKPEDWDEDAPY
    LIVNPDQSFQIRIDGAAVKNGTLLEDFSPAVNPEKEIDDPEDKKPEDWVDEAHIPDPEATKPEDWDEDAF
    DQSFQIRIDGAAVKNGTLLEDFSPAVNPEKEIDDPEDKKPEDWVDEAHIPDPEATKPEDWDEDAPYEIV
    NPDQSFQIRIDGAAVKNGTLLEDFSPAVNPEKEIDDPEDKKPEDWVDEAHIPDPEATKPEDWDEDAPYE
    VNPDQSFQIRIDGAAVKNGTLLEDFSPAVNPEKEIDDPEDKKPEDWVDEAHIPDPEATKPEDWDEDAP\
    .IVNPDQSFQIRIDGAAVKNGTLLEDFSPAVNPEKEIDDPEDKKPEDWVDEAHIPDPEATKPEDWDEDA
    DQSFQIRIDGAAVKNGTLLEDFSPAVNPEKEIDDPEDKKPEDWVDEAHIPDPEATKPEDWDEDAPYEIV
    LIVNPDQSFQIRIDGAAVKNGTLLEDFSPAVNPEKEIDDPEDKKPEDWVDEAHIPDPEATKPEDWDEDAI
    TLIVNPDQSFQIRIDGAAVKNGTLLEDFSPAVNPEKEIDDPEDKKPEDWVDEAHIPDPEATKPEDWDED.
    .IVNPDQSFQIRIDGAAVKNGTLLEDFSPAVNPEKEIDDPEDKKPEDWVDEAHIPDPEATKPEDWDEDAF
    TLIVNPDQSFQIRIDGAAVKNGTLLEDFSPAVNPEKEIDDPEDKKPEDWVDEAHIPDPEATKPEDWDEDA
    TLIVNPDQSFQIRIDGAAVKNGTLLEDFSPAVNPEKEIDDPEDKKPEDWVDEAHIPDPEATKPEDWDEDA
    /NPDQSFQIRIDGAAVKNGTLLEDFSPAVNPEKEIDDPEDKKPEDWVDEAHIPDPEATKPEDWDEDAPYI
    NPDQSFQIRIDGAAVKNGTLLEDFSPAVNPEKEIDDPEDKKPEDWVDEAHIPDPEATKPEDWDEDAPYE
    /NPDQSFQIRIDGAAVKNGTLLEDFSPAVNPEKEIDDPEDKKPEDWVDEAHIPDPEATKPEDWDEDAPYI
    QSFQIRIDGAAVKNGTLLEDFSPAVNPEKEIDDPEDKKPEDWVDEAHIPDPEATKPEDWDEDAPYEIVD
    VNPDQSFQIRIDGAAVKNGTLLEDFSPAVNPEKEIDDPEDKKPEDWVDEAHIPDPEATKPEDWDEDAPY
    IPDQSFQIRIDGAAVKNGTLLEDFSPAVNPEKEIDDPEDKKPEDWVDEAHIPDPEATKPEDWDEDAPYE
    JPDQSFQIRIDGAAVKNGTLLEDFSPAVNPEKEIDDPEDKKPEDWVDEAHIPDPEATKPEDWDEDAPYI
```

FIGURE 7 (CONTINUED) (SEQ ID NOs:37-87)

```
----310--------------320-------------330-------------340-------------350-------------360-------------370--------
VDTDATQPEDWLVDEPTSIPDPEAQKPEDWDDEEDGDWIPPTIPNPKCSEVSGCGMWEPPMKKNPEY
YEIVDTDATQPEDWLVDEPTSIPDPEAQKPEDWDDEEDGDWIPPTIPNPKCSEVSGCGMWEPPMKKNP
DAPYEIVDTDATQPEDWLVDEPTSIPDPEAQKPEDWDDEEDGDWIPPTIPNPKCSEVSGCGMWEPPM
DEDAPYEIVDTDATQPEDWLVDEPTSIPDPEAQKPEDWDDEEDGDWIPPTIPNPKCSEVSGCGMWEPP
DAPYEIVDTDATQPEDWLVDEPTSIPDPEAQKPEDWDDEEDGDWIPPTIPNPKCSEVSGCGMWEPPM
EDAPYEIVDTDATQPEDWLVDEPTSIPDPEAQKPEDWDDEEDGDWIPPTIPNPKCSEVSGCGMWEPP
EDAPYEIVDTDATQPEDWLVDEPTSIPDPEAQKPEDWDDEEDGDWIPPTIPNPKCSEVSGCGMWEPP
DAPYEIVDTDATQPEDWLVDEPTSIPDPEAQKPEDWDDEEDGDWIPPTIPNPKCSEVSGCGMWEPPM
DAPYEIVDTDATQPEDWLVDEPTSIPDPEAQKPEDWDDEEDGDWIPPTIPNPKCSEVSGCGMWEPPM
EDAPYEIVDTDATQPEDWLVDEPTSIPDPEAQKPEDWDDEEDGDWIPPTIPNPKCSEVSGCGMWEPP
EIVDTDATQPEDWLVDEPTSIPDPEAQKPEDWDDEEDGDWIPPTIPNPKCSEVSGCGMWEPPMKKNPE
APYEIVDTDATQPEDWLVDEPTSIPDPEAQKPEDWDDEEDGDWIPPTIPNPKCSEVSGCGMWEPPMKK
IVDTDATQPEDWLVDEPTSIPDPEAQKPEDWDDEEDGDWIPPTIPNPKCSEVSGCGMWEPPMKKNPE
APYEIVDTDATQPEDWLVDEPTSIPDPEAQKPEDWDDEEDGDWIPPTIPNPKCSEVSGCGMWEPPMKK
EIVDTDATQPEDWLVDEPTSIPDPEAQKPEDWDDEEDGDWIPPTIPNPKCSEVSGCGMWEPPMKKNPE
PYEIVDTDATQPEDWLVDEPTSIPDPEAQKPEDWDDEEDGDWIPPTIPNPKCSEVSGCGMWEPPMKK
DAPYEIVDTDATQPEDWLVDEPTSIPDPEAQKPEDWDDEEDGDWIPPTIPNPKCSEVSGCGMWEPPMK
APYEIVDTDATQPEDWLVDEPTSIPDPEAQKPEDWDDEEDGDWIPPTIPNPKCSEVSGCGMWEPPMK
YEIVDTDATQPEDWLVDEPTSIPDPEAQKPEDWDDEEDGDWIPPTIPNPKCSEVSGCGMWEPPMKKNP
APYEIVDTDATQPEDWLVDEPTSIPDPEAQKPEDWDDEEDGDWIPPTIPNPKCSEVSGCGMWEPPMKKN
PYEIVDTDATQPEDWLVDEPTSIPDPEAQKPEDWDDEEDGDWIPPTIPNPKCSEVSGCGMWEPPMKKN
DAPYEIVDTDATQPEDWLVDEPTSIPDPEAQKPEDWDDEEDGDWIPPTIPNPKCSEVSGCGMWEPPM
PYEIVDTDATQPEDWLVDEPTSIPDPEAQKPEDWDDEEDGDWIPPTIPNPKCSEVSGCGMWEPPMKKN
EIVDTDATQPEDWLVDEPTSIPDPEAQKPEDWDDEEDGDWIPPTIPNPKCSEVSGCGMWEPPMKKNPE
PYEIVDTDATQPEDWLVDEPTSIPDPEAQKPEDWDDEEDGDWIPPTIPNPKCSEVSGCGMWEPPMKKN
PYEIVDTDATQPEDWLVDEPTSIPDPEAQKPEDWDDEEDGDWIPPTIPNPKCSEVSGCGMWEPPMKKN
APYEIVDTDATQPEDWLVDEPTSIPDPEAQKPEDWDDEEDGDWIPPTIPNPKCSEVSGCGMWEPPMKK
PYEIVDTDATQPEDWLVDEPTSIPDPEAQKPEDWDDEEDGDWIPPTIPNPKCSEVSGCGMWEPPMKKN
APYEIVDTDATQPEDWLVDEPTSIPDPEAQKPEDWDDEEDGDWIPPTIPNPKCSEVSGCGMWEPPMKK
APYEIVDTDATQPEDWLVDEPTSIPDPEAQKPEDWDDEEDGDWIPPTIPNPKCSEVSGCGMWEPPMKK
EDAPYEIVDTDATQPEDWLVDEPTSIPDPEAQKPEDWDDEEDGDWIPPTIPNPKCSEVSGCGMWEPP
PYEIVDTDATQPEDWLVDEPTSIPDPEAQKPEDWDDEEDGDWIPPTIPNPKCSEVSGCGMWEPPMKKN
EIVDTDATQPEDWLVDEPTSIPDPEAQKPEDWDDEEDGDWIPPTIPNPKCSEVSGCGMWEPPMKKNPE
PYEIVDTDATQPEDWLVDEPTSIPDPEAQKPEDWDDEEDGDWIPPTIPNPKCSEVSGCGMWEPPMKKN
DTDATQPEDWLVDEPTSIPDPEAQKPEDWDDEEDGDWIPPTIPNPKCSEVSGCGMWEPPMKKNPEYK
IVDTDATQPEDWLVDEPTSIPDPEAQKPEDWDDEEDGDWIPPTIPNPKCSEVSGCGMWEPPMKKNPEY
EIVDTDATQPEDWLVDEPTSIPDPEAQKPEDWDDEEDGDWIPPTIPNPKCSEVSGCGMWEPPMKKNPE
PYEIVDTDATQPEDWLVDEPTSIPDPEAQKPEDWDDEEDGDWIPPTIPNPKCSEVSGCGMWEPPMKKN
DTDATQPEDWLVDEPTSIPDPEAQKPEDWDDEEDGDWIPPTIPNPKCSEVSGCGMWEPPMKKNPEYK
PYEIVDTDATQPEDWLVDEPTSIPDPEAQKPEDWDDEEDGDWIPPTIPNPKCSEVSGCGMWEPPMKKN
APYEIVDTDATQPEDWLVDEPTSIPDPEAQKPEDWDDEEDGDWIPPTIPNPKCSEVSGCGMWEPPMKK
PYEIVDTDATQPEDWLVDEPTSIPDPEAQKPEDWDDEEDGDWIPPTIPNPKCSEVSGCGMWEPPMKKN
PYEIVDTDATQPEDWLVDEPTSIPDPEAQKPEDWDDEEDGDWIPPTIPNPKCSEVSGCGMWEPPMKKN
PYEIVDTDATQPEDWLVDEPTSIPDPEAQKPEDWDDEEDGDWIPPTIPNPKCSEVSGCGMWEPPMKKN
EIVDTDATQPEDWLVDEPTSIPDPEAQKPEDWDDEEDGDWIPPTIPNPKCSEVSGCGMWEPPMKKNPE
EIVDTDATQPEDWLVDEPTSIPDPEAQKPEDWDDEEDGDWIPPTIPNPKCSEVSGCGMWEPPMKKNPE
EIVDTDATQPEDWLVDEPTSIPDPEAQKPEDWDDEEDGDWIPPTIPNPKCSEVSGCGMWEPPMKKNPE
TDATQPEDWLVDEPTSIPDPEAQKPEDWDDEEDGDWIPPTIPNPKCSEVSGCGMWEPPMKKNPEYKG
EIVDTDATQPEDWLVDEPTSIPDPEAQKPEDWDDEEDGDWIPPTIPNPKCSEVSGCGMWEPPMKKNPE
EIVDTDATQPEDWLVDEPTSIPDPEAQKPEDWDDEEDGDWIPPTIPNPKCSEVSGCGMWEPPMKKNPE
EIVDTDATQPEDWLVDEPTSIPDPEAQKPEDWDDEEDGDWIPPTIPNPKCSEVSGCGMWEPPMKKNPE
```

FIGURE 7 (CONTINUED) (SEQ ID NOs:37-87)

```
----------380-------------390-------------400--------------410-------------420-------------430--------------440-------------450--------
'KGKWTAPMIDNPAYKGPWAPRKIANPNYFEDKTPSNFEPMGAIGFEIWTMQNDILFDNIYIGHSVEDAEKLKAET'
PEYKGKWTAPMIDNPAYKGPWAPRKIANPNYFEDKTPSNFEPMGAIGFEIWTMQNDILFDNIYIGHSVEDAEKLKA
KKNPEYKGKWTAPMIDNPAYKGPWAPRKIANPNYFEDKTPSNFEPMGAIGFEIWTMQNDILFDNIYIGHSVEDAE
PMKKNPEYKGKWTAPMIDNPAYKGPWAPRKIANPNYFEDKTPSNFEPMGAIGFEIWTMQNDILFDNIYIGHSVE
KKNPEYKGKWTAPMIDNPAYKGPWAPRKIANPNYFEDKTPSNFEPMGAIGFEIWTMQNDILFDNIYIGHSVEDAE
MKKNPEYKGKWTAPMIDNPAYKGPWAPRKIANPNYFEDKTPSNFEPMGAIGFEIWTMQNDILFDNIYIGHSVEDA
MKKNPEYKGKWTAPMIDNPAYKGPWAPRKIANPNYFEDKTPSNFEPMGAIGFEIWTMQNDILFDNIYIGHSVEDA
KKNPEYKGKWTAPMIDNPAYKGPWAPRKIANPNYFEDKTPSNFEPMGAIGFEIWTMQNDILFDNIYIGHSVED
MKKNPEYKGKWTAPMIDNPAYKGPWAPRKIANPNYFEDKTPSNFEPMGAIGFEIWTMQNDILFDNIYIGHSVEDAE
PMKKNPEYKGKWTAPMIDNPAYKGPWAPRKIANPNYFEDKTPSNFEPMGAIGFEIWTMQNDILFDNIYIGHSVEDA
YKGKWTAPMIDNPAYKGPWAPRKIANPNYFEDKTPSNFEPMGAIGFEIWTMQNDILFDNIYIGHSVEDAEKLKAET'
NPEYKGKWTAPMIDNPAYKGPWAPRKIANPNYFEDKTPSNFEPMGAIGFEIWTMQNDILFDNIYIGHSVEDAEKLK
EYKGKWTAPMIDNPAYKGPWAPRKIANPNYFEDKTPSNFEPMGAIGFEIWTMQNDILFDNIYIGHSVEDAEKLKAET
NPEYKGKWTAPMIDNPAYKGPWAPRKIANPNYFEDKTPSNFEPMGAIGFEIWTMQNDILFDNIYIGHSVEDAEKLK
EYKGKWTAPMIDNPAYKGPWAPRKIANPNYFEDKTPSNFEPMGAIGFEIWTMQNDILFDNIYIGHSVEDAEKLKAET
NPEYKGKWTAPMIDNPAYKGPWAPRKIANPNYFEDKTPSNFEPMGAIGFEIWTMQNDILFDNIYIGHSVEDAEKL
KNPEYKGKWTAPMIDNPAYKGPWAPRKIANPNYFEDKTPSNFEPMGAIGFEIWTMQNDILFDNIYIGHSVEDAEKL
KKNPEYKGKWTAPMIDNPAYKGPWAPRKIANPNYFEDKTPSNFEPMGAIGFEIWTMQNDILFDNIYIGHSVEDAEK
PEYKGKWTAPMIDNPAYKGPWAPRKIANPNYFEDKTPSNFEPMGAIGFEIWTMQNDILFDNIYIGHSVEDAEKLKAE
NPEYKGKWTAPMIDNPAYKGPWAPRKIANPNYFEDKTPSNFEPMGAIGFEIWTMQNDILFDNIYIGHSVEDAEKLK
PEYKGKWTAPMIDNPAYKGPWAPRKIANPNYFEDKTPSNFEPMGAIGFEIWTMQNDILFDNIYIGHSVEDAEKL
KKNPEYKGKWTAPMIDNPAYKGPWAPRKIANPNYFEDKTPSNFEPMGAIGFEIWTMQNDILFDNIYIGHSVEDA
PEYKGKWTAPMIDNPAYKGPWAPRKIANPNYFEDKTPSNFEPMGAIGFEIWTMQNDILFDNIYIGHSVEDAEKLK
EYKGKWTAPMIDNPAYKGPWAPRKIANPNYFEDKTPSNFEPMGAIGFEIWTMQNDILFDNIYIGHSVEDAEKLKA
PEYKGKWTAPMIDNPAYKGPWAPRKIANPNYFEDKTPSNFEPMGAIGFEIWTMQNDILFDNIYIGHSVEDAEKLK
PEYKGKWTAPMIDNPAYKGPWAPRKIANPNYFEDKTPSNFEPMGAIGFEIWTMQNDILFDNIYIGHSVEDAEKLK
NPEYKGKWTAPMIDNPAYKGPWAPRKIANPNYFEDKTPSNFEPMGAIGFEIWTMQNDILFDNIYIGHSVEDAEKLK
PEYKGKWTAPMIDNPAYKGPWAPRKIANPNYFEDKTPSNFEPMGAIGFEIWTMQNDILFDNIYIGHSVEDAEKLK
KNPEYKGKWTAPMIDNPAYKGPWAPRKIANPNYFEDKTPSNFEPMGAIGFEIWTMQNDILFDNIYIGHSVEDAEKLK
KNPEYKGKWTAPMIDNPAYKGPWAPRKIANPNYFEDKTPSNFEPMGAIGFEIWTMQNDILFDNIYIGHSVEDAEKLK
PMKKNPEYKGKWTAPMIDNPAYKGPWAPRKIANPNYFEDKTPSNFEPMGAIGFEIWTMQNDILFDNIYIGHSVED
PEYKGKWTAPMIDNPAYKGPWAPRKIANPNYFEDKTPSNFEPMGAIGFEIWTMQNDILFDNIYIGHSVEDAEKL
EYKGKWTAPMIDNPAYKGPWAPRKIANPNYFEDKTPSNFEPMGAIGFEIWTMQNDILFDNIYIGHSVEDAEKLK
PEYKGKWTAPMIDNPAYKGPWAPRKIANPNYFEDKTPSNFEPMGAIGFEIWTMQNDILFDNIYIGHSVEDAEKLKAE
GKWTAPMIDNPAYKGPWAPRKIANPNYFEDKTPSNFEPMGAIGFEIWTMQNDILFDNIYIGHSVEDAEKLKAET'
YKGKWTAPMIDNPAYKGPWAPRKIANPNYFEDKTPSNFEPMGAIGFEIWTMQNDILFDNIYIGHSVEDAEKLKAET
EYKGKWTAPMIDNPAYKGPWAPRKIANPNYFEDKTPSNFEPMGAIGFEIWTMQNDILFDNIYIGHSVEDAEKLK
PEYKGKWTAPMIDNPAYKGPWAPRKIANPNYFEDKTPSNFEPMGAIGFEIWTMQNDILFDNIYIGHSVEDAEKLKA
GKWTAPMIDNPAYKGPWAPRKIANPNYFEDKTPSNFEPMGAIGFEIWTMQNDILFDNIYIGHSVEDAEKLKAET
PEYKGKWTAPMIDNPAYKGPWAPRKIANPNYFEDKTPSNFEPMGAIGFEIWTMQNDILFDNIYIGHSVEDAEKL
NPEYKGKWTAPMIDNPAYKGPWAPRKIANPNYFEDKTPSNFEPMGAIGFEIWTMQNDILFDNIYIGHSVEDAEKLK
PEYKGKWTAPMIDNPAYKGPWAPRKIANPNYFEDKTPSNFEPMGAIGFEIWTMQNDILFDNIYIGHSVEDAEKLKAE
PEYKGKWTAPMIDNPAYKGPWAPRKIANPNYFEDKTPSNFEPMGAIGFEIWTMQNDILFDNIYIGHSVEDAEKLKA
PEYKGKWTAPMIDNPAYKGPWAPRKIANPNYFEDKTPSNFEPMGAIGFEIWTMQNDILFDNIYIGHSVEDAEKL
YKGKWTAPMIDNPAYKGPWAPRKIANPNYFEDKTPSNFEPMGAIGFEIWTMQNDILFDNIYIGHSVEDAEKLKAE
YKGKWTAPMIDNPAYKGPWAPRKIANPNYFEDKTPSNFEPMGAIGFEIWTMQNDILFDNIYIGHSVEDAEKLKAET
YKGKWTAPMIDNPAYKGPWAPRKIANPNYFEDKTPSNFEPMGAIGFEIWTMQNDILFDNIYIGHSVEDAEKLKAET
KWTAPMIDNPAYKGPWAPRKIANPNYFEDKTPSNFEPMGAIGFEIWTMQNDILFDNIYIGHSVEDAEKLKAETWDLF
EYKGKWTAPMIDNPAYKGPWAPRKIANPNYFEDKTPSNFEPMGAIGFEIWTMQNDILFDNIYIGHSVEDAEKLKAET
YKGKWTAPMIDNPAYKGPWAPRKIANPNYFEDKTPSNFEPMGAIGFEIWTMQNDILFDNIYIGHSVEDAEKLKAE
YKGKWTAPMIDNPAYKGPWAPRKIANPNYFEDKTPSNFEPMGAIGFEIWTMQNDILFDNIYIGHSVEDAEKLKAE
```

FIGURE 7 (CONTINUED) (SEQ ID NOs:37-87)

```
----------460--------------470-----------480-------------490--------------500--------
`WDLKHPVEVAEEEAARPKDEEKKEGTLSFKEAPVKYIRGKIELFISLA
AETWDLKHPVEVAEEEAARPKDEEKKEGTLSFKEAPVKYIRGKIELFI
EKLKAETWDLKHPVEVAEEEAARPKDEEKKEGTLSFKEAPVKYIRGK
DAEKLKAETWDLKHPVEVAEEEAARPKDEEKKEGTLSFKEAPVKYI
KLKAETWDLKHPVEVAEEEAARPKDEEKKEGTLSFKEAPVKYIRGK
AEKLKAETWDLKHPVEVAEEEAARPKDEEKKEGTLSFKEAPVKYIRG
AEKLKAETWDLKHPVEVAEEEAARPKDEEKKEGTLSFKEAPVKYIRG
DAEKLKAETWDLKHPVEVAEEEAARPKDEEKKEGTLSFKEAPVKYIR
EKLKAETWDLKHPVEVAEEEAARPKDEEKKEGTLSFKEAPVKYIRGK
AEKLKAETWDLKHPVEVAEEEAARPKDEEKKEGTLSFKEAPVKYIRG
`WDLKHPVEVAEEEAARPKDEEKKEGTLSFKEAPVKYIRGKIELFISL
AETWDLKHPVEVAEEEAARPKDEEKKEGTLSFKEAPVKYIRGKIELF
TWDLKHPVEVAEEEAARPKDEEKKEGTLSFKEAPVKYIRGKIELFISL
AETWDLKHPVEVAEEEAARPKDEEKKEGTLSFKEAPVKYIRGKIELF
TWDLKHPVEVAEEEAARPKDEEKKEGTLSFKEAPVKYIRGKIELFISL
KAETWDLKHPVEVAEEEAARPKDEEKKEGTLSFKEAPVKYIRGKIEL
KAETWDLKHPVEVAEEEAARPKDEEKKEGTLSFKEAPVKYIRGKIEI
KLKAETWDLKHPVEVAEEEAARPKDEEKKEGTLSFKEAPVKYIRGKI
TWDLKHPVEVAEEEAARPKDEEKKEGTLSFKEAPVKYIRGKIELFIS
AETWDLKHPVEVAEEEAARPKDEEKKEGTLSFKEAPVKYIRGKIELF
KAETWDLKHPVEVAEEEAARPKDEEKKEGTLSFKEAPVKYIRGKIEI
AEKLKAETWDLKHPVEVAEEEAARPKDEEKKEGTLSFKEAPVKYIRG
AETWDLKHPVEVAEEEAARPKDEEKKEGTLSFKEAPVKYIRGKIEL
ETWDLKHPVEVAEEEAARPKDEEKKEGTLSFKEAPVKYIRGKIELF
AETWDLKHPVEVAEEEAARPKDEEKKEGTLSFKEAPVKYIRGKIELFI
AETWDLKHPVEVAEEEAARPKDEEKKEGTLSFKEAPVKYIRGKIEL
AETWDLKHPVEVAEEEAARPKDEEKKEGTLSFKEAPVKYIRGKIELF
ETWDLKHPVEVAEEEAARPKDEEKKEGTLSFKEAPVKYIRGKIELFIS
AETWDLKHPVEVAEEEAARPKDEEKKEGTLSFKEAPVKYIRGKIELF
AETWDLKHPVEVAEEEAARPKDEEKKEGTLSFKEAPVKYIRGKIELF
DAEKLKAETWDLKHPVEVAEEEAARPKDEEKKEGTLSFKEAPVKYIR
KAETWDLKHPVEVAEEEAARPKDEEKKEGTLSFKEAPVKYIRGKIEL
AETWDLKHPVEVAEEEAARPKDEEKKEGTLSFKEAPVKYIRGKIELFI
ETWDLKHPVEVAEEEAARPKDEEKKEGTLSFKEAPVKYIRGKIELFIS
`WDLKHPVEVAEEEAARPKDEEKKEGTLSFKEAPVKYIRGKIELFISLA
TWDLKHPVEVAEEEAARPKDEEKKEGTLSFKEAPVKYIRGKIELFISL
AETWDLKHPVEVAEEEAARPKDEEKKEGTLSFKEAPVKYIRGKIELF
AETWDLKHPVEVAEEEAARPKDEEKKEGTLSFKEAPVKYIRGKIELFIS
TWDLKHPVEVAEEEAARPKDEEKKEGTLSFKEAPVKYIRGKIELFISLA
LKAETWDLKHPVEVAEEEAARPKDEEKKEGTLSFKEAPVKYIRGKIEI
AETWDLKHPVEVAEEEAARPKDEEKKEGTLSFKEAPVKYIRGKIELF
ETWDLKHPVEVAEEEAARPKDEEKKEGTLSFKEAPVKYIRGKIELFIS
AETWDLKHPVEVAEEEAARPKDEEKKEGTLSFKEAPVKYIRGKIELFIS
LKAETWDLKHPVEVAEEEAARPKDEEKKEGTLSFKEAPVKYIRGKIE
TWDLKHPVEVAEEEAARPKDEEKKEGTLSFKEAPVKYIRGKIELFISL
TWDLKHPVEVAEEEAARPKDEEKKEGTLSFKEAPVKYIRGKIELFISL
`WDLKHPVEVAEEEAARPKDEEKKEGTLSFKEAPVKYIRGKIELFISL
KHPVEVAEEEAARPKDEEKKEGTLSFKEAPVKYIRGKIELFISLALE
TWDLKHPVEVAEEEAARPKDEEKKEGTLSFKEAPVKYIRGKIELFISL
TWDLKHPVEVAEEEAARPKDEEKKEGTLSFKEAPVKYIRGKIELFISL
ETWDLKHPVEVAEEEAARPKDEEKKEGTLSFKEAPVKYIRGKIELFISL
```

FIGURE 7 (CONTINUED) (SEQ ID NOs:37-87)

FIGURE 7 (CONTINUED) (SEQ ID NOs:37-87)

> B.d. 26199 calnexin (deduced from genomic sequence)
MRLNASLASLILSSIALIGNVHAEDEVKEDATSTSSVIEKPTFTPTTLKAPFLEQFTDGWET
RWTPSHAKKEDSKSEEDWAYVGTWAVEEPHVFNGMVGDKGLVVKNPAAHHAISAKFPK
KIDNKGKTLVVQYEVKLQNSLNCGGAYMKLLQDNKKLHAEEFSNTSPYVIMFGPDKCGVT
NKVHFIFKHKNPKTGEYEEKHMKLPPAVRVSKLSTLYTLIVNPDQSFQIRIDGAAVKNGTL
LEDFSPAVNPEKEIDDPEDKKPEDWVDEAHIPDPEATKPEDWDEDAPYEIVDTDATQPE
DWLVDEPTSIPDPEAQKPEDWDDEEDGDWIPPTIPNPKCSEVSGCGMWEPPMKKNPEY
KGKWTAPMIDNPAYKGPWAPRKIANPNYFEDKTPSNFEPMGAIGFEIWTMQNDILFDNI
YIGHSVEDAEKLKAETWDLKHPVEVAEEEAARPKDEEKKEGTLSFKEAPVKYIRGKIELFI
SLALENPVEAVKAVPEVAGGLGALLVTLVLIIVGAVGLGSPSPAPAAKKQAEKGKEKTAEA
VSTAADNVKGEAKKRSGKAGE Links to Calnexin Protein sequence in GenBank:

-Note that these links are for a the Calnexin sequence for the strain 18188, but the protein sequence is identical to that in strain 26199 www.ncbi.nlm.nih.gov/protein/327357651
Protein database Accession number: EGE86508
Broad Institute predicted Gene name: BDDG_09453

Figure 8(SEQ ID NO:35)

```
ClustalW (v1.83) multiple sequence alignment

7 Sequences Aligned              Processing time: 0.7 seconds
Gaps Inserted = 85               Conserved Identities = 152
Score = 51436

Pairwise Alignment Mode: Fast
Pairwise Alignment Parameters:
   Ktup = 1    Gap Penalty = 3      Top Diagonals = 5    Window Size = 5
   Similarity Matrix: gonnet Multiple Alignment Parameters:
   Open Gap Penalty = 10.0     Extend Gap Penalty = 0.2
   Delay Divergent = 40%       Gap Distance = 8
   Similarity Matrix: gonnet Identity Scores (%)
              B.d.  P.b.  C.i.  Pb C.i. RS H.c. G1 A.flavu C.a.531 C. neof
              26199 Pb01        86AR       s   4              orm.
B.d. 26199    100.0 82.9  78.9  87.1  73.9  32.5  49.0
P.b. Pb01     90.3  100.0 77.5  80.5  72.6  33.1  49.7
C.i. RS       87.6  85.9  100.0 77.5  72.3  33.8  50.0
H.c. G186AR   92.0  88.4  87.1  100.0 72.6  33.6  48.9
A. flavus     85.5  84.4  85.5  83.6  100.0 34.6  51.7
C.a.5314      46.0  47.8  47.3  46.8  46.6  100.0 33.5
C. neoform.   63.1  63.6  64.0  62.0  64.4  46.4  100.0
           Similarity Scores (%)
```

FIGURE 9

*Formatted Alignments*

```
B.d. 26199    1   MRLNASLASLILSSIALIGNVHAEDVKEDATSTSSVIEK    40
P.b. Pb01     1   MRLNASLASLITSIALIGNVHAEDVEGKPSSTSSVIEK    40
C.i. RS       1   MRLNARTASLILSYIALGQVHAESATKEEP-TATSISR    39
H.c. G186AR   1   MRLNASLASLILSSVALIGNVRAEEVKGDAPSPSSAIEK   40
A flavus      1   MRFNAAVASALVSSATLMG--YAHAEEAEKNPDATSVVEK  38
C.a.5314      1   ---------------MKYALVLLLSLVNALKYVPFDK    22
C. neoform.   1   MRP------------QNVAGVAGTGALIMAAGALADR    25

B.d. 26199    41  PTFTPTTLKAPFLEQFTDGW-ETRWTPSHAKKDSKSEED    79
P.b. Pb01     41  PLFTPTTLKAPFLEQFTDDW-ETRWTPSHAKKQDSSSEED  79
C.i. RS       40  PTFTPTTLKAPFLEQFTDDW-QTRWTPSHAKKEDSKSEEE  78
H.c. G186AR   41  PTFTPTTLKAPFLEQFTDDW-ETRWTPSHAKKEDSSDED   79
A flavus      39  PTFTPTTLKAPFLEQFTDDW-ESRWTPSHAKKDDSQTEED  77
C.a.5314      23  TQLDPSSVFEQHDYPSLNSS---PWQVSTAKKFDEGRDEI  59
C. neoform.   26  AVHHPTSLTAPHIEQHLESIPESRWTVSRATKQTPVGDEI  65

B.d. 26199    80  WAYVGTWAVEEPH-VHNGMVGDKGLVVKNPAAHHAISAKR 118
P.b. Pb01     80  WAYVGTWAVEEPH-VHNGMKGDKGLVIKNAAAHHAISAKR 118
C.i. RS       79  WAYVGEWAVEEPT-VHKGIDGDKGLVVKNAAAHHAISAKR 117
H.c. G186AR   80  WAYIGTWAVEEPH-VLNGMVGDKGLVVKNPAAHHAISAKR 118
A flavus      78  WAYVGEWSVEEPT-VHKGIDGDKGLVVKNPAAHHAISAKR 116
C.a.5314      60  VRYSGEWKIHSSTSKYPLEGDLGLVMKSRASHYAISYKL   99
C. neoform.   66  FSYVGQWEIEEPD-VYPGISGDKGLVLKTAAHHAISTLR  104

B.d. 26199    119 PKKID-----NKGKTLVVQYEVKLQNSLNCGGAYMKLLQ  152
P.b. Pb01     119 PKKID-----NKGNTLVVQYEVKLQNGLNCGGAYMKLLQ  152
C.i. RS       118 PQKID-----NKGKTLVVQYEVKLQNSLVCGGAYMKLLQ  151
H.c. G186AR   119 PKKID-----NKGKTLVVQYEVKLQNSLVCGGAYMKLLQ  152
A flavus      117 PKKID-----NKGKTLVVQYEVKPQNSLVCGGAYLKLLQ  150
C.a.5314      100 PHEVTNTNPNNKTQDLVLQYEVKLQQGLTCGGAYIKLLD  139
C. neoform.   105 DEPID-----PKGKSLVVQYEVKLQKGLECGGAYIKLLT  138

B.d. 26199    153 DNKK--LHA-EEFSNTSPYVIMFGPDKCGVTNKVHFIKH  189
P.b. Pb01     153 DNKK--LHA-EEFSNASPYVIMFGPDKCGVTNKVHFIFRH 189
C.i. RS       152 DNKK--LHA-EEFSNASPYVIMFGPDKCGATNKVHFIKH  188
H.c. G186AR   153 DNKK--LHA-EEFSNASPYVIMFGPDKCGVTNKVHFIFRH 189
A flavus      151 ENKK--LHA-EEFSNATPYVIMFGPDKCGATNKVHFIFRH 187
C.a.5314      140 SSPS----GYKFNSETPYQIMFGPDVCGSNKIHFIIRK  175
C. neoform.   139 DQQDEGLRAGEDYTDKTPFTIMFGPDKCGSTNKVHFIFRH 178
```

FIGURE 10

```
B.d. 26199   190  KNPKTGEYEEKHMKLPPAVRVSKLSTLYTLIVN--PDQSF  227
P.b. Pb01    190  KNPKTGEYEEKHLKNPPAARVSKLSTLYTLIVK--PDQSF  227
C.i. RS      189  KNPKTGEYEEKHLNNAPTARISKLSTLYTLIVK--PDQTF  226
H.c. G186AR  190  KNPKTGEYEEKHMNAAPAAKINKLSTLYTLIVK--PDQSF  227
A flavus     188  KNPKTGEYEEKHLKAPPAARTNKVTSLYTLIVR--PDQSF  225
C.a.5314     176  KLP-NGAIEEKHLKHKPMARTNELTNLYTLIIK--SNQDF  212
C. neoform.  179  KNPLTGEWEEKHLKNPPAPKITKTTALYTLITKTSPDQTF  218

B.d. 26199   228  QIRIDGAVKNGTLLED---HSPAVNPEKEIDDPEDKKPE   264
P.b. Pb01    228  QILIDGEAVKNGTLLED---HSPAVNPQKEIDDPEDKKPK  264
C.i. RS      227  QIQINGEAVKNGTLLED---HQPPVNPPKEIDDPNDKKPA  263
H.c. G186AR  228  QIRIDGKAVKNGTLLED---HSPAVNPPKEIDDPEDKKPE  264
A flavus     226  QILIDGEAVKNGTLLED---HNPPVNPEKEIDDPKDKKPD  262
C.a.5314     213  EIRVNGQVAKAGNLYKNQKLHNPPFEPPKEIPDVDDKKPD  252
C. neoform.  219  EILINDESVRKGSLLED---HDPPVNPPKEIDDPEDFKPE  255

B.d. 26199   265  DWVDEAHIPDPEATKPEDWDEDAPY-EIVDTDATQPEDWL  303
P.b. Pb01    265  DWVDETRIPDPTATKPDDWDEDAPY-EIIDTEATKPDDWL  303
C.i. RS      264  DWVDEAKIPDPEAKKPEDWDEDAPF-EIVDTEAKKPDDWL  302
H.c. G186AR  265  DWVDEARIADPDATKPEDWDEDAPY-EIVDADAVQPEDWL  303
A flavus     263  DWVDDVKIPDPEATKPEDWDEAPY-EIVDEEATKPEDWL   301
C.a.5314     253  DWDDRAYIPDPNVEKPEDYELKHEYPQIRDPNAVKPDEWD  292
C. neoform.  256  TWVDEAEIDDVTATKPDDWDEDAPI-MITDTSAVKPEDWL  294

B.d. 26199   304  VDEPTSIPDPEAQKPEDWDDEEDGDWIPPTIPNPKCSEVS  343
P.b. Pb01    304  DSEPDSIPDPEAQKPEDWDDEEDGDWAAPTIPNPKCSEVS  343
C.i. RS      303  DDEPSSIPDPEAQKPEDWDDEEDGDWVAPTVPNPKCEEAS  342
H.c. G186AR  304  IDEPTSIPDPEAEKPEDWDDEEDGDWTPPTIPNPKCSEVS  343
A flavus     302  EEEPTSIPDPEAEKPEDWDDEEDGDWIPPTVPNPKCNDVS  341
C.a.5314     293  ESAPRYIPDPDAVKPKDWNDAEK-QWEPPLIVNPKC--AT  329
C. neoform.  295  EEEPETIPDPEAEKPEWDDEEDGDWIPPMVPNPKCEDVS  334

B.d. 26199   344  GCGMWEPMKKNPEYKGKWTAPMIDNPAYKGPWAPRKIAN  383
P.b. Pb01    344  GCGKWEAPMKKNPDYKGKWTPPMIDNPAYKGPWTPRKIPN  383
C.i. RS      343  GCGKWEPMKRNPDYKGKWTAPLIDNPAYKGPWSPRKIAN  382
H.c. G186AR  344  GCGKWQQPMKKNPDYKGKWVAPMIDNPAYKGPWAPRKIPN  383
A flavus     342  GCGPWSAPMKKNPAYKGKWTAPMIDNPAYKGPWSPRKIAN  381
C.a.5314     330  GCGPWEAPLIPNHDYIGPWFPDIKNPNYNGIWTPRLIBN   369
C. neoform.  335  GCGPWTAPKVRNPAYKGKWTIPKIPNPDYKGPWAPRKIAN  374

B.d. 26199   384  PNYFEDKTPSNFEP-MGAIGFEIWTMQNDILFDNIYIGHS  422
P.b. Pb01    384  PNYFEDKTPANFEP-MGAIGFEIWTMQNDILFNNIYIGHS  422
C.i. RS      383  PDFEDKKPANFEP-MGAIGFEIWTMQNDILFDNIYIGHS   421
H.c. G186AR  384  PDYFEDKTPANFEP-MGAIGFEIWTMQSDILFNNIYIGHS  422
A flavus     382  PAYFEDKTPSNFEP-MGAIGFEIWTMQNDILFDNIYIGHS  420
C.a.5314     370  PYYYQVKTPGKLDKPIGGIGFELWSIESDILFDNIYLGNS  409
C. neoform.  375  PAFEDLHPSDHTK-IGGVGIELWTMTEDILFDNLYIGHD   413
```

FIGURE 10 - continued

```
B.d. 26199    423  VEDAEKLKAETWDKHPVEVAEEEARPK-DEKKEGTLS  461
P.b. Pb01     423  IEDAQKLKSETWDIKHPIEVAEEEATRPK-DDEKDSSFVS  461
C.i. RS       422  IEDAKKLKAETHDIKHPIEVAEEEAAKPK-DEPSTDSGLN  460
H.c. G186AR   423  IEDAEKLKAETWDLKHPVEVAEEEASRPK-DEKEAGT-S   460
A flavus      421  PEDAEQLRKETHDVKHPVEVAEEEASKPKKEETAPATSVS  460
C.a. 5314     410  IAEAELIGNITFKIKYELADQRRENKPRVKNEPVAPPRN   449
C. neoform.   414  AAQAKKFAEETYHVKKPIEKEAEGSNEDE--------LE   444

B.d. 26199    462  FKEAPVKYIRGKIELFISLALENPVEAVKAVP--------  493
P.b. Pb01     462  FKEAPVQFVREKINLFISIARKDPVQAAKSVP--------  493
C.i. RS       461  FKDDPVKYIRSKVDQFILMAKDNPVEAVKAVP--------  492
H.c. G186AR   461  FKEDPVQYIRKKIDLFISLALENPVEAVKTVP--------  492
A flavus      461  HQEDPITFVREKVDHHVGLAKQDPVNAVKQAP--------  492
C.a. 5314     450  HEDIIRDDSISTFQQHLIFIKLFWLKQYVQLKDFYFELTL  489
C. neoform.   445  EPSSLIDKVQLKVYELHLATFDISQAVKQMP--------  476

B.d. 26199    494  ----EVAGGLGALLVTLVLIIVGAVGLGSPSPAPAAKKQ   528
P.b. Pb01     494  ----EVAGGLGALVITLALIIVGAIGLSSPAPAPAVAKK  528
C.i. RS       493  ----EVAGGLAALUITLIVVHGAIGLSSPAPAPA-KKD   526
H.c. G186AR   493  ----EVAGGLGALLVTLILTIVSGISLGS-SSSPAPKKQ  526
A flavus      493  ----EVAGTLGALVLSMVLIIVGAIKASSPAPAPVKKGK  527
C.a. 5314     490  DPIGLIMANPLKTLLYAFLFLFSFTIFFGFASTIMFLLQG 529
C. neoform.   477  ----EVAAGLAAVHTLLGMLLALHGFIGSAPTKVKQTS   511

B.d. 26199    529  AEKGKEK-------TAEAVSTAADNV-----KGEAKRS   555
P.b. Pb01     529  VD-GKEKDGASKEKAAEAVSTTADNV-----KGAATRRS  561
C.i. RS       527  AGKGKEK---AKEKAAEAVSTGAENV-----KAGATKRS  557
H.c. G186AR   527  AEKGKEKE---KASASEAVSTGADNV-----KGGAKRS  557
A flavus      528  EAAGAAK----EKVSEAVSSSADTG-----KGGASKRT  556
C.a. 5314     530  GEAFGSSSSITTTTTDSNRKNVLTAEEIEMPSNHVQKIE  569
C. neoform.   512  VKTKSVAP---VAPAGEEKKALDQAGVEVPAVEGSKKRV  548

B.d. 26199    556  GKAGE-------  560
P.b. Pb01     562  GKANNE------  567
C.i. RS       558  -KSSE-------  561
H.c. G186AR   558  TKTSE-------  562
A flavus      557  TRSSAQ------  562
C.a. 5314     570  ILDEQIHVRQRK  581
C. neoform.   549  TRSTKE------  554
```

FIGURE 10 - continued

SEQUENCE LISTING

```
<160> NUMBER OF SEQ ID NOS: 95

<210> SEQ ID NO 1
<211> LENGTH: 13
<212> TYPE: PRT
<213> ORGANISM: Blastomyces dermatitidis strains 26199

<400> SEQUENCE: 1

Leu Val Val Lys Asn Pro Ala Ala His His Ala Ile Ser
1               5                   10

<210> SEQ ID NO 2
<211> LENGTH: 13
<212> TYPE: PRT
<213> ORGANISM: Blastomyces dermatitidis strains 26199

<400> SEQUENCE: 2

Leu Val Val Lys Asn Pro Ala Ala His His Ala Ile Ser
1               5                   10
```

-continued

```
<210> SEQ ID NO 3
<211> LENGTH: 13
<212> TYPE: PRT
<213> ORGANISM: Blastomyces dermatitidis strains

```
<212> TYPE: PRT
<213> ORGANISM: Paracoccidioides brasiliensis

<400> SEQUENCE: 10

Leu Val Ile Lys Asn Ala Ala Ala His His Ala Ile Ser
1               5                   10

<210> SEQ ID NO 11
<211> LENGTH: 13
<212> TYPE: PRT
<213> ORGANISM: Paracoccidioides lutzii

<400> SEQUENCE: 11

Leu Val Ile Lys Asn Ala Ala Ala His His Ala Ile Ser
1               5                   10

<210> SEQ ID NO 12
<211> LENGTH: 13
<212> TYPE: PRT
<213> ORGANISM: Coccidioides immitis

<400> SEQUENCE: 12

Leu Val Val Lys Asn Ala Ala Ala His His Ala Ile Ser
1               5                   10

<210> SEQ ID NO 13
<211> LENGTH: 13
<212> TYPE: PRT
<213> ORGANISM: Coccidioides posadasii C35 SOWgp

<400> SEQUENCE: 13

Leu Val Val Lys Asn Ala Ala Ala His His Ala Ile Ser
1               5                   10

<210> SEQ ID NO 14
<211> LENGTH: 13
<212> TYPE: PRT
<213> ORGANISM: Coccidioides posadasii Silveira

<400> SEQUENCE: 17

Leu Val Val Lys Asn Pro Ala Ala His His Ala Ile Ser
1               5                   10

<210> SEQ ID NO 18
<211> LENGTH: 13
<212> TYPE: PRT
<213> ORGANISM: Aspergillus oryzae

<400> SEQUENCE: 18

Leu Val Val Lys Asn Pro Ala Ala His His Ala Ile Ser
1               5                   10

<210> SEQ ID NO 19
<211> LENGTH: 13
<212> TYPE: PRT
<213> ORGANISM: Aspergillus terreus

<400> SEQUENCE: 19

Leu Val Val Lys Asn Pro Ala Ala His His Ala Ile Ser
1               5                   10

<210> SEQ ID NO 20
<211> LENGTH: 13
<212> TYPE: PRT
<213> ORGANISM: Aspergillus nidulans

<400> SEQUENCE: 20

Leu Val Val Lys Asn Val Ala Ala His His Ala Ile Ser
1               5                   10

<210> SEQ ID NO 21
<211> LENGTH: 13
<212> TYPE: PRT
<213> ORGANISM: Aspergillus kawachii

<400> SEQUENCE: 21

Leu Val Val Lys Asn Val Ala Ala His His Ala Ile Ser
1               5                   10

<210> SEQ ID NO 22
<211> LENGTH: 13
<212> TYPE: PRT
<213> ORGANISM: Aspergillus niger

<400> SEQUENCE: 22

Leu Val Val Lys Asn Val Ala Ala His His Ala Ile Ser
1               5                   10

<210> SEQ ID NO 23
<211> LENGTH: 13
<212> TYPE: PRT
<213> ORGANISM: Aspergillus fumigatus

<400> SEQUENCE: 23

Leu Val Val Lys Asn Val Ala Ala His His Ala Ile Ser
1               5                   10

<210> SEQ ID NO 24
<211> LENGTH: 13
<212> TYPE: PRT
<213> ORGANISM: Aspergillus clavatus

<400> SEQUENCE: 24

Leu Val Val Lys Asn Val Ala His His Ala Ile Ser
1               5                   10

<210> SEQ ID NO 25
<211> LENGTH: 13
<212> TYPE: PRT
<213> ORGANISM: Pneumocystis carinii

<400> SEQUENCE: 25

Leu Val Leu Lys Asn Glu Ala Ala His His Ala Ile Ser
1               5                   10

<210> SEQ ID NO 26
<211> LENGTH: 13
<212> TYPE: PRT
<213> ORGANISM: Magnaporthe oryzae

<400> SEQUENCE: 26

Leu Val Val Lys Asn Pro Ala Ala His His Ala Ile Ser
1               5                   10

<210> SEQ ID NO 27
<211> LENGTH: 13
<212> TYPE: PRT
<213> ORGANISM: Exophiala dermatitidis

<400> SEQUENCE: 27

Leu Val Val Lys Asn Ala Ala Ala His His Ala Ile Ser
1               5                   10

<210> SEQ ID NO 28
<211> LENGTH: 13
<212> TYPE: PRT
<213> ORGANISM: Neurospora crassa

<400> SEQUENCE: 28

Leu Val Val Lys Asn Ala Ala Ala His His Ala Ile Ser
1               5                   10

<210> SEQ ID NO 29
<211> LENGTH: 13
<212> TYPE: PRT
<213> ORGANISM: Cryptococcus neoformans

<400> SEQUENCE: 29

Leu Val Leu Lys Thr Lys Ala Ala His His Ala Ile Ser
1               5                   10

<210> SEQ ID NO 30
<211> LENGTH: 13
<212> TYPE: PRT
<213> ORGANISM: Schizophyllum commune

<400> SEQUENCE: 30

Leu Val Ala Lys Thr Lys Ala Ala His His Ala Ile Ser
1               5                   10

<210> SEQ ID NO 31
<211> LENGTH: 13
<212> TYPE: PRT
<213> ORGANISM: Candida albicans

<400> SEQUENCE: 31

Leu Val Met Lys Ser Arg Ala Ser His Tyr Ala Ile Ser

```
1               5                   10

<210> SEQ ID NO 32
<211> LENGTH: 13
<212> TYPE: PRT
<213> ORGANISM: Homo sapiens

<400> SEQUENCE: 32

Leu Val Leu Lys Ser Arg Ala Lys His His Ala Ile Ser
1               5                   10

<210> SEQ ID NO 33
<211> LENGTH: 13
<212> TYPE: PRT
<213> ORGANISM: Homo sapiens

<400> SEQUENCE: 33

Leu Val Leu Met Ser Arg Ala Lys His His Ala Ile Ser
1               5                   10

<210> SEQ ID NO 34
<211> LENGTH: 13
<212> TYPE: PRT
<213> ORGANISM: Geomyces destrctans now called Pseudogymnoascus
      destructans

<400> SEQUENCE: 34

Leu Val Val Lys Asn Ala Ala Ala His His Ala Ile Ser
1               5                   10

<210> SEQ ID NO 35
<211> LENGTH: 560
<212> TYPE: PRT
<213> ORGANISM: Blastomyces dermatitidis strains 26199

<400> SEQUENCE: 35

Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
                20                  25                  30

Ser Thr Ser Ser Val Ile Glu Lys Pro Thr Phe Thr Pro Thr Thr Leu
            35                  40                  45

Lys Ala Pro Phe Leu Glu Gln Phe Thr Asp Gly Trp Glu Thr Arg Trp
        50                  55                  60

Thr Pro Ser His Ala Lys Lys Glu Asp Ser Lys Ser Glu Glu Asp Trp
65                  70                  75                  80

Ala Tyr Val Gly Thr Trp Ala Val Glu Glu Pro His Val Phe Asn Gly
                85                  90                  95

Met Val Gly Asp Lys Gly Leu Val Val Lys Asn Pro Ala Ala His His
                100                 105                 110

Ala Ile Ser Ala Lys Phe Pro Lys Lys Ile Asp Asn Lys Gly Lys Thr
            115                 120                 125

Leu Val Val Gln Tyr Glu Val Lys Leu Gln Asn Ser Leu Asn Cys Gly
        130                 135                 140

Gly Ala Tyr Met Lys Leu Leu Gln Asp Asn Lys Lys Leu His Ala Glu
145                 150                 155                 160

Glu Phe Ser Asn Thr Ser Pro Tyr Val Ile Met Phe Gly Pro Asp Lys
                165                 170                 175

Cys Gly Val Thr Asn Lys Val His Phe Ile Phe Lys His Lys Asn Pro
                180                 185                 190
```

Lys Thr Gly Glu Tyr Glu Lys His Met Lys Leu Pro Pro Ala Val
            195                 200                 205

Arg Val Ser Lys Leu Ser Thr Leu Tyr Thr Leu Ile Val Asn Pro Asp
            210                 215                 220

Gln Ser Phe Gln Ile Arg Ile Asp Gly Ala Ala Val Lys Asn Gly Thr
225                 230                 235                 240

Leu Leu Glu Asp Phe Ser Pro Ala Val Asn Pro Glu Lys Glu Ile Asp
            245                 250                 255

Asp Pro Glu Asp Lys Lys Pro Glu Asp Trp Val Asp Glu Ala His Ile
            260                 265                 270

Pro Asp Pro Glu Ala Thr Lys Pro Glu Asp Trp Asp Asp Ala Pro
            275                 280                 285

Tyr Glu Ile Val Asp Thr Asp Ala Thr Gln Pro Glu Asp Trp Leu Val
            290                 295                 300

Asp Glu Pro Thr Ser Ile Pro Asp Pro Glu Ala Gln Lys Pro Glu Asp
305                 310                 315                 320

Trp Asp Asp Glu Glu Asp Gly Asp Trp Ile Pro Pro Thr Ile Pro Asn
            325                 330                 335

Pro Lys Cys Ser Glu Val Ser Gly Cys Gly Met Trp Glu Pro Pro Met
            340                 345                 350

Lys Lys Asn Pro Glu Tyr Lys Gly Lys Trp Thr Ala Pro Met Ile Asp
            355                 360                 365

Asn Pro Ala Tyr Lys Gly Pro Trp Ala Pro Arg Lys Ile Ala Asn Pro
370                 375                 380

Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
            405                 410                 415

Ile Tyr Ile Gly His Ser Val Glu Asp Ala Glu Lys Leu Lys Ala Glu
            420                 425                 430

Thr Trp Asp Leu Lys His Pro Val Glu Val Ala Glu Glu Ala Ala
            435                 440                 445

Arg Pro Lys Asp Glu Glu Lys Lys Glu Gly Thr Leu Ser Phe Lys Glu
            450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Glu Val Ala
            485                 490                 495

Gly Gly Leu Gly Ala Leu Leu Val Thr Leu Val Leu Ile Val Gly
            500                 505                 510

Ala Val Gly Leu Gly Ser Pro Ser Pro Ala Pro Ala Ala Lys Lys Gln
            515                 520                 525

Ala Glu Lys Gly Lys Glu Lys Thr Ala Glu Ala Val Ser Thr Ala Ala
            530                 535                 540

Asp Asn Val Lys Gly Glu Ala Lys Lys Arg Ser Gly Lys Ala Gly Glu
545                 550                 555                 560

<210> SEQ ID NO 36
<211> LENGTH: 560
<212> TYPE: PRT
<213> ORGANISM: Blastomyces dermatitidis strains 18188

<400> SEQUENCE: 36

```
Met Arg Leu Asn Ala Ser Leu Ala Ser Leu Ile Leu Ser Ser Ile Ala
```

```
1               5                    10                   15
Leu Ile Gly Asn Val His Ala Glu Asp Glu Val Lys Glu Asp Ala Thr
                    20                   25                   30

Ser Thr Ser Ser Val Ile Glu Lys Pro Thr Phe Thr Pro Thr Thr Leu
                35                   40                   45

Lys Ala Pro Phe Leu Glu Gln Phe Thr Asp Gly Trp Glu Thr Arg Trp
            50                   55                   60

Thr Pro Ser His Ala Lys Lys Glu Asp Ser Lys Ser Glu Glu Asp Trp
65                   70                   75                   80

Ala Tyr Val Gly Thr Trp Ala Val Glu Glu Pro His Val Phe Asn Gly
                    85                   90                   95

Met Val Gly Asp Lys Gly Leu Val Val Lys Asn Pro Ala Ala His His
                100                  105                  110

Ala Ile Ser Ala Lys Phe Pro Lys Lys Ile Asp Asn Lys Gly Lys Thr
            115                  120                  125

Leu Val Val Gln Tyr Glu Val Lys Leu Gln Asn Ser Leu Asn Cys Gly
    130                  135                  140

Gly Ala Tyr Met Lys Leu Leu Gln Asp Asn Lys Lys Leu His Ala Glu
145                  150                  155                  160

Glu Phe Ser Asn Thr Ser Pro Tyr Val Ile Met Phe Gly Pro Asp Lys
                    165                  170                  175

Cys Gly Val Thr Asn Lys Val His Phe Ile Phe Lys His Lys Asn Pro
                180                  185                  190

Lys Thr Gly Glu Tyr Glu Glu Lys His Met Lys Leu Pro Pro Ala Val
            195                  200                  205

Arg Val Ser Lys Leu Ser Thr Leu Tyr Thr Leu Ile Val Asn Pro Asp
    210                  215                  220

Gln Ser Phe Gln Ile Arg Ile Asp Gly Ala Ala Val Lys Asn Gly Thr
225                  230                  235                  240

Leu Leu Glu Asp Phe Ser Pro Ala Val Asn Pro Glu Lys Glu Ile Asp
                    245                  250                  255

Asp Pro Glu Asp Lys Lys Pro Glu Asp Trp Val Asp Glu Ala His Ile
                260                  265                  270

Pro Asp Pro Glu Ala Thr Lys Pro Glu Asp Trp Asp Glu Asp Ala Pro
            275                  280                  285

Tyr Glu Ile Val Asp Thr Asp Ala Thr Gln Pro Glu Asp Trp Leu Val
    290                  295                  300

Asp Glu Pro Thr Ser Ile Pro Asp Pro Glu Ala Gln Lys Pro Glu Asp
305                  310                  315                  320

Trp Asp Asp Glu Glu Asp Gly Asp Trp Ile Pro Pro Thr Ile Pro Asn
                    325                  330                  335

Pro Lys Cys Ser Glu Val Ser Gly Cys Gly Met Trp Glu Pro Pro Met
                340                  345                  350

Lys Lys Asn Pro Glu Tyr Lys Gly Lys Trp Thr Ala Pro Met Ile Asp
            355                  360                  365

Asn Pro Ala Tyr Lys Gly Pro Trp Ala Pro Arg Lys Ile Ala Asn Pro
    370                  375                  380

Asn Tyr Phe Glu Asp Lys Thr Pro Ser Asn Phe Glu Pro Met Gly Ala
385                  390                  395                  400

Ile Gly Phe Glu Ile Trp Thr Met Gln Asn Asp Ile Leu Phe Asp Asn
                    405                  410                  415

Ile Tyr Ile Gly His Ser Val Glu Asp Ala Glu Lys Leu Lys Ala Glu
                420                  425                  430
```

```
Thr Trp Asp Leu Lys His Pro Val Glu Val Ala Glu Glu Ala Ala
        435                 440                 445

Arg Pro Lys Asp Glu Glu Lys Lys Glu Gly Thr Leu Ser Phe Lys Glu
    450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Val Ala
                485                 490                 495

Gly Gly Leu Gly Ala Leu Leu Val Thr Leu Val Leu Ile Ile Val Gly
            500                 505                 510

Ala Val Gly Leu Gly Ser Pro Ser Pro Ala Pro Ala Ala Lys Lys Gln
            515                 520                 525

Ala Glu Lys Gly Lys Glu Lys Thr Ala Glu Ala Val Ser Thr Ala Ala
        530                 535                 540

Asp Asn Val Lys Gly Glu Ala Lys Lys Arg Ser Gly Lys Ala Gly Glu
545                 550                 555                 560
```

<210> SEQ ID NO 37
<211> LENGTH: 560
<212> TYPE: PRT
<213> ORGANISM: Homo sapiens
<220> FEATURE:
<221> NAME/KEY: BINDING SITE
<222> LOCATION: (1)..(9)
<220> FEATURE:
<221> NAME/KEY: BINDING SITE
<222> LOCATION: (129)..(143)
<220> FEATURE:
<221> NAME/KEY: BINDING SITE
<222> LOCATION: (162)..(176)
<220> FEATURE:
<221> NAME/KEY: BINDING SITE
<222> LOCATION: (202)..(210)
<220> FEATURE:
<221> NAME/KEY: BINDING SITE
<222> LOCATION: (395)..(403)
<220> FEATURE:
<221> NAME/KEY: BINDING SITE
<222> LOCATION: (474)..(482)
<220> FEATURE:
<221> NAME/KEY: BINDING SITE
<222> LOCATION: (503)..(516)

<400> SEQUENCE: 37

```
Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
            20                  25                  30

Ser Thr Ser Ser Val Ile Glu Lys Pro Thr Phe Thr Pro Thr Thr Leu
        35                  40                  45

Lys Ala Pro Phe Leu Glu Gln Phe Thr Asp Gly Trp Glu Thr Arg Trp
50                  55                  60

Thr Pro Ser His Ala Lys Lys Glu Asp Ser Lys Ser Glu Glu Asp Trp
65                  70                  75                  80

Ala Tyr Val Gly Thr Trp Ala Val Glu Glu Pro His Val Phe Asn Gly
                85                  90                  95

Met Val Gly Asp Lys Gly Leu Val Val Lys Asn Pro Ala Ala His His
                100                 105                 110

Ala Ile Ser Ala Lys Phe Pro Lys Lys Ile Asp Asn Lys Gly Lys Thr
            115                 120                 125

Leu Val Val Gln Tyr Glu Val Lys Leu Gln Asn Ser Leu Asn Cys Gly
```

```
            130                 135                 140
Gly Ala Tyr Met Lys Leu Leu Gln Asp Asn Lys Lys Leu His Ala Glu
145                 150                 155                 160

Glu Phe Ser Asn Thr Ser Pro Tyr Val Ile Met Phe Gly Pro Asp Lys
                165                 170                 175

Cys Gly Val Thr Asn Lys Val His Phe Ile Phe Lys His Lys Asn Pro
                180                 185                 190

Lys Thr Gly Glu Tyr Glu Glu Lys His Met Lys Leu Pro Pro Ala Val
                195                 200                 205

Arg Val Ser Lys Leu Ser Thr Leu Tyr Thr Leu Ile Val Asn Pro Asp
210                 215                 220

Gln Ser Phe Gln Ile Arg Ile Asp Gly Ala Ala Val Lys Asn Gly Thr
225                 230                 235                 240

Leu Leu Glu Asp Phe Ser Pro Ala Val Asn Pro Glu Lys Glu Ile Asp
                245                 250                 255

Asp Pro Glu Asp Lys Lys Pro Glu Asp Trp Val Asp Glu Ala His Ile
                260                 265                 270

Pro Asp Pro Glu Ala Thr Lys Pro Glu Asp Trp Asp Glu Asp Ala Pro
                275                 280                 285

Tyr Glu Ile Val Asp Thr Asp Ala Thr Gln Pro Glu Asp Trp Leu Val
                290                 295                 300

Asp Glu Pro Thr Ser Ile Pro Asp Pro Glu Ala Gln Lys Pro Glu Asp
305                 310                 315                 320

Trp Asp Asp Glu Glu Asp Gly Asp Trp Ile Pro Pro Thr Ile Pro Asn
                325                 330                 335

Pro Lys Cys Ser Glu Val Ser Gly Cys Gly Met Trp Glu Pro Pro Met
                340                 345                 350

Lys Lys Asn Pro Glu Tyr Lys Gly Lys Trp Thr Ala Pro Met Ile Asp
                355                 360                 365

Asn Pro Ala Tyr Lys Gly Pro Trp Ala Pro Arg Lys Ile Ala Asn Pro
370                 375                 380

Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
                405                 410                 415

Ile Tyr Ile Gly His Ser Val Glu Asp Ala Glu Lys Leu Lys Ala Glu
                420                 425                 430

Thr Trp Asp Leu Lys His Pro Val Glu Val Ala Glu Glu Ala Ala
                435                 440                 445

Arg Pro Lys Asp Glu Lys Lys Glu Gly Thr Leu Ser Phe Lys Glu
450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Glu Val Ala
                485                 490                 495

Gly Gly Leu Gly Ala Leu Leu Val Thr Leu Val Leu Ile Ile Val Gly
                500                 505                 510

Ala Val Gly Leu Gly Ser Pro Ser Pro Ala Pro Ala Ala Lys Lys Gln
                515                 520                 525

Ala Glu Lys Gly Lys Glu Lys Thr Ala Glu Ala Val Ser Thr Ala Ala
                530                 535                 540

Asp Asn Val Lys Gly Glu Ala Lys Lys Arg Ser Gly Lys Ala Gly Glu
545                 550                 555                 560
```

```
<210> SEQ ID NO 38
<211> LENGTH: 560
<212> TYPE: PRT
<213> ORGANISM: Homo sapiens
<220> FEATURE:
<221> NAME/KEY: BINDING SITE
<222> LOCATION: (1)..(9)
<220> FEATURE:
<221> NAME/KEY: BINDING SITE
<222> LOCATION: (15)..(23)
<220> FEATURE:
<221> NAME/KEY: BINDING SITE
<222> LOCATION: (104)..(112)
<220> FEATURE:
<221> NAME/KEY: BINDING SITE
<222> LOCATION: (128)..(142)
<220> FEATURE:
<221> NAME/KEY: BINDING SITE
<222> LOCATION: (168)..(176)
<220> FEATURE:
<221> NAME/KEY: BINDING SITE
<222> LOCATION: (202)..(210)
<220> FEATURE:
<221> NAME/KEY: BINDING SITE
<222> LOCATION: (395)..(403)
<220> FEATURE:
<221> NAME/KEY: BINDING SITE
<222> LOCATION: (474)..(488)
<220> FEATURE:
<221> NAME/KEY: BINDING SITE
<222> LOCATION: (503)..(516)

<400> SEQUENCE: 38

Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
            20                  25                  30

Ser Thr Ser Ser Val Ile Glu Lys Pro Thr Phe Thr Pro Thr Thr Leu
        35                  40                  45

Lys Ala Pro Phe Leu Glu Gln Phe Thr Asp Gly Trp Glu Thr Arg Trp
50                  55                  60

Thr Pro Ser His Ala Lys Lys Glu Asp Ser Lys Ser Glu Glu Asp Trp
65                  70                  75                  80

Ala Tyr Val Gly Thr Trp Ala Val Glu Glu Pro His Val Phe Asn Gly
                85                  90                  95

Met Val Gly Asp Lys Gly Leu Val Val Lys Asn Pro Ala Ala His His
            100                 105                 110

Ala Ile Ser Ala Lys Phe Pro Lys Lys Ile Asp Asn Lys Gly Lys Thr
        115                 120                 125

Leu Val Val Gln Tyr Glu Val Lys Leu Gln Asn Ser Leu Asn Cys Gly
    130                 135                 140

Gly Ala Tyr Met Lys Leu Leu Gln Asp Asn Lys Lys Leu His Ala Glu
145                 150                 155                 160

Glu Phe Ser Asn Thr Ser Pro Tyr Val Ile Met Phe Gly Pro Asp Lys
                165                 170                 175

Cys Gly Val Thr Asn Lys Val His Phe Ile Phe Lys His Lys Asn Pro
            180                 185                 190

Lys Thr Gly Glu Tyr Glu Glu Lys His Met Lys Leu Pro Pro Ala Val
        195                 200                 205

Arg Val Ser Lys Leu Ser Thr Leu Tyr Thr Leu Ile Val Asn Pro Asp
    210                 215                 220

Gln Ser Phe Gln Ile Arg Ile Asp Gly Ala Ala Val Lys Asn Gly Thr
```

```
                    225                 230                 235                 240

Leu Leu Glu Asp Phe Ser Pro Ala Val Asn Pro Glu Lys Glu Ile Asp
                        245                 250                 255

Asp Pro Glu Asp Lys Lys Pro Glu Asp Trp Val Asp Glu Ala His Ile
                        260                 265                 270

Pro Asp Pro Glu Ala Thr Lys Pro Glu Asp Trp Asp Glu Asp Ala Pro
                        275                 280                 285

Tyr Glu Ile Val Asp Thr Asp Ala Thr Gln Pro Glu Asp Trp Leu Val
                        290                 295                 300

Asp Glu Pro Thr Ser Ile Pro Asp Pro Glu Ala Gln Lys Pro Glu Asp
        305                 310                 315                 320

Trp Asp Asp Glu Glu Asp Gly Asp Trp Ile Pro Pro Thr Ile Pro Asn
                        325                 330                 335

Pro Lys Cys Ser Glu Val Ser Gly Cys Gly Met Trp Glu Pro Pro Met
                        340                 345                 350

Lys Lys Asn Pro Glu Tyr Lys Gly Lys Trp Thr Ala Pro Met Ile Asp
                        355                 360                 365

Asn Pro Ala Tyr Lys Gly Pro Trp Ala Pro Arg Lys Ile Ala Asn Pro
        370                 375                 380

Asn Tyr Phe Glu Asp Lys Thr Pro Ser Asn Phe Glu Pro Met Gly Ala
        385                 390                 395                 400

Ile Gly Phe Glu Ile Trp Thr Met Gln Asn Asp Ile Leu Phe Asp Asn
                        405                 410                 415

Ile Tyr Ile Gly His Ser Val Glu Asp Ala Glu Lys Leu Lys Ala Glu
                        420                 425                 430

Thr Trp Asp Leu Lys His Pro Val Glu Val Ala Glu Glu Ala Ala Ala
                        435                 440                 445

Arg Pro Lys Asp Glu Glu Lys Lys Glu Gly Thr Leu Ser Phe Lys Glu
                        450                 455                 460

Ala Pro Val Lys Tyr Ile Arg Gly Lys Ile Glu Leu Phe Ile Ser Leu
        465                 470                 475                 480

Ala Leu Glu Asn Pro Val Glu Ala Val Lys Ala Val Pro Glu Val Ala
                        485                 490                 495

Gly Gly Leu Gly Ala Leu Leu Val Thr Leu Val Leu Ile Ile Val Gly
                        500                 505                 510

Ala Val Gly Leu Gly Ser Pro Ser Pro Ala Pro Ala Ala Lys Lys Gln
                        515                 520                 525

Ala Glu Lys Gly Lys Glu Lys Thr Ala Glu Ala Val Ser Thr Ala Ala
                        530                 535                 540

Asp Asn Val Lys Gly Glu Ala Lys Lys Arg Ser Gly Lys Ala Gly Glu
        545                 550                 555                 560

<210> SEQ ID NO 39
<211> LENGTH: 560
<212> TYPE: PRT
<213> ORGANISM: Homo sapiens
<220> FEATURE:
<221> NAME/KEY: BINDING SITE
<222> LOCATION: (1)..(18)
<220> FEATURE:
<221> NAME/KEY: BINDING SITE
<222> LOCATION: (27)..(35)
<220> FEATURE:
<221> NAME/KEY: BINDING SITE
<222> LOCATION: (97)..(105)
<220> FEATURE:
<221> NAME/KEY: BINDING SITE
<222> LOCATION: (150)..(158)
```

```
<220> FEATURE:
<221> NAME/KEY: BINDING SITE
<222> LOCATION: (208)..(216)
<220> FEATURE:
<221> NAME/KEY: BINDING SITE
<222> LOCATION: (221)..(237)
<220> FEATURE:
<221> NAME/KEY: BINDING SITE
<222> LOCATION: (241)..(249)
<220> FEATURE:
<221> NAME/KEY: BINDING SITE
<222> LOCATION: (302)..(310)
<220> FEATURE:
<221> NAME/KEY: BINDING SITE
<222> LOCATION: (408)..(420)
<220> FEATURE:
<221> NAME/KEY: BINDING SITE
<222> LOCATION: (503)..(517)

<400> SEQUENCE: 39
```

Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
            20                  25                  30

Ser Thr Ser Ser Val Ile Glu Lys Pro Thr Phe Thr Pro Thr Thr Leu
        35                  40                  45

Lys Ala Pro Phe Leu Glu Gln Phe Thr Asp Gly Trp Glu Thr Arg Trp
    50                  55                  60

Thr Pro Ser His Ala Lys Lys Glu Asp Ser Lys Ser Glu Glu Asp Trp
65                  70                  75                  80

Ala Tyr Val Gly Thr Trp Ala Val Glu Glu Pro His Val Phe Asn Gly
                85                  90                  95

Met Val Gly Asp Lys Gly Leu Val Val Lys Asn Pro Ala Ala His His
            100                 105                 110

Ala Ile Ser Ala Lys Phe Pro Lys Lys Ile Asp Asn Lys Gly Lys Thr
        115                 120                 125

Leu Val Val Gln Tyr Glu Val Lys Leu Gln Asn Ser Leu Asn Cys Gly
    130                 135                 140

Gly Ala Tyr Met Lys Leu Leu Gln Asp Asn Lys Lys Leu His Ala Glu
145                 150                 155                 160

Glu Phe Ser Asn Thr Ser Pro Tyr Val Ile Met Phe Gly Pro Asp Lys
                165                 170                 175

Cys Gly Val Thr Asn Lys Val His Phe Ile Phe Lys His Lys Asn Pro
            180                 185                 190

Lys Thr Gly Glu Tyr Glu Glu Lys His Met Lys Leu Pro Pro Ala Val
        195                 200                 205

Arg Val Ser Lys Leu Ser Thr Leu Tyr Thr Leu Ile Val Asn Pro Asp
    210                 215                 220

Gln Ser Phe Gln Ile Arg Ile Asp Gly Ala Ala Val Lys Asn Gly Thr
225                 230                 235                 240

Leu Leu Glu Asp Phe Ser Pro Ala Val Asn Pro Glu Lys Glu Ile Asp
                245                 250                 255

Asp Pro Glu Asp Lys Lys Pro Glu Asp Trp Val Asp Glu Ala His Ile
            260                 265                 270

Pro Asp Pro Glu Ala Thr Lys Pro Glu Asp Trp Asp Glu Asp Ala Pro
        275                 280                 285

Tyr Glu Ile Val Asp Thr Asp Ala Thr Gln Pro Glu Asp Trp Leu Val
    290                 295                 300

Asp Glu Pro Thr Ser Ile Pro Asp Pro Glu Ala Gln Lys Pro Glu Asp

```
                305                 310                 315                 320
Trp Asp Asp Glu Glu Asp Gly Asp Trp Ile Pro Pro Thr Ile Pro Asn
                    325                 330                 335
Pro Lys Cys Ser Glu Val Ser Gly Cys Gly Met Trp Glu Pro Pro Met
                340                 345                 350
Lys Lys Asn Pro Glu Tyr Lys Gly Lys Trp Thr Ala Pro Met Ile Asp
                355                 360                 365
Asn Pro Ala Tyr Lys Gly Pro Trp Ala Pro Arg Lys Ile Ala Asn Pro
        370                 375                 380
Asn Tyr Phe Glu Asp Lys Thr Pro Ser Asn Phe Glu Pro Met Gly Ala
385                 390                 395                 400
Ile Gly Phe Glu Ile Trp Thr Met Gln Asn Asp Ile Leu Phe Asp Asn
                    405                 410                 415
Ile Tyr Ile Gly His Ser Val Glu Asp Ala Glu Lys Leu Lys Ala Glu
                420                 425                 430
Thr Trp Asp Leu Lys His Pro Val Glu Val Ala Glu Glu Ala Ala
                    435                 440                 445
Arg Pro Lys Asp Glu Lys Lys Glu Gly Thr Leu Ser Phe Lys Glu
    450                 455                 460
Ala Pro Val Lys Tyr Ile Arg Gly Lys Ile Glu Leu Phe Ile Ser Leu
465                 470                 475                 480
Ala Leu Glu Asn Pro Val Glu Ala Val Lys Ala Val Pro Glu Val Ala
                    485                 490                 495
Gly Gly Leu Gly Ala Leu Leu Val Thr Leu Val Leu Ile Ile Val Gly
                500                 505                 510
Ala Val Gly Leu Gly Ser Pro Ser Pro Ala Pro Ala Ala Lys Lys Gln
                515                 520                 525
Ala Glu Lys Gly Lys Glu Lys Thr Ala Glu Ala Val Ser Thr Ala Ala
                530                 535                 540
Asp Asn Val Lys Gly Glu Ala Lys Lys Arg Ser Gly Lys Ala Gly Glu
545                 550                 555                 560

<210> SEQ ID NO 40
<211> LENGTH: 560
<212> TYPE: PRT
<213> ORGANISM: Homo sapiens
<220> FEATURE:
<221> NAME/KEY: BINDING SITE
<222> LOCATION: (1)..(18)
<220> FEATURE:
<221> NAME/KEY: BINDING SITE
<222> LOCATION: (27)..(35)
<220> FEATURE:
<221> NAME/KEY: BINDING SITE
<222> LOCATION: (93)..(105)
<220> FEATURE:
<221> NAME/KEY: BINDING SITE
<222> LOCATION: (150)..(158)
<220> FEATURE:
<221> NAME/KEY: BINDING SITE
<222> LOCATION: (168)..(180)
<220> FEATURE:
<221> NAME/KEY: BINDING SITE
<222> LOCATION: (185)..(193)
<220> FEATURE:
<221> NAME/KEY: BINDING SITE
<222> LOCATION: (217)..(237)
<220> FEATURE:
<221> NAME/KEY: BINDING SITE
<222> LOCATION: (302)..(310)
<220> FEATURE:
<221> NAME/KEY: BINDING SITE
<222> LOCATION: (386)..(394)
```

```
<220> FEATURE:
<221> NAME/KEY: BINDING SITE
<222> LOCATION: (408)..(426)
<220> FEATURE:
<221> NAME/KEY: BINDING SITE
<222> LOCATION: (469)..(477)
<220> FEATURE:
<221> NAME/KEY: BINDING SITE
<222> LOCATION: (505)..(514)

<400> SEQUENCE: 40
```

Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
            20                  25                  30

Ser Thr Ser Ser Val Ile Glu Lys Pro Thr Phe Thr Pro Thr Thr Leu
        35                  40                  45

Lys Ala Pro Phe Leu Glu Gln Phe Thr Asp Gly Trp Glu Thr Arg Trp
    50                  55                  60

Thr Pro Ser His Ala Lys Lys Glu Asp Ser Lys Ser Glu Glu Asp Trp
65                  70                  75                  80

Ala Tyr Val Gly Thr Trp Ala Val Glu Glu Pro His Val Phe Asn Gly
                85                  90                  95

Met Val Gly Asp Lys Gly Leu Val Val Lys Asn Pro Ala Ala His His
            100                 105                 110

Ala Ile Ser Ala Lys Phe Pro Lys Ile Asp Asn Lys Gly Lys Thr
        115                 120                 125

Leu Val Val Gln Tyr Glu Val Lys Leu Gln Asn Ser Leu Asn Cys Gly
    130                 135                 140

Gly Ala Tyr Met Lys Leu Leu Gln Asp Asn Lys Lys Leu His Ala Glu
145                 150                 155                 160

Glu Phe Ser Asn Thr Ser Pro Tyr Val Ile Met Phe Gly Pro Asp Lys
                165                 170                 175

Cys Gly Val Thr Asn Lys Val His Phe Ile Phe Lys His Lys Asn Pro
            180                 185                 190

Lys Thr Gly Glu Tyr Glu Glu Lys His Met Lys Leu Pro Pro Ala Val
        195                 200                 205

Arg Val Ser Lys Leu Ser Thr Leu Tyr Thr Leu Ile Val Asn Pro Asp
    210                 215                 220

Gln Ser Phe Gln Ile Arg Ile Asp Gly Ala Ala Val Lys Asn Gly Thr
225                 230                 235                 240

Leu Leu Glu Asp Phe Ser Pro Ala Val Asn Pro Glu Lys Glu Ile Asp
                245                 250                 255

Asp Pro Glu Asp Lys Lys Pro Glu Asp Trp Val Asp Glu Ala His Ile
            260                 265                 270

Pro Asp Pro Glu Ala Thr Lys Pro Glu Asp Trp Asp Glu Asp Ala Pro
        275                 280                 285

Tyr Glu Ile Val Asp Thr Asp Ala Thr Gln Pro Glu Asp Trp Leu Val
    290                 295                 300

Asp Glu Pro Thr Ser Ile Pro Asp Pro Glu Ala Gln Lys Pro Glu Asp
305                 310                 315                 320

Trp Asp Asp Glu Glu Asp Gly Asp Trp Ile Pro Thr Ile Pro Asn
                325                 330                 335

Pro Lys Cys Ser Glu Val Ser Gly Cys Gly Met Trp Glu Pro Pro Met
            340                 345                 350

Lys Lys Asn Pro Glu Tyr Lys Gly Lys Trp Thr Ala Pro Met Ile Asp

```
                    355                 360                 365
Asn Pro Ala Tyr Lys Gly Pro Trp Ala Pro Arg Lys Ile Ala Asn Pro
    370                 375                 380

Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
                405                 410                 415

Ile Tyr Ile Gly His Ser Val Glu Asp Ala Glu Lys Leu Lys Ala Glu
            420                 425                 430

Thr Trp Asp Leu Lys His Pro Val Glu Val Ala Glu Glu Ala Ala
                435                 440                 445

Arg Pro Lys Asp Glu Glu Lys Glu Gly Thr Leu Ser Phe Lys Glu
    450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Glu Val Ala
                485                 490                 495

Gly Gly Leu Gly Ala Leu Leu Val Thr Leu Val Leu Ile Ile Val Gly
            500                 505                 510

Ala Val Gly Leu Gly Ser Pro Ser Pro Ala Pro Ala Ala Lys Lys Gln
                515                 520                 525

Ala Glu Lys Gly Lys Glu Lys Thr Ala Glu Ala Val Ser Thr Ala Ala
    530                 535                 540

Asp Asn Val Lys Gly Glu Ala Lys Lys Arg Ser Gly Lys Ala Gly Glu
545                 550                 555                 560

<210> SEQ ID NO 41
<211> LENGTH: 560
<212> TYPE: PRT
<213> ORGANISM: Homo sapiens
<220> FEATURE:
<221> NAME/KEY: BINDING SITE
<222> LOCATION: (1)..(18)
<220> FEATURE:
<221> NAME/KEY: BINDING SITE
<222> LOCATION: (97)..(112)
<220> FEATURE:
<221> NAME/KEY: BINDING SITE
<222> LOCATION: (130)..(143)
<220> FEATURE:
<221> NAME/KEY: BINDING SITE
<222> LOCATION: (150)..(159)
<220> FEATURE:
<221> NAME/KEY: BINDING SITE
<222> LOCATION: (208)..(216)
<220> FEATURE:
<221> NAME/KEY: BINDING SITE
<222> LOCATION: (229)..(237)
<220> FEATURE:
<221> NAME/KEY: BINDING SITE
<222> LOCATION: (302)..(310)
<220> FEATURE:
<221> NAME/KEY: BINDING SITE
<222> LOCATION: (412)..(420)
<220> FEATURE:
<221> NAME/KEY: BINDING SITE
<222> LOCATION: (476)..(484)
<220> FEATURE:
<221> NAME/KEY: BINDING SITE
<222> LOCATION: (502)..(522)

<400> SEQUENCE: 41

Met Arg Leu Asn Ala Ser Leu Ala Ser Leu Ile Leu Ser Ser Ile Ala
1               5                   10                  15
```

```
Leu Ile Gly Asn Val His Ala Glu Asp Val Lys Glu Asp Ala Thr
            20                  25                  30
Ser Thr Ser Ser Val Ile Glu Lys Pro Thr Phe Thr Pro Thr Thr Leu
        35                  40                  45
Lys Ala Pro Phe Leu Glu Gln Phe Thr Asp Gly Trp Glu Thr Arg Trp
50                  55                  60
Thr Pro Ser His Ala Lys Lys Glu Asp Ser Lys Ser Glu Glu Asp Trp
65                  70                  75                  80
Ala Tyr Val Gly Thr Trp Ala Val Glu Glu Pro His Val Phe Asn Gly
                85                  90                  95
Met Val Gly Asp Lys Gly Leu Val Val Lys Asn Pro Ala Ala His His
            100                 105                 110
Ala Ile Ser Ala Lys Phe Pro Lys Lys Ile Asp Asn Lys Gly Lys Thr
            115                 120                 125
Leu Val Val Gln Tyr Glu Val Lys Leu Gln Asn Ser Leu Asn Cys Gly
            130                 135                 140
Gly Ala Tyr Met Lys Leu Leu Gln Asp Asn Lys Lys Leu His Ala Glu
145                 150                 155                 160
Glu Phe Ser Asn Thr Ser Pro Tyr Val Ile Met Phe Gly Pro Asp Lys
                165                 170                 175
Cys Gly Val Thr Asn Lys Val His Phe Ile Phe Lys His Lys Asn Pro
            180                 185                 190
Lys Thr Gly Glu Tyr Glu Lys His Met Lys Leu Pro Pro Ala Val
                195                 200                 205
Arg Val Ser Lys Leu Ser Thr Leu Tyr Thr Leu Ile Val Asn Pro Asp
210                 215                 220
Gln Ser Phe Gln Ile Arg Ile Asp Gly Ala Ala Val Lys Asn Gly Thr
225                 230                 235                 240
Leu Leu Glu Asp Phe Ser Pro Ala Val Asn Pro Lys Glu Ile Asp
                245                 250                 255
Asp Pro Glu Asp Lys Lys Pro Glu Asp Trp Val Asp Glu Ala His Ile
            260                 265                 270
Pro Asp Pro Glu Ala Thr Lys Pro Glu Asp Trp Asp Glu Asp Ala Pro
            275                 280                 285
Tyr Glu Ile Val Asp Thr Asp Ala Thr Gln Pro Glu Asp Trp Leu Val
290                 295                 300
Asp Glu Pro Thr Ser Ile Pro Asp Pro Glu Ala Gln Lys Pro Glu Asp
305                 310                 315                 320
Trp Asp Asp Glu Glu Asp Gly Asp Trp Ile Pro Pro Thr Ile Pro Asn
                325                 330                 335
Pro Lys Cys Ser Glu Val Ser Gly Cys Gly Met Trp Glu Pro Pro Met
            340                 345                 350
Lys Lys Asn Pro Glu Tyr Lys Gly Lys Trp Thr Ala Pro Met Ile Asp
            355                 360                 365
Asn Pro Ala Tyr Lys Gly Pro Trp Ala Pro Arg Lys Ile Ala Asn Pro
            370                 375                 380
Asn Tyr Phe Glu Asp Lys Thr Pro Ser Asn Phe Glu Pro Met Gly Ala
385                 390                 395                 400
Ile Gly Phe Glu Ile Trp Thr Met Gln Asn Asp Ile Leu Phe Asp Asn
                405                 410                 415
Ile Tyr Ile Gly His Ser Val Glu Asp Ala Glu Lys Leu Lys Ala Glu
                420                 425                 430
Thr Trp Asp Leu Lys His Pro Val Glu Val Ala Glu Glu Glu Ala Ala
```

```
            435                 440                 445
Arg Pro Lys Asp Glu Lys Lys Glu Gly Thr Leu Ser Phe Lys Glu
    450                 455                 460

Ala Pro Val Lys Tyr Ile Arg Gly Lys Ile Glu Leu Phe Ile Ser Leu
465                 470                 475                 480

Ala Leu Glu Asn Pro Val Glu Val Lys Ala Val Pro Glu Val Ala
                485                 490                 495

Gly Gly Leu Gly Ala Leu Leu Val Thr Leu Val Leu Ile Ile Val Gly
                500                 505                 510

Ala Val Gly Leu Gly Ser Pro Ser Pro Ala Pro Ala Ala Lys Lys Gln
            515                 520                 525

Ala Glu Lys Gly Lys Glu Lys Thr Ala Glu Ala Val Ser Thr Ala Ala
        530                 535                 540

Asp Asn Val Lys Gly Glu Ala Lys Lys Arg Ser Gly Lys Ala Gly Glu
545                 550                 555                 560

<210> SEQ ID NO 42
<211> LENGTH: 560
<212> TYPE: PRT
<213> ORGANISM: Homo sapiens
<220> FEATURE:
<221> NAME/KEY: BINDING SITE
<222> LOCATION: (1)..(18)
<220> FEATURE:
<221> NAME/KEY: BINDING SITE
<222> LOCATION: (27)..(35)
<220> FEATURE:
<221> NAME/KEY: BINDING SITE
<222> LOCATION: (97)..(112)
<220> FEATURE:
<221> NAME/KEY: BINDING SITE
<222> LOCATION: (130)..(143)
<220> FEATURE:
<221> NAME/KEY: BINDING SITE
<222> LOCATION: (150)..(159)
<220> FEATURE:
<221> NAME/KEY: BINDING SITE
<222> LOCATION: (208)..(216)
<220> FEATURE:
<221> NAME/KEY: BINDING SITE
<222> LOCATION: (229)..(237)
<220> FEATURE:
<221> NAME/KEY: BINDING SITE
<222> LOCATION: (302)..(310)
<220> FEATURE:
<221> NAME/KEY: BINDING SITE
<222> LOCATION: (412)..(420)
<220> FEATURE:
<221> NAME/KEY: BINDING SITE
<222> LOCATION: (476)..(484)
<220> FEATURE:
<221> NAME/KEY: BINDING SITE
<222> LOCATION: (502)..(522)

<400> SEQUENCE: 42

Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
                20                  25                  30

Ser Thr Ser Ser Val Ile Glu Lys Pro Thr Phe Thr Pro Thr Thr Leu
            35                  40                  45

Lys Ala Pro Phe Leu Glu Gln Phe Thr Asp Gly Trp Glu Thr Arg Trp
        50                  55                  60

Thr Pro Ser His Ala Lys Lys Glu Asp Ser Lys Ser Glu Glu Asp Trp
65                  70                  75                  80
```

```
Ala Tyr Val Gly Thr Trp Ala Val Glu Glu Pro His Val Phe Asn Gly
                 85                  90                  95

Met Val Gly Asp Lys Gly Leu Val Val Lys Asn Pro Ala Ala His His
            100                 105                 110

Ala Ile Ser Ala Lys Phe Pro Lys Lys Ile Asp Asn Lys Gly Lys Thr
            115                 120                 125

Leu Val Val Gln Tyr Glu Val Lys Leu Gln Asn Ser Leu Asn Cys Gly
        130                 135                 140

Gly Ala Tyr Met Lys Leu Leu Gln Asp Asn Lys Lys Leu His Ala Glu
145                 150                 155                 160

Glu Phe Ser Asn Thr Ser Pro Tyr Val Ile Met Phe Gly Pro Asp Lys
                165                 170                 175

Cys Gly Val Thr Asn Lys Val His Phe Ile Phe Lys His Lys Asn Pro
            180                 185                 190

Lys Thr Gly Glu Tyr Glu Lys His Met Lys Leu Pro Pro Ala Val
        195                 200                 205

Arg Val Ser Lys Leu Ser Thr Leu Tyr Thr Leu Ile Val Asn Pro Asp
    210                 215                 220

Gln Ser Phe Gln Ile Arg Ile Asp Gly Ala Ala Val Lys Asn Gly Thr
225                 230                 235                 240

Leu Leu Glu Asp Phe Ser Pro Ala Val Asn Pro Glu Lys Glu Ile Asp
                245                 250                 255

Asp Pro Glu Asp Lys Lys Pro Glu Asp Trp Val Asp Glu Ala His Ile
            260                 265                 270

Pro Asp Pro Glu Ala Thr Lys Pro Glu Asp Trp Asp Glu Asp Ala Pro
            275                 280                 285

Tyr Glu Ile Val Asp Thr Asp Ala Thr Gln Pro Glu Asp Trp Leu Val
        290                 295                 300

Asp Glu Pro Thr Ser Ile Pro Asp Pro Glu Ala Gln Lys Pro Glu Asp
305                 310                 315                 320

Trp Asp Asp Glu Glu Asp Gly Asp Trp Ile Pro Pro Thr Ile Pro Asn
                325                 330                 335

Pro Lys Cys Ser Glu Val Ser Gly Cys Gly Met Trp Glu Pro Pro Met
            340                 345                 350

Lys Lys Asn Pro Glu Tyr Lys Gly Lys Trp Thr Ala Pro Met Ile Asp
        355                 360                 365

Asn Pro Ala Tyr Lys Gly Pro Trp Ala Pro Arg Lys Ile Ala Asn Pro
    370                 375                 380

Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
                405                 410                 415

Ile Tyr Ile Gly His Ser Val Glu Asp Ala Glu Lys Leu Lys Ala Glu
            420                 425                 430

Thr Trp Asp Leu Lys His Pro Val Glu Val Ala Glu Glu Ala Ala
        435                 440                 445

Arg Pro Lys Asp Glu Lys Lys Glu Gly Thr Leu Ser Phe Lys Glu
    450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Glu Val Ala
                485                 490                 495

Gly Gly Leu Gly Ala Leu Leu Val Thr Leu Val Leu Ile Ile Val Gly
```

```
                        500                 505                 510
Ala Val Gly Leu Gly Ser Pro Ser Pro Ala Pro Ala Ala Lys Lys Gln
            515                 520                 525

Ala Glu Lys Gly Lys Glu Lys Thr Ala Glu Ala Val Ser Thr Ala Ala
    530                 535                 540

Asp Asn Val Lys Gly Glu Ala Lys Lys Arg Ser Gly Lys Ala Gly Glu
545                 550                 555                 560

<210> SEQ ID NO 43
<211> LENGTH: 560
<212> TYPE: PRT
<213> ORGANISM: Homo sapiens
<220> FEATURE:
<221> NAME/KEY: BINDING SITE
<222> LOCATION: (1)..(18)
<220> FEATURE:
<221> NAME/KEY: BINDING SITE
<222> LOCATION: (27)..(35)
<220> FEATURE:
<221> NAME/KEY: BINDING SITE
<222> LOCATION: (97)..(102)
<220> FEATURE:
<221> NAME/KEY: BINDING SITE
<222> LOCATION: (130)..(143)
<220> FEATURE:
<221> NAME/KEY: BINDING SITE
<222> LOCATION: (150)..(159)
<220> FEATURE:
<221> NAME/KEY: BINDING SITE
<222> LOCATION: (208)..(216)
<220> FEATURE:
<221> NAME/KEY: BINDING SITE
<222> LOCATION: (229)..(237)
<220> FEATURE:
<221> NAME/KEY: BINDING SITE
<222> LOCATION: (302)..(310)
<220> FEATURE:
<221> NAME/KEY: BINDING SITE
<222> LOCATION: (412)..(420)
<220> FEATURE:
<221> NAME/KEY: BINDING SITE
<222> LOCATION: (476)..(484)
<220> FEATURE:
<221> NAME/KEY: BINDING SITE
<222> LOCATION: (502)..(522)

<400> SEQUENCE: 43

Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
            20                  25                  30

Ser Thr Ser Ser Val Ile Glu Lys Pro Thr Phe Thr Pro Thr Thr Leu
        35                  40                  45

Lys Ala Pro Phe Leu Glu Gln Phe Thr Asp Gly Trp Glu Thr Arg Trp
    50                  55                  60

Thr Pro Ser His Ala Lys Lys Glu Asp Ser Lys Ser Glu Glu Asp Trp
65                  70                  75                  80

Ala Tyr Val Gly Thr Trp Ala Val Glu Glu Pro His Val Phe Asn Gly
                85                  90                  95

Met Val Gly Asp Lys Gly Leu Val Val Lys Asn Pro Ala Ala His His
            100                 105                 110

Ala Ile Ser Ala Lys Phe Pro Lys Lys Ile Asp Asn Lys Gly Lys Thr
        115                 120                 125

Leu Val Val Gln Tyr Glu Val Lys Leu Gln Asn Ser Leu Asn Cys Gly
    130                 135                 140
```

```
Gly Ala Tyr Met Lys Leu Leu Gln Asp Asn Lys Lys Leu His Ala Glu
145                 150                 155                 160

Glu Phe Ser Asn Thr Ser Pro Tyr Val Ile Met Phe Gly Pro Asp Lys
            165                 170                 175

Cys Gly Val Thr Asn Lys Val His Phe Ile Phe Lys His Lys Asn Pro
            180                 185                 190

Lys Thr Gly Glu Tyr Glu Lys His Met Lys Leu Pro Pro Ala Val
            195                 200                 205

Arg Val Ser Lys Leu Ser Thr Leu Tyr Thr Leu Ile Val Asn Pro Asp
            210                 215                 220

Gln Ser Phe Gln Ile Arg Ile Asp Gly Ala Ala Val Lys Asn Gly Thr
225                 230                 235                 240

Leu Leu Glu Asp Phe Ser Pro Ala Val Asn Pro Glu Lys Glu Ile Asp
                245                 250                 255

Asp Pro Glu Asp Lys Lys Pro Glu Asp Trp Val Asp Glu Ala His Ile
            260                 265                 270

Pro Asp Pro Glu Ala Thr Lys Pro Glu Asp Trp Asp Glu Asp Ala Pro
            275                 280                 285

Tyr Glu Ile Val Asp Thr Asp Ala Thr Gln Pro Glu Asp Trp Leu Val
            290                 295                 300

Asp Glu Pro Thr Ser Ile Pro Asp Pro Glu Ala Gln Lys Pro Glu Asp
305                 310                 315                 320

Trp Asp Asp Glu Glu Asp Gly Asp Trp Ile Pro Pro Thr Ile Pro Asn
                325                 330                 335

Pro Lys Cys Ser Glu Val Ser Gly Cys Gly Met Trp Glu Pro Pro Met
            340                 345                 350

Lys Lys Asn Pro Glu Tyr Lys Gly Lys Trp Thr Ala Pro Met Ile Asp
            355                 360                 365

Asn Pro Ala Tyr Lys Gly Pro Trp Ala Pro Arg Lys Ile Ala Asn Pro
            370                 375                 380

Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
                405                 410                 415

Ile Tyr Ile Gly His Ser Val Glu Asp Ala Glu Lys Leu Lys Ala Glu
            420                 425                 430

Thr Trp Asp Leu Lys His Pro Val Glu Val Ala Glu Glu Ala Ala
            435                 440                 445

Arg Pro Lys Asp Glu Lys Lys Glu Gly Thr Leu Ser Phe Lys Glu
450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Glu Val Ala
                485                 490                 495

Gly Gly Leu Gly Ala Leu Leu Val Thr Leu Val Leu Ile Ile Val Gly
                500                 505                 510

Ala Val Gly Leu Gly Ser Pro Ser Pro Ala Pro Ala Ala Lys Lys Gln
            515                 520                 525

Ala Glu Lys Gly Lys Glu Lys Thr Ala Glu Ala Val Ser Thr Ala Ala
            530                 535                 540

Asp Asn Val Lys Gly Glu Ala Lys Lys Arg Ser Gly Lys Ala Gly Glu
545                 550                 555                 560
```

-continued

```
<210> SEQ ID NO 44
<211> LENGTH: 560
<212> TYPE: PRT
<213> ORGANISM: Homo sapiens
<220> FEATURE:
<221> NAME/KEY: BINDING SITE
<222> LOCATION: (1)..(18)
<220> FEATURE:
<221> NAME/KEY: BINDING SITE
<222> LOCATION: (27)..(35)
<220> FEATURE:
<221> NAME/KEY: BINDING SITE
<222> LOCATION: (97)..(105)
<220> FEATURE:
<221> NAME/KEY: BINDING SITE
<222> LOCATION: (168)..(180)
<220> FEATURE:
<221> NAME/KEY: BINDING SITE
<222> LOCATION: (208)..(216)
<220> FEATURE:
<221> NAME/KEY: BINDING SITE
<222> LOCATION: (221)..(237)
<220> FEATURE:
<221> NAME/KEY: BINDING SITE
<222> LOCATION: (302)..(310)
<220> FEATURE:
<221> NAME/KEY: BINDING SITE
<222> LOCATION: (386)..(394)
<220> FEATURE:
<221> NAME/KEY: BINDING SITE
<222> LOCATION: (408)..(420)
<220> FEATURE:
<221> NAME/KEY: BINDING SITE
<222> LOCATION: (469)..(477)
<220> FEATURE:
<221> NAME/KEY: BINDING SITE
<222> LOCATION: (506)..(517)

<400> SEQUENCE: 44

Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
            20                  25                  30

Ser Thr Ser Ser Val Ile Glu Lys Pro Thr Phe Thr Pro Thr Thr Leu
        35                  40                  45

Lys Ala Pro Phe Leu Glu Gln Phe Thr Asp Gly Trp Glu Thr Arg Trp
    50                  55                  60

Thr Pro Ser His Ala Lys Lys Glu Asp Ser Lys Ser Glu Glu Asp Trp
65                  70                  75                  80

Ala Tyr Val Gly Thr Trp Ala Val Glu Glu Pro His Val Phe Asn Gly
                85                  90                  95

Met Val Gly Asp Lys Gly Leu Val Val Lys Asn Pro Ala Ala His His
            100                 105                 110

Ala Ile Ser Ala Lys Phe Pro Lys Lys Ile Asp Asn Lys Gly Lys Thr
        115                 120                 125

Leu Val Val Gln Tyr Glu Val Lys Leu Gln Asn Ser Leu Asn Cys Gly
    130                 135                 140

Gly Ala Tyr Met Lys Leu Leu Gln Asp Asn Lys Lys Leu His Ala Glu
145                 150                 155                 160

Glu Phe Ser Asn Thr Ser Pro Tyr Val Ile Met Phe Gly Pro Asp Lys
                165                 170                 175

Cys Gly Val Thr Asn Lys Val His Phe Ile Phe Lys His Lys Asn Pro
            180                 185                 190

Lys Thr Gly Glu Tyr Glu Glu Lys His Met Lys Leu Pro Pro Ala Val
        195                 200                 205
```

```
Arg Val Ser Lys Leu Ser Thr Leu Tyr Thr Leu Ile Val Asn Pro Asp
            210                 215                 220

Gln Ser Phe Gln Ile Arg Ile Asp Gly Ala Ala Val Lys Asn Gly Thr
225                 230                 235                 240

Leu Leu Glu Asp Phe Ser Pro Ala Val Asn Pro Glu Lys Glu Ile Asp
                245                 250                 255

Asp Pro Glu Asp Lys Lys Pro Glu Asp Trp Val Asp Glu Ala His Ile
            260                 265                 270

Pro Asp Pro Glu Ala Thr Lys Pro Glu Asp Trp Asp Glu Asp Ala Pro
        275                 280                 285

Tyr Glu Ile Val Asp Thr Asp Ala Thr Gln Pro Glu Asp Trp Leu Val
    290                 295                 300

Asp Glu Pro Thr Ser Ile Pro Asp Pro Glu Ala Gln Lys Pro Glu Asp
305                 310                 315                 320

Trp Asp Asp Glu Glu Asp Gly Asp Trp Ile Pro Pro Thr Ile Pro Asn
                325                 330                 335

Pro Lys Cys Ser Glu Val Ser Gly Cys Gly Met Trp Glu Pro Pro Met
            340                 345                 350

Lys Lys Asn Pro Glu Tyr Lys Gly Lys Trp Thr Ala Pro Met Ile Asp
        355                 360                 365

Asn Pro Ala Tyr Lys Gly Pro Trp Ala Pro Arg Lys Ile Ala Asn Pro
    370                 375                 380

Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
                405                 410                 415

Ile Tyr Ile Gly His Ser Val Glu Asp Ala Glu Lys Leu Lys Ala Glu
            420                 425                 430

Thr Trp Asp Leu Lys His Pro Val Glu Val Ala Glu Glu Ala Ala
        435                 440                 445

Arg Pro Lys Asp Glu Glu Lys Lys Glu Gly Thr Leu Ser Phe Lys Glu
    450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Glu Val Ala
                485                 490                 495

Gly Gly Leu Gly Ala Leu Leu Val Thr Leu Val Leu Ile Ile Val Gly
            500                 505                 510

Ala Val Gly Leu Gly Ser Pro Ser Pro Ala Pro Ala Ala Lys Lys Gln
        515                 520                 525

Ala Glu Lys Gly Lys Glu Lys Thr Ala Glu Ala Val Ser Thr Ala Ala
    530                 535                 540

Asp Asn Val Lys Gly Glu Ala Lys Lys Arg Ser Gly Lys Ala Gly Glu
545                 550                 555                 560

<210> SEQ ID NO 45
<211> LENGTH: 560
<212> TYPE: PRT
<213> ORGANISM: Homo sapiens
<220> FEATURE:
<221> NAME/KEY: BINDING SITE
<222> LOCATION: (1)..(18)
<220> FEATURE:
<221> NAME/KEY: BINDING SITE
<222> LOCATION: (27)..(35)
<220> FEATURE:
<221> NAME/KEY: BINDING SITE
```

```
<222> LOCATION: (97)..(102)
<220> FEATURE:
<221> NAME/KEY: BINDING SITE
<222> LOCATION: (130)..(143)
<220> FEATURE:
<221> NAME/KEY: BINDING SITE
<222> LOCATION: (150)..(159)
<220> FEATURE:
<221> NAME/KEY: BINDING SITE
<222> LOCATION: (208)..(216)
<220> FEATURE:
<221> NAME/KEY: BINDING SITE
<222> LOCATION: (229)..(237)
<220> FEATURE:
<221> NAME/KEY: BINDING SITE
<222> LOCATION: (302)..(310)
<220> FEATURE:
<221> NAME/KEY: BINDING SITE
<222> LOCATION: (412)..(420)
<220> FEATURE:
<221> NAME/KEY: BINDING SITE
<222> LOCATION: (476)..(484)
<220> FEATURE:
<221> NAME/KEY: BINDING SITE
<222> LOCATION: (502)..(522)

<400> SEQUENCE: 45
```

Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
            20                  25                  30

Ser Thr Ser Ser Val Ile Glu Lys Pro Thr Phe Thr Pro Thr Thr Leu
        35                  40                  45

Lys Ala Pro Phe Leu Glu Gln Phe Thr Asp Gly Trp Glu Thr Arg Trp
50                  55                  60

Thr Pro Ser His Ala Lys Lys Glu Asp Ser Lys Ser Glu Glu Asp Trp
65                  70                  75                  80

Ala Tyr Val Gly Thr Trp Ala Val Glu Glu Pro His Val Phe Asn Gly
            85                  90                  95

Met Val Gly Asp Lys Gly Leu Val Val Lys Asn Pro Ala Ala His His
            100                 105                 110

Ala Ile Ser Ala Lys Phe Pro Lys Lys Ile Asp Asn Lys Gly Lys Thr
            115                 120                 125

Leu Val Val Gln Tyr Glu Val Lys Leu Gln Asn Ser Leu Asn Cys Gly
    130                 135                 140

Gly Ala Tyr Met Lys Leu Leu Gln Asp Asn Lys Lys Leu His Ala Glu
145                 150                 155                 160

Glu Phe Ser Asn Thr Ser Pro Tyr Val Ile Met Phe Gly Pro Asp Lys
                165                 170                 175

Cys Gly Val Thr Asn Lys Val His Phe Ile Phe Lys His Lys Asn Pro
            180                 185                 190

Lys Thr Gly Glu Tyr Glu Glu Lys His Met Lys Leu Pro Pro Ala Val
        195                 200                 205

Arg Val Ser Lys Leu Ser Thr Leu Tyr Thr Leu Ile Val Asn Pro Asp
    210                 215                 220

Gln Ser Phe Gln Ile Arg Ile Asp Gly Ala Ala Val Lys Asn Gly Thr
225                 230                 235                 240

Leu Leu Glu Asp Phe Ser Pro Ala Val Asn Pro Glu Lys Glu Ile Asp
                245                 250                 255

Asp Pro Glu Asp Lys Lys Pro Glu Asp Trp Val Asp Glu Ala His Ile
            260                 265                 270

```
Pro Asp Pro Glu Ala Thr Lys Pro Glu Asp Trp Asp Glu Asp Ala Pro
            275                 280                 285

Tyr Glu Ile Val Asp Thr Asp Ala Thr Gln Pro Glu Asp Trp Leu Val
        290                 295                 300

Asp Glu Pro Thr Ser Ile Pro Asp Pro Glu Ala Gln Lys Pro Glu Asp
305                 310                 315                 320

Trp Asp Asp Glu Glu Asp Gly Asp Trp Ile Pro Pro Thr Ile Pro Asn
                325                 330                 335

Pro Lys Cys Ser Glu Val Ser Gly Cys Gly Met Trp Glu Pro Pro Met
            340                 345                 350

Lys Lys Asn Pro Glu Tyr Lys Gly Lys Trp Thr Ala Pro Met Ile Asp
        355                 360                 365

Asn Pro Ala Tyr Lys Gly Pro Trp Ala Pro Arg Lys Ile Ala Asn Pro
    370                 375                 380

Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
                405                 410                 415

Ile Tyr Ile Gly His Ser Val Glu Asp Ala Glu Lys Leu Lys Ala Glu
            420                 425                 430

Thr Trp Asp Leu Lys His Pro Val Glu Val Ala Glu Glu Ala Ala
        435                 440                 445

Arg Pro Lys Asp Glu Glu Lys Lys Glu Gly Thr Leu Ser Phe Lys Glu
    450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Glu Val Ala
                485                 490                 495

Gly Gly Leu Gly Ala Leu Leu Val Thr Leu Val Leu Ile Ile Val Gly
            500                 505                 510

Ala Val Gly Leu Gly Ser Pro Ser Pro Ala Pro Ala Ala Lys Lys Gln
        515                 520                 525

Ala Glu Lys Gly Lys Glu Lys Thr Ala Glu Ala Val Ser Thr Ala Ala
    530                 535                 540

Asp Asn Val Lys Gly Glu Ala Lys Lys Arg Ser Gly Lys Ala Gly Glu
545                 550                 555                 560

<210> SEQ ID NO 46
<211> LENGTH: 560
<212> TYPE: PRT
<213> ORGANISM: Homo sapiens
<220> FEATURE:
<221> NAME/KEY: BINDING SITE
<222> LOCATION: (1)..(23)
<220> FEATURE:
<221> NAME/KEY: BINDING SITE
<222> LOCATION: (27)..(35)
<220> FEATURE:
<221> NAME/KEY: BINDING SITE
<222> LOCATION: (104)..(112)
<220> FEATURE:
<221> NAME/KEY: BINDING SITE
<222> LOCATION: (135)..(145)
<220> FEATURE:
<221> NAME/KEY: BINDING SITE
<222> LOCATION: (168)..(176)
<220> FEATURE:
<221> NAME/KEY: BINDING SITE
<222> LOCATION: (217)..(225)
<220> FEATURE:
<221> NAME/KEY: BINDING SITE
```

```
<222> LOCATION: (229)..(237)
<220> FEATURE:
<221> NAME/KEY: BINDING SITE
<222> LOCATION: (302)..(311)
<220> FEATURE:
<221> NAME/KEY: BINDING SITE
<222> LOCATION: (418)..(426)
<220> FEATURE:
<221> NAME/KEY: BINDING SITE
<222> LOCATION: (480)..(488)
<220> FEATURE:
<221> NAME/KEY: BINDING SITE
<222> LOCATION: (502)..(514)

<400> SEQUENCE: 46
```

Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
            20                  25                  30

Ser Thr Ser Ser Val Ile Glu Lys Pro Thr Phe Thr Pro Thr Thr Leu
        35                  40                  45

Lys Ala Pro Phe Leu Glu Gln Phe Thr Asp Gly Trp Glu Thr Arg Trp
    50                  55                  60

Thr Pro Ser His Ala Lys Lys Glu Asp Ser Lys Ser Glu Glu Asp Trp
65                  70                  75                  80

Ala Tyr Val Gly Thr Trp Ala Val Glu Glu Pro His Val Phe Asn Gly
                85                  90                  95

Met Val Gly Asp Lys Gly Leu Val Val Lys Asn Pro Ala Ala His His
            100                 105                 110

Ala Ile Ser Ala Lys Phe Pro Lys Lys Ile Asp Asn Lys Gly Lys Thr
        115                 120                 125

Leu Val Val Gln Tyr Glu Val Lys Leu Gln Asn Ser Leu Asn Cys Gly
    130                 135                 140

Gly Ala Tyr Met Lys Leu Leu Gln Asp Asn Lys Lys Leu His Ala Glu
145                 150                 155                 160

Glu Phe Ser Asn Thr Ser Pro Tyr Val Ile Met Phe Gly Pro Asp Lys
                165                 170                 175

Cys Gly Val Thr Asn Lys Val His Phe Ile Phe Lys His Lys Asn Pro
            180                 185                 190

Lys Thr Gly Glu Tyr Glu Glu Lys His Met Lys Leu Pro Pro Ala Val
        195                 200                 205

Arg Val Ser Lys Leu Ser Thr Leu Tyr Thr Leu Ile Val Asn Pro Asp
    210                 215                 220

Gln Ser Phe Gln Ile Arg Ile Asp Gly Ala Ala Val Lys Asn Gly Thr
225                 230                 235                 240

Leu Leu Glu Asp Phe Ser Pro Ala Val Asn Pro Glu Lys Glu Ile Asp
                245                 250                 255

Asp Pro Glu Asp Lys Lys Pro Glu Asp Trp Val Asp Glu Ala His Ile
            260                 265                 270

Pro Asp Pro Glu Ala Thr Lys Pro Glu Asp Trp Asp Glu Asp Ala Pro
        275                 280                 285

Tyr Glu Ile Val Asp Thr Asp Ala Thr Gln Pro Glu Asp Trp Leu Val
    290                 295                 300

Asp Glu Pro Thr Ser Ile Pro Asp Pro Glu Ala Gln Lys Pro Glu Asp
305                 310                 315                 320

Trp Asp Asp Glu Glu Asp Gly Asp Trp Ile Pro Pro Thr Ile Pro Asn
                325                 330                 335

```
Pro Lys Cys Ser Glu Val Ser Gly Cys Gly Met Trp Glu Pro Pro Met
            340                 345                 350

Lys Lys Asn Pro Glu Tyr Lys Gly Lys Trp Thr Ala Pro Met Ile Asp
            355                 360                 365

Asn Pro Ala Tyr Lys Gly Pro Trp Ala Pro Arg Lys Ile Ala Asn Pro
370                 375                 380

Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
                405                 410                 415

Ile Tyr Ile Gly His Ser Val Glu Asp Ala Glu Lys Leu Lys Ala Glu
            420                 425                 430

Thr Trp Asp Leu Lys His Pro Val Glu Val Ala Glu Glu Ala Ala
            435                 440                 445

Arg Pro Lys Asp Glu Glu Lys Lys Glu Gly Thr Leu Ser Phe Lys Glu
            450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Glu Val Ala
                485                 490                 495

Gly Gly Leu Gly Ala Leu Leu Val Thr Leu Val Leu Ile Ile Val Gly
            500                 505                 510

Ala Val Gly Leu Gly Ser Pro Ser Pro Ala Pro Ala Ala Lys Lys Gln
            515                 520                 525

Ala Glu Lys Gly Lys Lys Thr Ala Glu Ala Val Ser Thr Ala Ala
            530                 535                 540

Asp Asn Val Lys Gly Glu Ala Lys Lys Arg Ser Gly Lys Ala Gly Glu
545                 550                 555                 560

<210> SEQ ID NO 47
<211> LENGTH: 560
<212> TYPE: PRT
<213> ORGANISM: Homo sapiens
<220> FEATURE:
<221> NAME/KEY: BINDING SITE
<222> LOCATION: (1)..(9)
<220> FEATURE:
<221> NAME/KEY: BINDING SITE
<222> LOCATION: (15)..(23)
<220> FEATURE:
<221> NAME/KEY: BINDING SITE
<222> LOCATION: (103)..(111)
<220> FEATURE:
<221> NAME/KEY: BINDING SITE
<222> LOCATION: (130)..(143)
<220> FEATURE:
<221> NAME/KEY: BINDING SITE
<222> LOCATION: (358)..(366)
<220> FEATURE:
<221> NAME/KEY: BINDING SITE
<222> LOCATION: (474)..(482)
<220> FEATURE:
<221> NAME/KEY: BINDING SITE
<222> LOCATION: (502)..(518)

<400> SEQUENCE: 47

Met Arg Leu Asn Ala Ser Leu Ala Ser Leu Ile Leu Ser Ile Ala
1               5                   10                  15

Leu Ile Gly Asn Val His Ala Glu Asp Glu Val Lys Glu Asp Ala Thr
            20                  25                  30

Ser Thr Ser Ser Val Ile Glu Lys Pro Thr Phe Thr Pro Thr Thr Leu
        35                  40                  45
```

```
Lys Ala Pro Phe Leu Glu Gln Phe Thr Asp Gly Trp Glu Thr Arg Trp
 50                  55                  60
Thr Pro Ser His Ala Lys Glu Asp Ser Lys Ser Glu Glu Asp Trp
 65                  70                  75                  80
Ala Tyr Val Gly Thr Trp Ala Val Glu Glu Pro His Val Phe Asn Gly
                 85                  90                  95
Met Val Gly Asp Lys Gly Leu Val Val Lys Asn Pro Ala Ala His His
            100                 105                 110
Ala Ile Ser Ala Lys Phe Pro Lys Lys Ile Asp Asn Lys Gly Lys Thr
            115                 120                 125
Leu Val Val Gln Tyr Glu Val Lys Leu Gln Asn Ser Leu Asn Cys Gly
130                 135                 140
Gly Ala Tyr Met Lys Leu Leu Gln Asp Asn Lys Lys Leu His Ala Glu
145                 150                 155                 160
Glu Phe Ser Asn Thr Ser Pro Tyr Val Ile Met Phe Gly Pro Asp Lys
                165                 170                 175
Cys Gly Val Thr Asn Lys Val His Phe Ile Phe Lys His Lys Asn Pro
                180                 185                 190
Lys Thr Gly Glu Tyr Glu Glu Lys His Met Lys Leu Pro Pro Ala Val
            195                 200                 205
Arg Val Ser Lys Leu Ser Thr Leu Tyr Thr Leu Ile Val Asn Pro Asp
210                 215                 220
Gln Ser Phe Gln Ile Arg Ile Asp Gly Ala Ala Val Lys Asn Gly Thr
225                 230                 235                 240
Leu Leu Glu Asp Phe Ser Pro Ala Val Asn Pro Glu Lys Glu Ile Asp
                245                 250                 255
Asp Pro Glu Asp Lys Lys Pro Glu Asp Trp Val Asp Glu Ala His Ile
            260                 265                 270
Pro Asp Pro Glu Ala Thr Lys Pro Glu Asp Trp Asp Glu Asp Ala Pro
            275                 280                 285
Tyr Glu Ile Val Asp Thr Asp Ala Thr Gln Pro Glu Asp Trp Leu Val
290                 295                 300
Asp Glu Pro Thr Ser Ile Pro Asp Pro Glu Ala Gln Lys Pro Glu Asp
305                 310                 315                 320
Trp Asp Asp Glu Glu Asp Gly Asp Trp Ile Pro Pro Thr Ile Pro Asn
                325                 330                 335
Pro Lys Cys Ser Glu Val Ser Gly Cys Gly Met Trp Glu Pro Pro Met
            340                 345                 350
Lys Lys Asn Pro Glu Tyr Lys Gly Lys Trp Thr Ala Pro Met Ile Asp
            355                 360                 365
Asn Pro Ala Tyr Lys Gly Pro Trp Ala Pro Arg Lys Ile Ala Asn Pro
370                 375                 380
Asn Tyr Phe Glu Asp Lys Thr Pro Ser Asn Phe Glu Pro Met Gly Ala
385                 390                 395                 400
Ile Gly Phe Glu Ile Trp Thr Met Gln Asn Asp Ile Leu Phe Asp Asn
                405                 410                 415
Ile Tyr Ile Gly His Ser Val Glu Asp Ala Glu Lys Leu Lys Ala Glu
            420                 425                 430
Thr Trp Asp Leu Lys His Pro Val Glu Val Ala Glu Glu Ala Ala
            435                 440                 445
Arg Pro Lys Asp Glu Glu Lys Lys Glu Gly Thr Leu Ser Phe Lys Glu
450                 455                 460
```

-continued

```
Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Glu Val Ala
            485                 490                 495

Gly Gly Leu Gly Ala Leu Leu Val Thr Leu Val Leu Ile Ile Val Gly
        500                 505                 510

Ala Val Gly Leu Gly Ser Pro Ser Pro Ala Pro Ala Ala Lys Lys Gln
        515                 520                 525

Ala Glu Lys Gly Lys Glu Lys Thr Ala Glu Ala Val Ser Thr Ala Ala
        530                 535                 540

Asp Asn Val Lys Gly Glu Ala Lys Lys Arg Ser Gly Lys Ala Gly Glu
545                 550                 555                 560

<210> SEQ ID NO 48
<211> LENGTH: 560
<212> TYPE: PRT
<213> ORGANISM: Homo sapiens
<220> FEATURE:
<221> NAME/KEY: BINDING SITE
<222> LOCATION: (1)..(9)
<220> FEATURE:
<221> NAME/KEY: BINDING SITE
<222> LOCATION: (19)..(23)
<220> FEATURE:
<221> NAME/KEY: BINDING SITE
<222> LOCATION: (27)..(35)
<220> FEATURE:
<221> NAME/KEY: BINDING SITE
<222> LOCATION: (130)..(143)
<220> FEATURE:
<221> NAME/KEY: BINDING SITE
<222> LOCATION: (148)..(156)
<220> FEATURE:
<221> NAME/KEY: BINDING SITE
<222> LOCATION: (168)..(176)
<220> FEATURE:
<221> NAME/KEY: BINDING SITE
<222> LOCATION: (213)..(225)
<220> FEATURE:
<221> NAME/KEY: BINDING SITE
<222> LOCATION: (229)..(237)
<220> FEATURE:
<221> NAME/KEY: BINDING SITE
<222> LOCATION: (474)..(482)
<220> FEATURE:
<221> NAME/KEY: BINDING SITE
<222> LOCATION: (499)..(518)

<400> SEQUENCE: 48

Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
            20                  25                  30

Ser Thr Ser Ser Val Ile Glu Lys Pro Thr Phe Thr Pro Thr Thr Leu
        35                  40                  45

Lys Ala Pro Phe Leu Glu Gln Phe Thr Asp Gly Trp Glu Thr Arg Trp
    50                  55                  60

Thr Pro Ser His Ala Lys Lys Glu Asp Ser Lys Ser Glu Glu Asp Trp
65                  70                  75                  80

Ala Tyr Val Gly Thr Trp Ala Val Glu Glu Pro His Val Phe Asn Gly
                85                  90                  95

Met Val Gly Asp Lys Gly Leu Val Val Lys Asn Pro Ala Ala His His
            100                 105                 110

Ala Ile Ser Ala Lys Phe Pro Lys Lys Ile Asp Asn Lys Gly Lys Thr
        115                 120                 125
```

```
Leu Val Val Gln Tyr Glu Val Lys Leu Gln Asn Ser Leu Asn Cys Gly
        130                 135                 140

Gly Ala Tyr Met Lys Leu Leu Gln Asp Asn Lys Lys Leu His Ala Glu
145                 150                 155                 160

Glu Phe Ser Asn Thr Ser Pro Tyr Val Ile Met Phe Gly Pro Asp Lys
                165                 170                 175

Cys Gly Val Thr Asn Lys Val His Phe Ile Phe Lys His Lys Asn Pro
                180                 185                 190

Lys Thr Gly Glu Tyr Glu Lys His Met Lys Leu Pro Pro Ala Val
                195                 200                 205

Arg Val Ser Lys Leu Ser Thr Leu Tyr Thr Leu Ile Val Asn Pro Asp
        210                 215                 220

Gln Ser Phe Gln Ile Arg Ile Asp Gly Ala Ala Val Lys Asn Gly Thr
225                 230                 235                 240

Leu Leu Glu Asp Phe Ser Pro Ala Val Asn Pro Glu Lys Glu Ile Asp
                245                 250                 255

Asp Pro Glu Asp Lys Lys Pro Glu Asp Trp Val Asp Glu Ala His Ile
                260                 265                 270

Pro Asp Pro Glu Ala Thr Lys Pro Glu Asp Trp Asp Glu Asp Ala Pro
                275                 280                 285

Tyr Glu Ile Val Asp Thr Asp Ala Thr Gln Pro Glu Asp Trp Leu Val
        290                 295                 300

Asp Glu Pro Thr Ser Ile Pro Asp Pro Glu Ala Gln Lys Pro Glu Asp
305                 310                 315                 320

Trp Asp Asp Glu Glu Asp Gly Asp Trp Ile Pro Pro Thr Ile Pro Asn
                325                 330                 335

Pro Lys Cys Ser Glu Val Ser Gly Cys Gly Met Trp Glu Pro Pro Met
                340                 345                 350

Lys Lys Asn Pro Glu Tyr Lys Gly Lys Trp Thr Ala Pro Met Ile Asp
                355                 360                 365

Asn Pro Ala Tyr Lys Gly Pro Trp Ala Pro Arg Lys Ile Ala Asn Pro
        370                 375                 380

Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
                405                 410                 415

Ile Tyr Ile Gly His Ser Val Glu Asp Ala Glu Lys Leu Lys Ala Glu
                420                 425                 430

Thr Trp Asp Leu Lys His Pro Val Glu Val Ala Glu Glu Ala Ala
        435                 440                 445

Arg Pro Lys Asp Glu Lys Lys Glu Gly Thr Leu Ser Phe Lys Glu
450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Glu Val Ala
                485                 490                 495

Gly Gly Leu Gly Ala Leu Leu Val Thr Leu Val Leu Ile Ile Val Gly
                500                 505                 510

Ala Val Gly Leu Gly Ser Pro Ser Pro Ala Pro Ala Ala Lys Lys Gln
        515                 520                 525

Ala Glu Lys Gly Lys Glu Lys Thr Ala Glu Ala Val Ser Thr Ala Ala
530                 535                 540
```

```
Asp Asn Val Lys Gly Glu Ala Lys Lys Arg Ser Gly Lys Ala Gly Glu
545                 550                 555                 560

<210> SEQ ID NO 49
<211> LENGTH: 560
<212> TYPE: PRT
<213> ORGANISM: Homo sapiens
<220> FEATURE:
<221> NAME/KEY: BINDING SITE
<222> LOCATION: (1)..(9)
<220> FEATURE:
<221> NAME/KEY: BINDING SITE
<222> LOCATION: (15)..(23)
<220> FEATURE:
<221> NAME/KEY: BINDING SITE
<222> LOCATION: (80)..(90)
<220> FEATURE:
<221> NAME/KEY: BINDING SITE
<222> LOCATION: (135)..(143)
<220> FEATURE:
<221> NAME/KEY: BINDING SITE
<222> LOCATION: (216)..(225)
<220> FEATURE:
<221> NAME/KEY: BINDING SITE
<222> LOCATION: (289)..(297)
<220> FEATURE:
<221> NAME/KEY: BINDING SITE
<222> LOCATION: (358)..(366)
<220> FEATURE:
<221> NAME/KEY: BINDING SITE
<222> LOCATION: (474)..(482)
<220> FEATURE:
<221> NAME/KEY: BINDING SITE
<222> LOCATION: (506)..(516)

<400> SEQUENCE: 49

Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
                20                  25                  30

Ser Thr Ser Ser Val Ile Glu Lys Pro Thr Phe Thr Pro Thr Thr Leu
            35                  40                  45

Lys Ala Pro Phe Leu Glu Gln Phe Thr Asp Gly Trp Glu Thr Arg Trp
50                  55                  60

Thr Pro Ser His Ala Lys Lys Glu Asp Ser Lys Ser Glu Glu Asp Trp
65                  70                  75                  80

Ala Tyr Val Gly Thr Trp Ala Val Glu Glu Pro His Val Phe Asn Gly
                85                  90                  95

Met Val Gly Asp Lys Gly Leu Val Lys Asn Pro Ala Ala His His
                100                 105                 110

Ala Ile Ser Ala Lys Phe Pro Lys Ile Asp Asn Lys Gly Lys Thr
            115                 120                 125

Leu Val Val Gln Tyr Glu Val Lys Leu Gln Asn Ser Leu Asn Cys Gly
130                 135                 140

Gly Ala Tyr Met Lys Leu Leu Gln Asp Asn Lys Lys Leu His Ala Glu
145                 150                 155                 160

Glu Phe Ser Asn Thr Ser Pro Tyr Val Ile Met Phe Gly Pro Asp Lys
                165                 170                 175

Cys Gly Val Thr Asn Lys Val His Phe Ile Phe Lys His Lys Asn Pro
            180                 185                 190

Lys Thr Gly Glu Tyr Glu Glu Lys His Met Lys Leu Pro Pro Ala Val
        195                 200                 205

Arg Val Ser Lys Leu Ser Thr Leu Tyr Thr Leu Ile Val Asn Pro Asp
    210                 215                 220
```

Gln Ser Phe Gln Ile Arg Ile Asp Gly Ala Ala Val Lys Asn Gly Thr
225                 230                 235                 240

Leu Leu Glu Asp Phe Ser Pro Ala Val Asn Pro Glu Lys Glu Ile Asp
            245                 250                 255

Asp Pro Asp Lys Lys Pro Glu Asp Trp Val Asp Glu Ala His Ile
        260                 265                 270

Pro Asp Pro Glu Ala Thr Lys Pro Glu Asp Trp Asp Glu Asp Ala Pro
        275                 280                 285

Tyr Glu Ile Val Asp Thr Asp Ala Thr Gln Pro Glu Asp Trp Leu Val
        290                 295                 300

Asp Glu Pro Thr Ser Ile Pro Asp Pro Glu Ala Gln Lys Pro Glu Asp
305                 310                 315                 320

Trp Asp Asp Glu Glu Asp Gly Asp Trp Ile Pro Pro Thr Ile Pro Asn
                325                 330                 335

Pro Lys Cys Ser Glu Val Ser Gly Cys Gly Met Trp Glu Pro Pro Met
            340                 345                 350

Lys Lys Asn Pro Glu Tyr Lys Gly Lys Trp Thr Ala Pro Met Ile Asp
            355                 360                 365

Asn Pro Ala Tyr Lys Gly Pro Trp Ala Pro Arg Lys Ile Ala Asn Pro
370                 375                 380

Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
                405                 410                 415

Ile Tyr Ile Gly His Ser Val Glu Asp Ala Glu Lys Leu Lys Ala Glu
            420                 425                 430

Thr Trp Asp Leu Lys His Pro Val Glu Val Ala Glu Glu Ala Ala
            435                 440                 445

Arg Pro Lys Asp Glu Glu Lys Lys Glu Gly Thr Leu Ser Phe Lys Glu
        450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Glu Val Ala
            485                 490                 495

Gly Gly Leu Gly Ala Leu Leu Val Thr Leu Val Leu Ile Ile Val Gly
            500                 505                 510

Ala Val Gly Leu Gly Ser Pro Ser Pro Ala Pro Ala Ala Lys Lys Gln
            515                 520                 525

Ala Glu Lys Gly Lys Glu Lys Thr Ala Glu Ala Val Ser Thr Ala Ala
            530                 535                 540

Asp Asn Val Lys Gly Glu Ala Lys Lys Arg Ser Gly Lys Ala Gly Glu
545                 550                 555                 560

```
<210> SEQ ID NO 50
<211> LENGTH: 560
<212> TYPE: PRT
<213> ORGANISM: Homo sapiens
<220> FEATURE:
<221> NAME/KEY: BINDING SITE
<222> LOCATION: (1)..(9)
<220> FEATURE:
<221> NAME/KEY: BINDING SITE
<222> LOCATION: (15)..(23)
<220> FEATURE:
<221> NAME/KEY: BINDING SITE
<222> LOCATION: (80)..(88)
<220> FEATURE:
```

<220> FEATURE:
<221> NAME/KEY: BINDING SITE
<222> LOCATION: (135)..(143)
<220> FEATURE:
<221> NAME/KEY: BINDING SITE
<222> LOCATION: (148)..(156)
<220> FEATURE:
<221> NAME/KEY: BINDING SITE
<222> LOCATION: (168)..(177)
<220> FEATURE:
<221> NAME/KEY: BINDING SITE
<222> LOCATION: (213)..(225)
<220> FEATURE:
<221> NAME/KEY: BINDING SITE
<222> LOCATION: (229)..(237)
<220> FEATURE:
<221> NAME/KEY: BINDING SITE
<222> LOCATION: (289)..(297)
<220> FEATURE:
<221> NAME/KEY: BINDING SITE
<222> LOCATION: (358)..(366)
<220> FEATURE:
<221> NAME/KEY: BINDING SITE
<222> LOCATION: (395)..(403)
<220> FEATURE:
<221> NAME/KEY: BINDING SITE
<222> LOCATION: (474)..(482)
<220> FEATURE:
<221> NAME/KEY: BINDING SITE
<222> LOCATION: (506)..(514)

<400> SEQUENCE: 50

```
Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
            20                  25                  30

Ser Thr Ser Ser Val Ile Glu Lys Pro Thr Phe Thr Pro Thr Thr Leu
        35                  40                  45

Lys Ala Pro Phe Leu Glu Gln Phe Thr Asp Gly Trp Glu Thr Arg Trp
    50                  55                  60

Thr Pro Ser His Ala Lys Lys Glu Asp Ser Lys Ser Glu Glu Asp Trp
65                  70                  75                  80

Ala Tyr Val Gly Thr Trp Ala Val Glu Glu Pro His Val Phe Asn Gly
                85                  90                  95

Met Val Gly Asp Lys Gly Leu Val Val Lys Asn Pro Ala Ala His His
            100                 105                 110

Ala Ile Ser Ala Lys Phe Pro Lys Lys Ile Asp Asn Lys Gly Lys Thr
        115                 120                 125

Leu Val Val Gln Tyr Glu Val Lys Leu Gln Asn Ser Leu Asn Cys Gly
    130                 135                 140

Gly Ala Tyr Met Lys Leu Leu Gln Asp Asn Lys Lys Leu His Ala Glu
145                 150                 155                 160

Glu Phe Ser Asn Thr Ser Pro Tyr Val Ile Met Phe Gly Pro Asp Lys
                165                 170                 175

Cys Gly Val Thr Asn Lys Val His Phe Ile Phe Lys His Lys Asn Pro
            180                 185                 190

Lys Thr Gly Glu Tyr Glu Glu Lys His Met Lys Leu Pro Pro Ala Val
        195                 200                 205

Arg Val Ser Lys Leu Ser Thr Leu Tyr Thr Leu Ile Val Asn Pro Asp
    210                 215                 220

Gln Ser Phe Gln Ile Arg Ile Asp Gly Ala Ala Val Lys Asn Gly Thr
225                 230                 235                 240

Leu Leu Glu Asp Phe Ser Pro Ala Val Asn Pro Glu Lys Glu Ile Asp
                245                 250                 255
```

```
Asp Pro Glu Asp Lys Pro Glu Asp Trp Val Asp Glu Ala His Ile
            260                 265                 270

Pro Asp Pro Glu Ala Thr Lys Pro Glu Asp Trp Asp Glu Asp Ala Pro
            275                 280                 285

Tyr Glu Ile Val Asp Thr Asp Ala Thr Gln Pro Glu Asp Trp Leu Val
            290                 295                 300

Asp Glu Pro Thr Ser Ile Pro Asp Pro Glu Ala Gln Lys Pro Glu Asp
305                 310                 315                 320

Trp Asp Asp Glu Glu Asp Gly Asp Trp Ile Pro Pro Thr Ile Pro Asn
                325                 330                 335

Pro Lys Cys Ser Glu Val Ser Gly Cys Gly Met Trp Glu Pro Pro Met
            340                 345                 350

Lys Lys Asn Pro Glu Tyr Lys Gly Lys Trp Thr Ala Pro Met Ile Asp
            355                 360                 365

Asn Pro Ala Tyr Lys Gly Pro Trp Ala Pro Arg Lys Ile Ala Asn Pro
            370                 375                 380

Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
                405                 410                 415

Ile Tyr Ile Gly His Ser Val Glu Asp Ala Glu Lys Leu Lys Ala Glu
                420                 425                 430

Thr Trp Asp Leu Lys His Pro Val Glu Val Ala Glu Glu Ala Ala
            435                 440                 445

Arg Pro Lys Asp Glu Lys Lys Glu Gly Thr Leu Ser Phe Lys Glu
            450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Glu Val Ala
                485                 490                 495

Gly Gly Leu Gly Ala Leu Leu Val Thr Leu Val Leu Ile Ile Val Gly
            500                 505                 510

Ala Val Gly Leu Gly Ser Pro Ser Pro Ala Pro Ala Ala Lys Lys Gln
            515                 520                 525

Ala Glu Lys Gly Lys Glu Lys Thr Ala Glu Ala Val Ser Thr Ala Ala
            530                 535                 540

Asp Asn Val Lys Gly Glu Ala Lys Arg Ser Gly Lys Ala Gly Glu
545                 550                 555                 560
```

<210> SEQ ID NO 51
<211> LENGTH: 560
<212> TYPE: PRT
<213> ORGANISM: Homo sapiens
<220> FEATURE:
<221> NAME/KEY: BINDING SITE
<222> LOCATION: (1)..(9)
<220> FEATURE:
<221> NAME/KEY: BINDING SITE
<222> LOCATION: (104)..(112)
<220> FEATURE:
<221> NAME/KEY: BINDING SITE
<222> LOCATION: (130)..(145)
<220> FEATURE:
<221> NAME/KEY: BINDING SITE
<222> LOCATION: (210)..(225)
<220> FEATURE:
<221> NAME/KEY: BINDING SITE
<222> LOCATION: (474)..(482)
<220> FEATURE:

```
<221> NAME/KEY: BINDING SITE
<222> LOCATION: (506)..(516)

<400> SEQUENCE: 51
```

| | | | | | | | | | | | | | | |
|---|---|---|---|---|---|---|---|---|---|---|---|---|---|---|
| Met | Arg | Leu | Asn | Ala | Ser | Leu | Ala | Ser | Leu | Ile | Leu | Ser | Ser | Ile | Ala |
| 1 | | | | 5 | | | | | 10 | | | | | 15 | |

| Leu | Ile | Gly | Asn | Val | His | Ala | Glu | Asp | Glu | Val | Lys | Glu | Asp | Ala | Thr |
| | | | 20 | | | | | 25 | | | | | 30 | | |

| Ser | Thr | Ser | Ser | Val | Ile | Glu | Lys | Pro | Thr | Phe | Thr | Pro | Thr | Thr | Leu |
| | | 35 | | | | | 40 | | | | | 45 | | | |

| Lys | Ala | Pro | Phe | Leu | Glu | Gln | Phe | Thr | Asp | Gly | Trp | Glu | Thr | Arg | Trp |
| 50 | | | | | 55 | | | | | 60 | | | | | |

| Thr | Pro | Ser | His | Ala | Lys | Lys | Glu | Asp | Ser | Lys | Ser | Glu | Glu | Asp | Trp |
| 65 | | | | | 70 | | | | | 75 | | | | | 80 |

| Ala | Tyr | Val | Gly | Thr | Trp | Ala | Val | Glu | Glu | Pro | His | Val | Phe | Asn | Gly |
| | | | | 85 | | | | | 90 | | | | | 95 | |

| Met | Val | Gly | Asp | Lys | Gly | Leu | Val | Val | Lys | Asn | Pro | Ala | Ala | His | His |
| | | | 100 | | | | | 105 | | | | | 110 | | |

| Ala | Ile | Ser | Ala | Lys | Phe | Pro | Lys | Lys | Ile | Asp | Asn | Lys | Gly | Lys | Thr |
| | | 115 | | | | | 120 | | | | | 125 | | | |

| Leu | Val | Val | Gln | Tyr | Glu | Val | Lys | Leu | Gln | Asn | Ser | Leu | Asn | Cys | Gly |
| 130 | | | | | 135 | | | | | 140 | | | | | |

| Gly | Ala | Tyr | Met | Lys | Leu | Leu | Gln | Asp | Asn | Lys | Lys | Leu | His | Ala | Glu |
| 145 | | | | | 150 | | | | | 155 | | | | | 160 |

| Glu | Phe | Ser | Asn | Thr | Ser | Pro | Tyr | Val | Ile | Met | Phe | Gly | Pro | Asp | Lys |
| | | | | 165 | | | | | 170 | | | | | 175 | |

| Cys | Gly | Val | Thr | Asn | Lys | Val | His | Phe | Ile | Phe | Lys | His | Lys | Asn | Pro |
| | | | 180 | | | | | 185 | | | | | 190 | | |

| Lys | Thr | Gly | Glu | Tyr | Glu | Glu | Lys | His | Met | Lys | Leu | Pro | Pro | Ala | Val |
| | | | 195 | | | | | 200 | | | | | 205 | | |

| Arg | Val | Ser | Lys | Leu | Ser | Thr | Leu | Tyr | Thr | Leu | Ile | Val | Asn | Pro | Asp |
| 210 | | | | | 215 | | | | | 220 | | | | | |

| Gln | Ser | Phe | Gln | Ile | Arg | Ile | Asp | Gly | Ala | Ala | Val | Lys | Asn | Gly | Thr |
| 225 | | | | | 230 | | | | | 235 | | | | | 240 |

| Leu | Leu | Glu | Asp | Phe | Ser | Pro | Ala | Val | Asn | Pro | Glu | Lys | Glu | Ile | Asp |
| | | | | 245 | | | | | 250 | | | | | 255 | |

| Asp | Pro | Glu | Asp | Lys | Lys | Pro | Glu | Asp | Trp | Val | Asp | Glu | Ala | His | Ile |
| | | | 260 | | | | | 265 | | | | | 270 | | |

| Pro | Asp | Pro | Glu | Ala | Thr | Lys | Pro | Glu | Asp | Trp | Asp | Glu | Asp | Ala | Pro |
| | | 275 | | | | | 280 | | | | | 285 | | | |

| Tyr | Glu | Ile | Val | Asp | Thr | Asp | Ala | Thr | Gln | Pro | Glu | Asp | Trp | Leu | Val |
| | 290 | | | | | 295 | | | | | 300 | | | | |

| Asp | Glu | Pro | Thr | Ser | Ile | Pro | Asp | Pro | Glu | Ala | Gln | Lys | Pro | Glu | Asp |
| 305 | | | | | 310 | | | | | 315 | | | | | 320 |

| Trp | Asp | Asp | Glu | Glu | Asp | Gly | Asp | Trp | Ile | Pro | Pro | Thr | Ile | Pro | Asn |
| | | | | 325 | | | | | 330 | | | | | 335 | |

| Pro | Lys | Cys | Ser | Glu | Val | Ser | Gly | Cys | Gly | Met | Trp | Glu | Pro | Pro | Met |
| | | | 340 | | | | | 345 | | | | | 350 | | |

| Lys | Lys | Asn | Pro | Glu | Tyr | Lys | Gly | Lys | Trp | Thr | Ala | Pro | Met | Ile | Asp |
| | | 355 | | | | | 360 | | | | | 365 | | | |

| Asn | Pro | Ala | Tyr | Lys | Gly | Pro | Trp | Ala | Pro | Arg | Lys | Ile | Ala | Asn | Pro |
| 370 | | | | | 375 | | | | | 380 | | | | | |

| Asn | Tyr | Phe | Glu | Asp | Lys | Thr | Pro | Ser | Asn | Phe | Glu | Pro | Met | Gly | Ala |
| 385 | | | | | 390 | | | | | 395 | | | | | 400 |

```
Ile Gly Phe Glu Ile Trp Thr Met Gln Asn Asp Ile Leu Phe Asp Asn
                405                 410                 415

Ile Tyr Ile Gly His Ser Val Glu Asp Ala Glu Lys Leu Lys Ala Glu
            420                 425                 430

Thr Trp Asp Leu Lys His Pro Val Glu Val Ala Glu Glu Ala Ala
        435                 440                 445

Arg Pro Lys Asp Glu Lys Lys Gly Thr Leu Ser Phe Lys Glu
450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Glu Val Ala
                485                 490                 495

Gly Gly Leu Gly Ala Leu Leu Val Thr Leu Val Leu Ile Ile Val Gly
            500                 505                 510

Ala Val Gly Leu Gly Ser Pro Ser Pro Ala Pro Ala Ala Lys Lys Gln
            515                 520                 525

Ala Glu Lys Gly Lys Glu Lys Thr Ala Glu Ala Val Ser Thr Ala Ala
        530                 535                 540

Asp Asn Val Lys Gly Glu Ala Lys Lys Arg Ser Gly Lys Ala Gly Glu
545                 550                 555                 560

<210> SEQ ID NO 52
<211> LENGTH: 560
<212> TYPE: PRT
<213> ORGANISM: Homo sapiens
<220> FEATURE:
<221> NAME/KEY: BINDING SITE
<222> LOCATION: (1)..(18)
<220> FEATURE:
<221> NAME/KEY: BINDING SITE
<222> LOCATION: (27)..(35)
<220> FEATURE:
<221> NAME/KEY: BINDING SITE
<222> LOCATION: (82)..(94)
<220> FEATURE:
<221> NAME/KEY: BINDING SITE
<222> LOCATION: (135)..(145)
<220> FEATURE:
<221> NAME/KEY: BINDING SITE
<222> LOCATION: (213)..(221)
<220> FEATURE:
<221> NAME/KEY: BINDING SITE
<222> LOCATION: (229)..(237)
<220> FEATURE:
<221> NAME/KEY: BINDING SITE
<222> LOCATION: (302)..(311)
<220> FEATURE:
<221> NAME/KEY: BINDING SITE
<222> LOCATION: (358)..(366)
<220> FEATURE:
<221> NAME/KEY: BINDING SITE
<222> LOCATION: (418)..(426)
<220> FEATURE:
<221> NAME/KEY: BINDING SITE
<222> LOCATION: (502)..(514)

<400> SEQUENCE: 52

Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
                20                  25                  30

Ser Thr Ser Ser Val Ile Glu Lys Pro Thr Phe Thr Pro Thr Thr Leu
            35                  40                  45

Lys Ala Pro Phe Leu Glu Gln Phe Thr Asp Gly Trp Glu Thr Arg Trp
```

-continued

```
                50                  55                  60
Thr Pro Ser His Ala Lys Lys Glu Asp Ser Lys Ser Glu Glu Asp Trp
65                  70                  75                  80
Ala Tyr Val Gly Thr Trp Ala Val Glu Glu Pro His Val Phe Asn Gly
                    85                  90                  95
Met Val Gly Asp Lys Gly Leu Val Val Lys Asn Pro Ala Ala His His
                100                 105                 110
Ala Ile Ser Ala Lys Phe Pro Lys Lys Ile Asp Asn Lys Gly Lys Thr
                115                 120                 125
Leu Val Val Gln Tyr Glu Val Lys Leu Gln Asn Ser Leu Asn Cys Gly
                130                 135                 140
Gly Ala Tyr Met Lys Leu Leu Gln Asp Asn Lys Lys Leu His Ala Glu
145                 150                 155                 160
Glu Phe Ser Asn Thr Ser Pro Tyr Val Ile Met Phe Gly Pro Asp Lys
                165                 170                 175
Cys Gly Val Thr Asn Lys Val His Phe Ile Phe Lys His Lys Asn Pro
                180                 185                 190
Lys Thr Gly Glu Tyr Glu Lys His Met Lys Leu Pro Pro Ala Val
                195                 200                 205
Arg Val Ser Lys Leu Ser Thr Leu Tyr Thr Leu Ile Val Asn Pro Asp
210                 215                 220
Gln Ser Phe Gln Ile Arg Ile Asp Gly Ala Val Lys Asn Gly Thr
225                 230                 235                 240
Leu Leu Glu Asp Phe Ser Pro Ala Val Asn Pro Glu Lys Glu Ile Asp
                245                 250                 255
Asp Pro Glu Asp Lys Lys Pro Glu Asp Trp Val Asp Glu Ala His Ile
                260                 265                 270
Pro Asp Pro Glu Ala Thr Lys Pro Glu Asp Trp Asp Glu Asp Ala Pro
                275                 280                 285
Tyr Glu Ile Val Asp Thr Asp Ala Thr Gln Pro Glu Asp Trp Leu Val
290                 295                 300
Asp Glu Pro Thr Ser Ile Pro Asp Pro Glu Ala Gln Lys Pro Glu Asp
305                 310                 315                 320
Trp Asp Asp Glu Glu Asp Gly Asp Trp Ile Pro Pro Thr Ile Pro Asn
                325                 330                 335
Pro Lys Cys Ser Glu Val Ser Gly Cys Gly Met Trp Glu Pro Pro Met
                340                 345                 350
Lys Lys Asn Pro Glu Tyr Lys Gly Lys Trp Thr Ala Pro Met Ile Asp
                355                 360                 365
Asn Pro Ala Tyr Lys Gly Pro Trp Ala Pro Arg Lys Ile Ala Asn Pro
                370                 375                 380
Asn Tyr Phe Glu Asp Lys Thr Pro Ser Asn Phe Glu Pro Met Gly Ala
385                 390                 395                 400
Ile Gly Phe Glu Ile Trp Thr Met Gln Asn Asp Ile Leu Phe Asp Asn
                405                 410                 415
Ile Tyr Ile Gly His Ser Val Glu Asp Ala Glu Lys Leu Lys Ala Glu
                420                 425                 430
Thr Trp Asp Leu Lys His Pro Val Glu Val Ala Glu Glu Ala Ala
                435                 440                 445
Arg Pro Lys Asp Glu Lys Lys Glu Gly Thr Leu Ser Phe Lys Glu
450                 455                 460
Ala Pro Val Lys Tyr Ile Arg Gly Lys Ile Glu Leu Phe Ile Ser Leu
465                 470                 475                 480
```

Ala Leu Glu Asn Pro Val Ala Val Lys Ala Val Pro Glu Val Ala
            485                 490                 495

Gly Gly Leu Gly Ala Leu Leu Val Thr Leu Val Leu Ile Ile Val Gly
        500                 505                 510

Ala Val Gly Leu Gly Ser Pro Ser Pro Ala Pro Ala Ala Lys Lys Gln
        515                 520                 525

Ala Glu Lys Gly Lys Glu Lys Thr Ala Glu Ala Val Ser Thr Ala Ala
        530                 535                 540

Asp Asn Val Lys Gly Glu Ala Lys Lys Arg Ser Gly Lys Ala Gly Glu
545                 550                 555                 560

```
<210> SEQ ID NO 53
<211> LENGTH: 560
<212> TYPE: PRT
<213> ORGANISM: Homo sapiens
<220> FEATURE:
<221> NAME/KEY: BINDING SITE
<222> LOCATION: (1)..(9)
<220> FEATURE:
<221> NAME/KEY: BINDING SITE
<222> LOCATION: (15)..(23)
<220> FEATURE:
<221> NAME/KEY: BINDING SITE
<222> LOCATION: (27)..(35)
<220> FEATURE:
<221> NAME/KEY: BINDING SITE
<222> LOCATION: (130)..(143)
<220> FEATURE:
<221> NAME/KEY: BINDING SITE
<222> LOCATION: (148)..(156)
<220> FEATURE:
<221> NAME/KEY: BINDING SITE
<222> LOCATION: (169)..(177)
<220> FEATURE:
<221> NAME/KEY: BINDING SITE
<222> LOCATION: (210)..(225)
<220> FEATURE:
<221> NAME/KEY: BINDING SITE
<222> LOCATION: (229)..(237)
<220> FEATURE:
<221> NAME/KEY: BINDING SITE
<222> LOCATION: (474)..(482)
<220> FEATURE:
<221> NAME/KEY: BINDING SITE
<222> LOCATION: (499)..(518)
```

<400> SEQUENCE: 53

Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
            20                  25                  30

Ser Thr Ser Ser Val Ile Glu Lys Pro Thr Phe Thr Pro Thr Thr Leu
        35                  40                  45

Lys Ala Pro Phe Leu Glu Gln Phe Thr Asp Gly Trp Glu Thr Arg Trp
    50                  55                  60

Thr Pro Ser His Ala Lys Lys Glu Asp Ser Lys Ser Glu Glu Asp Trp
65                  70                  75                  80

Ala Tyr Val Gly Thr Trp Ala Val Glu Glu Pro His Val Phe Asn Gly
                85                  90                  95

Met Val Gly Asp Lys Gly Leu Val Val Lys Asn Pro Ala Ala His His
            100                 105                 110

Ala Ile Ser Ala Lys Phe Pro Lys Lys Ile Asp Asn Lys Gly Lys Thr
        115                 120                 125

Leu Val Val Gln Tyr Glu Val Lys Leu Gln Asn Ser Leu Asn Cys Gly

-continued

```
                130                 135                 140
Gly Ala Tyr Met Lys Leu Leu Gln Asp Asn Lys Lys Leu His Ala Glu
145                 150                 155                 160

Glu Phe Ser Asn Thr Ser Pro Tyr Val Ile Met Phe Gly Pro Asp Lys
                165                 170                 175

Cys Gly Val Thr Asn Lys Val His Phe Ile Phe Lys His Lys Asn Pro
                180                 185                 190

Lys Thr Gly Glu Tyr Glu Glu Lys His Met Lys Leu Pro Pro Ala Val
                195                 200                 205

Arg Val Ser Lys Leu Ser Thr Leu Tyr Thr Leu Ile Val Asn Pro Asp
210                 215                 220

Gln Ser Phe Gln Ile Arg Ile Asp Gly Ala Ala Val Lys Asn Gly Thr
225                 230                 235                 240

Leu Leu Glu Asp Phe Ser Pro Ala Val Asn Pro Glu Lys Glu Ile Asp
                245                 250                 255

Asp Pro Glu Asp Lys Lys Pro Glu Asp Trp Val Asp Glu Ala His Ile
                260                 265                 270

Pro Asp Pro Glu Ala Thr Lys Pro Glu Asp Trp Asp Glu Asp Ala Pro
                275                 280                 285

Tyr Glu Ile Val Asp Thr Asp Ala Thr Gln Pro Glu Asp Trp Leu Val
                290                 295                 300

Asp Glu Pro Thr Ser Ile Pro Asp Pro Glu Ala Gln Lys Pro Glu Asp
305                 310                 315                 320

Trp Asp Asp Glu Glu Asp Gly Asp Trp Ile Pro Pro Thr Ile Pro Asn
                325                 330                 335

Pro Lys Cys Ser Glu Val Ser Gly Cys Gly Met Trp Glu Pro Pro Met
                340                 345                 350

Lys Lys Asn Pro Glu Tyr Lys Gly Lys Trp Thr Ala Pro Met Ile Asp
                355                 360                 365

Asn Pro Ala Tyr Lys Gly Pro Trp Ala Pro Arg Lys Ile Ala Asn Pro
                370                 375                 380

Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
                405                 410                 415

Ile Tyr Ile Gly His Ser Val Glu Asp Ala Glu Lys Leu Lys Ala Glu
                420                 425                 430

Thr Trp Asp Leu Lys His Pro Val Glu Val Ala Glu Glu Ala Ala
                435                 440                 445

Arg Pro Lys Asp Glu Lys Lys Glu Gly Thr Leu Ser Phe Lys Glu
450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Glu Val Ala
                485                 490                 495

Gly Gly Leu Gly Ala Leu Leu Val Thr Leu Val Leu Ile Ile Val Gly
                500                 505                 510

Ala Val Gly Leu Gly Ser Pro Ser Pro Ala Pro Ala Ala Lys Lys Gln
                515                 520                 525

Ala Glu Lys Gly Lys Glu Lys Thr Ala Glu Ala Val Ser Thr Ala Ala
                530                 535                 540

Asp Asn Val Lys Gly Glu Ala Lys Lys Arg Ser Gly Lys Ala Gly Glu
545                 550                 555                 560
```

<210> SEQ ID NO 54
<211> LENGTH: 560
<212> TYPE: PRT
<213> ORGANISM: Homo sapiens
<220> FEATURE:
<221> NAME/KEY: BINDING SITE
<222> LOCATION: (1)..(9)
<220> FEATURE:
<221> NAME/KEY: BINDING SITE
<222> LOCATION: (15)..(23)
<220> FEATURE:
<221> NAME/KEY: BINDING SITE
<222> LOCATION: (27)..(35)
<220> FEATURE:
<221> NAME/KEY: BINDING SITE
<222> LOCATION: (104)..(112)
<220> FEATURE:
<221> NAME/KEY: BINDING SITE
<222> LOCATION: (135)..(145)
<220> FEATURE:
<221> NAME/KEY: BINDING SITE
<222> LOCATION: (168)..(176)
<220> FEATURE:
<221> NAME/KEY: BINDING SITE
<222> LOCATION: (217)..(225)
<220> FEATURE:
<221> NAME/KEY: BINDING SITE
<222> LOCATION: (229)..(237)
<220> FEATURE:
<221> NAME/KEY: BINDING SITE
<222> LOCATION: (302)..(311)
<220> FEATURE:
<221> NAME/KEY: BINDING SITE
<222> LOCATION: (418)..(426)
<220> FEATURE:
<221> NAME/KEY: BINDING SITE
<222> LOCATION: (502)..(514)

<400> SEQUENCE: 54

Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
            20                  25                  30

Ser Thr Ser Ser Val Ile Glu Lys Pro Thr Phe Thr Pro Thr Thr Leu
        35                  40                  45

Lys Ala Pro Phe Leu Glu Gln Phe Thr Asp Gly Trp Glu Thr Arg Trp
    50                  55                  60

Thr Pro Ser His Ala Lys Lys Glu Asp Ser Lys Ser Glu Glu Asp Trp
65                  70                  75                  80

Ala Tyr Val Gly Thr Trp Ala Val Glu Glu Pro His Val Phe Asn Gly
                85                  90                  95

Met Val Gly Asp Lys Gly Leu Val Val Lys Asn Pro Ala Ala His His
            100                 105                 110

Ala Ile Ser Ala Lys Phe Pro Lys Lys Ile Asp Asn Lys Gly Lys Thr
        115                 120                 125

Leu Val Val Gln Tyr Glu Val Lys Leu Gln Asn Ser Leu Asn Cys Gly
    130                 135                 140

Gly Ala Tyr Met Lys Leu Leu Gln Asp Asn Lys Lys Leu His Ala Glu
145                 150                 155                 160

Glu Phe Ser Asn Thr Ser Pro Tyr Val Ile Met Phe Gly Pro Asp Lys
                165                 170                 175

Cys Gly Val Thr Asn Lys Val His Phe Ile Phe Lys His Lys Asn Pro
            180                 185                 190

Lys Thr Gly Glu Tyr Glu Glu Lys His Met Lys Leu Pro Pro Ala Val

```
            195                 200                 205
Arg Val Ser Lys Leu Ser Thr Leu Tyr Thr Leu Ile Val Asn Pro Asp
210                 215                 220

Gln Ser Phe Gln Ile Arg Ile Asp Gly Ala Ala Val Lys Asn Gly Thr
225                 230                 235                 240

Leu Leu Glu Asp Phe Ser Pro Ala Val Asn Pro Glu Lys Glu Ile Asp
                245                 250                 255

Asp Pro Glu Asp Lys Lys Pro Glu Asp Trp Val Asp Glu Ala His Ile
            260                 265                 270

Pro Asp Pro Glu Ala Thr Lys Pro Glu Asp Trp Asp Glu Asp Ala Pro
        275                 280                 285

Tyr Glu Ile Val Asp Thr Asp Ala Thr Gln Pro Glu Asp Trp Leu Val
290                 295                 300

Asp Glu Pro Thr Ser Ile Pro Asp Pro Glu Ala Gln Lys Pro Glu Asp
305                 310                 315                 320

Trp Asp Asp Glu Glu Asp Gly Asp Trp Ile Pro Pro Thr Ile Pro Asn
                325                 330                 335

Pro Lys Cys Ser Glu Val Ser Gly Cys Gly Met Trp Glu Pro Pro Met
            340                 345                 350

Lys Lys Asn Pro Glu Tyr Lys Gly Lys Trp Thr Ala Pro Met Ile Asp
        355                 360                 365

Asn Pro Ala Tyr Lys Gly Pro Trp Ala Pro Arg Lys Ile Ala Asn Pro
370                 375                 380

Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
                405                 410                 415

Ile Tyr Ile Gly His Ser Val Glu Asp Ala Glu Lys Leu Lys Ala Glu
            420                 425                 430

Thr Trp Asp Leu Lys His Pro Val Glu Val Ala Glu Glu Ala Ala
        435                 440                 445

Arg Pro Lys Asp Glu Glu Lys Lys Glu Gly Thr Leu Ser Phe Lys Glu
450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Glu Val Ala
                485                 490                 495

Gly Gly Leu Gly Ala Leu Leu Val Thr Leu Val Leu Ile Ile Val Gly
            500                 505                 510

Ala Val Gly Leu Gly Ser Pro Ser Pro Ala Pro Ala Ala Lys Lys Gln
        515                 520                 525

Ala Glu Lys Gly Lys Glu Lys Thr Ala Glu Ala Val Ser Thr Ala Ala
530                 535                 540

Asp Asn Val Lys Gly Glu Ala Lys Lys Arg Ser Gly Lys Ala Gly Glu
545                 550                 555                 560

<210> SEQ ID NO 55
<211> LENGTH: 560
<212> TYPE: PRT
<213> ORGANISM: Homo sapiens
<220> FEATURE:
<221> NAME/KEY: BINDING SITE
<222> LOCATION: (3)..(18)
<220> FEATURE:
<221> NAME/KEY: BINDING SITE
<222> LOCATION: (80)..(90)
```

```
<220> FEATURE:
<221> NAME/KEY: BINDING SITE
<222> LOCATION: (162)..(170)
<220> FEATURE:
<221> NAME/KEY: BINDING SITE
<222> LOCATION: (208)..(216)
<220> FEATURE:
<221> NAME/KEY: BINDING SITE
<222> LOCATION: (221)..(229)
<220> FEATURE:
<221> NAME/KEY: BINDING SITE
<222> LOCATION: (395)..(403)
<220> FEATURE:
<221> NAME/KEY: BINDING SITE
<222> LOCATION: (474)..(484)
<220> FEATURE:
<221> NAME/KEY: BINDING SITE
<222> LOCATION: (502)..(516)

<400> SEQUENCE: 55
```

Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
            20                  25                  30

Ser Thr Ser Ser Val Ile Glu Lys Pro Thr Phe Thr Pro Thr Thr Leu
        35                  40                  45

Lys Ala Pro Phe Leu Glu Gln Phe Thr Asp Gly Trp Glu Thr Arg Trp
50                  55                  60

Thr Pro Ser His Ala Lys Lys Glu Asp Ser Lys Ser Glu Glu Asp Trp
65                  70                  75                  80

Ala Tyr Val Gly Thr Trp Ala Val Glu Glu Pro His Val Phe Asn Gly
                85                  90                  95

Met Val Gly Asp Lys Gly Leu Val Val Lys Asn Pro Ala Ala His His
            100                 105                 110

Ala Ile Ser Ala Lys Phe Pro Lys Lys Ile Asp Asn Lys Gly Lys Thr
        115                 120                 125

Leu Val Val Gln Tyr Glu Val Lys Leu Gln Asn Ser Leu Asn Cys Gly
    130                 135                 140

Gly Ala Tyr Met Lys Leu Leu Gln Asp Asn Lys Lys Leu His Ala Glu
145                 150                 155                 160

Glu Phe Ser Asn Thr Ser Pro Tyr Val Ile Met Phe Gly Pro Asp Lys
                165                 170                 175

Cys Gly Val Thr Asn Lys Val His Phe Ile Phe Lys His Lys Asn Pro
            180                 185                 190

Lys Thr Gly Glu Tyr Glu Glu Lys His Met Lys Leu Pro Pro Ala Val
        195                 200                 205

Arg Val Ser Lys Leu Ser Thr Leu Tyr Thr Leu Ile Val Asn Pro Asp
    210                 215                 220

Gln Ser Phe Gln Ile Arg Ile Asp Gly Ala Ala Val Lys Asn Gly Thr
225                 230                 235                 240

Leu Leu Glu Asp Phe Ser Pro Ala Val Asn Pro Glu Lys Glu Ile Asp
                245                 250                 255

Asp Pro Glu Asp Lys Lys Pro Glu Asp Trp Val Asp Glu Ala His Ile
            260                 265                 270

Pro Asp Pro Glu Ala Thr Lys Pro Glu Asp Trp Asp Glu Asp Ala Pro
        275                 280                 285

Tyr Glu Ile Val Asp Thr Asp Ala Thr Gln Pro Glu Asp Trp Leu Val
    290                 295                 300

Asp Glu Pro Thr Ser Ile Pro Asp Pro Glu Ala Gln Lys Pro Glu Asp

-continued

```
            305                 310                 315                 320
        Trp Asp Asp Glu Glu Asp Gly Asp Trp Ile Pro Pro Thr Ile Pro Asn
                        325                 330                 335
        Pro Lys Cys Ser Glu Val Ser Gly Cys Gly Met Trp Glu Pro Pro Met
                        340                 345                 350
        Lys Lys Asn Pro Glu Tyr Lys Gly Lys Trp Thr Ala Pro Met Ile Asp
                        355                 360                 365
        Asn Pro Ala Tyr Lys Gly Pro Trp Ala Pro Arg Lys Ile Ala Asn Pro
        370                 375                 380
        Asn Tyr Phe Glu Asp Lys Thr Pro Ser Asn Phe Glu Pro Met Gly Ala
        385                 390                 395                 400
        Ile Gly Phe Glu Ile Trp Thr Met Gln Asn Asp Ile Leu Phe Asp Asn
                        405                 410                 415
        Ile Tyr Ile Gly His Ser Val Glu Asp Ala Glu Lys Leu Lys Ala Glu
                        420                 425                 430
        Thr Trp Asp Leu Lys His Pro Val Glu Val Ala Glu Glu Ala Ala
                        435                 440                 445
        Arg Pro Lys Asp Glu Lys Lys Glu Gly Thr Leu Ser Phe Lys Glu
        450                 455                 460
        Ala Pro Val Lys Tyr Ile Arg Gly Lys Ile Glu Leu Phe Ile Ser Leu
        465                 470                 475                 480
        Ala Leu Glu Asn Pro Val Glu Ala Val Lys Ala Val Pro Glu Val Ala
                        485                 490                 495
        Gly Gly Leu Gly Ala Leu Leu Val Thr Leu Val Leu Ile Ile Val Gly
                        500                 505                 510
        Ala Val Gly Leu Gly Ser Pro Ser Pro Ala Pro Ala Ala Lys Lys Gln
                        515                 520                 525
        Ala Glu Lys Gly Lys Glu Lys Thr Ala Glu Ala Val Ser Thr Ala Ala
                        530                 535                 540
        Asp Asn Val Lys Gly Glu Ala Lys Lys Arg Ser Gly Lys Ala Gly Glu
        545                 550                 555                 560

<210> SEQ ID NO 56
<211> LENGTH: 560
<212> TYPE: PRT
<213> ORGANISM: Homo sapiens
<220> FEATURE:
<221> NAME/KEY: BINDING SITE
<222> LOCATION: (3)..(18)
<220> FEATURE:
<221> NAME/KEY: BINDING SITE
<222> LOCATION: (80)..(90)
<220> FEATURE:
<221> NAME/KEY: BINDING SITE
<222> LOCATION: (162)..(170)
<220> FEATURE:
<221> NAME/KEY: BINDING SITE
<222> LOCATION: (208)..(216)
<220> FEATURE:
<221> NAME/KEY: BINDING SITE
<222> LOCATION: (221)..(229)
<220> FEATURE:
<221> NAME/KEY: BINDING SITE
<222> LOCATION: (395)..(403)
<220> FEATURE:
<221> NAME/KEY: BINDING SITE
<222> LOCATION: (474)..(484)
<220> FEATURE:
<221> NAME/KEY: BINDING SITE
<222> LOCATION: (502)..(516)

<400> SEQUENCE: 56
```

-continued

```
Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
            20                  25                  30

Ser Thr Ser Ser Val Ile Glu Lys Pro Thr Phe Thr Pro Thr Thr Leu
        35                  40                  45

Lys Ala Pro Phe Leu Glu Gln Phe Thr Asp Gly Trp Glu Thr Arg Trp
50                  55                  60

Thr Pro Ser His Ala Lys Lys Glu Asp Ser Ser Glu Glu Asp Trp
65                  70                  75                  80

Ala Tyr Val Gly Thr Trp Ala Val Glu Glu Pro His Val Phe Asn Gly
                85                  90                  95

Met Val Gly Asp Lys Gly Leu Val Val Lys Asn Pro Ala Ala His His
            100                 105                 110

Ala Ile Ser Ala Lys Phe Pro Lys Lys Ile Asp Asn Lys Gly Lys Thr
            115                 120                 125

Leu Val Val Gln Tyr Glu Val Lys Leu Gln Asn Ser Leu Asn Cys Gly
            130                 135                 140

Gly Ala Tyr Met Lys Leu Leu Gln Asp Asn Lys Lys Leu His Ala Glu
145                 150                 155                 160

Glu Phe Ser Asn Thr Ser Pro Tyr Val Ile Met Phe Gly Pro Asp Lys
                165                 170                 175

Cys Gly Val Thr Asn Lys Val His Phe Ile Phe Lys His Lys Asn Pro
            180                 185                 190

Lys Thr Gly Glu Tyr Glu Glu Lys His Met Lys Leu Pro Pro Ala Val
            195                 200                 205

Arg Val Ser Lys Leu Ser Thr Leu Tyr Thr Leu Ile Val Asn Pro Asp
210                 215                 220

Gln Ser Phe Gln Ile Arg Ile Asp Gly Ala Ala Val Lys Asn Gly Thr
225                 230                 235                 240

Leu Leu Glu Asp Phe Ser Pro Ala Val Asn Pro Glu Lys Glu Ile Asp
                245                 250                 255

Asp Pro Glu Asp Lys Lys Pro Glu Asp Trp Val Asp Glu Ala His Ile
            260                 265                 270

Pro Asp Pro Glu Ala Thr Lys Pro Glu Asp Trp Asp Glu Asp Ala Pro
            275                 280                 285

Tyr Glu Ile Val Asp Thr Asp Ala Thr Gln Pro Glu Asp Trp Leu Val
            290                 295                 300

Asp Glu Pro Thr Ser Ile Pro Asp Pro Glu Ala Gln Lys Pro Glu Asp
305                 310                 315                 320

Trp Asp Asp Glu Glu Asp Gly Asp Trp Ile Pro Pro Thr Ile Pro Asn
                325                 330                 335

Pro Lys Cys Ser Glu Val Ser Gly Cys Gly Met Trp Glu Pro Pro Met
            340                 345                 350

Lys Lys Asn Pro Glu Tyr Lys Gly Lys Trp Thr Ala Pro Met Ile Asp
            355                 360                 365

Asn Pro Ala Tyr Lys Gly Pro Trp Ala Pro Arg Lys Ile Ala Asn Pro
            370                 375                 380

Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
                405                 410                 415

Ile Tyr Ile Gly His Ser Val Glu Asp Ala Glu Lys Leu Lys Ala Glu
```

```
            420                 425                 430
Thr Trp Asp Leu Lys His Pro Val Glu Val Ala Glu Glu Ala Ala
        435                 440                 445
Arg Pro Lys Asp Glu Lys Lys Glu Gly Thr Leu Ser Phe Lys Glu
        450                 455                 460
Ala Pro Val Lys Tyr Ile Arg Gly Lys Ile Glu Leu Phe Ile Ser Leu
465                 470                 475                 480
Ala Leu Glu Asn Pro Val Glu Ala Val Lys Ala Val Pro Glu Val Ala
                485                 490                 495
Gly Gly Leu Gly Ala Leu Leu Val Thr Leu Val Leu Ile Ile Val Gly
                500                 505                 510
Ala Val Gly Leu Gly Ser Pro Ser Pro Ala Pro Ala Ala Lys Lys Gln
        515                 520                 525
Ala Glu Lys Gly Lys Glu Lys Thr Ala Glu Ala Val Ser Thr Ala Ala
        530                 535                 540
Asp Asn Val Lys Gly Glu Ala Lys Lys Arg Ser Gly Lys Ala Gly Glu
545                 550                 555                 560
```

<210> SEQ ID NO 57
<211> LENGTH: 560
<212> TYPE: PRT
<213> ORGANISM: Homo sapiens
<220> FEATURE:
<221> NAME/KEY: BINDING SITE
<222> LOCATION: (1)..(9)
<220> FEATURE:
<221> NAME/KEY: BINDING SITE
<222> LOCATION: (60)..(68)
<220> FEATURE:
<221> NAME/KEY: BINDING SITE
<222> LOCATION: (103)..(112)
<220> FEATURE:
<221> NAME/KEY: BINDING SITE
<222> LOCATION: (130)..(138)
<220> FEATURE:
<221> NAME/KEY: BINDING SITE
<222> LOCATION: (168)..(176)
<220> FEATURE:
<221> NAME/KEY: BINDING SITE
<222> LOCATION: (183)..(195)
<220> FEATURE:
<221> NAME/KEY: BINDING SITE
<222> LOCATION: (227)..(235)
<220> FEATURE:
<221> NAME/KEY: BINDING SITE
<222> LOCATION: (358)..(366)
<220> FEATURE:
<221> NAME/KEY: BINDING SITE
<222> LOCATION: (376)..(384)
<220> FEATURE:
<221> NAME/KEY: BINDING SITE
<222> LOCATION: (470)..(478)
<220> FEATURE:
<221> NAME/KEY: BINDING SITE
<222> LOCATION: (506)..(514)

<400> SEQUENCE: 57

```
Met Arg Leu Asn Ala Ser Leu Ala Ser Leu Ile Leu Ser Ser Ile Ala
1               5                   10                  15
Leu Ile Gly Asn Val His Ala Glu Asp Glu Val Lys Glu Asp Ala Thr
                20                  25                  30
Ser Thr Ser Ser Val Ile Glu Lys Pro Thr Phe Thr Pro Thr Thr Leu
        35                  40                  45
Lys Ala Pro Phe Leu Glu Gln Phe Thr Asp Gly Trp Glu Thr Arg Trp
        50                  55                  60
```

```
Thr Pro Ser His Ala Lys Lys Glu Asp Ser Lys Ser Glu Glu Asp Trp
 65                  70                  75                  80

Ala Tyr Val Gly Thr Trp Ala Val Glu Glu Pro His Val Phe Asn Gly
                 85                  90                  95

Met Val Gly Asp Lys Gly Leu Val Val Lys Asn Pro Ala Ala His His
            100                 105                 110

Ala Ile Ser Ala Lys Phe Pro Lys Lys Ile Asp Asn Lys Gly Lys Thr
        115                 120                 125

Leu Val Val Gln Tyr Glu Val Lys Leu Gln Asn Ser Leu Asn Cys Gly
    130                 135                 140

Gly Ala Tyr Met Lys Leu Leu Gln Asp Asn Lys Lys Leu His Ala Glu
145                 150                 155                 160

Glu Phe Ser Asn Thr Ser Pro Tyr Val Ile Met Phe Gly Pro Asp Lys
                165                 170                 175

Cys Gly Val Thr Asn Lys Val His Phe Ile Phe Lys His Lys Asn Pro
            180                 185                 190

Lys Thr Gly Glu Tyr Glu Glu Lys His Met Lys Leu Pro Pro Ala Val
        195                 200                 205

Arg Val Ser Lys Leu Ser Thr Leu Tyr Thr Leu Ile Val Asn Pro Asp
    210                 215                 220

Gln Ser Phe Gln Ile Arg Ile Asp Gly Ala Ala Val Lys Asn Gly Thr
225                 230                 235                 240

Leu Leu Glu Asp Phe Ser Pro Ala Val Asn Pro Glu Lys Glu Ile Asp
                245                 250                 255

Asp Pro Glu Asp Lys Lys Pro Glu Asp Trp Val Asp Glu Ala His Ile
            260                 265                 270

Pro Asp Pro Glu Ala Thr Lys Pro Glu Asp Trp Asp Glu Asp Ala Pro
        275                 280                 285

Tyr Glu Ile Val Asp Thr Asp Ala Thr Gln Pro Glu Asp Trp Leu Val
    290                 295                 300

Asp Glu Pro Thr Ser Ile Pro Asp Pro Glu Ala Gln Lys Pro Glu Asp
305                 310                 315                 320

Trp Asp Asp Glu Glu Asp Gly Asp Trp Ile Pro Pro Thr Ile Pro Asn
                325                 330                 335

Pro Lys Cys Ser Glu Val Ser Gly Cys Gly Met Trp Glu Pro Pro Met
            340                 345                 350

Lys Lys Asn Pro Glu Tyr Lys Gly Lys Trp Thr Ala Pro Met Ile Asp
        355                 360                 365

Asn Pro Ala Tyr Lys Gly Pro Trp Ala Pro Arg Lys Ile Ala Asn Pro
    370                 375                 380

Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
                405                 410                 415

Ile Tyr Ile Gly His Ser Val Glu Asp Ala Glu Lys Leu Lys Ala Glu
            420                 425                 430

Thr Trp Asp Leu Lys His Pro Val Glu Val Ala Glu Glu Ala Ala
        435                 440                 445

Arg Pro Lys Asp Glu Glu Lys Lys Glu Gly Thr Leu Ser Phe Lys Glu
    450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Glu Val Ala
```

```
                         485                 490                 495
Gly Gly Leu Gly Ala Leu Leu Val Thr Leu Val Leu Ile Ile Val Gly
                500                 505                 510

Ala Val Gly Leu Gly Ser Pro Ser Pro Ala Pro Ala Ala Lys Lys Gln
            515                 520                 525

Ala Glu Lys Gly Lys Glu Lys Thr Ala Glu Ala Val Ser Thr Ala Ala
        530                 535                 540

Asp Asn Val Lys Gly Glu Ala Lys Lys Arg Ser Gly Lys Ala Gly Glu
545                 550                 555                 560

<210> SEQ ID NO 58
<211> LENGTH: 560
<212> TYPE: PRT
<213> ORGANISM: Homo sapiens
<220> FEATURE:
<221> NAME/KEY: BINDING SITE
<222> LOCATION: (1)..(9)
<220> FEATURE:
<221> NAME/KEY: BINDING SITE
<222> LOCATION: (60)..(68)
<220> FEATURE:
<221> NAME/KEY: BINDING SITE
<222> LOCATION: (103)..(112)
<220> FEATURE:
<221> NAME/KEY: BINDING SITE
<222> LOCATION: (130)..(138)
<220> FEATURE:
<221> NAME/KEY: BINDING SITE
<222> LOCATION: (168)..(176)
<220> FEATURE:
<221> NAME/KEY: BINDING SITE
<222> LOCATION: (185)..(195)
<220> FEATURE:
<221> NAME/KEY: BINDING SITE
<222> LOCATION: (227)..(237)
<220> FEATURE:
<221> NAME/KEY: BINDING SITE
<222> LOCATION: (358)..(366)
<220> FEATURE:
<221> NAME/KEY: BINDING SITE
<222> LOCATION: (376)..(384)
<220> FEATURE:
<221> NAME/KEY: BINDING SITE
<222> LOCATION: (470)..(478)
<220> FEATURE:
<221> NAME/KEY: BINDING SITE
<222> LOCATION: (506)..(518)

<400> SEQUENCE: 58

Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
            20                  25                  30

Ser Thr Ser Ser Val Ile Glu Lys Pro Thr Phe Thr Pro Thr Thr Leu
        35                  40                  45

Lys Ala Pro Phe Leu Glu Gln Phe Thr Asp Gly Trp Glu Thr Arg Trp
    50                  55                  60

Thr Pro Ser His Ala Lys Lys Glu Asp Ser Lys Ser Glu Glu Asp Trp
65                  70                  75                  80

Ala Tyr Val Gly Thr Trp Ala Val Glu Glu Pro His Val Phe Asn Gly
                85                  90                  95

Met Val Gly Asp Lys Gly Leu Val Val Lys Asn Pro Ala Ala His His
            100                 105                 110

Ala Ile Ser Ala Lys Phe Pro Lys Lys Ile Asp Asn Lys Gly Lys Thr
        115                 120                 125
```

Leu Val Val Gln Tyr Glu Val Lys Leu Gln Asn Ser Leu Asn Cys Gly
    130                 135                 140

Gly Ala Tyr Met Lys Leu Leu Gln Asp Asn Lys Lys Leu His Ala Glu
145                 150                 155                 160

Glu Phe Ser Asn Thr Ser Pro Tyr Val Ile Met Phe Gly Pro Asp Lys
                165                 170                 175

Cys Gly Val Thr Asn Lys Val His Phe Ile Phe Lys His Lys Asn Pro
            180                 185                 190

Lys Thr Gly Glu Tyr Glu Lys His Met Lys Leu Pro Pro Ala Val
        195                 200                 205

Arg Val Ser Lys Leu Ser Thr Leu Tyr Thr Leu Ile Val Asn Pro Asp
210                 215                 220

Gln Ser Phe Gln Ile Arg Ile Asp Gly Ala Ala Val Lys Asn Gly Thr
225                 230                 235                 240

Leu Leu Glu Asp Phe Ser Pro Ala Val Asn Pro Glu Lys Glu Ile Asp
                245                 250                 255

Asp Pro Glu Asp Lys Lys Pro Glu Asp Trp Val Asp Glu Ala His Ile
            260                 265                 270

Pro Asp Pro Glu Ala Thr Lys Pro Glu Asp Trp Asp Glu Asp Ala Pro
        275                 280                 285

Tyr Glu Ile Val Asp Thr Asp Ala Thr Gln Pro Glu Asp Trp Leu Val
    290                 295                 300

Asp Glu Pro Thr Ser Ile Pro Asp Pro Glu Ala Gln Lys Pro Glu Asp
305                 310                 315                 320

Trp Asp Asp Glu Glu Asp Gly Asp Trp Ile Pro Pro Thr Ile Pro Asn
                325                 330                 335

Pro Lys Cys Ser Glu Val Ser Gly Cys Gly Met Trp Glu Pro Pro Met
            340                 345                 350

Lys Lys Asn Pro Glu Tyr Lys Gly Lys Trp Thr Ala Pro Met Ile Asp
        355                 360                 365

Asn Pro Ala Tyr Lys Gly Pro Trp Ala Pro Arg Lys Ile Ala Asn Pro
    370                 375                 380

Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
                405                 410                 415

Ile Tyr Ile Gly His Ser Val Glu Asp Ala Glu Lys Leu Lys Ala Glu
            420                 425                 430

Thr Trp Asp Leu Lys His Pro Val Glu Val Ala Glu Glu Ala Ala
        435                 440                 445

Arg Pro Lys Asp Glu Lys Lys Glu Gly Thr Leu Ser Phe Lys Glu
    450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Glu Val Ala
                485                 490                 495

Gly Gly Leu Gly Ala Leu Leu Val Thr Leu Val Leu Ile Ile Val Gly
            500                 505                 510

Ala Val Gly Leu Gly Ser Pro Ala Pro Ala Lys Lys Gln
        515                 520                 525

Ala Glu Lys Gly Lys Glu Lys Thr Ala Glu Ala Val Ser Thr Ala Ala
530                 535                 540

Asp Asn Val Lys Gly Glu Ala Lys Lys Arg Ser Gly Lys Ala Gly Glu

<210> SEQ ID NO 59
<211> LENGTH: 560
<212> TYPE: PRT
<213> ORGANISM: Homo sapiens
<220> FEATURE:
<221> NAME/KEY: BINDING SITE
<222> LOCATION: (1)..(9)
<220> FEATURE:
<221> NAME/KEY: BINDING SITE
<222> LOCATION: (103)..(112)
<220> FEATURE:
<221> NAME/KEY: BINDING SITE
<222> LOCATION: (130)..(138)
<220> FEATURE:
<221> NAME/KEY: BINDING SITE
<222> LOCATION: (168)..(176)
<220> FEATURE:
<221> NAME/KEY: BINDING SITE
<222> LOCATION: (185)..(193)
<220> FEATURE:
<221> NAME/KEY: BINDING SITE
<222> LOCATION: (229)..(237)
<220> FEATURE:
<221> NAME/KEY: BINDING SITE
<222> LOCATION: (358)..(366)
<220> FEATURE:
<221> NAME/KEY: BINDING SITE
<222> LOCATION: (470)..(478)
<220> FEATURE:
<221> NAME/KEY: BINDING SITE
<222> LOCATION: (506)..(518)

<400> SEQUENCE: 59

```
Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
            20                  25                  30

Ser Thr Ser Ser Val Ile Glu Lys Pro Thr Phe Thr Pro Thr Thr Leu
        35                  40                  45

Lys Ala Pro Phe Leu Glu Gln Phe Thr Asp Gly Trp Glu Thr Arg Trp
    50                  55                  60

Thr Pro Ser His Ala Lys Lys Glu Asp Ser Lys Ser Glu Glu Asp Trp
65                  70                  75                  80

Ala Tyr Val Gly Thr Trp Ala Val Glu Glu Pro His Val Phe Asn Gly
                85                  90                  95

Met Val Gly Asp Lys Gly Leu Val Val Lys Asn Pro Ala Ala His His
            100                 105                 110

Ala Ile Ser Ala Lys Phe Pro Lys Ile Asp Asn Lys Gly Lys Thr
        115                 120                 125

Leu Val Val Gln Tyr Glu Val Lys Leu Gln Asn Ser Leu Asn Cys Gly
    130                 135                 140

Gly Ala Tyr Met Lys Leu Leu Gln Asp Asn Lys Lys Leu His Ala Glu
145                 150                 155                 160

Glu Phe Ser Asn Thr Ser Pro Tyr Val Ile Met Phe Gly Pro Asp Lys
                165                 170                 175

Cys Gly Val Thr Asn Lys Val His Phe Ile Phe Lys His Lys Asn Pro
            180                 185                 190

Lys Thr Gly Glu Tyr Glu Glu Lys His Met Lys Leu Pro Pro Ala Val
        195                 200                 205

Arg Val Ser Lys Leu Ser Thr Leu Tyr Thr Leu Ile Val Asn Pro Asp
    210                 215                 220
```

```
Gln Ser Phe Gln Ile Arg Ile Asp Gly Ala Ala Val Lys Asn Gly Thr
225                 230                 235                 240

Leu Leu Glu Asp Phe Ser Pro Ala Val Asn Pro Glu Lys Glu Ile Asp
            245                 250                 255

Asp Pro Glu Asp Lys Lys Pro Glu Asp Trp Val Asp Glu Ala His Ile
        260                 265                 270

Pro Asp Pro Glu Ala Thr Lys Pro Glu Asp Trp Asp Glu Asp Ala Pro
    275                 280                 285

Tyr Glu Ile Val Asp Thr Asp Ala Thr Gln Pro Glu Asp Trp Leu Val
290                 295                 300

Asp Glu Pro Thr Ser Ile Pro Asp Pro Glu Ala Gln Lys Pro Glu Asp
305                 310                 315                 320

Trp Asp Asp Glu Glu Asp Gly Asp Trp Ile Pro Pro Thr Ile Pro Asn
                325                 330                 335

Pro Lys Cys Ser Glu Val Ser Gly Cys Gly Met Trp Glu Pro Pro Met
                340                 345                 350

Lys Lys Asn Pro Glu Tyr Lys Gly Lys Trp Thr Ala Pro Met Ile Asp
                355                 360                 365

Asn Pro Ala Tyr Lys Gly Pro Trp Ala Pro Arg Lys Ile Ala Asn Pro
370                 375                 380

Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
                405                 410                 415

Ile Tyr Ile Gly His Ser Val Glu Asp Ala Glu Lys Lys Ala Lys Glu
                420                 425                 430

Thr Trp Asp Leu Lys His Pro Val Glu Val Ala Glu Glu Ala Ala
                435                 440                 445

Arg Pro Lys Asp Glu Lys Lys Glu Gly Thr Leu Ser Phe Lys Glu
                450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Glu Val Ala
                485                 490                 495

Gly Gly Leu Gly Ala Leu Leu Val Thr Leu Val Leu Ile Ile Val Gly
            500                 505                 510

Ala Val Gly Leu Gly Ser Pro Ser Pro Ala Pro Ala Ala Lys Lys Gln
                515                 520                 525

Ala Glu Lys Gly Lys Glu Lys Thr Ala Glu Ala Val Ser Thr Ala Ala
                530                 535                 540

Asp Asn Val Lys Gly Glu Ala Lys Lys Arg Ser Gly Lys Ala Gly Glu
545                 550                 555                 560

<210> SEQ ID NO 60
<211> LENGTH: 560
<212> TYPE: PRT
<213> ORGANISM: Homo sapiens
<220> FEATURE:
<221> NAME/KEY: BINDING SITE
<222> LOCATION: (1)..(9)
<220> FEATURE:
<221> NAME/KEY: BINDING SITE
<222> LOCATION: (103)..(112)
<220> FEATURE:
<221> NAME/KEY: BINDING SITE
<222> LOCATION: (130)..(139)
<220> FEATURE:
<221> NAME/KEY: BINDING SITE
```

```
<222> LOCATION: (183)..(195)
<220> FEATURE:
<221> NAME/KEY: BINDING SITE
<222> LOCATION: (216)..(224)
<220> FEATURE:
<221> NAME/KEY: BINDING SITE
<222> LOCATION: (358)..(366)
<220> FEATURE:
<221> NAME/KEY: BINDING SITE
<222> LOCATION: (470)..(478)
<220> FEATURE:
<221> NAME/KEY: BINDING SITE
<222> LOCATION: (506)..(515)

<400> SEQUENCE: 60

Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
            20                  25                  30

Ser Thr Ser Ser Val Ile Glu Lys Pro Thr Phe Thr Pro Thr Thr Leu
        35                  40                  45

Lys Ala Pro Phe Leu Glu Gln Phe Thr Asp Gly Trp Glu Thr Arg Trp
    50                  55                  60

Thr Pro Ser His Ala Lys Lys Glu Asp Ser Lys Ser Glu Glu Asp Trp
65                  70                  75                  80

Ala Tyr Val Gly Thr Trp Ala Val Glu Pro His Val Phe Asn Gly
                85                  90                  95

Met Val Gly Asp Lys Gly Leu Val Val Lys Asn Pro Ala Ala His His
                100                 105                 110

Ala Ile Ser Ala Lys Phe Pro Lys Lys Ile Asp Asn Lys Gly Lys Thr
            115                 120                 125

Leu Val Val Gln Tyr Glu Val Lys Leu Gln Asn Ser Leu Asn Cys Gly
130                 135                 140

Gly Ala Tyr Met Lys Leu Leu Gln Asp Asn Lys Lys Leu His Ala Glu
145                 150                 155                 160

Glu Phe Ser Asn Thr Ser Pro Tyr Val Ile Met Phe Gly Pro Asp Lys
                165                 170                 175

Cys Gly Val Thr Asn Lys Val His Phe Ile Phe Lys His Lys Asn Pro
            180                 185                 190

Lys Thr Gly Glu Tyr Glu Glu Lys His Met Lys Leu Pro Pro Ala Val
        195                 200                 205

Arg Val Ser Lys Leu Ser Thr Leu Tyr Thr Leu Ile Val Asn Pro Asp
    210                 215                 220

Gln Ser Phe Gln Ile Arg Ile Asp Gly Ala Ala Val Lys Asn Gly Thr
225                 230                 235                 240

Leu Leu Glu Asp Phe Ser Pro Ala Val Asn Pro Glu Lys Glu Ile Asp
                245                 250                 255

Asp Pro Glu Asp Lys Lys Pro Glu Asp Trp Val Asp Glu Ala His Ile
            260                 265                 270

Pro Asp Pro Glu Ala Thr Lys Pro Glu Asp Trp Asp Glu Asp Ala Pro
        275                 280                 285

Tyr Glu Ile Val Asp Thr Asp Ala Thr Gln Pro Glu Asp Trp Leu Val
    290                 295                 300

Asp Glu Pro Thr Ser Ile Pro Asp Pro Glu Ala Gln Lys Pro Glu Asp
305                 310                 315                 320

Trp Asp Asp Glu Glu Asp Gly Asp Trp Ile Pro Pro Thr Ile Pro Asn
                325                 330                 335
```

-continued

```
Pro Lys Cys Ser Glu Val Ser Cys Gly Met Trp Glu Pro Pro Met
            340                 345                 350

Lys Lys Asn Pro Glu Tyr Lys Gly Lys Trp Thr Ala Pro Met Ile Asp
        355                 360                 365

Asn Pro Ala Tyr Lys Gly Pro Trp Ala Pro Arg Lys Ile Ala Asn Pro
    370                 375                 380

Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
                405                 410                 415

Ile Tyr Ile Gly His Ser Val Glu Asp Ala Glu Lys Leu Lys Ala Glu
            420                 425                 430

Thr Trp Asp Leu Lys His Pro Val Glu Val Ala Glu Glu Ala Ala
            435                 440                 445

Arg Pro Lys Asp Glu Glu Lys Lys Glu Gly Thr Leu Ser Phe Lys Glu
    450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Glu Val Ala
                485                 490                 495

Gly Gly Leu Gly Ala Leu Leu Val Thr Leu Val Leu Ile Ile Val Gly
            500                 505                 510

Ala Val Gly Leu Gly Ser Pro Ser Pro Ala Pro Ala Ala Lys Lys Gln
            515                 520                 525

Ala Glu Lys Gly Lys Lys Thr Ala Glu Ala Val Ser Thr Ala Ala
    530                 535                 540

Asp Asn Val Lys Gly Glu Ala Lys Lys Arg Ser Gly Lys Ala Gly Glu
545                 550                 555                 560

<210> SEQ ID NO 61
<211> LENGTH: 560
<212> TYPE: PRT
<213> ORGANISM: Homo sapiens
<220> FEATURE:
<221> NAME/KEY: BINDING SITE
<222> LOCATION: (1)..(9)
<220> FEATURE:
<221> NAME/KEY: BINDING SITE
<222> LOCATION: (60)..(68)
<220> FEATURE:
<221> NAME/KEY: BINDING SITE
<222> LOCATION: (103)..(111)
<220> FEATURE:
<221> NAME/KEY: BINDING SITE
<222> LOCATION: (130)..(141)
<220> FEATURE:
<221> NAME/KEY: BINDING SITE
<222> LOCATION: (168)..(176)
<220> FEATURE:
<221> NAME/KEY: BINDING SITE
<222> LOCATION: (185)..(193)
<220> FEATURE:
<221> NAME/KEY: BINDING SITE
<222> LOCATION: (358)..(366)
<220> FEATURE:
<221> NAME/KEY: BINDING SITE
<222> LOCATION: (376)..(384)
<220> FEATURE:
<221> NAME/KEY: BINDING SITE
<222> LOCATION: (470)..(478)

<400> SEQUENCE: 61

Met Arg Leu Asn Ala Ser Leu Ala Ser Leu Ile Leu Ser Ser Ile Ala
1               5                   10                  15
```

Leu Ile Gly Asn Val His Ala Glu Asp Glu Val Lys Glu Asp Ala Thr
                20                  25                  30

Ser Thr Ser Ser Val Ile Glu Lys Pro Thr Phe Thr Pro Thr Thr Leu
            35                  40                  45

Lys Ala Pro Phe Leu Glu Gln Phe Thr Asp Gly Trp Glu Thr Arg Trp
 50                  55                  60

Thr Pro Ser His Ala Lys Lys Glu Asp Ser Lys Ser Glu Glu Asp Trp
 65                  70                  75                  80

Ala Tyr Val Gly Thr Trp Ala Val Glu Glu Pro His Val Phe Asn Gly
                85                  90                  95

Met Val Gly Asp Lys Gly Leu Val Val Lys Asn Pro Ala Ala His His
            100                 105                 110

Ala Ile Ser Ala Lys Phe Pro Lys Lys Ile Asp Asn Lys Gly Lys Thr
            115                 120                 125

Leu Val Val Gln Tyr Glu Val Lys Leu Gln Asn Ser Leu Asn Cys Gly
    130                 135                 140

Gly Ala Tyr Met Lys Leu Leu Gln Asp Asn Lys Lys Leu His Ala Glu
145                 150                 155                 160

Glu Phe Ser Asn Thr Ser Pro Tyr Val Ile Met Phe Gly Pro Asp Lys
                165                 170                 175

Cys Gly Val Thr Asn Lys Val His Phe Ile Phe Lys His Lys Asn Pro
            180                 185                 190

Lys Thr Gly Glu Tyr Glu Glu Lys His Met Lys Leu Pro Pro Ala Val
            195                 200                 205

Arg Val Ser Lys Leu Ser Thr Leu Tyr Thr Leu Ile Val Asn Pro Asp
    210                 215                 220

Gln Ser Phe Gln Ile Arg Ile Asp Gly Ala Ala Val Lys Asn Gly Thr
225                 230                 235                 240

Leu Leu Glu Asp Phe Ser Pro Ala Val Asn Pro Glu Lys Glu Ile Asp
                245                 250                 255

Asp Pro Glu Asp Lys Lys Pro Glu Asp Trp Val Asp Glu Ala His Ile
            260                 265                 270

Pro Asp Pro Glu Ala Thr Lys Pro Glu Asp Trp Asp Glu Asp Ala Pro
            275                 280                 285

Tyr Glu Ile Val Asp Thr Asp Ala Thr Gln Pro Glu Asp Trp Leu Val
    290                 295                 300

Asp Glu Pro Thr Ser Ile Pro Asp Pro Glu Ala Gln Lys Pro Glu Asp
305                 310                 315                 320

Trp Asp Asp Glu Glu Asp Gly Asp Trp Ile Pro Pro Thr Ile Pro Asn
                325                 330                 335

Pro Lys Cys Ser Glu Val Ser Gly Cys Gly Met Trp Glu Pro Pro Met
            340                 345                 350

Lys Lys Asn Pro Glu Tyr Lys Gly Lys Trp Thr Ala Pro Met Ile Asp
            355                 360                 365

Asn Pro Ala Tyr Lys Gly Pro Trp Ala Pro Arg Lys Ile Ala Asn Pro
    370                 375                 380

Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
                405                 410                 415

Ile Tyr Ile Gly His Ser Val Glu Asp Ala Glu Lys Leu Lys Ala Glu
            420                 425                 430

```
Thr Trp Asp Leu Lys His Pro Val Glu Val Ala Glu Glu Ala Ala
            435                 440                 445

Arg Pro Lys Asp Glu Glu Lys Lys Glu Gly Thr Leu Ser Phe Lys Glu
450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Glu Val Ala
            485                 490                 495

Gly Gly Leu Gly Ala Leu Leu Val Thr Leu Val Leu Ile Ile Val Gly
            500                 505                 510

Ala Val Gly Leu Gly Ser Pro Ser Pro Ala Pro Ala Ala Lys Lys Gln
            515                 520                 525

Ala Glu Lys Gly Lys Glu Lys Thr Ala Glu Ala Val Ser Thr Ala Ala
            530                 535                 540

Asp Asn Val Lys Gly Glu Ala Lys Lys Arg Ser Gly Lys Ala Gly Glu
545                 550                 555                 560
```

<210> SEQ ID NO 62
<211> LENGTH: 560
<212> TYPE: PRT
<213> ORGANISM: Homo sapiens
<220> FEATURE:
<221> NAME/KEY: BINDING SITE
<222> LOCATION: (1)..(9)
<220> FEATURE:
<221> NAME/KEY: BINDING SITE
<222> LOCATION: (60)..(68)
<220> FEATURE:
<221> NAME/KEY: BINDING SITE
<222> LOCATION: (102)..(110)
<220> FEATURE:
<221> NAME/KEY: BINDING SITE
<222> LOCATION: (129)..(138)
<220> FEATURE:
<221> NAME/KEY: BINDING SITE
<222> LOCATION: (167)..(175)
<220> FEATURE:
<221> NAME/KEY: BINDING SITE
<222> LOCATION: (184)..(194)
<220> FEATURE:
<221> NAME/KEY: BINDING SITE
<222> LOCATION: (357)..(365)
<220> FEATURE:
<221> NAME/KEY: BINDING SITE
<222> LOCATION: (469)..(477)
<220> FEATURE:
<221> NAME/KEY: BINDING SITE
<222> LOCATION: (505)..(517)

<400> SEQUENCE: 62

```
Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
            20                  25                  30

Ser Thr Ser Ser Val Ile Glu Lys Pro Thr Phe Thr Pro Thr Thr Leu
        35                  40                  45

Lys Ala Pro Phe Leu Glu Gln Phe Thr Asp Gly Trp Glu Thr Arg Trp
50                  55                  60

Thr Pro Ser His Ala Lys Lys Glu Asp Ser Lys Ser Glu Glu Asp Trp
65                  70                  75                  80

Ala Tyr Val Gly Thr Trp Ala Val Glu Glu Pro His Val Phe Asn Gly
            85                  90                  95

Met Val Gly Asp Lys Gly Leu Val Val Lys Asn Pro Ala Ala His His
            100                 105                 110
```

-continued

```
Ala Ile Ser Ala Lys Phe Pro Lys Ile Asp Asn Lys Gly Lys Thr
        115                 120                 125
Leu Val Val Gln Tyr Glu Val Lys Leu Gln Asn Ser Leu Asn Cys Gly
    130                 135                 140
Gly Ala Tyr Met Lys Leu Leu Gln Asp Asn Lys Lys Leu His Ala Glu
145                 150                 155                 160
Glu Phe Ser Asn Thr Ser Pro Tyr Val Ile Met Phe Gly Pro Asp Lys
                165                 170                 175
Cys Gly Val Thr Asn Lys Val His Phe Ile Phe Lys His Lys Asn Pro
            180                 185                 190
Lys Thr Gly Glu Tyr Glu Glu Lys His Met Lys Leu Pro Pro Ala Val
        195                 200                 205
Arg Val Ser Lys Leu Ser Thr Leu Tyr Thr Leu Ile Val Asn Pro Asp
    210                 215                 220
Gln Ser Phe Gln Ile Arg Ile Asp Gly Ala Ala Val Lys Asn Gly Thr
225                 230                 235                 240
Leu Leu Glu Asp Phe Ser Pro Ala Val Asn Pro Glu Lys Glu Ile Asp
                245                 250                 255
Asp Pro Glu Asp Lys Lys Pro Glu Asp Trp Val Asp Glu Ala His Ile
            260                 265                 270
Pro Asp Pro Glu Ala Thr Lys Pro Glu Asp Trp Asp Glu Asp Ala Pro
        275                 280                 285
Tyr Glu Ile Val Asp Thr Asp Ala Thr Gln Pro Glu Asp Trp Leu Val
    290                 295                 300
Asp Glu Pro Thr Ser Ile Pro Asp Pro Glu Ala Gln Lys Pro Glu Asp
305                 310                 315                 320
Trp Asp Asp Glu Glu Asp Gly Asp Trp Ile Pro Pro Thr Ile Pro Asn
                325                 330                 335
Pro Lys Cys Ser Glu Val Ser Gly Cys Gly Met Trp Glu Pro Pro Met
            340                 345                 350
Lys Lys Asn Pro Glu Tyr Lys Gly Lys Trp Thr Ala Pro Met Ile Asp
        355                 360                 365
Asn Pro Ala Tyr Lys Gly Pro Trp Ala Pro Arg Lys Ile Ala Asn Pro
    370                 375                 380
Asn Tyr Phe Glu Asp Lys Thr Pro Ser Asn Phe Glu Pro Met Gly Ala
385                 390                 395                 400
Ile Gly Phe Glu Ile Trp Thr Met Gln Asn Asp Ile Leu Phe Asp Asn
                405                 410                 415
Ile Tyr Ile Gly His Ser Val Glu Asp Ala Glu Lys Leu Lys Ala Glu
            420                 425                 430
Thr Trp Asp Leu Lys His Pro Val Glu Val Ala Glu Glu Ala Ala
        435                 440                 445
Arg Pro Lys Asp Glu Lys Lys Glu Gly Thr Leu Ser Phe Lys Glu
    450                 455                 460
Ala Pro Val Lys Tyr Ile Arg Gly Lys Ile Glu Leu Phe Ile Ser Leu
465                 470                 475                 480
Ala Leu Glu Asn Pro Val Glu Ala Val Lys Ala Val Pro Glu Val Ala
                485                 490                 495
Gly Gly Leu Gly Ala Leu Leu Val Thr Leu Val Leu Ile Ile Val Gly
            500                 505                 510
Ala Val Gly Leu Gly Ser Pro Ser Pro Ala Pro Ala Ala Lys Lys Gln
        515                 520                 525
```

-continued

```
Ala Glu Lys Gly Lys Glu Lys Thr Ala Glu Ala Val Ser Thr Ala Ala
            530                 535                 540

Asp Asn Val Lys Gly Glu Ala Lys Lys Arg Ser Gly Lys Ala Gly Glu
545                 550                 555                 560

<210> SEQ ID NO 63
<211> LENGTH: 560
<212> TYPE: PRT
<213> ORGANISM: Homo sapiens
<220> FEATURE:
<221> NAME/KEY: BINDING SITE
<222> LOCATION: (1)..(9)
<220> FEATURE:
<221> NAME/KEY: BINDING SITE
<222> LOCATION: (103)..(112)
<220> FEATURE:
<221> NAME/KEY: BINDING SITE
<222> LOCATION: (130)..(143)
<220> FEATURE:
<221> NAME/KEY: BINDING SITE
<222> LOCATION: (151)..(159)
<220> FEATURE:
<221> NAME/KEY: BINDING SITE
<222> LOCATION: (168)..(176)
<220> FEATURE:
<221> NAME/KEY: BINDING SITE
<222> LOCATION: (183)..(193)
<220> FEATURE:
<221> NAME/KEY: BINDING SITE
<222> LOCATION: (213)..(225)
<220> FEATURE:
<221> NAME/KEY: BINDING SITE
<222> LOCATION: (358)..(366)
<220> FEATURE:
<221> NAME/KEY: BINDING SITE
<222> LOCATION: (395)..(403)
<220> FEATURE:
<221> NAME/KEY: BINDING SITE
<222> LOCATION: (414)..(422)
<220> FEATURE:
<221> NAME/KEY: BINDING SITE
<222> LOCATION: (502)..(518)

<400> SEQUENCE: 63

Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
                20                  25                  30

Ser Thr Ser Ser Val Ile Glu Lys Pro Thr Phe Thr Pro Thr Thr Leu
            35                  40                  45

Lys Ala Pro Phe Leu Glu Gln Phe Thr Asp Gly Trp Glu Thr Arg Trp
50                  55                  60

Thr Pro Ser His Ala Lys Lys Glu Asp Ser Lys Ser Glu Glu Asp Trp
65                  70                  75                  80

Ala Tyr Val Gly Thr Trp Ala Val Glu Glu Pro His Val Phe Asn Gly
                85                  90                  95

Met Val Gly Asp Lys Gly Leu Val Lys Asn Pro Ala Ala His His
            100                 105                 110

Ala Ile Ser Ala Lys Phe Pro Lys Lys Ile Asp Asn Lys Gly Lys Thr
        115                 120                 125

Leu Val Val Gln Tyr Glu Val Lys Leu Gln Asn Ser Leu Asn Cys Gly
    130                 135                 140

Gly Ala Tyr Met Lys Leu Leu Gln Asp Asn Lys Lys Leu His Ala Glu
145                 150                 155                 160

Glu Phe Ser Asn Thr Ser Pro Tyr Val Ile Met Phe Gly Pro Asp Lys
                165                 170                 175
```

Cys Gly Val Thr Asn Lys Val His Phe Ile Phe Lys His Lys Asn Pro
            180                 185                 190

Lys Thr Gly Glu Tyr Glu Lys His Met Lys Leu Pro Ala Val
        195                 200                 205

Arg Val Ser Lys Leu Ser Thr Leu Tyr Thr Leu Ile Val Asn Pro Asp
210                 215                 220

Gln Ser Phe Gln Ile Arg Ile Asp Gly Ala Val Lys Asn Gly Thr
225                 230                 235                 240

Leu Leu Glu Asp Phe Ser Pro Ala Val Asn Pro Lys Glu Ile Asp
                245                 250                 255

Asp Pro Glu Asp Lys Lys Pro Glu Asp Trp Val Asp Glu Ala His Ile
                260                 265                 270

Pro Asp Pro Glu Ala Thr Lys Pro Glu Asp Trp Asp Glu Asp Ala Pro
                275                 280                 285

Tyr Glu Ile Val Asp Thr Asp Ala Thr Gln Pro Glu Asp Trp Leu Val
290                 295                 300

Asp Glu Pro Thr Ser Ile Pro Asp Pro Glu Ala Gln Lys Pro Glu Asp
305                 310                 315                 320

Trp Asp Asp Glu Glu Asp Gly Asp Trp Ile Pro Pro Thr Ile Pro Asn
                325                 330                 335

Pro Lys Cys Ser Glu Val Ser Gly Cys Gly Met Trp Glu Pro Pro Met
                340                 345                 350

Lys Lys Asn Pro Glu Tyr Lys Gly Lys Trp Thr Ala Pro Met Ile Asp
                355                 360                 365

Asn Pro Ala Tyr Lys Gly Pro Trp Ala Pro Arg Lys Ile Ala Asn Pro
370                 375                 380

Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
                405                 410                 415

Ile Tyr Ile Gly His Ser Val Glu Asp Ala Glu Lys Leu Lys Ala Glu
                420                 425                 430

Thr Trp Asp Leu Lys His Pro Val Glu Val Ala Glu Glu Ala Ala
                435                 440                 445

Arg Pro Lys Asp Glu Lys Lys Glu Gly Thr Leu Ser Phe Lys Glu
450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Glu Val Ala
                485                 490                 495

Gly Gly Leu Gly Ala Leu Leu Val Thr Leu Val Leu Ile Ile Val Gly
                500                 505                 510

Ala Val Gly Leu Gly Ser Pro Ser Pro Ala Pro Ala Ala Lys Lys Gln
                515                 520                 525

Ala Glu Lys Gly Lys Glu Lys Thr Ala Glu Ala Val Ser Thr Ala Ala
                530                 535                 540

Asp Asn Val Lys Gly Glu Ala Lys Lys Arg Ser Gly Lys Ala Gly Glu
545                 550                 555                 560

<210> SEQ ID NO 64
<211> LENGTH: 560
<212> TYPE: PRT
<213> ORGANISM: Homo sapiens
<220> FEATURE:

```
<221> NAME/KEY: BINDING SITE
<222> LOCATION: (1)..(18)
<220> FEATURE:
<221> NAME/KEY: BINDING SITE
<222> LOCATION: (103)..(112)
<220> FEATURE:
<221> NAME/KEY: BINDING SITE
<222> LOCATION: (130)..(143)
<220> FEATURE:
<221> NAME/KEY: BINDING SITE
<222> LOCATION: (168)..(177)
<220> FEATURE:
<221> NAME/KEY: BINDING SITE
<222> LOCATION: (185)..(193)
<220> FEATURE:
<221> NAME/KEY: BINDING SITE
<222> LOCATION: (229)..(237)
<220> FEATURE:
<221> NAME/KEY: BINDING SITE
<222> LOCATION: (418)..(426)
<220> FEATURE:
<221> NAME/KEY: BINDING SITE
<222> LOCATION: (470)..(478)
<220> FEATURE:
<221> NAME/KEY: BINDING SITE
<222> LOCATION: (510)..(518)
<220> FEATURE:
<221> NAME/KEY: BINDING SITE
<222> LOCATION: (547)..(555)

<400> SEQUENCE: 64
```

Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
            20                  25                  30

Ser Thr Ser Ser Val Ile Glu Lys Pro Thr Phe Thr Pro Thr Thr Leu
        35                  40                  45

Lys Ala Pro Phe Leu Glu Gln Phe Thr Asp Gly Trp Glu Thr Arg Trp
    50                  55                  60

Thr Pro Ser His Ala Lys Lys Glu Asp Ser Lys Ser Glu Glu Asp Trp
65                  70                  75                  80

Ala Tyr Val Gly Thr Trp Ala Val Glu Glu Pro His Val Phe Asn Gly
                85                  90                  95

Met Val Gly Asp Lys Gly Leu Val Val Lys Asn Pro Ala Ala His His
            100                 105                 110

Ala Ile Ser Ala Lys Phe Pro Lys Lys Ile Asp Asn Lys Gly Lys Thr
        115                 120                 125

Leu Val Val Gln Tyr Glu Val Lys Leu Gln Asn Ser Leu Asn Cys Gly
    130                 135                 140

Gly Ala Tyr Met Lys Leu Leu Gln Asp Asn Lys Lys Leu His Ala Glu
145                 150                 155                 160

Glu Phe Ser Asn Thr Ser Pro Tyr Val Ile Met Phe Gly Pro Asp Lys
                165                 170                 175

Cys Gly Val Thr Asn Lys Val His Phe Ile Phe Lys His Lys Asn Pro
            180                 185                 190

Lys Thr Gly Glu Tyr Glu Glu Lys His Met Lys Leu Pro Pro Ala Val
        195                 200                 205

Arg Val Ser Lys Leu Ser Thr Leu Tyr Thr Leu Ile Val Asn Pro Asp
    210                 215                 220

Gln Ser Phe Gln Ile Arg Ile Asp Gly Ala Ala Val Lys Asn Gly Thr
225                 230                 235                 240

Leu Leu Glu Asp Phe Ser Pro Ala Val Asn Pro Glu Lys Glu Ile Asp
                245                 250                 255

```
Asp Pro Glu Asp Lys Pro Glu Asp Trp Val Asp Glu Ala His Ile
        260                 265                 270

Pro Asp Pro Glu Ala Thr Lys Pro Glu Asp Trp Asp Glu Asp Ala Pro
                275                 280                 285

Tyr Glu Ile Val Asp Thr Asp Ala Thr Gln Pro Glu Asp Trp Leu Val
        290                 295                 300

Asp Glu Pro Thr Ser Ile Pro Asp Pro Glu Ala Gln Lys Pro Glu Asp
305                 310                 315                 320

Trp Asp Asp Glu Glu Asp Gly Asp Trp Ile Pro Pro Thr Ile Pro Asn
                325                 330                 335

Pro Lys Cys Ser Glu Val Ser Gly Cys Gly Met Trp Glu Pro Pro Met
                340                 345                 350

Lys Lys Asn Pro Glu Tyr Lys Gly Lys Trp Thr Ala Pro Met Ile Asp
                355                 360                 365

Asn Pro Ala Tyr Lys Gly Pro Trp Ala Pro Arg Lys Ile Ala Asn Pro
370                 375                 380

Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
                405                 410                 415

Ile Tyr Ile Gly His Ser Val Glu Asp Ala Glu Lys Lys Ala Glu
                420                 425                 430

Thr Trp Asp Leu Lys His Pro Val Glu Val Ala Glu Glu Ala Ala
                435                 440                 445

Arg Pro Lys Asp Glu Glu Lys Lys Glu Gly Thr Leu Ser Phe Lys Glu
                450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Glu Val Ala
                485                 490                 495

Gly Gly Leu Gly Ala Leu Leu Val Thr Leu Val Leu Ile Ile Val Gly
                500                 505                 510

Ala Val Gly Leu Gly Ser Pro Ser Pro Ala Pro Ala Ala Lys Lys Gln
                515                 520                 525

Ala Glu Lys Gly Lys Glu Lys Thr Ala Glu Ala Val Ser Thr Ala Ala
                530                 535                 540

Asp Asn Val Lys Gly Glu Ala Lys Lys Arg Ser Gly Lys Ala Gly Glu
545                 550                 555                 560

<210> SEQ ID NO 65
<211> LENGTH: 560
<212> TYPE: PRT
<213> ORGANISM: Homo sapiens
<220> FEATURE:
<221> NAME/KEY: BINDING SITE
<222> LOCATION: (1)..(9)
<220> FEATURE:
<221> NAME/KEY: BINDING SITE
<222> LOCATION: (103)..(112)
<220> FEATURE:
<221> NAME/KEY: BINDING SITE
<222> LOCATION: (130)..(143)
<220> FEATURE:
<221> NAME/KEY: BINDING SITE
<222> LOCATION: (151)..(159)
<220> FEATURE:
<221> NAME/KEY: BINDING SITE
<222> LOCATION: (168)..(176)
<220> FEATURE:
```

```
<221> NAME/KEY: BINDING SITE
<222> LOCATION: (183)..(191)
<220> FEATURE:
<221> NAME/KEY: BINDING SITE
<222> LOCATION: (213)..(221)
<220> FEATURE:
<221> NAME/KEY: BINDING SITE
<222> LOCATION: (502)..(518)

<400> SEQUENCE: 65
```

| | | | | | | | | | | | | | | |
|---|---|---|---|---|---|---|---|---|---|---|---|---|---|---|
| Met | Arg | Leu | Asn | Ala | Ser | Leu | Ala | Ser | Leu | Ile | Leu | Ser | Ser | Ile | Ala |
| 1 | | | | 5 | | | | | 10 | | | | | 15 | |

Leu Ile Gly Asn Val His Ala Glu Asp Glu Val Lys Glu Asp Ala Thr
                20                  25                  30

Ser Thr Ser Ser Val Ile Glu Lys Pro Thr Phe Thr Pro Thr Thr Leu
            35                  40                  45

Lys Ala Pro Phe Leu Glu Gln Phe Thr Asp Gly Trp Glu Thr Arg Trp
 50                  55                  60

Thr Pro Ser His Ala Lys Lys Glu Asp Ser Lys Ser Glu Glu Asp Trp
 65                  70                  75                  80

Ala Tyr Val Gly Thr Trp Ala Val Glu Glu Pro His Val Phe Asn Gly
                85                  90                  95

Met Val Gly Asp Lys Gly Leu Val Val Lys Asn Pro Ala Ala His His
            100                 105                 110

Ala Ile Ser Ala Lys Phe Pro Lys Lys Ile Asp Asn Lys Gly Lys Thr
        115                 120                 125

Leu Val Val Gln Tyr Glu Val Lys Leu Gln Asn Ser Leu Asn Cys Gly
130                 135                 140

Gly Ala Tyr Met Lys Leu Leu Gln Asp Asn Lys Lys Leu His Ala Glu
145                 150                 155                 160

Glu Phe Ser Asn Thr Ser Pro Tyr Val Ile Met Phe Gly Pro Asp Lys
                165                 170                 175

Cys Gly Val Thr Asn Lys Val His Phe Ile Phe Lys His Lys Asn Pro
            180                 185                 190

Lys Thr Gly Glu Tyr Glu Glu Lys His Met Lys Leu Pro Pro Ala Val
        195                 200                 205

Arg Val Ser Lys Leu Ser Thr Leu Tyr Thr Leu Ile Val Asn Pro Asp
    210                 215                 220

Gln Ser Phe Gln Ile Arg Ile Asp Gly Ala Ala Val Lys Asn Gly Thr
225                 230                 235                 240

Leu Leu Glu Asp Phe Ser Pro Ala Val Asn Pro Glu Lys Glu Ile Asp
                245                 250                 255

Asp Pro Glu Asp Lys Lys Pro Glu Asp Trp Val Asp Glu Ala His Ile
            260                 265                 270

Pro Asp Pro Glu Ala Thr Lys Pro Glu Asp Trp Asp Asp Ala Pro Pro
        275                 280                 285

Tyr Glu Ile Val Asp Thr Asp Ala Thr Gln Pro Glu Asp Trp Leu Val
290                 295                 300

Asp Glu Pro Thr Ser Ile Pro Asp Pro Glu Ala Gln Lys Pro Glu Asp
305                 310                 315                 320

Trp Asp Asp Glu Glu Asp Gly Asp Trp Ile Pro Pro Thr Ile Pro Asn
                325                 330                 335

Pro Lys Cys Ser Glu Val Ser Gly Cys Gly Met Trp Glu Pro Pro Met
            340                 345                 350

Lys Lys Asn Pro Glu Tyr Lys Gly Lys Trp Thr Ala Pro Met Ile Asp
        355                 360                 365

Asn Pro Ala Tyr Lys Gly Pro Trp Ala Pro Arg Lys Ile Ala Asn Pro
        370                 375                 380

Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
                405                 410                 415

Ile Tyr Ile Gly His Ser Val Glu Asp Ala Glu Lys Leu Lys Ala Glu
                420                 425                 430

Thr Trp Asp Leu Lys His Pro Val Glu Val Ala Glu Glu Ala Ala
        435                 440                 445

Arg Pro Lys Asp Glu Glu Lys Lys Glu Gly Thr Leu Ser Phe Lys Glu
        450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Val Ala
                485                 490                 495

Gly Gly Leu Gly Ala Leu Leu Val Thr Leu Val Leu Ile Ile Val Gly
                500                 505                 510

Ala Val Gly Leu Gly Ser Pro Ser Pro Ala Pro Ala Ala Lys Lys Gln
        515                 520                 525

Ala Glu Lys Gly Lys Glu Lys Thr Ala Glu Ala Val Ser Thr Ala Ala
        530                 535                 540

Asp Asn Val Lys Gly Glu Ala Lys Lys Arg Ser Gly Lys Ala Gly Glu
545                 550                 555                 560

<210> SEQ ID NO 66
<211> LENGTH: 560
<212> TYPE: PRT
<213> ORGANISM: Homo sapiens
<220> FEATURE:
<221> NAME/KEY: BINDING SITE
<222> LOCATION: (1)..(9)
<220> FEATURE:
<221> NAME/KEY: BINDING SITE
<222> LOCATION: (103)..(112)
<220> FEATURE:
<221> NAME/KEY: BINDING SITE
<222> LOCATION: (130)..(143)
<220> FEATURE:
<221> NAME/KEY: BINDING SITE
<222> LOCATION: (151)..(159)
<220> FEATURE:
<221> NAME/KEY: BINDING SITE
<222> LOCATION: (168)..(176)
<220> FEATURE:
<221> NAME/KEY: BINDING SITE
<222> LOCATION: (183)..(191)
<220> FEATURE:
<221> NAME/KEY: BINDING SITE
<222> LOCATION: (213)..(221)
<220> FEATURE:
<221> NAME/KEY: BINDING SITE
<222> LOCATION: (502)..(518)

<400> SEQUENCE: 66

Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
                20                  25                  30

Ser Thr Ser Ser Val Ile Glu Lys Pro Thr Phe Thr Pro Thr Thr Leu
        35                  40                  45

Lys Ala Pro Phe Leu Glu Gln Phe Thr Asp Gly Trp Glu Thr Arg Trp

```
            50                  55                  60
Thr Pro Ser His Ala Lys Lys Glu Asp Ser Lys Ser Glu Glu Asp Trp
65                  70                  75                  80

Ala Tyr Val Gly Thr Trp Ala Val Glu Glu Pro His Val Phe Asn Gly
                85                  90                  95

Met Val Gly Asp Lys Gly Leu Val Val Lys Asn Pro Ala Ala His His
            100                 105                 110

Ala Ile Ser Ala Lys Phe Pro Lys Lys Ile Asp Asn Lys Gly Lys Thr
        115                 120                 125

Leu Val Val Gln Tyr Glu Val Lys Leu Gln Asn Ser Leu Asn Cys Gly
    130                 135                 140

Gly Ala Tyr Met Lys Leu Leu Gln Asp Asn Lys Lys Leu His Ala Glu
145                 150                 155                 160

Glu Phe Ser Asn Thr Ser Pro Tyr Val Ile Met Phe Gly Pro Asp Lys
                165                 170                 175

Cys Gly Val Thr Asn Lys Val His Phe Ile Phe Lys His Lys Asn Pro
            180                 185                 190

Lys Thr Gly Glu Tyr Glu Glu Lys His Met Lys Leu Pro Pro Ala Val
        195                 200                 205

Arg Val Ser Lys Leu Ser Thr Leu Tyr Thr Leu Ile Val Asn Pro Asp
    210                 215                 220

Gln Ser Phe Gln Ile Arg Ile Asp Gly Ala Ala Val Lys Asn Gly Thr
225                 230                 235                 240

Leu Leu Glu Asp Phe Ser Pro Ala Val Asn Pro Glu Lys Glu Ile Asp
                245                 250                 255

Asp Pro Glu Asp Lys Lys Pro Glu Asp Trp Val Asp Glu Ala His Ile
            260                 265                 270

Pro Asp Pro Glu Ala Thr Lys Pro Glu Asp Trp Asp Glu Asp Ala Pro
        275                 280                 285

Tyr Glu Ile Val Asp Thr Asp Ala Thr Gln Pro Glu Asp Trp Leu Val
    290                 295                 300

Asp Glu Pro Thr Ser Ile Pro Asp Pro Glu Ala Gln Lys Pro Glu Asp
305                 310                 315                 320

Trp Asp Asp Glu Glu Asp Gly Asp Trp Ile Pro Pro Thr Ile Pro Asn
                325                 330                 335

Pro Lys Cys Ser Glu Val Ser Gly Cys Gly Met Trp Glu Pro Pro Met
            340                 345                 350

Lys Lys Asn Pro Glu Tyr Lys Gly Lys Trp Thr Ala Pro Met Ile Asp
        355                 360                 365

Asn Pro Ala Tyr Lys Gly Pro Trp Ala Pro Arg Lys Ile Ala Asn Pro
    370                 375                 380

Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
                405                 410                 415

Ile Tyr Ile Gly His Ser Val Glu Asp Ala Glu Lys Leu Lys Ala Glu
            420                 425                 430

Thr Trp Asp Leu Lys His Pro Val Glu Val Ala Glu Glu Ala Ala
        435                 440                 445

Arg Pro Lys Asp Glu Lys Lys Glu Gly Thr Leu Ser Phe Lys Glu
    450                 455                 460

Ala Pro Val Lys Tyr Ile Arg Gly Lys Ile Glu Leu Phe Ile Ser Leu
465                 470                 475                 480
```

```
Ala Leu Glu Asn Pro Val Ala Val Lys Ala Val Pro Glu Val Ala
            485                 490                 495

Gly Gly Leu Gly Ala Leu Leu Val Thr Leu Val Leu Ile Ile Val Gly
        500                 505                 510

Ala Val Gly Leu Gly Ser Pro Ser Pro Ala Pro Ala Ala Lys Lys Gln
        515                 520                 525

Ala Glu Lys Gly Lys Glu Lys Thr Ala Glu Ala Val Ser Thr Ala Ala
        530                 535                 540

Asp Asn Val Lys Gly Glu Ala Lys Lys Arg Ser Gly Lys Ala Gly Glu
545                 550                 555                 560

<210> SEQ ID NO 67
<211> LENGTH: 560
<212> TYPE: PRT
<213> ORGANISM: Homo sapiens
<220> FEATURE:
<221> NAME/KEY: BINDING SITE
<222> LOCATION: (1)..(18)
<220> FEATURE:
<221> NAME/KEY: BINDING SITE
<222> LOCATION: (27)..(35)
<220> FEATURE:
<221> NAME/KEY: BINDING SITE
<222> LOCATION: (93)..(112)
<220> FEATURE:
<221> NAME/KEY: BINDING SITE
<222> LOCATION: (135)..(143)
<220> FEATURE:
<221> NAME/KEY: BINDING SITE
<222> LOCATION: (150)..(158)
<220> FEATURE:
<221> NAME/KEY: BINDING SITE
<222> LOCATION: (168)..(176)
<220> FEATURE:
<221> NAME/KEY: BINDING SITE
<222> LOCATION: (221)..(237)
<220> FEATURE:
<221> NAME/KEY: BINDING SITE
<222> LOCATION: (302)..(310)
<220> FEATURE:
<221> NAME/KEY: BINDING SITE
<222> LOCATION: (408)..(420)
<220> FEATURE:
<221> NAME/KEY: BINDING SITE
<222> LOCATION: (506)..(522)

<400> SEQUENCE: 67

Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
            20                  25                  30

Ser Thr Ser Ser Val Ile Glu Lys Pro Thr Phe Thr Pro Thr Thr Leu
        35                  40                  45

Lys Ala Pro Phe Leu Glu Gln Phe Thr Asp Gly Trp Glu Thr Arg Trp
    50                  55                  60

Thr Pro Ser His Ala Lys Lys Glu Asp Ser Lys Ser Glu Glu Asp Trp
65                  70                  75                  80

Ala Tyr Val Gly Thr Trp Ala Val Glu Glu Pro His Val Phe Asn Gly
                85                  90                  95

Met Val Gly Asp Lys Gly Leu Val Val Lys Asn Pro Ala Ala His His
            100                 105                 110

Ala Ile Ser Ala Lys Phe Pro Lys Lys Ile Asp Asn Lys Gly Lys Thr
        115                 120                 125

Leu Val Val Gln Tyr Glu Val Lys Leu Gln Asn Ser Leu Asn Cys Gly
```

```
              130                 135                 140
Gly Ala Tyr Met Lys Leu Leu Gln Asp Asn Lys Lys Leu His Ala Glu
145                 150                 155                 160

Glu Phe Ser Asn Thr Ser Pro Tyr Val Ile Met Phe Gly Pro Asp Lys
                165                 170                 175

Cys Gly Val Thr Asn Lys Val His Phe Ile Phe Lys His Lys Asn Pro
                180                 185                 190

Lys Thr Gly Glu Tyr Glu Glu Lys His Met Lys Leu Pro Pro Ala Val
                195                 200                 205

Arg Val Ser Lys Leu Ser Thr Leu Tyr Thr Leu Ile Val Asn Pro Asp
        210                 215                 220

Gln Ser Phe Gln Ile Arg Ile Asp Gly Ala Ala Val Lys Asn Gly Thr
225                 230                 235                 240

Leu Leu Glu Asp Phe Ser Pro Ala Val Asn Pro Glu Lys Glu Ile Asp
                245                 250                 255

Asp Pro Glu Asp Lys Lys Pro Glu Asp Trp Val Asp Glu Ala His Ile
                260                 265                 270

Pro Asp Pro Glu Ala Thr Lys Pro Glu Asp Trp Asp Glu Asp Ala Pro
        275                 280                 285

Tyr Glu Ile Val Asp Thr Asp Ala Thr Gln Pro Glu Asp Trp Leu Val
        290                 295                 300

Asp Glu Pro Thr Ser Ile Pro Asp Pro Glu Ala Gln Lys Pro Glu Asp
305                 310                 315                 320

Trp Asp Asp Glu Glu Asp Gly Asp Trp Ile Pro Pro Thr Ile Pro Asn
                325                 330                 335

Pro Lys Cys Ser Glu Val Ser Gly Cys Gly Met Trp Glu Pro Pro Met
                340                 345                 350

Lys Lys Asn Pro Glu Tyr Lys Gly Lys Trp Thr Ala Pro Met Ile Asp
                355                 360                 365

Asn Pro Ala Tyr Lys Gly Pro Trp Ala Pro Arg Lys Ile Ala Asn Pro
        370                 375                 380

Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
                405                 410                 415

Ile Tyr Ile Gly His Ser Val Glu Asp Ala Glu Lys Leu Lys Ala Glu
                420                 425                 430

Thr Trp Asp Leu Lys His Pro Val Glu Val Ala Glu Glu Ala Ala
                435                 440                 445

Arg Pro Lys Asp Glu Lys Lys Glu Gly Thr Leu Ser Phe Lys Glu
        450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Glu Val Ala
                485                 490                 495

Gly Gly Leu Gly Ala Leu Leu Val Thr Leu Val Leu Ile Ile Val Gly
                500                 505                 510

Ala Val Gly Leu Gly Ser Pro Ser Pro Ala Pro Ala Ala Lys Lys Gln
                515                 520                 525

Ala Glu Lys Gly Lys Glu Lys Thr Ala Glu Ala Val Ser Thr Ala Ala
        530                 535                 540

Asp Asn Val Lys Gly Glu Ala Lys Lys Arg Ser Gly Lys Ala Gly Glu
545                 550                 555                 560
```

```
<210> SEQ ID NO 68
<211> LENGTH: 560
<212> TYPE: PRT
<213> ORGANISM: Homo sapiens
<220> FEATURE:
<221> NAME/KEY: BINDING SITE
<222> LOCATION: (1)..(9)
<220> FEATURE:
<221> NAME/KEY: BINDING SITE
<222> LOCATION: (103)..(111)
<220> FEATURE:
<221> NAME/KEY: BINDING SITE
<222> LOCATION: (130)..(143)
<220> FEATURE:
<221> NAME/KEY: BINDING SITE
<222> LOCATION: (168)..(177)
<220> FEATURE:
<221> NAME/KEY: BINDING SITE
<222> LOCATION: (185)..(195)
<220> FEATURE:
<221> NAME/KEY: BINDING SITE
<222> LOCATION: (358)..(366)
<220> FEATURE:
<221> NAME/KEY: BINDING SITE
<222> LOCATION: (418)..(426)
<220> FEATURE:
<221> NAME/KEY: BINDING SITE
<222> LOCATION: (510)..(518)

<400> SEQUENCE: 68

Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
            20                  25                  30

Ser Thr Ser Ser Val Ile Glu Lys Pro Thr Phe Thr Pro Thr Thr Leu
        35                  40                  45

Lys Ala Pro Phe Leu Glu Gln Phe Thr Asp Gly Trp Glu Thr Arg Trp
    50                  55                  60

Thr Pro Ser His Ala Lys Lys Glu Asp Ser Lys Ser Glu Glu Asp Trp
65                  70                  75                  80

Ala Tyr Val Gly Thr Trp Ala Val Glu Glu Pro His Val Phe Asn Gly
                85                  90                  95

Met Val Gly Asp Lys Gly Leu Val Val Lys Asn Pro Ala Ala His His
            100                 105                 110

Ala Ile Ser Ala Lys Phe Pro Lys Lys Ile Asp Asn Lys Gly Lys Thr
        115                 120                 125

Leu Val Val Gln Tyr Glu Val Lys Leu Gln Asn Ser Leu Asn Cys Gly
    130                 135                 140

Gly Ala Tyr Met Lys Leu Leu Gln Asp Asn Lys Lys Leu His Ala Glu
145                 150                 155                 160

Glu Phe Ser Asn Thr Ser Pro Tyr Val Ile Met Phe Gly Pro Asp Lys
                165                 170                 175

Cys Gly Val Thr Asn Lys Val His Phe Ile Phe Lys His Lys Asn Pro
            180                 185                 190

Lys Thr Gly Glu Tyr Glu Glu Lys His Met Lys Leu Pro Pro Ala Val
        195                 200                 205

Arg Val Ser Lys Leu Ser Thr Leu Tyr Thr Leu Ile Val Asn Pro Asp
    210                 215                 220

Gln Ser Phe Gln Ile Arg Ile Asp Gly Ala Ala Val Lys Asn Gly Thr
225                 230                 235                 240

Leu Leu Glu Asp Phe Ser Pro Ala Val Asn Pro Glu Lys Glu Ile Asp
```

```
                245                 250                 255
Asp Pro Glu Asp Lys Pro Glu Asp Trp Val Asp Glu Ala His Ile
            260                 265                 270

Pro Asp Pro Glu Ala Thr Lys Pro Glu Asp Trp Asp Glu Asp Ala Pro
        275                 280                 285

Tyr Glu Ile Val Asp Thr Asp Ala Thr Gln Pro Glu Asp Trp Leu Val
    290                 295                 300

Asp Glu Pro Thr Ser Ile Pro Asp Pro Glu Ala Gln Lys Pro Glu Asp
305                 310                 315                 320

Trp Asp Asp Glu Glu Asp Gly Asp Trp Ile Pro Pro Thr Ile Pro Asn
                325                 330                 335

Pro Lys Cys Ser Glu Val Ser Gly Cys Gly Met Trp Glu Pro Pro Met
            340                 345                 350

Lys Lys Asn Pro Glu Tyr Lys Gly Lys Trp Thr Ala Pro Met Ile Asp
        355                 360                 365

Asn Pro Ala Tyr Lys Gly Pro Trp Ala Pro Arg Lys Ile Ala Asn Pro
370                 375                 380

Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
                405                 410                 415

Ile Tyr Ile Gly His Ser Val Glu Asp Ala Glu Lys Leu Lys Ala Glu
            420                 425                 430

Thr Trp Asp Leu Lys His Pro Val Glu Val Ala Glu Glu Ala Ala
        435                 440                 445

Arg Pro Lys Asp Glu Lys Lys Glu Gly Thr Leu Ser Phe Lys Glu
    450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Glu Val Ala
                485                 490                 495

Gly Gly Leu Gly Ala Leu Leu Val Thr Leu Val Leu Ile Ile Val Gly
            500                 505                 510

Ala Val Gly Leu Gly Ser Pro Ser Pro Ala Pro Ala Ala Lys Lys Gln
        515                 520                 525

Ala Glu Lys Gly Lys Glu Lys Thr Ala Glu Ala Val Ser Thr Ala Ala
    530                 535                 540

Asp Asn Val Lys Gly Glu Ala Lys Lys Arg Ser Gly Lys Ala Gly Glu
545                 550                 555                 560

<210> SEQ ID NO 69
<211> LENGTH: 560
<212> TYPE: PRT
<213> ORGANISM: Homo sapiens
<220> FEATURE:
<221> NAME/KEY: BINDING SITE
<222> LOCATION: (1)..(9)
<220> FEATURE:
<221> NAME/KEY: BINDING SITE
<222> LOCATION: (103)..(111)
<220> FEATURE:
<221> NAME/KEY: BINDING SITE
<222> LOCATION: (130)..(138)
<220> FEATURE:
<221> NAME/KEY: BINDING SITE
<222> LOCATION: (168)..(176)
<220> FEATURE:
<221> NAME/KEY: BINDING SITE
<222> LOCATION: (185)..(195)
```

```
<220> FEATURE:
<221> NAME/KEY: BINDING SITE
<222> LOCATION: (358)..(366)
<220> FEATURE:
<221> NAME/KEY: BINDING SITE
<222> LOCATION: (418)..(426)
<220> FEATURE:
<221> NAME/KEY: BINDING SITE
<222> LOCATION: (510)..(518)

<400> SEQUENCE: 69
```

| | | | | | | | | | | | | | | | |
|---|---|---|---|---|---|---|---|---|---|---|---|---|---|---|---|
| Met | Arg | Leu | Asn | Ala | Ser | Leu | Ala | Ser | Leu | Ile | Leu | Ser | Ser | Ile | Ala |
| 1 | | | | 5 | | | | | 10 | | | | | 15 | |
| Leu | Ile | Gly | Asn | Val | His | Ala | Glu | Asp | Glu | Val | Lys | Glu | Asp | Ala | Thr |
| | | | 20 | | | | | 25 | | | | | 30 | | |
| Ser | Thr | Ser | Ser | Val | Ile | Glu | Lys | Pro | Thr | Phe | Thr | Pro | Thr | Thr | Leu |
| | | 35 | | | | | 40 | | | | | 45 | | | |
| Lys | Ala | Pro | Phe | Leu | Glu | Gln | Phe | Thr | Asp | Gly | Trp | Glu | Thr | Arg | Trp |
| | 50 | | | | | 55 | | | | | 60 | | | | |
| Thr | Pro | Ser | His | Ala | Lys | Lys | Glu | Asp | Ser | Lys | Ser | Glu | Glu | Asp | Trp |
| 65 | | | | | 70 | | | | | 75 | | | | | 80 |
| Ala | Tyr | Val | Gly | Thr | Trp | Ala | Val | Glu | Glu | Pro | His | Val | Phe | Asn | Gly |
| | | | | 85 | | | | | 90 | | | | | 95 | |
| Met | Val | Gly | Asp | Lys | Gly | Leu | Val | Val | Lys | Asn | Pro | Ala | Ala | His | His |
| | | | 100 | | | | | 105 | | | | | 110 | | |
| Ala | Ile | Ser | Ala | Lys | Phe | Pro | Lys | Lys | Ile | Asp | Asn | Lys | Gly | Lys | Thr |
| | | | 115 | | | | | 120 | | | | | 125 | | |
| Leu | Val | Val | Gln | Tyr | Glu | Val | Lys | Leu | Gln | Asn | Ser | Leu | Asn | Cys | Gly |
| 130 | | | | | 135 | | | | | 140 | | | | | |
| Gly | Ala | Tyr | Met | Lys | Leu | Leu | Gln | Asp | Asn | Lys | Lys | Leu | His | Ala | Glu |
| 145 | | | | | 150 | | | | | 155 | | | | | 160 |
| Glu | Phe | Ser | Asn | Thr | Ser | Pro | Tyr | Val | Ile | Met | Phe | Gly | Pro | Asp | Lys |
| | | | | 165 | | | | | 170 | | | | | 175 | |
| Cys | Gly | Val | Thr | Asn | Lys | Val | His | Phe | Ile | Phe | Lys | His | Lys | Asn | Pro |
| | | | 180 | | | | | 185 | | | | | 190 | | |
| Lys | Thr | Gly | Glu | Tyr | Glu | Glu | Lys | His | Met | Lys | Leu | Pro | Pro | Ala | Val |
| | | 195 | | | | | 200 | | | | | 205 | | | |
| Arg | Val | Ser | Lys | Leu | Ser | Thr | Leu | Tyr | Thr | Leu | Ile | Val | Asn | Pro | Asp |
| 210 | | | | | 215 | | | | | 220 | | | | | |
| Gln | Ser | Phe | Gln | Ile | Arg | Ile | Asp | Gly | Ala | Ala | Val | Lys | Asn | Gly | Thr |
| 225 | | | | | 230 | | | | | 235 | | | | | 240 |
| Leu | Leu | Glu | Asp | Phe | Ser | Pro | Ala | Val | Asn | Pro | Glu | Lys | Glu | Ile | Asp |
| | | | | 245 | | | | | 250 | | | | | 255 | |
| Asp | Pro | Glu | Asp | Lys | Lys | Pro | Glu | Asp | Trp | Val | Asp | Glu | Ala | His | Ile |
| | | | 260 | | | | | 265 | | | | | 270 | | |
| Pro | Asp | Pro | Glu | Ala | Thr | Lys | Pro | Glu | Asp | Trp | Asp | Glu | Asp | Ala | Pro |
| | | 275 | | | | | 280 | | | | | 285 | | | |
| Tyr | Glu | Ile | Val | Asp | Thr | Asp | Ala | Thr | Gln | Pro | Glu | Asp | Trp | Leu | Val |
| 290 | | | | | 295 | | | | | 300 | | | | | |
| Asp | Glu | Pro | Thr | Ser | Ile | Pro | Asp | Pro | Glu | Ala | Gln | Lys | Pro | Glu | Asp |
| 305 | | | | | 310 | | | | | 315 | | | | | 320 |
| Trp | Asp | Asp | Glu | Glu | Asp | Gly | Asp | Trp | Ile | Pro | Thr | Ile | Pro | Asn | |
| | | | | 325 | | | | | 330 | | | | | 335 | |
| Pro | Lys | Cys | Ser | Glu | Val | Ser | Gly | Cys | Gly | Met | Trp | Glu | Pro | Pro | Met |
| | | | 340 | | | | | 345 | | | | | 350 | | |
| Lys | Lys | Asn | Pro | Glu | Tyr | Lys | Gly | Lys | Trp | Thr | Ala | Pro | Met | Ile | Asp |

```
            355                 360                 365
Asn Pro Ala Tyr Lys Gly Pro Trp Ala Pro Arg Lys Ile Ala Asn Pro
    370                 375                 380

Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
                405                 410                 415

Ile Tyr Ile Gly His Ser Val Glu Asp Ala Glu Lys Leu Lys Ala Glu
            420                 425                 430

Thr Trp Asp Leu Lys His Pro Val Glu Val Ala Glu Glu Ala Ala
            435                 440                 445

Arg Pro Lys Asp Glu Glu Lys Glu Gly Thr Leu Ser Phe Lys Glu
    450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Glu Val Ala
                485                 490                 495

Gly Gly Leu Gly Ala Leu Leu Val Thr Leu Val Leu Ile Ile Val Gly
            500                 505                 510

Ala Val Gly Leu Gly Ser Pro Ser Pro Ala Pro Ala Ala Lys Lys Gln
            515                 520                 525

Ala Glu Lys Gly Lys Glu Lys Thr Ala Glu Ala Val Ser Thr Ala Ala
            530                 535                 540

Asp Asn Val Lys Gly Glu Ala Lys Lys Arg Ser Gly Lys Ala Gly Glu
545                 550                 555                 560

<210> SEQ ID NO 70
<211> LENGTH: 560
<212> TYPE: PRT
<213> ORGANISM: Homo sapiens
<220> FEATURE:
<221> NAME/KEY: BINDING SITE
<222> LOCATION: (1)..(18)
<220> FEATURE:
<221> NAME/KEY: BINDING SITE
<222> LOCATION: (103)..(112)
<220> FEATURE:
<221> NAME/KEY: BINDING SITE
<222> LOCATION: (130)..(143)
<220> FEATURE:
<221> NAME/KEY: BINDING SITE
<222> LOCATION: (168)..(177)
<220> FEATURE:
<221> NAME/KEY: BINDING SITE
<222> LOCATION: (185)..(193)
<220> FEATURE:
<221> NAME/KEY: BINDING SITE
<222> LOCATION: (229)..(237)
<220> FEATURE:
<221> NAME/KEY: BINDING SITE
<222> LOCATION: (418)..(426)
<220> FEATURE:
<221> NAME/KEY: BINDING SITE
<222> LOCATION: (470)..(478)
<220> FEATURE:
<221> NAME/KEY: BINDING SITE
<222> LOCATION: (510)..(518)
<220> FEATURE:
<221> NAME/KEY: BINDING SITE
<222> LOCATION: (547)..(555)

<400> SEQUENCE: 70

Met Arg Leu Asn Ala Ser Leu Ala Ser Leu Ile Leu Ser Ser Ile Ala
1               5                   10                  15
```

```
Leu Ile Gly Asn Val His Ala Glu Asp Glu Val Lys Glu Asp Ala Thr
            20                  25                  30
Ser Thr Ser Ser Val Ile Glu Lys Pro Thr Phe Thr Pro Thr Thr Leu
         35                  40                  45
Lys Ala Pro Phe Leu Glu Gln Phe Thr Asp Gly Trp Glu Thr Arg Trp
 50                  55                  60
Thr Pro Ser His Ala Lys Lys Glu Asp Ser Lys Ser Glu Glu Asp Trp
 65                  70                  75                  80
Ala Tyr Val Gly Thr Trp Ala Val Glu Glu Pro His Val Phe Asn Gly
                 85                  90                  95
Met Val Gly Asp Lys Gly Leu Val Val Lys Asn Pro Ala Ala His His
             100                 105                 110
Ala Ile Ser Ala Lys Phe Pro Lys Lys Ile Asp Asn Lys Gly Lys Thr
         115                 120                 125
Leu Val Val Gln Tyr Glu Val Lys Leu Gln Asn Ser Leu Asn Cys Gly
130                 135                 140
Gly Ala Tyr Met Lys Leu Leu Gln Asp Asn Lys Lys Leu His Ala Glu
145                 150                 155                 160
Glu Phe Ser Asn Thr Ser Pro Tyr Val Ile Met Phe Gly Pro Asp Lys
                165                 170                 175
Cys Gly Val Thr Asn Lys Val His Phe Ile Phe Lys His Lys Asn Pro
             180                 185                 190
Lys Thr Gly Glu Tyr Glu Lys His Met Lys Leu Pro Pro Ala Val
         195                 200                 205
Arg Val Ser Lys Leu Ser Thr Leu Tyr Thr Leu Ile Val Asn Pro Asp
210                 215                 220
Gln Ser Phe Gln Ile Arg Ile Asp Gly Ala Ala Val Lys Asn Gly Thr
225                 230                 235                 240
Leu Leu Glu Asp Phe Ser Pro Ala Val Asn Pro Glu Lys Glu Ile Asp
                245                 250                 255
Asp Pro Glu Asp Lys Pro Glu Asp Trp Val Asp Glu Ala His Ile
             260                 265                 270
Pro Asp Pro Glu Ala Thr Lys Pro Glu Asp Trp Asp Glu Asp Ala Pro
         275                 280                 285
Tyr Glu Ile Val Asp Thr Asp Ala Thr Gln Pro Glu Asp Trp Leu Val
290                 295                 300
Asp Glu Pro Thr Ser Ile Pro Asp Pro Glu Ala Gln Lys Pro Glu Asp
305                 310                 315                 320
Trp Asp Asp Glu Glu Asp Gly Asp Trp Ile Pro Pro Thr Ile Pro Asn
                325                 330                 335
Pro Lys Cys Ser Glu Val Ser Gly Cys Gly Met Trp Glu Pro Pro Met
             340                 345                 350
Lys Lys Asn Pro Glu Tyr Lys Gly Lys Trp Thr Ala Pro Met Ile Asp
         355                 360                 365
Asn Pro Ala Tyr Lys Gly Pro Trp Ala Pro Arg Lys Ile Ala Asn Pro
370                 375                 380
Asn Tyr Phe Glu Asp Lys Thr Pro Ser Asn Phe Glu Pro Met Gly Ala
385                 390                 395                 400
Ile Gly Phe Glu Ile Trp Thr Met Gln Asn Asp Ile Leu Phe Asp Asn
                405                 410                 415
Ile Tyr Ile Gly His Ser Val Glu Asp Ala Glu Lys Leu Lys Ala Glu
             420                 425                 430
Thr Trp Asp Leu Lys His Pro Val Glu Val Ala Glu Glu Glu Ala Ala
```

```
                    435                 440                 445
Arg Pro Lys Asp Glu Lys Lys Glu Gly Thr Leu Ser Phe Lys Glu
450                 455                 460

Ala Pro Val Lys Tyr Ile Arg Gly Lys Ile Glu Leu Phe Ile Ser Leu
465                 470                 475                 480

Ala Leu Glu Asn Pro Val Glu Val Lys Ala Val Pro Glu Val Ala
                485                 490                 495

Gly Gly Leu Gly Ala Leu Leu Val Thr Leu Val Leu Ile Ile Val Gly
                500                 505                 510

Ala Val Gly Leu Gly Ser Pro Ser Pro Ala Pro Ala Ala Lys Lys Gln
                515                 520                 525

Ala Glu Lys Gly Lys Glu Lys Thr Ala Glu Ala Val Ser Thr Ala Ala
530                 535                 540

Asp Asn Val Lys Gly Glu Ala Lys Lys Arg Ser Gly Lys Ala Gly Glu
545                 550                 555                 560

<210> SEQ ID NO 71
<211> LENGTH: 560
<212> TYPE: PRT
<213> ORGANISM: Homo sapiens
<220> FEATURE:
<221> NAME/KEY: BINDING SITE
<222> LOCATION: (1)..(9)
<220> FEATURE:
<221> NAME/KEY: BINDING SITE
<222> LOCATION: (168)..(176)
<220> FEATURE:
<221> NAME/KEY: BINDING SITE
<222> LOCATION: (213)..(221)
<220> FEATURE:
<221> NAME/KEY: BINDING SITE
<222> LOCATION: (358)..(366)
<220> FEATURE:
<221> NAME/KEY: BINDING SITE
<222> LOCATION: (395)..(403)
<220> FEATURE:
<221> NAME/KEY: BINDING SITE
<222> LOCATION: (502)..(514)

<400> SEQUENCE: 71

Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
                20                  25                  30

Ser Thr Ser Ser Val Ile Glu Lys Pro Thr Phe Thr Pro Thr Thr Leu
                35                  40                  45

Lys Ala Pro Phe Leu Glu Gln Phe Thr Asp Gly Trp Glu Thr Arg Trp
50                  55                  60

Thr Pro Ser His Ala Lys Lys Glu Asp Ser Lys Ser Glu Glu Asp Trp
65                  70                  75                  80

Ala Tyr Val Gly Thr Trp Ala Val Glu Glu Pro His Val Phe Asn Gly
                85                  90                  95

Met Val Gly Asp Lys Gly Leu Val Val Lys Asn Pro Ala Ala His His
                100                 105                 110

Ala Ile Ser Ala Lys Phe Pro Lys Lys Ile Asp Asn Lys Gly Lys Thr
                115                 120                 125

Leu Val Val Gln Tyr Glu Val Lys Leu Gln Asn Ser Leu Asn Cys Gly
                130                 135                 140

Gly Ala Tyr Met Lys Leu Leu Gln Asp Asn Lys Lys Leu His Ala Glu
145                 150                 155                 160
```

```
Glu Phe Ser Asn Thr Ser Pro Tyr Val Ile Met Phe Gly Pro Asp Lys
                165                 170                 175
Cys Gly Val Thr Asn Lys Val His Phe Ile Phe Lys His Lys Asn Pro
            180                 185                 190
Lys Thr Gly Glu Tyr Glu Lys His Met Lys Leu Pro Pro Ala Val
        195                 200                 205
Arg Val Ser Lys Leu Ser Thr Leu Tyr Thr Leu Ile Val Asn Pro Asp
        210                 215                 220
Gln Ser Phe Gln Ile Arg Ile Asp Gly Ala Ala Val Lys Asn Gly Thr
225                 230                 235                 240
Leu Leu Glu Asp Phe Ser Pro Ala Val Asn Pro Glu Lys Glu Ile Asp
                245                 250                 255
Asp Pro Glu Asp Lys Pro Glu Asp Trp Val Asp Glu Ala His Ile
            260                 265                 270
Pro Asp Pro Glu Ala Thr Lys Pro Glu Asp Trp Asp Glu Asp Ala Pro
        275                 280                 285
Tyr Glu Ile Val Asp Thr Asp Ala Thr Gln Pro Glu Asp Trp Leu Val
        290                 295                 300
Asp Glu Pro Thr Ser Ile Pro Asp Pro Glu Ala Gln Lys Pro Glu Asp
305                 310                 315                 320
Trp Asp Asp Glu Glu Asp Gly Asp Trp Ile Pro Pro Thr Ile Pro Asn
                325                 330                 335
Pro Lys Cys Ser Glu Val Ser Gly Cys Gly Met Trp Glu Pro Pro Met
                340                 345                 350
Lys Lys Asn Pro Glu Tyr Lys Gly Lys Trp Thr Ala Pro Met Ile Asp
            355                 360                 365
Asn Pro Ala Tyr Lys Gly Pro Trp Ala Pro Arg Lys Ile Ala Asn Pro
        370                 375                 380
Asn Tyr Phe Glu Asp Lys Thr Pro Ser Asn Phe Glu Pro Met Gly Ala
385                 390                 395                 400
Ile Gly Phe Glu Ile Trp Thr Met Gln Asn Asp Ile Leu Phe Asp Asn
                405                 410                 415
Ile Tyr Ile Gly His Ser Val Glu Asp Ala Glu Lys Leu Lys Ala Glu
            420                 425                 430
Thr Trp Asp Leu Lys His Pro Val Glu Val Ala Glu Glu Ala Ala
        435                 440                 445
Arg Pro Lys Asp Glu Lys Lys Glu Gly Thr Leu Ser Phe Lys Glu
        450                 455                 460
Ala Pro Val Lys Tyr Ile Arg Gly Lys Ile Glu Leu Phe Ile Ser Leu
465                 470                 475                 480
Ala Leu Glu Asn Pro Val Glu Ala Val Lys Ala Val Pro Glu Val Ala
                485                 490                 495
Gly Gly Leu Gly Ala Leu Leu Val Thr Leu Val Leu Ile Ile Val Gly
            500                 505                 510
Ala Val Gly Leu Gly Ser Pro Ser Pro Ala Pro Ala Ala Lys Lys Gln
        515                 520                 525
Ala Glu Lys Gly Lys Glu Lys Thr Ala Glu Ala Val Ser Thr Ala Ala
        530                 535                 540
Asp Asn Val Lys Gly Glu Ala Lys Lys Arg Ser Gly Lys Ala Gly Glu
545                 550                 555                 560

<210> SEQ ID NO 72
<211> LENGTH: 560
<212> TYPE: PRT
```

-continued

```
<213> ORGANISM: Homo sapiens
<220> FEATURE:
<221> NAME/KEY: BINDING SITE
<222> LOCATION: (1)..(18)
<220> FEATURE:
<221> NAME/KEY: BINDING SITE
<222> LOCATION: (103)..(111)
<220> FEATURE:
<221> NAME/KEY: BINDING SITE
<222> LOCATION: (130)..(143)
<220> FEATURE:
<221> NAME/KEY: BINDING SITE
<222> LOCATION: (179)..(193)
<220> FEATURE:
<221> NAME/KEY: BINDING SITE
<222> LOCATION: (358)..(366)
<220> FEATURE:
<221> NAME/KEY: BINDING SITE
<222> LOCATION: (470)..(478)
<220> FEATURE:
<221> NAME/KEY: BINDING SITE
<222> LOCATION: (502)..(518)
<220> FEATURE:
<221> NAME/KEY: BINDING SITE
<222> LOCATION: (547)..(555)

<400> SEQUENCE: 72

Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
            20                  25                  30

Ser Thr Ser Ser Val Ile Glu Lys Pro Thr Phe Thr Pro Thr Thr Leu
        35                  40                  45

Lys Ala Pro Phe Leu Glu Gln Phe Thr Asp Gly Trp Glu Thr Arg Trp
50                  55                  60

Thr Pro Ser His Ala Lys Lys Glu Asp Ser Lys Ser Glu Glu Asp Trp
65                  70                  75                  80

Ala Tyr Val Gly Thr Trp Ala Val Glu Glu Pro His Val Phe Asn Gly
                85                  90                  95

Met Val Gly Asp Lys Gly Leu Val Val Lys Asn Pro Ala Ala His His
            100                 105                 110

Ala Ile Ser Ala Lys Phe Pro Lys Lys Ile Asp Asn Lys Gly Lys Thr
        115                 120                 125

Leu Val Val Gln Tyr Glu Val Lys Leu Gln Asn Ser Leu Asn Cys Gly
    130                 135                 140

Gly Ala Tyr Met Lys Leu Leu Gln Asp Asn Lys Lys Leu His Ala Glu
145                 150                 155                 160

Glu Phe Ser Asn Thr Ser Pro Tyr Val Ile Met Phe Gly Pro Asp Lys
                165                 170                 175

Cys Gly Val Thr Asn Lys Val His Phe Ile Phe Lys His Lys Asn Pro
            180                 185                 190

Lys Thr Gly Glu Tyr Glu Glu Lys His Met Lys Leu Pro Pro Ala Val
        195                 200                 205

Arg Val Ser Lys Leu Ser Thr Leu Tyr Thr Leu Ile Val Asn Pro Asp
    210                 215                 220

Gln Ser Phe Gln Ile Arg Ile Asp Gly Ala Ala Val Lys Asn Gly Thr
225                 230                 235                 240

Leu Leu Glu Asp Phe Ser Pro Ala Val Asn Pro Glu Lys Glu Ile Asp
                245                 250                 255

Asp Pro Glu Asp Lys Lys Pro Glu Asp Trp Val Asp Glu Ala His Ile
            260                 265                 270
```

```
Pro Asp Pro Glu Ala Thr Lys Pro Glu Asp Trp Asp Glu Asp Ala Pro
            275                 280                 285

Tyr Glu Ile Val Asp Thr Asp Ala Thr Gln Pro Glu Asp Trp Leu Val
        290                 295                 300

Asp Glu Pro Thr Ser Ile Pro Asp Pro Glu Ala Gln Lys Pro Glu Asp
305                 310                 315                 320

Trp Asp Asp Glu Glu Asp Gly Asp Trp Ile Pro Pro Thr Ile Pro Asn
                325                 330                 335

Pro Lys Cys Ser Glu Val Ser Gly Cys Gly Met Trp Glu Pro Pro Met
            340                 345                 350

Lys Lys Asn Pro Glu Tyr Lys Gly Lys Trp Thr Ala Pro Met Ile Asp
        355                 360                 365

Asn Pro Ala Tyr Lys Gly Pro Trp Ala Pro Arg Lys Ile Ala Asn Pro
    370                 375                 380

Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
                405                 410                 415

Ile Tyr Ile Gly His Ser Val Glu Asp Ala Glu Lys Leu Lys Ala Glu
            420                 425                 430

Thr Trp Asp Leu Lys His Pro Val Glu Val Ala Glu Glu Ala Ala
        435                 440                 445

Arg Pro Lys Asp Glu Glu Lys Lys Glu Gly Thr Leu Ser Phe Lys Glu
    450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Glu Val Ala
                485                 490                 495

Gly Gly Leu Gly Ala Leu Leu Val Thr Leu Val Leu Ile Ile Val Gly
            500                 505                 510

Ala Val Gly Leu Gly Ser Pro Ser Pro Ala Pro Ala Ala Lys Lys Gln
        515                 520                 525

Ala Glu Lys Gly Lys Glu Lys Thr Ala Glu Ala Val Ser Thr Ala Ala
    530                 535                 540

Asp Asn Val Lys Gly Glu Ala Lys Lys Arg Ser Gly Lys Ala Gly Glu
545                 550                 555                 560

<210> SEQ ID NO 73
<211> LENGTH: 560
<212> TYPE: PRT
<213> ORGANISM: Homo sapiens
<220> FEATURE:
<221> NAME/KEY: BINDING SITE
<222> LOCATION: (1)..(9)
<220> FEATURE:
<221> NAME/KEY: BINDING SITE
<222> LOCATION: (103)..(111)
<220> FEATURE:
<221> NAME/KEY: BINDING SITE
<222> LOCATION: (130)..(138)
<220> FEATURE:
<221> NAME/KEY: BINDING SITE
<222> LOCATION: (168)..(176)
<220> FEATURE:
<221> NAME/KEY: BINDING SITE
<222> LOCATION: (185)..(195)
<220> FEATURE:
<221> NAME/KEY: BINDING SITE
<222> LOCATION: (358)..(366)
<220> FEATURE:
<221> NAME/KEY: BINDING SITE
```

```
<222> LOCATION: (418)..(426)
<220> FEATURE:
<221> NAME/KEY: BINDING SITE
<222> LOCATION: (510)..(518)

<400> SEQUENCE: 73
```

| | | | | | | | | | | | | | | |
|---|---|---|---|---|---|---|---|---|---|---|---|---|---|---|
| Met | Arg | Leu | Asn | Ala | Ser | Leu | Ala | Ser | Leu | Ile | Leu | Ser | Ser | Ile | Ala |
| 1 | | | | 5 | | | | | 10 | | | | | 15 | |

| Leu | Ile | Gly | Asn | Val | His | Ala | Glu | Asp | Glu | Val | Lys | Glu | Asp | Ala | Thr |
| | | | 20 | | | | | 25 | | | | | 30 | | |

| Ser | Thr | Ser | Ser | Val | Ile | Glu | Lys | Pro | Thr | Phe | Thr | Pro | Thr | Thr | Leu |
| | | 35 | | | | | 40 | | | | | 45 | | | |

| Lys | Ala | Pro | Phe | Leu | Glu | Gln | Phe | Thr | Asp | Gly | Trp | Glu | Thr | Arg | Trp |
| 50 | | | | | 55 | | | | | 60 | | | | | |

| Thr | Pro | Ser | His | Ala | Lys | Lys | Glu | Asp | Ser | Lys | Ser | Glu | Glu | Asp | Trp |
| 65 | | | | 70 | | | | | 75 | | | | | 80 | |

| Ala | Tyr | Val | Gly | Thr | Trp | Ala | Val | Glu | Glu | Pro | His | Val | Phe | Asn | Gly |
| | | | | 85 | | | | | 90 | | | | | 95 | |

| Met | Val | Gly | Asp | Lys | Gly | Leu | Val | Val | Lys | Asn | Pro | Ala | Ala | His | His |
| | | | 100 | | | | | 105 | | | | | 110 | | |

| Ala | Ile | Ser | Ala | Lys | Phe | Pro | Lys | Lys | Ile | Asp | Asn | Lys | Gly | Lys | Thr |
| | | | 115 | | | | | 120 | | | | | 125 | | |

| Leu | Val | Val | Gln | Tyr | Glu | Val | Lys | Leu | Gln | Asn | Ser | Leu | Asn | Cys | Gly |
| | 130 | | | | | 135 | | | | | 140 | | | | |

| Gly | Ala | Tyr | Met | Lys | Leu | Leu | Gln | Asp | Asn | Lys | Lys | Leu | His | Ala | Glu |
| 145 | | | | | 150 | | | | | 155 | | | | | 160 |

| Glu | Phe | Ser | Asn | Thr | Ser | Pro | Tyr | Val | Ile | Met | Phe | Gly | Pro | Asp | Lys |
| | | | | 165 | | | | | 170 | | | | | 175 | |

| Cys | Gly | Val | Thr | Asn | Lys | Val | His | Phe | Ile | Phe | Lys | His | Lys | Asn | Pro |
| | | | 180 | | | | | 185 | | | | | 190 | | |

| Lys | Thr | Gly | Glu | Tyr | Glu | Glu | Lys | His | Met | Lys | Leu | Pro | Pro | Ala | Val |
| | | | 195 | | | | | 200 | | | | | 205 | | |

| Arg | Val | Ser | Lys | Leu | Ser | Thr | Leu | Tyr | Thr | Leu | Ile | Val | Asn | Pro | Asp |
| | 210 | | | | | 215 | | | | | 220 | | | | |

| Gln | Ser | Phe | Gln | Ile | Arg | Ile | Asp | Gly | Ala | Ala | Val | Lys | Asn | Gly | Thr |
| 225 | | | | | 230 | | | | | 235 | | | | | 240 |

| Leu | Leu | Glu | Asp | Phe | Ser | Pro | Ala | Val | Asn | Pro | Glu | Lys | Glu | Ile | Asp |
| | | | | 245 | | | | | 250 | | | | | 255 | |

| Asp | Pro | Glu | Asp | Lys | Lys | Pro | Glu | Asp | Trp | Val | Asp | Glu | Ala | His | Ile |
| | | | 260 | | | | | 265 | | | | | 270 | | |

| Pro | Asp | Pro | Glu | Ala | Thr | Lys | Pro | Glu | Asp | Trp | Asp | Glu | Asp | Ala | Pro |
| | | | 275 | | | | | 280 | | | | | 285 | | |

| Tyr | Glu | Ile | Val | Asp | Thr | Asp | Ala | Thr | Gln | Pro | Glu | Asp | Trp | Leu | Val |
| | 290 | | | | | 295 | | | | | 300 | | | | |

| Asp | Glu | Pro | Thr | Ser | Ile | Pro | Asp | Pro | Glu | Ala | Gln | Lys | Pro | Glu | Asp |
| 305 | | | | | 310 | | | | | 315 | | | | | 320 |

| Trp | Asp | Asp | Glu | Glu | Asp | Gly | Asp | Trp | Ile | Pro | Thr | Ile | Pro | Asn | |
| | | | | 325 | | | | | 330 | | | | | 335 | |

| Pro | Lys | Cys | Ser | Glu | Val | Ser | Gly | Cys | Gly | Met | Trp | Glu | Pro | Pro | Met |
| | | | 340 | | | | | 345 | | | | | 350 | | |

| Lys | Lys | Asn | Pro | Glu | Tyr | Lys | Gly | Lys | Trp | Thr | Ala | Pro | Met | Ile | Asp |
| | | 355 | | | | | 360 | | | | | 365 | | | |

| Asn | Pro | Ala | Tyr | Lys | Gly | Pro | Trp | Ala | Pro | Arg | Lys | Ile | Ala | Asn | Pro |
| | 370 | | | | | 375 | | | | | 380 | | | | |

-continued

```
Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
                405                 410                 415

Ile Tyr Ile Gly His Ser Val Glu Asp Ala Glu Lys Leu Lys Ala Glu
            420                 425                 430

Thr Trp Asp Leu Lys His Pro Val Glu Val Ala Glu Glu Ala Ala
        435                 440                 445

Arg Pro Lys Asp Glu Glu Lys Glu Gly Thr Leu Ser Phe Lys Glu
    450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Glu Val Ala
                485                 490                 495

Gly Gly Leu Gly Ala Leu Leu Val Thr Leu Val Leu Ile Ile Val Gly
            500                 505                 510

Ala Val Gly Leu Gly Ser Pro Ser Pro Ala Pro Ala Ala Lys Lys Gln
        515                 520                 525

Ala Glu Lys Gly Lys Glu Lys Thr Ala Glu Ala Val Ser Thr Ala Ala
    530                 535                 540

Asp Asn Val Lys Gly Glu Ala Lys Lys Arg Ser Gly Lys Ala Gly Glu
545                 550                 555                 560
```

<210> SEQ ID NO 74
<211> LENGTH: 560
<212> TYPE: PRT
<213> ORGANISM: Homo sapiens
<220> FEATURE:
<221> NAME/KEY: BINDING SITE
<222> LOCATION: (1)..(9)
<220> FEATURE:
<221> NAME/KEY: BINDING SITE
<222> LOCATION: (103)..(112)
<220> FEATURE:
<221> NAME/KEY: BINDING SITE
<222> LOCATION: (130)..(143)
<220> FEATURE:
<221> NAME/KEY: BINDING SITE
<222> LOCATION: (183)..(191)
<220> FEATURE:
<221> NAME/KEY: BINDING SITE
<222> LOCATION: (216)..(224)
<220> FEATURE:
<221> NAME/KEY: BINDING SITE
<222> LOCATION: (358)..(366)
<220> FEATURE:
<221> NAME/KEY: BINDING SITE
<222> LOCATION: (476)..(484)
<220> FEATURE:
<221> NAME/KEY: BINDING SITE
<222> LOCATION: (510)..(518)

<400> SEQUENCE: 74

```
Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
                20                  25                  30

Ser Thr Ser Ser Val Ile Glu Lys Pro Thr Phe Thr Pro Thr Thr Leu
            35                  40                  45

Lys Ala Pro Phe Leu Glu Gln Phe Thr Asp Gly Trp Glu Thr Arg Trp
        50                  55                  60

Thr Pro Ser His Ala Lys Lys Glu Asp Ser Lys Ser Glu Glu Asp Trp
65                  70                  75                  80
```

```
Ala Tyr Val Gly Thr Trp Ala Val Glu Glu Pro His Val Phe Asn Gly
                 85                  90                  95
Met Val Gly Asp Lys Gly Leu Val Val Lys Asn Pro Ala Ala His His
            100                 105                 110
Ala Ile Ser Ala Lys Phe Pro Lys Lys Ile Asp Asn Lys Gly Lys Thr
        115                 120                 125
Leu Val Val Gln Tyr Glu Val Lys Leu Gln Asn Ser Leu Asn Cys Gly
    130                 135                 140
Gly Ala Tyr Met Lys Leu Leu Gln Asp Asn Lys Lys Leu His Ala Glu
145                 150                 155                 160
Glu Phe Ser Asn Thr Ser Pro Tyr Val Ile Met Phe Gly Pro Asp Lys
                165                 170                 175
Cys Gly Val Thr Asn Lys Val His Phe Ile Phe Lys His Lys Asn Pro
            180                 185                 190
Lys Thr Gly Glu Tyr Glu Glu Lys His Met Lys Leu Pro Pro Ala Val
        195                 200                 205
Arg Val Ser Lys Leu Ser Thr Leu Tyr Thr Leu Ile Val Asn Pro Asp
    210                 215                 220
Gln Ser Phe Gln Ile Arg Ile Asp Gly Ala Ala Val Lys Asn Gly Thr
225                 230                 235                 240
Leu Leu Glu Asp Phe Ser Pro Ala Val Asn Pro Glu Lys Glu Ile Asp
                245                 250                 255
Asp Pro Glu Asp Lys Lys Pro Glu Asp Trp Val Asp Glu Ala His Ile
            260                 265                 270
Pro Asp Pro Glu Ala Thr Lys Pro Glu Asp Trp Asp Glu Asp Ala Pro
        275                 280                 285
Tyr Glu Ile Val Asp Thr Asp Ala Thr Gln Pro Glu Asp Trp Leu Val
    290                 295                 300
Asp Glu Pro Thr Ser Ile Pro Asp Pro Glu Ala Gln Lys Pro Glu Asp
305                 310                 315                 320
Trp Asp Asp Glu Glu Asp Gly Asp Trp Ile Pro Pro Thr Ile Pro Asn
                325                 330                 335
Pro Lys Cys Ser Glu Val Ser Gly Cys Gly Met Trp Glu Pro Pro Met
            340                 345                 350
Lys Lys Asn Pro Glu Tyr Lys Gly Lys Trp Thr Ala Pro Met Ile Asp
        355                 360                 365
Asn Pro Ala Tyr Lys Gly Pro Trp Ala Pro Arg Lys Ile Ala Asn Pro
    370                 375                 380
Asn Tyr Phe Glu Asp Lys Thr Pro Ser Asn Phe Glu Pro Met Gly Ala
385                 390                 395                 400
Ile Gly Phe Glu Ile Trp Thr Met Gln Asn Asp Ile Leu Phe Asp Asn
                405                 410                 415
Ile Tyr Ile Gly His Ser Val Glu Asp Ala Glu Lys Leu Lys Ala Glu
            420                 425                 430
Thr Trp Asp Leu Lys His Pro Val Glu Val Ala Glu Glu Ala Ala
        435                 440                 445
Arg Pro Lys Asp Glu Lys Lys Glu Gly Thr Leu Ser Phe Lys Glu
    450                 455                 460
Ala Pro Val Lys Tyr Ile Arg Gly Lys Ile Glu Leu Phe Ile Ser Leu
465                 470                 475                 480
Ala Leu Glu Asn Pro Val Glu Ala Val Lys Ala Val Pro Glu Val Ala
                485                 490                 495
```

```
Gly Gly Leu Gly Ala Leu Leu Val Thr Leu Val Leu Ile Ile Val Gly
            500                 505                 510
Ala Val Gly Leu Gly Ser Pro Ser Pro Ala Pro Ala Ala Lys Lys Gln
        515                 520                 525
Ala Glu Lys Gly Lys Glu Lys Thr Ala Glu Ala Val Ser Thr Ala Ala
    530                 535                 540
Asp Asn Val Lys Gly Glu Ala Lys Lys Arg Ser Gly Lys Ala Gly Glu
545                 550                 555                 560

<210> SEQ ID NO 75
<211> LENGTH: 560
<212> TYPE: PRT
<213> ORGANISM: Homo sapiens
<220> FEATURE:
<221> NAME/KEY: BINDING SITE
<222> LOCATION: (1)..(9)
<220> FEATURE:
<221> NAME/KEY: BINDING SITE
<222> LOCATION: (168)..(176)
<220> FEATURE:
<221> NAME/KEY: BINDING SITE
<222> LOCATION: (213)..(221)
<220> FEATURE:
<221> NAME/KEY: BINDING SITE
<222> LOCATION: (358)..(366)
<220> FEATURE:
<221> NAME/KEY: BINDING SITE
<222> LOCATION: (395)..(403)
<220> FEATURE:
<221> NAME/KEY: BINDING SITE
<222> LOCATION: (502)..(514)

<400> SEQUENCE: 75

Met Arg Leu Asn Ala Ser Leu Ala Ser Leu Ile Leu Ser Ser Ile Ala
1               5                   10                  15
Leu Ile Gly Asn Val His Ala Glu Asp Glu Val Lys Glu Asp Ala Thr
            20                  25                  30
Ser Thr Ser Ser Val Ile Glu Lys Pro Thr Phe Thr Pro Thr Thr Leu
        35                  40                  45
Lys Ala Pro Phe Leu Glu Gln Phe Thr Asp Gly Trp Glu Thr Arg Trp
    50                  55                  60
Thr Pro Ser His Ala Lys Lys Glu Asp Ser Lys Ser Glu Glu Asp Trp
65                  70                  75                  80
Ala Tyr Val Gly Thr Trp Ala Val Glu Glu Pro His Val Phe Asn Gly
            85                  90                  95
Met Val Gly Asp Lys Gly Leu Val Val Lys Asn Pro Ala Ala His His
            100                 105                 110
Ala Ile Ser Ala Lys Phe Pro Lys Lys Ile Asp Asn Lys Gly Lys Thr
        115                 120                 125
Leu Val Val Gln Tyr Glu Val Lys Leu Gln Asn Ser Leu Asn Cys Gly
    130                 135                 140
Gly Ala Tyr Met Lys Leu Leu Gln Asp Asn Lys Lys Leu His Ala Glu
145                 150                 155                 160
Glu Phe Ser Asn Thr Ser Pro Tyr Val Ile Met Phe Gly Pro Asp Lys
            165                 170                 175
Cys Gly Val Thr Asn Lys Val His Phe Ile Phe Lys His Lys Asn Pro
            180                 185                 190
Lys Thr Gly Glu Tyr Glu Glu Lys His Met Lys Leu Pro Pro Ala Val
        195                 200                 205
Arg Val Ser Lys Leu Ser Thr Leu Tyr Thr Leu Ile Val Asn Pro Asp
    210                 215                 220
```

```
Gln Ser Phe Gln Ile Arg Ile Asp Gly Ala Ala Val Lys Asn Gly Thr
225                 230                 235                 240

Leu Leu Glu Asp Phe Ser Pro Ala Val Asn Pro Glu Lys Glu Ile Asp
            245                 250                 255

Asp Pro Asp Lys Lys Pro Glu Asp Trp Val Asp Glu Ala His Ile
        260                 265                 270

Pro Asp Pro Glu Ala Thr Lys Pro Glu Asp Trp Asp Glu Asp Ala Pro
        275                 280                 285

Tyr Glu Ile Val Asp Thr Asp Ala Thr Gln Pro Glu Asp Trp Leu Val
        290                 295                 300

Asp Glu Pro Thr Ser Ile Pro Asp Pro Glu Ala Gln Lys Pro Glu Asp
305                 310                 315                 320

Trp Asp Asp Glu Glu Asp Gly Asp Trp Ile Pro Pro Thr Ile Pro Asn
                325                 330                 335

Pro Lys Cys Ser Glu Val Ser Gly Cys Gly Met Trp Glu Pro Pro Met
                340                 345                 350

Lys Lys Asn Pro Glu Tyr Lys Gly Lys Trp Thr Ala Pro Met Ile Asp
            355                 360                 365

Asn Pro Ala Tyr Lys Gly Pro Trp Ala Pro Arg Lys Ile Ala Asn Pro
370                 375                 380

Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
                405                 410                 415

Ile Tyr Ile Gly His Ser Val Glu Asp Ala Glu Lys Leu Lys Ala Glu
            420                 425                 430

Thr Trp Asp Leu Lys His Pro Val Glu Val Ala Glu Glu Ala Ala
            435                 440                 445

Arg Pro Lys Asp Glu Glu Lys Lys Glu Gly Thr Leu Ser Phe Lys Glu
    450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Glu Val Ala
                485                 490                 495

Gly Gly Leu Gly Ala Leu Leu Val Thr Leu Val Leu Ile Ile Val Gly
            500                 505                 510

Ala Val Gly Leu Gly Ser Pro Ser Pro Ala Pro Ala Ala Lys Lys Gln
            515                 520                 525

Ala Glu Lys Gly Lys Glu Lys Thr Ala Glu Ala Val Ser Thr Ala Ala
        530                 535                 540

Asp Asn Val Lys Gly Glu Ala Lys Lys Arg Ser Gly Lys Ala Gly Glu
545                 550                 555                 560

<210> SEQ ID NO 76
<211> LENGTH: 560
<212> TYPE: PRT
<213> ORGANISM: Homo sapiens
<220> FEATURE:
<221> NAME/KEY: BINDING SITE
<222> LOCATION: (1)..(18)
<220> FEATURE:
<221> NAME/KEY: BINDING SITE
<222> LOCATION: (103)..(112)
<220> FEATURE:
<221> NAME/KEY: BINDING SITE
<222> LOCATION: (130)..(138)
<220> FEATURE:
```

```
<221> NAME/KEY: BINDING SITE
<222> LOCATION: (168)..(176)
<220> FEATURE:
<221> NAME/KEY: BINDING SITE
<222> LOCATION: (185)..(193)
<220> FEATURE:
<221> NAME/KEY: BINDING SITE
<222> LOCATION: (217)..(225)
<220> FEATURE:
<221> NAME/KEY: BINDING SITE
<222> LOCATION: (229)..(237)
<220> FEATURE:
<221> NAME/KEY: BINDING SITE
<222> LOCATION: (358)..(366)
<220> FEATURE:
<221> NAME/KEY: BINDING SITE
<222> LOCATION: (414)..(422)
<220> FEATURE:
<221> NAME/KEY: BINDING SITE
<222> LOCATION: (503)..(518)

<400> SEQUENCE: 76
```

Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
            20                  25                  30

Ser Thr Ser Ser Val Ile Glu Lys Pro Thr Phe Thr Pro Thr Thr Leu
        35                  40                  45

Lys Ala Pro Phe Leu Glu Gln Phe Thr Asp Gly Trp Glu Thr Arg Trp
50                  55                  60

Thr Pro Ser His Ala Lys Lys Glu Asp Ser Lys Ser Glu Glu Asp Trp
65                  70                  75                  80

Ala Tyr Val Gly Thr Trp Ala Val Glu Glu Pro His Val Phe Asn Gly
                85                  90                  95

Met Val Gly Asp Lys Gly Leu Val Val Lys Asn Pro Ala Ala His His
            100                 105                 110

Ala Ile Ser Ala Lys Phe Pro Lys Lys Ile Asp Asn Lys Gly Lys Thr
        115                 120                 125

Leu Val Val Gln Tyr Glu Val Lys Leu Gln Asn Ser Leu Asn Cys Gly
130                 135                 140

Gly Ala Tyr Met Lys Leu Leu Gln Asp Asn Lys Lys Leu His Ala Glu
145                 150                 155                 160

Glu Phe Ser Asn Thr Ser Pro Tyr Val Ile Met Phe Gly Pro Asp Lys
                165                 170                 175

Cys Gly Val Thr Asn Lys Val His Phe Ile Phe Lys His Lys Asn Pro
            180                 185                 190

Lys Thr Gly Glu Tyr Glu Glu Lys His Met Lys Leu Pro Pro Ala Val
        195                 200                 205

Arg Val Ser Lys Leu Ser Thr Leu Tyr Thr Leu Ile Val Asn Pro Asp
210                 215                 220

Gln Ser Phe Gln Ile Arg Ile Asp Gly Ala Ala Val Lys Asn Gly Thr
225                 230                 235                 240

Leu Leu Glu Asp Phe Ser Pro Ala Val Asn Pro Glu Lys Glu Ile Asp
                245                 250                 255

Asp Pro Glu Asp Lys Lys Pro Glu Asp Trp Val Asp Glu Ala His Ile
            260                 265                 270

Pro Asp Pro Glu Ala Thr Lys Pro Glu Asp Trp Asp Glu Asp Ala Pro
        275                 280                 285

Tyr Glu Ile Val Asp Thr Asp Ala Thr Gln Pro Glu Asp Trp Leu Val
290                 295                 300

```
Asp Glu Pro Thr Ser Ile Pro Asp Pro Glu Ala Gln Lys Pro Glu Asp
305                 310                 315                 320

Trp Asp Asp Glu Glu Asp Gly Asp Trp Ile Pro Pro Thr Ile Pro Asn
                325                 330                 335

Pro Lys Cys Ser Glu Val Ser Gly Cys Gly Met Trp Glu Pro Pro Met
            340                 345                 350

Lys Lys Asn Pro Glu Tyr Lys Gly Lys Trp Thr Ala Pro Met Ile Asp
        355                 360                 365

Asn Pro Ala Tyr Lys Gly Pro Trp Ala Pro Arg Lys Ile Ala Asn Pro
    370                 375                 380

Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
                405                 410                 415

Ile Tyr Ile Gly His Ser Val Glu Asp Ala Glu Lys Leu Lys Ala Glu
            420                 425                 430

Thr Trp Asp Leu Lys His Pro Val Glu Val Ala Glu Glu Ala Ala
        435                 440                 445

Arg Pro Lys Asp Glu Lys Lys Glu Gly Thr Leu Ser Phe Lys Glu
    450                 455                 460

Ala Pro Val Lys Tyr Ile Arg Gly Lys Ile Glu Leu Phe Ile Ser Leu
465                 470                 475                 480

Ala Leu Glu Asn Pro Val Ala Val Lys Ala Val Pro Glu Val Ala
                485                 490                 495

Gly Gly Leu Gly Ala Leu Leu Val Thr Leu Val Leu Ile Ile Val Gly
            500                 505                 510

Ala Val Gly Leu Gly Ser Pro Ser Pro Ala Pro Ala Ala Lys Lys Gln
        515                 520                 525

Ala Glu Lys Gly Lys Glu Lys Thr Ala Glu Ala Val Ser Thr Ala Ala
        530                 535                 540

Asp Asn Val Lys Gly Glu Ala Lys Lys Arg Ser Gly Lys Ala Gly Glu
545                 550                 555                 560

<210> SEQ ID NO 77
<211> LENGTH: 560
<212> TYPE: PRT
<213> ORGANISM: Homo sapiens
<220> FEATURE:
<221> NAME/KEY: BINDING SITE
<222> LOCATION: (1)..(9)
<220> FEATURE:
<221> NAME/KEY: BINDING SITE
<222> LOCATION: (103)..(112)
<220> FEATURE:
<221> NAME/KEY: BINDING SITE
<222> LOCATION: (130)..(143)
<220> FEATURE:
<221> NAME/KEY: BINDING SITE
<222> LOCATION: (151)..(159)
<220> FEATURE:
<221> NAME/KEY: BINDING SITE
<222> LOCATION: (168)..(176)
<220> FEATURE:
<221> NAME/KEY: BINDING SITE
<222> LOCATION: (183)..(191)
<220> FEATURE:
<221> NAME/KEY: BINDING SITE
<222> LOCATION: (213)..(221)
<220> FEATURE:
<221> NAME/KEY: BINDING SITE
<222> LOCATION: (502)..(518)
```

<400> SEQUENCE: 77

```
Met Arg Leu Asn Ala Ser Leu Ala Ser Leu Ile Leu Ser Ser Ile Ala
1               5                   10                  15
Leu Ile Gly Asn Val His Ala Glu Asp Glu Val Lys Glu Asp Ala Thr
            20                  25                  30
Ser Thr Ser Ser Val Ile Glu Lys Pro Thr Phe Pro Thr Thr Leu
        35                  40                  45
Lys Ala Pro Phe Leu Glu Gln Phe Thr Asp Gly Trp Glu Thr Arg Trp
    50                  55                  60
Thr Pro Ser His Ala Lys Lys Glu Asp Ser Lys Ser Glu Glu Asp Trp
65                  70                  75                  80
Ala Tyr Val Gly Thr Trp Ala Val Glu Glu Pro His Val Phe Asn Gly
                85                  90                  95
Met Val Gly Asp Lys Gly Leu Val Val Lys Asn Pro Ala Ala His His
            100                 105                 110
Ala Ile Ser Ala Lys Phe Pro Lys Lys Ile Asp Asn Lys Gly Lys Thr
        115                 120                 125
Leu Val Val Gln Tyr Glu Val Lys Leu Gln Asn Ser Leu Asn Cys Gly
    130                 135                 140
Gly Ala Tyr Met Lys Leu Leu Gln Asp Asn Lys Lys Leu His Ala Glu
145                 150                 155                 160
Glu Phe Ser Asn Thr Ser Pro Tyr Val Ile Met Phe Gly Pro Asp Lys
                165                 170                 175
Cys Gly Val Thr Asn Lys Val His Phe Ile Phe Lys His Lys Asn Pro
            180                 185                 190
Lys Thr Gly Glu Tyr Glu Glu Lys His Met Lys Leu Pro Pro Ala Val
        195                 200                 205
Arg Val Ser Lys Leu Ser Thr Leu Tyr Thr Leu Ile Val Asn Pro Asp
    210                 215                 220
Gln Ser Phe Gln Ile Arg Ile Asp Gly Ala Ala Val Lys Asn Gly Thr
225                 230                 235                 240
Leu Leu Glu Asp Phe Ser Pro Ala Val Asn Pro Glu Lys Glu Ile Asp
                245                 250                 255
Asp Pro Glu Asp Lys Lys Pro Glu Asp Trp Val Asp Glu Ala His Ile
            260                 265                 270
Pro Asp Pro Glu Ala Thr Lys Pro Glu Asp Trp Asp Glu Asp Ala Pro
        275                 280                 285
Tyr Glu Ile Val Asp Thr Asp Ala Thr Gln Pro Glu Asp Trp Leu Val
    290                 295                 300
Asp Glu Pro Thr Ser Ile Pro Asp Pro Glu Ala Gln Lys Pro Glu Asp
305                 310                 315                 320
Trp Asp Asp Glu Glu Asp Gly Asp Trp Ile Pro Pro Thr Ile Pro Asn
                325                 330                 335
Pro Lys Cys Ser Glu Val Ser Gly Cys Gly Met Trp Glu Pro Pro Met
            340                 345                 350
Lys Lys Asn Pro Glu Tyr Lys Gly Lys Trp Thr Ala Pro Met Ile Asp
        355                 360                 365
Asn Pro Ala Tyr Lys Gly Pro Trp Ala Pro Arg Lys Ile Ala Asn Pro
    370                 375                 380
Asn Tyr Phe Glu Asp Lys Thr Pro Ser Asn Phe Glu Pro Met Gly Ala
385                 390                 395                 400
Ile Gly Phe Glu Ile Trp Thr Met Gln Asn Asp Ile Leu Phe Asp Asn
                405                 410                 415
```

```
Ile Tyr Ile Gly His Ser Val Glu Asp Ala Glu Lys Leu Lys Ala Glu
            420                 425                 430

Thr Trp Asp Leu Lys His Pro Val Glu Val Ala Glu Glu Ala Ala
            435                 440                 445

Arg Pro Lys Asp Glu Lys Lys Glu Gly Thr Leu Ser Phe Lys Glu
450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Glu Val Ala
                485                 490                 495

Gly Gly Leu Gly Ala Leu Leu Val Thr Leu Val Leu Ile Ile Val Gly
                500                 505                 510

Ala Val Gly Leu Gly Ser Pro Ser Pro Ala Pro Ala Ala Lys Lys Gln
            515                 520                 525

Ala Glu Lys Gly Lys Glu Lys Thr Ala Glu Ala Val Ser Thr Ala Ala
            530                 535                 540

Asp Asn Val Lys Gly Glu Ala Lys Lys Arg Ser Gly Lys Ala Gly Glu
545                 550                 555                 560

<210> SEQ ID NO 78
<211> LENGTH: 560
<212> TYPE: PRT
<213> ORGANISM: Homo sapiens
<220> FEATURE:
<221> NAME/KEY: BINDING SITE
<222> LOCATION: (1)..(9)
<220> FEATURE:
<221> NAME/KEY: BINDING SITE
<222> LOCATION: (82)..(90)
<220> FEATURE:
<221> NAME/KEY: BINDING SITE
<222> LOCATION: (103)..(112)
<220> FEATURE:
<221> NAME/KEY: BINDING SITE
<222> LOCATION: (130)..(139)
<220> FEATURE:
<221> NAME/KEY: BINDING SITE
<222> LOCATION: (168)..(176)
<220> FEATURE:
<221> NAME/KEY: BINDING SITE
<222> LOCATION: (183)..(191)
<220> FEATURE:
<221> NAME/KEY: BINDING SITE
<222> LOCATION: (216)..(224)
<220> FEATURE:
<221> NAME/KEY: BINDING SITE
<222> LOCATION: (358)..(366)
<220> FEATURE:
<221> NAME/KEY: BINDING SITE
<222> LOCATION: (467)..(484)
<220> FEATURE:
<221> NAME/KEY: BINDING SITE
<222> LOCATION: (502)..(514)

<400> SEQUENCE: 78

Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
                20                  25                  30

Ser Thr Ser Ser Val Ile Glu Lys Pro Thr Phe Thr Pro Thr Thr Leu
            35                  40                  45

Lys Ala Pro Phe Leu Glu Gln Phe Thr Asp Gly Trp Glu Thr Arg Trp
50                  55                  60

Thr Pro Ser His Ala Lys Lys Glu Asp Ser Lys Ser Glu Glu Asp Trp
```

```
                65                  70                  75                  80
Ala Tyr Val Gly Thr Trp Ala Val Glu Glu Pro His Val Phe Asn Gly
                    85                  90                  95

Met Val Gly Asp Lys Gly Leu Val Val Lys Asn Pro Ala Ala His His
                    100                 105                 110

Ala Ile Ser Ala Lys Phe Pro Lys Ile Asp Asn Lys Gly Lys Thr
                115                 120                 125

Leu Val Val Gln Tyr Glu Val Lys Leu Gln Asn Ser Leu Asn Cys Gly
            130                 135                 140

Gly Ala Tyr Met Lys Leu Leu Gln Asp Asn Lys Lys Leu His Ala Glu
145                 150                 155                 160

Glu Phe Ser Asn Thr Ser Pro Tyr Val Ile Met Phe Gly Pro Asp Lys
                    165                 170                 175

Cys Gly Val Thr Asn Lys Val His Phe Ile Phe Lys His Lys Asn Pro
                180                 185                 190

Lys Thr Gly Glu Tyr Glu Glu Lys His Met Lys Leu Pro Pro Ala Val
                195                 200                 205

Arg Val Ser Lys Leu Ser Thr Leu Tyr Thr Leu Ile Val Asn Pro Asp
210                 215                 220

Gln Ser Phe Gln Ile Arg Ile Asp Gly Ala Ala Val Lys Asn Gly Thr
225                 230                 235                 240

Leu Leu Glu Asp Phe Ser Pro Ala Val Asn Pro Glu Lys Glu Ile Asp
                245                 250                 255

Asp Pro Glu Asp Lys Lys Pro Glu Asp Trp Val Asp Glu Ala His Ile
                260                 265                 270

Pro Asp Pro Glu Ala Thr Lys Pro Glu Asp Trp Asp Glu Asp Ala Pro
            275                 280                 285

Tyr Glu Ile Val Asp Thr Asp Ala Thr Gln Pro Glu Asp Trp Leu Val
                290                 295                 300

Asp Glu Pro Thr Ser Ile Pro Asp Pro Glu Ala Gln Lys Pro Glu Asp
305                 310                 315                 320

Trp Asp Asp Glu Glu Asp Gly Asp Trp Ile Pro Pro Thr Ile Pro Asn
                    325                 330                 335

Pro Lys Cys Ser Glu Val Ser Gly Cys Gly Met Trp Glu Pro Pro Met
                340                 345                 350

Lys Lys Asn Pro Glu Tyr Lys Gly Lys Trp Thr Ala Pro Met Ile Asp
                355                 360                 365

Asn Pro Ala Tyr Lys Gly Pro Trp Ala Pro Arg Lys Ile Ala Asn Pro
                370                 375                 380

Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
                    405                 410                 415

Ile Tyr Ile Gly His Ser Val Glu Asp Ala Glu Lys Leu Lys Ala Glu
                420                 425                 430

Thr Trp Asp Leu Lys His Pro Val Glu Val Ala Glu Glu Ala Ala
            435                 440                 445

Arg Pro Lys Asp Glu Lys Lys Glu Gly Thr Leu Ser Phe Lys Glu
                450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Glu Val Ala
                485                 490                 495
```

```
Gly Gly Leu Gly Ala Leu Leu Val Thr Leu Val Leu Ile Ile Val Gly
            500                 505                 510

Ala Val Gly Leu Gly Ser Pro Ser Pro Ala Pro Ala Ala Lys Lys Gln
            515                 520                 525

Ala Glu Lys Gly Lys Glu Lys Thr Ala Glu Ala Val Ser Thr Ala Ala
530                 535                 540

Asp Asn Val Lys Gly Glu Ala Lys Lys Arg Ser Gly Lys Ala Gly Glu
545                 550                 555                 560

<210> SEQ ID NO 79
<211> LENGTH: 560
<212> TYPE: PRT
<213> ORGANISM: Homo sapiens
<220> FEATURE:
<221> NAME/KEY: BINDING SITE
<222> LOCATION: (1)..(18)
<220> FEATURE:
<221> NAME/KEY: BINDING SITE
<222> LOCATION: (103)..(112)
<220> FEATURE:
<221> NAME/KEY: BINDING SITE
<222> LOCATION: (130)..(143)
<220> FEATURE:
<221> NAME/KEY: BINDING SITE
<222> LOCATION: (168)..(177)
<220> FEATURE:
<221> NAME/KEY: BINDING SITE
<222> LOCATION: (185)..(193)
<220> FEATURE:
<221> NAME/KEY: BINDING SITE
<222> LOCATION: (229)..(237)
<220> FEATURE:
<221> NAME/KEY: BINDING SITE
<222> LOCATION: (418)..(426)
<220> FEATURE:
<221> NAME/KEY: BINDING SITE
<222> LOCATION: (470)..(478)
<220> FEATURE:
<221> NAME/KEY: BINDING SITE
<222> LOCATION: (510)..(518)
<220> FEATURE:
<221> NAME/KEY: BINDING SITE
<222> LOCATION: (547)..(555)

<400> SEQUENCE: 79

Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
            20                  25                  30

Ser Thr Ser Ser Val Ile Glu Lys Pro Thr Phe Thr Pro Thr Thr Leu
        35                  40                  45

Lys Ala Pro Phe Leu Glu Gln Phe Thr Asp Gly Trp Glu Thr Arg Trp
    50                  55                  60

Thr Pro Ser His Ala Lys Lys Glu Asp Ser Lys Ser Glu Glu Asp Trp
65                  70                  75                  80

Ala Tyr Val Gly Thr Trp Ala Val Glu Glu Pro His Val Phe Asn Gly
                85                  90                  95

Met Val Gly Asp Lys Gly Leu Val Val Lys Asn Pro Ala Ala His His
            100                 105                 110

Ala Ile Ser Ala Lys Phe Pro Lys Lys Ile Asp Asn Lys Gly Lys Thr
        115                 120                 125

Leu Val Val Gln Tyr Glu Val Lys Leu Gln Asn Ser Leu Asn Cys Gly
    130                 135                 140

Gly Ala Tyr Met Lys Leu Leu Gln Asp Asn Lys Lys Leu His Ala Glu
```

```
            145                 150                 155                 160
        Glu Phe Ser Asn Thr Ser Pro Tyr Val Ile Met Phe Gly Pro Asp Lys
                        165                 170                 175

Cys Gly Val Thr Asn Lys Val His Phe Ile Phe Lys His Lys Asn Pro
                        180                 185                 190

Lys Thr Gly Glu Tyr Glu Lys His Met Lys Leu Pro Ala Val
                        195                 200                 205

Arg Val Ser Lys Leu Ser Thr Leu Tyr Thr Leu Ile Val Asn Pro Asp
        210                 215                 220

Gln Ser Phe Gln Ile Arg Ile Asp Gly Ala Ala Val Lys Asn Gly Thr
        225                 230                 235                 240

Leu Leu Glu Asp Phe Ser Pro Ala Val Asn Pro Glu Lys Glu Ile Asp
                        245                 250                 255

Asp Pro Glu Asp Lys Pro Glu Asp Trp Val Asp Glu Ala His Ile
                        260                 265                 270

Pro Asp Pro Glu Ala Thr Lys Pro Glu Asp Trp Asp Glu Asp Ala Pro
                        275                 280                 285

Tyr Glu Ile Val Asp Thr Asp Ala Thr Gln Pro Glu Asp Trp Leu Val
                        290                 295                 300

Asp Glu Pro Thr Ser Ile Pro Asp Pro Glu Ala Gln Lys Pro Glu Asp
        305                 310                 315                 320

Trp Asp Asp Glu Glu Asp Gly Asp Trp Ile Pro Pro Thr Ile Pro Asn
                        325                 330                 335

Pro Lys Cys Ser Glu Val Ser Gly Cys Gly Met Trp Glu Pro Pro Met
                        340                 345                 350

Lys Lys Asn Pro Glu Tyr Lys Gly Lys Trp Thr Ala Pro Met Ile Asp
                        355                 360                 365

Asn Pro Ala Tyr Lys Gly Pro Trp Ala Pro Arg Lys Ile Ala Asn Pro
                        370                 375                 380

Asn Tyr Phe Glu Asp Lys Thr Pro Ser Asn Phe Glu Pro Met Gly Ala
        385                 390                 395                 400

Ile Gly Phe Glu Ile Trp Thr Met Gln Asn Asp Ile Leu Phe Asp Asn
                        405                 410                 415

Ile Tyr Ile Gly His Ser Val Glu Asp Ala Glu Lys Leu Lys Ala Glu
                        420                 425                 430

Thr Trp Asp Leu Lys His Pro Val Glu Val Ala Glu Glu Ala Ala
                        435                 440                 445

Arg Pro Lys Asp Glu Lys Lys Glu Gly Thr Leu Ser Phe Lys Glu
        450                 455                 460

Ala Pro Val Lys Tyr Ile Arg Gly Lys Ile Glu Leu Phe Ile Ser Leu
        465                 470                 475                 480

Ala Leu Glu Asn Pro Val Glu Ala Val Lys Ala Val Pro Glu Val Ala
                        485                 490                 495

Gly Gly Leu Gly Ala Leu Leu Val Thr Leu Val Leu Ile Ile Val Gly
                        500                 505                 510

Ala Val Gly Leu Gly Ser Pro Ser Pro Ala Pro Ala Ala Lys Lys Gln
                        515                 520                 525

Ala Glu Lys Gly Lys Glu Lys Thr Ala Glu Ala Val Ser Thr Ala Ala
                        530                 535                 540

Asp Asn Val Lys Gly Glu Ala Lys Lys Arg Ser Gly Lys Ala Gly Glu
        545                 550                 555                 560

<210> SEQ ID NO 80
```

```
<211> LENGTH: 560
<212> TYPE: PRT
<213> ORGANISM: Homo sapiens
<220> FEATURE:
<221> NAME/KEY: BINDING SITE
<222> LOCATION: (1)..(9)
<220> FEATURE:
<221> NAME/KEY: BINDING SITE
<222> LOCATION: (103)..(111)
<220> FEATURE:
<221> NAME/KEY: BINDING SITE
<222> LOCATION: (130)..(143)
<220> FEATURE:
<221> NAME/KEY: BINDING SITE
<222> LOCATION: (168)..(177)
<220> FEATURE:
<221> NAME/KEY: BINDING SITE
<222> LOCATION: (185)..(195)
<220> FEATURE:
<221> NAME/KEY: BINDING SITE
<222> LOCATION: (358)..(366)
<220> FEATURE:
<221> NAME/KEY: BINDING SITE
<222> LOCATION: (418)..(426)
<220> FEATURE:
<221> NAME/KEY: BINDING SITE
<222> LOCATION: (510)..(518)

<400> SEQUENCE: 80
```

Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
            20                  25                  30

Ser Thr Ser Ser Val Ile Glu Lys Pro Thr Phe Thr Pro Thr Thr Leu
        35                  40                  45

Lys Ala Pro Phe Leu Glu Gln Phe Thr Asp Gly Trp Glu Thr Arg Trp
    50                  55                  60

Thr Pro Ser His Ala Lys Lys Glu Asp Ser Lys Ser Glu Glu Asp Trp
65                  70                  75                  80

Ala Tyr Val Gly Thr Trp Ala Val Glu Glu Pro His Val Phe Asn Gly
                85                  90                  95

Met Val Gly Asp Lys Gly Leu Val Val Lys Asn Pro Ala Ala His His
            100                 105                 110

Ala Ile Ser Ala Lys Phe Pro Lys Lys Ile Asp Asn Lys Gly Lys Thr
        115                 120                 125

Leu Val Val Gln Tyr Glu Val Lys Leu Gln Asn Ser Leu Asn Cys Gly
    130                 135                 140

Gly Ala Tyr Met Lys Leu Leu Gln Asp Asn Lys Lys Leu His Ala Glu
145                 150                 155                 160

Glu Phe Ser Asn Thr Ser Pro Tyr Val Ile Met Phe Gly Pro Asp Lys
                165                 170                 175

Cys Gly Val Thr Asn Lys Val His Phe Ile Phe Lys His Lys Asn Pro
            180                 185                 190

Lys Thr Gly Glu Tyr Glu Glu Lys His Met Lys Leu Pro Pro Ala Val
        195                 200                 205

Arg Val Ser Lys Leu Ser Thr Leu Tyr Thr Leu Ile Val Asn Pro Asp
    210                 215                 220

Gln Ser Phe Gln Ile Arg Ile Asp Gly Ala Ala Val Lys Asn Gly Thr
225                 230                 235                 240

Leu Leu Glu Asp Phe Ser Pro Ala Val Asn Pro Glu Lys Glu Ile Asp
                245                 250                 255

Asp Pro Glu Asp Lys Lys Pro Glu Asp Trp Val Asp Glu Ala His Ile

```
            260                 265                 270
Pro Asp Pro Glu Ala Thr Lys Pro Glu Asp Trp Asp Glu Asp Ala Pro
            275                 280                 285

Tyr Glu Ile Val Asp Thr Asp Ala Thr Gln Pro Glu Asp Trp Leu Val
            290                 295                 300

Asp Glu Pro Thr Ser Ile Pro Asp Pro Glu Ala Gln Lys Pro Glu Asp
305                 310                 315                 320

Trp Asp Asp Glu Glu Asp Gly Asp Trp Ile Pro Pro Thr Ile Pro Asn
                325                 330                 335

Pro Lys Cys Ser Glu Val Ser Gly Cys Gly Met Trp Glu Pro Pro Met
                340                 345                 350

Lys Lys Asn Pro Glu Tyr Lys Gly Lys Trp Thr Ala Pro Met Ile Asp
                355                 360                 365

Asn Pro Ala Tyr Lys Gly Pro Trp Ala Pro Arg Lys Ile Ala Asn Pro
                370                 375                 380

Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
                405                 410                 415

Ile Tyr Ile Gly His Ser Val Glu Asp Ala Glu Lys Leu Lys Ala Glu
                420                 425                 430

Thr Trp Asp Leu Lys His Pro Val Glu Val Ala Glu Glu Ala Ala
                435                 440                 445

Arg Pro Lys Asp Glu Lys Lys Gly Thr Leu Ser Phe Lys Glu
            450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Glu Val Ala
                485                 490                 495

Gly Gly Leu Gly Ala Leu Leu Val Thr Leu Val Leu Ile Ile Val Gly
                500                 505                 510

Ala Val Gly Leu Gly Ser Pro Ser Pro Ala Pro Ala Ala Lys Lys Gln
                515                 520                 525

Ala Glu Lys Gly Lys Glu Lys Thr Ala Glu Ala Val Ser Thr Ala Ala
            530                 535                 540

Asp Asn Val Lys Gly Glu Ala Lys Lys Arg Ser Gly Lys Ala Gly Glu
545                 550                 555                 560

<210> SEQ ID NO 81
<211> LENGTH: 560
<212> TYPE: PRT
<213> ORGANISM: Homo sapiens
<220> FEATURE:
<221> NAME/KEY: BINDING SITE
<222> LOCATION: (1)..(18)
<220> FEATURE:
<221> NAME/KEY: BINDING SITE
<222> LOCATION: (103)..(111)
<220> FEATURE:
<221> NAME/KEY: BINDING SITE
<222> LOCATION: (130)..(143)
<220> FEATURE:
<221> NAME/KEY: BINDING SITE
<222> LOCATION: (179)..(193)
<220> FEATURE:
<221> NAME/KEY: BINDING SITE
<222> LOCATION: (358)..(366)
<220> FEATURE:
<221> NAME/KEY: BINDING SITE
<222> LOCATION: (470)..(478)
```

```
<220> FEATURE:
<221> NAME/KEY: BINDING SITE
<222> LOCATION: (502)..(518)
<220> FEATURE:
<221> NAME/KEY: BINDING SITE
<222> LOCATION: (547)..(555)

<400> SEQUENCE: 81
```

Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
            20                  25                  30

Ser Thr Ser Ser Val Ile Glu Lys Pro Thr Phe Thr Pro Thr Thr Leu
        35                  40                  45

Lys Ala Pro Phe Leu Glu Gln Phe Thr Asp Gly Trp Glu Thr Arg Trp
50                  55                  60

Thr Pro Ser His Ala Lys Lys Glu Asp Ser Lys Ser Glu Glu Asp Trp
65                  70                  75                  80

Ala Tyr Val Gly Thr Trp Ala Val Glu Glu Pro His Val Phe Asn Gly
                85                  90                  95

Met Val Gly Asp Lys Gly Leu Val Val Lys Asn Pro Ala Ala His His
            100                 105                 110

Ala Ile Ser Ala Lys Phe Pro Lys Lys Ile Asp Asn Lys Gly Lys Thr
        115                 120                 125

Leu Val Val Gln Tyr Glu Val Lys Leu Gln Asn Ser Leu Asn Cys Gly
130                 135                 140

Gly Ala Tyr Met Lys Leu Leu Gln Asp Asn Lys Lys Leu His Ala Glu
145                 150                 155                 160

Glu Phe Ser Asn Thr Ser Pro Tyr Val Ile Met Phe Gly Pro Asp Lys
                165                 170                 175

Cys Gly Val Thr Asn Lys Val His Phe Ile Phe Lys His Lys Asn Pro
            180                 185                 190

Lys Thr Gly Glu Tyr Glu Glu Lys His Met Lys Leu Pro Pro Ala Val
        195                 200                 205

Arg Val Ser Lys Leu Ser Thr Leu Tyr Thr Leu Ile Val Asn Pro Asp
210                 215                 220

Gln Ser Phe Gln Ile Arg Ile Asp Gly Ala Ala Val Lys Asn Gly Thr
225                 230                 235                 240

Leu Leu Glu Asp Phe Ser Pro Ala Val Asn Pro Glu Lys Glu Ile Asp
                245                 250                 255

Asp Pro Glu Asp Lys Lys Pro Glu Asp Trp Val Asp Glu Ala His Ile
            260                 265                 270

Pro Asp Pro Glu Ala Thr Lys Pro Glu Asp Trp Asp Glu Asp Ala Pro
        275                 280                 285

Tyr Glu Ile Val Asp Thr Asp Ala Thr Gln Pro Glu Asp Trp Leu Val
290                 295                 300

Asp Glu Pro Thr Ser Ile Pro Asp Pro Glu Ala Gln Lys Pro Glu Asp
305                 310                 315                 320

Trp Asp Asp Glu Glu Asp Gly Asp Trp Ile Pro Pro Thr Ile Pro Asn
                325                 330                 335

Pro Lys Cys Ser Glu Val Ser Gly Cys Gly Met Trp Glu Pro Pro Met
            340                 345                 350

Lys Lys Asn Pro Glu Tyr Lys Gly Lys Trp Thr Ala Pro Met Ile Asp
        355                 360                 365

Asn Pro Ala Tyr Lys Gly Pro Trp Ala Pro Arg Lys Ile Ala Asn Pro

```
                     370                 375                 380
Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
                405                 410                 415

Ile Tyr Ile Gly His Ser Val Glu Asp Ala Glu Lys Leu Lys Ala Glu
                420                 425                 430

Thr Trp Asp Leu Lys His Pro Val Glu Val Ala Glu Glu Ala Ala
                435                 440                 445

Arg Pro Lys Asp Glu Lys Lys Gly Thr Leu Ser Phe Lys Glu
    450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Glu Val Ala
                485                 490                 495

Gly Gly Leu Gly Ala Leu Leu Val Thr Leu Val Leu Ile Ile Val Gly
                500                 505                 510

Ala Val Gly Leu Gly Ser Pro Ser Pro Ala Pro Ala Ala Lys Lys Gln
                515                 520                 525

Ala Glu Lys Gly Lys Glu Lys Thr Ala Glu Ala Val Ser Thr Ala Ala
                530                 535                 540

Asp Asn Val Lys Gly Glu Ala Lys Lys Arg Ser Gly Lys Ala Gly Glu
545                 550                 555                 560

<210> SEQ ID NO 82
<211> LENGTH: 560
<212> TYPE: PRT
<213> ORGANISM: Homo sapiens
<220> FEATURE:
<221> NAME/KEY: BINDING SITE
<222> LOCATION: (1)..(18)
<220> FEATURE:
<221> NAME/KEY: BINDING SITE
<222> LOCATION: (103)..(111)
<220> FEATURE:
<221> NAME/KEY: BINDING SITE
<222> LOCATION: (130)..(143)
<220> FEATURE:
<221> NAME/KEY: BINDING SITE
<222> LOCATION: (179)..(193)
<220> FEATURE:
<221> NAME/KEY: BINDING SITE
<222> LOCATION: (358)..(366)
<220> FEATURE:
<221> NAME/KEY: BINDING SITE
<222> LOCATION: (470)..(478)
<220> FEATURE:
<221> NAME/KEY: BINDING SITE
<222> LOCATION: (502)..(518)
<220> FEATURE:
<221> NAME/KEY: BINDING SITE
<222> LOCATION: (547)..(555)

<400> SEQUENCE: 82

Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
                20                  25                  30

Ser Thr Ser Ser Val Ile Glu Lys Pro Thr Phe Thr Pro Thr Thr Leu
            35                  40                  45

Lys Ala Pro Phe Leu Glu Gln Phe Thr Asp Gly Trp Glu Thr Arg Trp
        50                  55                  60
```

-continued

Thr Pro Ser His Ala Lys Lys Glu Asp Ser Lys Ser Glu Glu Asp Trp
 65                  70                  75                  80

Ala Tyr Val Gly Thr Trp Ala Val Glu Glu Pro His Val Phe Asn Gly
                 85                  90                  95

Met Val Gly Asp Lys Gly Leu Val Val Lys Asn Pro Ala Ala His His
                100                 105                 110

Ala Ile Ser Ala Lys Phe Pro Lys Lys Ile Asp Asn Lys Gly Lys Thr
            115                 120                 125

Leu Val Val Gln Tyr Glu Val Lys Leu Gln Asn Ser Leu Asn Cys Gly
        130                 135                 140

Gly Ala Tyr Met Lys Leu Leu Gln Asp Asn Lys Lys Leu His Ala Glu
145                 150                 155                 160

Glu Phe Ser Asn Thr Ser Pro Tyr Val Ile Met Phe Gly Pro Asp Lys
                165                 170                 175

Cys Gly Val Thr Asn Lys Val His Phe Ile Phe Lys His Lys Asn Pro
                180                 185                 190

Lys Thr Gly Glu Tyr Glu Glu Lys His Met Lys Leu Pro Pro Ala Val
            195                 200                 205

Arg Val Ser Lys Leu Ser Thr Leu Tyr Thr Leu Ile Val Asn Pro Asp
        210                 215                 220

Gln Ser Phe Gln Ile Arg Ile Asp Gly Ala Ala Val Lys Asn Gly Thr
225                 230                 235                 240

Leu Leu Glu Asp Phe Ser Pro Ala Val Asn Pro Glu Lys Glu Ile Asp
                245                 250                 255

Asp Pro Glu Asp Lys Lys Pro Glu Asp Trp Val Asp Glu Ala His Ile
                260                 265                 270

Pro Asp Pro Glu Ala Thr Lys Pro Glu Asp Trp Asp Glu Asp Ala Pro
            275                 280                 285

Tyr Glu Ile Val Asp Thr Asp Ala Thr Gln Pro Glu Asp Trp Leu Val
        290                 295                 300

Asp Glu Pro Thr Ser Ile Pro Asp Pro Glu Ala Gln Lys Pro Glu Asp
305                 310                 315                 320

Trp Asp Asp Glu Glu Asp Gly Asp Trp Ile Pro Pro Thr Ile Pro Asn
                325                 330                 335

Pro Lys Cys Ser Glu Val Ser Gly Cys Gly Met Trp Glu Pro Pro Met
            340                 345                 350

Lys Lys Asn Pro Glu Tyr Lys Gly Lys Trp Thr Ala Pro Met Ile Asp
        355                 360                 365

Asn Pro Ala Tyr Lys Gly Pro Trp Ala Pro Arg Lys Ile Ala Asn Pro
        370                 375                 380

Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
                405                 410                 415

Ile Tyr Ile Gly His Ser Val Glu Asp Ala Glu Lys Leu Lys Ala Glu
            420                 425                 430

Thr Trp Asp Leu Lys His Pro Val Glu Val Ala Glu Glu Ala Ala
        435                 440                 445

Arg Pro Lys Asp Glu Glu Lys Lys Glu Gly Thr Leu Ser Phe Lys Glu
        450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Glu Val Ala

```
                       485                 490                 495
Gly Gly Leu Gly Ala Leu Leu Val Thr Leu Val Leu Ile Ile Val Gly
            500                 505                 510

Ala Val Gly Leu Gly Ser Pro Ser Pro Ala Pro Ala Ala Lys Lys Gln
            515                 520                 525

Ala Glu Lys Gly Lys Glu Lys Thr Ala Glu Ala Val Ser Thr Ala Ala
        530                 535                 540

Asp Asn Val Lys Gly Glu Ala Lys Lys Arg Ser Gly Lys Ala Gly Glu
545                 550                 555                 560

<210> SEQ ID NO 83
<211> LENGTH: 560
<212> TYPE: PRT
<213> ORGANISM: Homo sapiens
<220> FEATURE:
<221> NAME/KEY: BINDING SITE
<222> LOCATION: (1)..(9)
<220> FEATURE:
<221> NAME/KEY: BINDING SITE
<222> LOCATION: (97)..(105)
<220> FEATURE:
<221> NAME/KEY: BINDING SITE
<222> LOCATION: (135)..(143)
<220> FEATURE:
<221> NAME/KEY: BINDING SITE
<222> LOCATION: (169)..(177)
<220> FEATURE:
<221> NAME/KEY: BINDING SITE
<222> LOCATION: (208)..(216)
<220> FEATURE:
<221> NAME/KEY: BINDING SITE
<222> LOCATION: (221)..(229)
<220> FEATURE:
<221> NAME/KEY: BINDING SITE
<222> LOCATION: (470)..(482)
<220> FEATURE:
<221> NAME/KEY: BINDING SITE
<222> LOCATION: (502)..(516)

<400> SEQUENCE: 83

Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
            20                  25                  30

Ser Thr Ser Ser Val Ile Glu Lys Pro Thr Phe Thr Pro Thr Thr Leu
        35                  40                  45

Lys Ala Pro Phe Leu Glu Gln Phe Thr Asp Gly Trp Glu Thr Arg Trp
    50                  55                  60

Thr Pro Ser His Ala Lys Lys Glu Asp Ser Lys Ser Glu Glu Asp Trp
65                  70                  75                  80

Ala Tyr Val Gly Thr Trp Ala Val Glu Glu Pro His Val Phe Asn Gly
                85                  90                  95

Met Val Gly Asp Lys Gly Leu Val Val Lys Asn Pro Ala Ala His His
            100                 105                 110

Ala Ile Ser Ala Lys Phe Pro Lys Ile Asp Asn Lys Gly Lys Thr
        115                 120                 125

Leu Val Val Gln Tyr Glu Val Lys Leu Gln Asn Ser Leu Asn Cys Gly
    130                 135                 140

Gly Ala Tyr Met Lys Leu Leu Gln Asp Asn Lys Lys Leu His Ala Glu
145                 150                 155                 160

Glu Phe Ser Asn Thr Ser Pro Tyr Val Ile Met Phe Gly Pro Asp Lys
                165                 170                 175
```

Cys Gly Val Thr Asn Lys Val His Phe Ile Phe Lys His Lys Asn Pro
            180                 185                 190

Lys Thr Gly Glu Tyr Glu Glu Lys His Met Lys Leu Pro Pro Ala Val
        195                 200                 205

Arg Val Ser Lys Leu Ser Thr Leu Tyr Thr Leu Ile Val Asn Pro Asp
        210                 215                 220

Gln Ser Phe Gln Ile Arg Ile Asp Gly Ala Ala Val Lys Asn Gly Thr
225                 230                 235                 240

Leu Leu Glu Asp Phe Ser Pro Ala Val Asn Pro Glu Lys Glu Ile Asp
                245                 250                 255

Asp Pro Glu Asp Lys Lys Pro Glu Asp Trp Val Asp Glu Ala His Ile
                260                 265                 270

Pro Asp Pro Glu Ala Thr Lys Pro Glu Asp Trp Asp Glu Asp Ala Pro
            275                 280                 285

Tyr Glu Ile Val Asp Thr Asp Ala Thr Gln Pro Glu Asp Trp Leu Val
        290                 295                 300

Asp Glu Pro Thr Ser Ile Pro Asp Pro Glu Ala Gln Lys Pro Glu Asp
305                 310                 315                 320

Trp Asp Asp Glu Glu Asp Gly Asp Trp Ile Pro Pro Thr Ile Pro Asn
                325                 330                 335

Pro Lys Cys Ser Glu Val Ser Gly Cys Gly Met Trp Glu Pro Pro Met
                340                 345                 350

Lys Lys Asn Pro Glu Tyr Lys Gly Lys Trp Thr Ala Pro Met Ile Asp
            355                 360                 365

Asn Pro Ala Tyr Lys Gly Pro Trp Ala Pro Arg Lys Ile Ala Asn Pro
370                 375                 380

Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
                405                 410                 415

Ile Tyr Ile Gly His Ser Val Glu Asp Ala Glu Lys Leu Lys Ala Glu
            420                 425                 430

Thr Trp Asp Leu Lys His Pro Val Glu Val Ala Glu Glu Ala Ala
            435                 440                 445

Arg Pro Lys Asp Glu Lys Lys Glu Gly Thr Leu Ser Phe Lys Glu
450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Glu Val Ala
                485                 490                 495

Gly Gly Leu Gly Ala Leu Leu Val Thr Leu Val Leu Ile Ile Val Gly
            500                 505                 510

Ala Val Gly Leu Gly Ser Pro Ser Pro Ala Pro Ala Ala Lys Lys Gln
            515                 520                 525

Ala Glu Lys Gly Lys Glu Lys Thr Ala Glu Ala Val Ser Thr Ala Ala
            530                 535                 540

Asp Asn Val Lys Gly Glu Ala Lys Lys Arg Ser Gly Lys Ala Gly Glu
545                 550                 555                 560

<210> SEQ ID NO 84
<211> LENGTH: 560
<212> TYPE: PRT
<213> ORGANISM: Homo sapiens
<220> FEATURE:
<221> NAME/KEY: BINDING SITE

```
<222> LOCATION: (1)..(9)
<220> FEATURE:
<221> NAME/KEY: BINDING SITE
<222> LOCATION: (97)..(105)
<220> FEATURE:
<221> NAME/KEY: BINDING SITE
<222> LOCATION: (168)..(176)
<220> FEATURE:
<221> NAME/KEY: BINDING SITE
<222> LOCATION: (474)..(482)
<220> FEATURE:
<221> NAME/KEY: BINDING SITE
<222> LOCATION: (503)..(518)

<400> SEQUENCE: 84
```

| | | | | | | | | | | | | | | |
|---|---|---|---|---|---|---|---|---|---|---|---|---|---|---|
|Met|Arg|Leu|Asn|Ala|Ser|Leu|Ala|Ser|Leu|Ile|Leu|Ser|Ser|Ile|Ala|
|1| | | |5| | | | |10| | | | |15| |
|Leu|Ile|Gly|Asn|Val|His|Ala|Glu|Asp|Glu|Val|Lys|Glu|Asp|Ala|Thr|
| | | | |20| | | | |25| | | | |30| |
|Ser|Thr|Ser|Ser|Val|Ile|Glu|Lys|Pro|Thr|Phe|Thr|Pro|Thr|Thr|Leu|
| | | | |35| | | | |40| | | | |45| |
|Lys|Ala|Pro|Phe|Leu|Glu|Gln|Phe|Thr|Asp|Gly|Trp|Glu|Thr|Arg|Trp|
| |50| | | | |55| | | | |60| | | | |
|Thr|Pro|Ser|His|Ala|Lys|Lys|Glu|Asp|Ser|Lys|Ser|Glu|Glu|Asp|Trp|
|65| | | | |70| | | | |75| | | | |80|
|Ala|Tyr|Val|Gly|Thr|Trp|Ala|Val|Glu|Glu|Pro|His|Val|Phe|Asn|Gly|
| | | | |85| | | | |90| | | | |95| |
|Met|Val|Gly|Asp|Lys|Gly|Leu|Val|Val|Lys|Asn|Pro|Ala|Ala|His|His|
| | | | |100| | | | |105| | | | |110| |
|Ala|Ile|Ser|Ala|Lys|Phe|Pro|Lys|Lys|Ile|Asp|Asn|Lys|Gly|Lys|Thr|
| | | | |115| | | | |120| | | | |125| |
|Leu|Val|Val|Gln|Tyr|Glu|Val|Lys|Leu|Gln|Asn|Ser|Leu|Asn|Cys|Gly|
| | | | |130| | | | |135| | | | |140| |
|Gly|Ala|Tyr|Met|Lys|Leu|Leu|Gln|Asp|Asn|Lys|Lys|Leu|His|Ala|Glu|
|145| | | | |150| | | | |155| | | | |160|
|Glu|Phe|Ser|Asn|Thr|Ser|Pro|Tyr|Val|Ile|Met|Phe|Gly|Pro|Asp|Lys|
| | | | |165| | | | |170| | | | |175| |
|Cys|Gly|Val|Thr|Asn|Lys|Val|His|Phe|Ile|Phe|Lys|His|Lys|Asn|Pro|
| | | | |180| | | | |185| | | | |190| |
|Lys|Thr|Gly|Glu|Tyr|Glu|Glu|Lys|His|Met|Lys|Leu|Pro|Pro|Ala|Val|
| | | | |195| | | | |200| | | | |205| |
|Arg|Val|Ser|Lys|Leu|Ser|Thr|Leu|Tyr|Thr|Leu|Ile|Val|Asn|Pro|Asp|
| |210| | | | |215| | | | |220| | | | |
|Gln|Ser|Phe|Gln|Ile|Arg|Ile|Asp|Gly|Ala|Ala|Val|Lys|Asn|Gly|Thr|
|225| | | | |230| | | | |235| | | | |240|
|Leu|Leu|Glu|Asp|Phe|Ser|Pro|Ala|Val|Asn|Pro|Glu|Lys|Glu|Ile|Asp|
| | | | |245| | | | |250| | | | |255| |
|Asp|Pro|Glu|Asp|Lys|Lys|Pro|Glu|Asp|Trp|Val|Asp|Glu|Ala|His|Ile|
| | | | |260| | | | |265| | | | |270| |
|Pro|Asp|Pro|Glu|Ala|Thr|Lys|Pro|Glu|Asp|Trp|Asp|Glu|Asp|Ala|Pro|
| | |275| | | | |280| | | | |285| | | |
|Tyr|Glu|Ile|Val|Asp|Thr|Asp|Ala|Thr|Gln|Pro|Glu|Asp|Trp|Leu|Val|
| |290| | | | |295| | | | |300| | | | |
|Asp|Glu|Pro|Thr|Ser|Ile|Pro|Asp|Pro|Glu|Ala|Gln|Lys|Pro|Glu|Asp|
|305| | | | |310| | | | |315| | | | |320|
|Trp|Asp|Asp|Glu|Glu|Asp|Gly|Asp|Trp|Ile|Pro|Pro|Thr|Ile|Pro|Asn|
| | | | |325| | | | |330| | | | |335| |

```
Pro Lys Cys Ser Glu Val Ser Gly Cys Gly Met Trp Glu Pro Pro Met
                340                 345                 350

Lys Lys Asn Pro Glu Tyr Lys Gly Lys Trp Thr Ala Pro Met Ile Asp
            355                 360                 365

Asn Pro Ala Tyr Lys Gly Pro Trp Ala Pro Arg Lys Ile Ala Asn Pro
370                 375                 380

Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
                405                 410                 415

Ile Tyr Ile Gly His Ser Val Glu Asp Ala Glu Lys Leu Lys Ala Glu
            420                 425                 430

Thr Trp Asp Leu Lys His Pro Val Glu Val Ala Glu Glu Ala Ala
            435                 440                 445

Arg Pro Lys Asp Glu Glu Lys Lys Glu Gly Thr Leu Ser Phe Lys Glu
            450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Glu Val Ala
                485                 490                 495

Gly Gly Leu Gly Ala Leu Leu Val Thr Leu Val Leu Ile Ile Val Gly
            500                 505                 510

Ala Val Gly Leu Gly Ser Pro Ser Pro Ala Pro Ala Ala Lys Lys Gln
            515                 520                 525

Ala Glu Lys Gly Lys Lys Thr Ala Glu Ala Val Ser Thr Ala Ala
            530                 535                 540

Asp Asn Val Lys Gly Glu Ala Lys Lys Arg Ser Gly Lys Ala Gly Glu
545                 550                 555                 560

<210> SEQ ID NO 85
<211> LENGTH: 560
<212> TYPE: PRT
<213> ORGANISM: Homo sapiens
<220> FEATURE:
<221> NAME/KEY: BINDING SITE
<222> LOCATION: (1)..(9)
<220> FEATURE:
<221> NAME/KEY: BINDING SITE
<222> LOCATION: (97)..(105)
<220> FEATURE:
<221> NAME/KEY: BINDING SITE
<222> LOCATION: (135)..(143)
<220> FEATURE:
<221> NAME/KEY: BINDING SITE
<222> LOCATION: (169)..(177)
<220> FEATURE:
<221> NAME/KEY: BINDING SITE
<222> LOCATION: (208)..(216)
<220> FEATURE:
<221> NAME/KEY: BINDING SITE
<222> LOCATION: (221)..(229)
<220> FEATURE:
<221> NAME/KEY: BINDING SITE
<222> LOCATION: (470)..(482)
<220> FEATURE:
<221> NAME/KEY: BINDING SITE
<222> LOCATION: (502)..(516)

<400> SEQUENCE: 85

Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
            20                  25                  30
```

```
Ser Thr Ser Ser Val Ile Glu Lys Pro Thr Phe Thr Pro Thr Thr Leu
            35                  40                  45

Lys Ala Pro Phe Leu Glu Gln Phe Thr Asp Gly Trp Glu Thr Arg Trp
    50                  55                  60

Thr Pro Ser His Ala Lys Lys Glu Asp Ser Lys Ser Glu Glu Asp Trp
65                  70                  75                  80

Ala Tyr Val Gly Thr Trp Ala Val Glu Glu Pro His Val Phe Asn Gly
                85                  90                  95

Met Val Gly Asp Lys Gly Leu Val Val Lys Asn Pro Ala Ala His His
                100                 105                 110

Ala Ile Ser Ala Lys Phe Pro Lys Lys Ile Asp Asn Lys Gly Lys Thr
            115                 120                 125

Leu Val Val Gln Tyr Glu Val Lys Leu Gln Asn Ser Leu Asn Cys Gly
    130                 135                 140

Gly Ala Tyr Met Lys Leu Leu Gln Asp Asn Lys Lys Leu His Ala Glu
145                 150                 155                 160

Glu Phe Ser Asn Thr Ser Pro Tyr Val Ile Met Phe Gly Pro Asp Lys
                165                 170                 175

Cys Gly Val Thr Asn Lys Val His Phe Ile Phe Lys His Lys Asn Pro
            180                 185                 190

Lys Thr Gly Glu Tyr Glu Glu Lys His Met Lys Leu Pro Pro Ala Val
    195                 200                 205

Arg Val Ser Lys Leu Ser Thr Leu Tyr Thr Leu Ile Val Asn Pro Asp
210                 215                 220

Gln Ser Phe Gln Ile Arg Ile Asp Gly Ala Ala Val Lys Asn Gly Thr
225                 230                 235                 240

Leu Leu Glu Asp Phe Ser Pro Ala Val Asn Pro Glu Lys Glu Ile Asp
                245                 250                 255

Asp Pro Glu Asp Lys Lys Pro Glu Asp Trp Val Asp Glu Ala His Ile
            260                 265                 270

Pro Asp Pro Glu Ala Thr Lys Pro Glu Asp Trp Asp Glu Asp Ala Pro
    275                 280                 285

Tyr Glu Ile Val Asp Thr Asp Ala Thr Gln Pro Glu Asp Trp Leu Val
290                 295                 300

Asp Glu Pro Thr Ser Ile Pro Asp Pro Glu Ala Gln Lys Pro Glu Asp
305                 310                 315                 320

Trp Asp Asp Glu Glu Asp Gly Asp Trp Ile Pro Pro Thr Ile Pro Asn
                325                 330                 335

Pro Lys Cys Ser Glu Val Ser Gly Cys Gly Met Trp Glu Pro Pro Met
            340                 345                 350

Lys Lys Asn Pro Glu Tyr Lys Gly Lys Trp Thr Ala Pro Met Ile Asp
    355                 360                 365

Asn Pro Ala Tyr Lys Gly Pro Trp Ala Pro Arg Lys Ile Ala Asn Pro
370                 375                 380

Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
                405                 410                 415

Ile Tyr Ile Gly His Ser Val Glu Asp Ala Glu Lys Leu Lys Ala Glu
            420                 425                 430

Thr Trp Asp Leu Lys His Pro Val Glu Val Ala Glu Glu Glu Ala Ala
    435                 440                 445
```

```
Arg Pro Lys Asp Glu Glu Lys Glu Gly Thr Leu Ser Phe Lys Glu
    450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Glu Val Ala
                485                 490                 495

Gly Gly Leu Gly Ala Leu Leu Val Thr Leu Val Leu Ile Ile Val Gly
            500                 505                 510

Ala Val Gly Leu Gly Ser Pro Ser Pro Ala Pro Ala Ala Lys Lys Gln
        515                 520                 525

Ala Glu Lys Gly Lys Lys Thr Ala Glu Ala Val Ser Thr Ala Ala
    530                 535                 540

Asp Asn Val Lys Gly Glu Ala Lys Lys Arg Ser Gly Lys Ala Gly Glu
545                 550                 555                 560

<210> SEQ ID NO 86
<211> LENGTH: 560
<212> TYPE: PRT
<213> ORGANISM: Homo sapiens
<220> FEATURE:
<221> NAME/KEY: BINDING SITE
<222> LOCATION: (148)..(156)
<220> FEATURE:
<221> NAME/KEY: BINDING SITE
<222> LOCATION: (162)..(176)
<220> FEATURE:
<221> NAME/KEY: BINDING SITE
<222> LOCATION: (229)..(237)
<220> FEATURE:
<221> NAME/KEY: BINDING SITE
<222> LOCATION: (330)..(338)
<220> FEATURE:
<221> NAME/KEY: BINDING SITE
<222> LOCATION: (395)..(403)
<220> FEATURE:
<221> NAME/KEY: BINDING SITE
<222> LOCATION: (506)..(518)

<400> SEQUENCE: 86

Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
                20                  25                  30

Ser Thr Ser Ser Val Ile Glu Lys Pro Thr Phe Thr Pro Thr Thr Leu
        35                  40                  45

Lys Ala Pro Phe Leu Glu Gln Phe Thr Asp Gly Trp Glu Thr Arg Trp
50                  55                  60

Thr Pro Ser His Ala Lys Lys Glu Asp Ser Lys Ser Glu Glu Asp Trp
65                  70                  75                  80

Ala Tyr Val Gly Thr Trp Ala Val Glu Glu Pro His Val Phe Asn Gly
                85                  90                  95

Met Val Gly Asp Lys Gly Leu Val Lys Asn Pro Ala Ala His His
                100                 105                 110

Ala Ile Ser Ala Lys Phe Pro Lys Lys Ile Asp Asn Lys Gly Lys Thr
        115                 120                 125

Leu Val Val Gln Tyr Glu Val Lys Leu Gln Asn Ser Leu Asn Cys Gly
        130                 135                 140

Gly Ala Tyr Met Lys Leu Leu Gln Asp Asn Lys Lys Leu His Ala Glu
145                 150                 155                 160

Glu Phe Ser Asn Thr Ser Pro Tyr Val Ile Met Phe Gly Pro Asp Lys
                165                 170                 175
```

Cys Gly Val Thr Asn Lys Val His Phe Ile Phe Lys His Lys Asn Pro
           180                 185                 190

Lys Thr Gly Glu Tyr Glu Lys His Met Lys Leu Pro Ala Val
            195                 200                 205

Arg Val Ser Lys Leu Ser Thr Leu Tyr Thr Leu Ile Val Asn Pro Asp
210                 215                 220

Gln Ser Phe Gln Ile Arg Ile Asp Gly Ala Ala Val Lys Asn Gly Thr
225                 230                 235                 240

Leu Leu Glu Asp Phe Ser Pro Ala Val Asn Pro Lys Glu Ile Asp
                245                 250                 255

Asp Pro Glu Asp Lys Lys Pro Glu Asp Trp Val Asp Glu Ala His Ile
            260                 265                 270

Pro Asp Pro Glu Ala Thr Lys Pro Glu Asp Trp Asp Glu Asp Ala Pro
            275                 280                 285

Tyr Glu Ile Val Asp Thr Asp Ala Thr Gln Pro Glu Asp Trp Leu Val
            290                 295                 300

Asp Glu Pro Thr Ser Ile Pro Asp Pro Glu Ala Gln Lys Pro Glu Asp
305                 310                 315                 320

Trp Asp Asp Glu Glu Asp Gly Asp Trp Ile Pro Pro Thr Ile Pro Asn
                325                 330                 335

Pro Lys Cys Ser Glu Val Ser Gly Cys Gly Met Trp Glu Pro Pro Met
            340                 345                 350

Lys Lys Asn Pro Glu Tyr Lys Gly Lys Trp Thr Ala Pro Met Ile Asp
            355                 360                 365

Asn Pro Ala Tyr Lys Gly Pro Trp Ala Pro Arg Lys Ile Ala Asn Pro
            370                 375                 380

Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
                405                 410                 415

Ile Tyr Ile Gly His Ser Val Glu Asp Ala Glu Lys Leu Lys Ala Glu
            420                 425                 430

Thr Trp Asp Leu Lys His Pro Val Glu Val Ala Glu Glu Ala Ala
            435                 440                 445

Arg Pro Lys Asp Glu Lys Lys Glu Gly Thr Leu Ser Phe Lys Glu
450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Glu Val Ala
                485                 490                 495

Gly Gly Leu Gly Ala Leu Leu Val Thr Leu Val Leu Ile Ile Val Gly
            500                 505                 510

Ala Val Gly Leu Gly Ser Pro Ser Pro Ala Pro Ala Ala Lys Lys Gln
            515                 520                 525

Ala Glu Lys Gly Lys Glu Lys Thr Ala Glu Ala Val Ser Thr Ala Ala
            530                 535                 540

Asp Asn Val Lys Gly Glu Ala Lys Lys Arg Ser Gly Lys Ala Gly Glu
545                 550                 555                 560

<210> SEQ ID NO 87
<211> LENGTH: 560
<212> TYPE: PRT
<213> ORGANISM: Homo sapiens
<220> FEATURE:

```
<221> NAME/KEY: BINDING SITE
<222> LOCATION: (148)..(156)
<220> FEATURE:
<221> NAME/KEY: BINDING SITE
<222> LOCATION: (162)..(176)
<220> FEATURE:
<221> NAME/KEY: BINDING SITE
<222> LOCATION: (229)..(237)
<220> FEATURE:
<221> NAME/KEY: BINDING SITE
<222> LOCATION: (330)..(338)
<220> FEATURE:
<221> NAME/KEY: BINDING SITE
<222> LOCATION: (395)..(403)
<220> FEATURE:
<221> NAME/KEY: BINDING SITE
<222> LOCATION: (506)..(518)

<400> SEQUENCE: 87
```

Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
            20                  25                  30

Ser Thr Ser Ser Val Ile Glu Lys Pro Thr Phe Thr Pro Thr Thr Leu
        35                  40                  45

Lys Ala Pro Phe Leu Glu Gln Phe Thr Asp Gly Trp Glu Thr Arg Trp
50                  55                  60

Thr Pro Ser His Ala Lys Lys Glu Asp Ser Lys Ser Glu Glu Asp Trp
65                  70                  75                  80

Ala Tyr Val Gly Thr Trp Ala Val Glu Glu Pro His Val Phe Asn Gly
                85                  90                  95

Met Val Gly Asp Lys Gly Leu Val Val Lys Asn Pro Ala Ala His His
            100                 105                 110

Ala Ile Ser Ala Lys Phe Pro Lys Lys Ile Asp Asn Lys Gly Lys Thr
        115                 120                 125

Leu Val Val Gln Tyr Glu Val Lys Leu Gln Asn Ser Leu Asn Cys Gly
    130                 135                 140

Gly Ala Tyr Met Lys Leu Leu Gln Asp Asn Lys Lys Leu His Ala Glu
145                 150                 155                 160

Glu Phe Ser Asn Thr Ser Pro Tyr Val Ile Met Phe Gly Pro Asp Lys
                165                 170                 175

Cys Gly Val Thr Asn Lys Val His Phe Ile Phe Lys His Lys Asn Pro
            180                 185                 190

Lys Thr Gly Glu Tyr Glu Glu Lys His Met Lys Leu Pro Pro Ala Val
        195                 200                 205

Arg Val Ser Lys Leu Ser Thr Leu Tyr Thr Leu Ile Val Asn Pro Asp
    210                 215                 220

Gln Ser Phe Gln Ile Arg Ile Asp Gly Ala Ala Val Lys Asn Gly Thr
225                 230                 235                 240

Leu Leu Glu Asp Phe Ser Pro Ala Val Asn Pro Glu Lys Glu Ile Asp
                245                 250                 255

Asp Pro Glu Asp Lys Lys Pro Glu Asp Trp Val Asp Glu Ala His Ile
            260                 265                 270

Pro Asp Pro Glu Ala Thr Lys Pro Glu Asp Trp Asp Glu Asp Ala Pro
        275                 280                 285

Tyr Glu Ile Val Asp Thr Asp Ala Thr Gln Pro Glu Asp Trp Leu Val
    290                 295                 300

Asp Glu Pro Thr Ser Ile Pro Asp Pro Glu Ala Gln Lys Pro Glu Asp
305                 310                 315                 320

Trp Asp Asp Glu Glu Asp Gly Asp Trp Ile Pro Pro Thr Ile Pro Asn
                325                 330                 335

Pro Lys Cys Ser Glu Val Ser Gly Cys Gly Met Trp Glu Pro Pro Met
            340                 345                 350

Lys Lys Asn Pro Glu Tyr Lys Gly Lys Trp Thr Ala Pro Met Ile Asp
        355                 360                 365

Asn Pro Ala Tyr Lys Gly Pro Trp Ala Pro Arg Lys Ile Ala Asn Pro
370                 375                 380

Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
                405                 410                 415

Ile Tyr Ile Gly His Ser Val Glu Asp Ala Glu Lys Leu Lys Ala Glu
                420                 425                 430

Thr Trp Asp Leu Lys His Pro Val Glu Val Ala Glu Glu Ala Ala
                435                 440                 445

Arg Pro Lys Asp Glu Glu Lys Lys Glu Gly Thr Leu Ser Phe Lys Glu
            450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Glu Val Ala
                485                 490                 495

Gly Gly Leu Gly Ala Leu Leu Val Thr Leu Val Leu Ile Ile Val Gly
                500                 505                 510

Ala Val Gly Leu Gly Ser Pro Ser Pro Ala Pro Ala Lys Lys Gln
            515                 520                 525

Ala Glu Lys Gly Lys Glu Lys Thr Ala Glu Ala Val Ser Thr Ala Ala
            530                 535                 540

Asp Asn Val Lys Gly Glu Ala Lys Lys Arg Ser Gly Lys Ala Gly Glu
545                 550                 555                 560

<210> SEQ ID NO 88
<211> LENGTH: 562
<212> TYPE: PRT
<213> ORGANISM: Histoplasma capsulatum of strains G217B

<400> SEQUENCE: 88

Met Arg Leu Asn Ala Ser Leu Ala Ser Leu Ile Leu Ser Ser Val Ala
1               5                   10                  15

Leu Ile Gly Asn Val Arg Ala Glu Glu Glu Val Lys Gly Asp Ala Pro
            20                  25                  30

Ser Pro Ser Ser Ala Ile Glu Lys Pro Thr Phe Thr Pro Thr Thr Leu
        35                  40                  45

Lys Ala Pro Phe Leu Glu Gln Phe Thr Asp Asp Trp Glu Thr Arg Trp
50                  55                  60

Thr Pro Ser His Ala Lys Lys Glu Asp Ser Ser Asp Glu Asp Trp
65                  70                  75                  80

Ala Tyr Ile Gly Thr Trp Ala Val Glu Glu Pro His Val Leu Asn Gly
                85                  90                  95

Met Val Gly Asp Lys Gly Leu Val Val Lys Asn Pro Ala Ala His His
                100                 105                 110

Ala Ile Ser Ala Lys Phe Pro Lys Lys Ile Asp Asn Lys Gly Lys Thr
            115                 120                 125

Leu Val Val Gln Tyr Glu Val Lys Leu Gln Asp Ser Leu Val Cys Gly

```
            130                 135                 140
Gly Ala Tyr Met Lys Leu Leu Gln Asp Asn Lys Lys Leu His Ala Glu
145                 150                 155                 160

Glu Phe Ser Asn Ala Ser Pro Tyr Val Ile Met Phe Gly Pro Asp Lys
                165                 170                 175

Cys Gly Val Thr Asn Lys Val His Phe Ile Phe Arg His Lys Asn Pro
            180                 185                 190

Lys Thr Gly Glu Tyr Glu Glu Lys His Met Asn Ala Ala Pro Ala Ala
                195                 200                 205

Lys Ile Asn Lys Leu Ser Thr Leu Tyr Thr Leu Ile Val Lys Pro Asp
            210                 215                 220

Gln Ser Phe Gln Ile Arg Ile Asp Gly Lys Ala Val Lys Asn Gly Thr
225                 230                 235                 240

Leu Leu Glu Asp Phe Ser Pro Ala Val Asn Pro Pro Lys Glu Ile Asp
                245                 250                 255

Asp Pro Glu Asp Lys Lys Pro Glu Asp Trp Val Asp Glu Ala Arg Ile
                260                 265                 270

Ala Asp Pro Asp Ala Thr Lys Pro Glu Asp Trp Asp Glu Asp Ala Pro
            275                 280                 285

Tyr Glu Ile Val Asp Thr Asp Ala Val Gln Pro Glu Asp Trp Leu Val
            290                 295                 300

Asp Glu Pro Thr Ser Ile Pro Asp Pro Glu Ala Glu Lys Pro Glu Asp
305                 310                 315                 320

Trp Asp Asp Glu Glu Asp Gly Asp Trp Thr Pro Pro Thr Ile Pro Asn
                325                 330                 335

Pro Lys Cys Ser Glu Val Ser Gly Cys Gly Lys Trp Gln Gln Pro Met
                340                 345                 350

Lys Lys Asn Pro Asp Tyr Lys Gly Lys Trp Val Ala Pro Met Ile Asp
            355                 360                 365

Asn Pro Ala Tyr Lys Gly Pro Trp Ala Pro Arg Lys Ile Pro Asn Pro
            370                 375                 380

Asp Tyr Phe Glu Asp Lys Thr Pro Ser Asn Phe Glu Pro Met Gly Ala
385                 390                 395                 400

Ile Gly Phe Glu Ile Trp Thr Met Gln Ser Asp Ile Leu Phe Asn Asn
                405                 410                 415

Ile Tyr Ile Gly His Ser Ile Glu Asp Ala Glu Lys Leu Lys Ala Glu
            420                 425                 430

Thr Trp Asp Leu Lys His Pro Val Glu Val Ala Glu Glu Ala Ser
            435                 440                 445

Arg Pro Lys Asp Glu Lys Glu Ala Gly Thr Ser Phe Lys Glu Asp
450                 455                 460

Pro Val Gln Tyr Ile Arg Lys Lys Ile Asp Leu Phe Ile Ser Leu Ala
465                 470                 475                 480

Leu Glu Asn Pro Val Glu Ala Val Lys Ala Val Pro Glu Val Ala Gly
                485                 490                 495

Gly Leu Cys Ala Leu Leu Val Thr Leu Ile Leu Ile Ile Val Ser Gly
            500                 505                 510

Leu Ser Leu Gly Ser Ser Ser Pro Ala Pro Lys Lys Gln Ala Glu
            515                 520                 525

Lys Gly Lys Glu Lys Glu Lys Ala Ser Ala Ser Glu Ala Val Ser Thr
            530                 535                 540

Gly Ala Asp Asn Val Lys Gly Gly Ala Lys Lys Arg Ser Thr Lys Thr
545                 550                 555                 560
```

Ser Glu

<210> SEQ ID NO 89
<211> LENGTH: 561
<212> TYPE: PRT
<213> ORGANISM: Coccidioides posadasii strain PB01

<400> SEQUENCE: 89

Met Arg Leu Asn Ala Arg Thr Ala Ser Leu Ile Leu Ser Tyr Ile Ala
1 5 10 15

Leu Leu Gly Gln Val His Ala Glu Ser Glu Ala Thr Lys Glu Glu Pro
20 25 30

Thr Ala Thr Ser Ile Ser Arg Pro Thr Phe Thr Pro Thr Thr Leu Lys
35 40 45

Ala Pro Phe Leu Glu Gln Phe Thr Asp Asp Trp Gln Thr Arg Trp Thr
50 55 60

Pro Ser His Ala Lys Lys Glu Asp Ser Lys Ser Glu Glu Glu Trp Ala
65 70 75 80

Tyr Val Gly Glu Trp Ala Val Glu Glu Pro Thr Val Phe Lys Gly Ile
85 90 95

Asp Gly Asp Lys Gly Leu Val Val Lys Asn Ala Ala Ala His His Ala
100 105 110

Ile Ser Ala Lys Phe Pro Lys Lys Ile Asp Asn Lys Gly Lys Thr Leu
115 120 125

Val Val Gln Tyr Glu Val Lys Leu Gln Asn Ser Leu Val Cys Gly Gly
130 135 140

Ala Tyr Met Lys Leu Leu Gln Asp Asn Lys Lys Leu His Ala Glu Glu
145 150 155 160

Phe Ser Asn Ala Ser Pro Tyr Val Ile Met Phe Gly Pro Asp Lys Cys
165 170 175

Gly Ala Thr Asn Lys Val His Phe Ile Phe Lys His Lys Asn Pro Lys
180 185 190

Thr Gly Glu Tyr Glu Glu Lys His Leu Asn Asn Ala Pro Thr Ala Arg
195 200 205

Val Ser Lys Leu Ser Thr Leu Tyr Thr Leu Ile Val Lys Pro Asp Gln
210 215 220

Thr Phe Gln Ile Gln Ile Asn Gly Glu Ala Val Lys Asn Gly Thr Leu
225 230 235 240

Leu Glu Asp Phe Gln Pro Pro Val Asn Pro Pro Lys Glu Ile Asp Asp
245 250 255

Pro Asn Asp Lys Lys Pro Ala Asp Trp Val Asp Glu Ala Lys Ile Pro
260 265 270

Asp Pro Glu Ala Lys Lys Pro Glu Asp Trp Asp Glu Asp Ala Pro Phe
275 280 285

Glu Ile Val Asp Thr Glu Ala Lys Lys Pro Asp Asp Trp Leu Asp Asp
290 295 300

Glu Pro Ser Ser Ile Pro Asp Pro Glu Ala Gln Lys Pro Glu Asp Trp
305 310 315 320

Asp Asp Glu Glu Asp Gly Asp Trp Phe Ala Pro Thr Val Pro Asn Pro
325 330 335

Lys Cys Glu Glu Ala Ser Gly Cys Gly Lys Trp Glu Pro Pro Met Lys
340 345 350

Arg Asn Pro Asp Tyr Lys Gly Lys Trp Thr Ala Pro Leu Ile Asp Asn
355 360 365

```
Pro Ala Tyr Lys Gly Pro Trp Ser Pro Arg Lys Ile Ala Asn Pro Asp
    370                 375                 380

Phe Phe Glu Asp Lys Lys Pro Ala Asn Phe Glu Pro Met Gly Ala Ile
385                 390                 395                 400

Gly Phe Glu Ile Trp Thr Met Gln Asn Asp Ile Leu Phe Asp Asn Ile
                405                 410                 415

Tyr Ile Gly His Ser Ile Glu Asp Ala Lys Lys Leu Lys Ala Glu Thr
                420                 425                 430

Phe Asp Ile Lys Gln Pro Ile Glu Val Ala Glu Glu Ala Ala Lys
        435                 440                 445

Pro Lys Asp Glu Pro Ser Thr Asp Ser Gly Leu Asn Phe Lys Asp Asp
    450                 455                 460

Pro Val Lys Tyr Ile Arg Ser Lys Val Asp Gln Phe Ile Leu Met Ala
465                 470                 475                 480

Lys Asp Asn Pro Val Glu Ala Val Lys Thr Val Pro Glu Val Ala Gly
                485                 490                 495

Gly Leu Ala Ala Leu Leu Ile Thr Leu Ile Leu Val Val Phe Gly Ala
                500                 505                 510

Ile Gly Leu Ser Ser Pro Ala Pro Ala Pro Ala Lys Lys Asp Ala Gly
        515                 520                 525

Lys Gly Lys Glu Lys Ala Lys Glu Lys Ala Ala Glu Ala Val Ser Thr
    530                 535                 540

Gly Ala Glu Asn Ile Lys Ala Gly Ala Thr Lys Arg Ser Lys Ser Ser
545                 550                 555                 560

Glu

<210> SEQ ID NO 90
<211> LENGTH: 567
<212> TYPE: PRT
<213> ORGANISM: Paracoccidioides brasiliensis

<400> SEQUENCE: 90

Met Arg Leu Asn Ala Ser Leu Ala Ser Leu Ile Leu Thr Ser Ile Ala
1               5                   10                  15

Leu Ile Gly Asn Val His Ala Glu Asp Glu Val Glu Gly Lys Pro Ser
                20                  25                  30

Ser Thr Ser Ser Val Ile Glu Lys Pro Leu Phe Thr Pro Thr Thr Leu
            35                  40                  45

Lys Ala Pro Phe Leu Glu Gln Phe Thr Asp Asp Trp Glu Thr Arg Trp
    50                  55                  60

Thr Pro Ser His Ala Lys Lys Gln Asp Ser Ser Ser Glu Glu Asp Trp
65                  70                  75                  80

Ala Tyr Val Gly Thr Trp Ala Val Glu Glu Pro His Val Phe Asn Gly
                85                  90                  95

Met Lys Gly Asp Lys Gly Leu Val Ile Lys Asn Ala Ala Ala His His
                100                 105                 110

Ala Ile Ser Ala Lys Phe Pro Lys Lys Ile Asp Asn Lys Gly Asn Thr
            115                 120                 125

Leu Val Val Gln Tyr Glu Val Lys Leu Gln Asn Gly Leu Asn Cys Gly
    130                 135                 140

Gly Ala Tyr Met Lys Leu Leu Gln Asp Asn Lys Lys Leu His Ala Glu
145                 150                 155                 160

Glu Phe Ser Asn Ala Ser Pro Tyr Val Ile Met Phe Gly Pro Asp Lys
                165                 170                 175
```

```
Cys Gly Val Thr Asn Lys Val His Phe Ile Phe Arg His Lys Asn Pro
            180                 185                 190

Lys Thr Gly Glu Tyr Glu Lys His Leu Lys Asn Pro Pro Ala Ala
            195                 200                 205

Arg Val Ser Lys Leu Ser Thr Leu Tyr Thr Leu Ile Val Lys Pro Asp
210                 215                 220

Gln Ser Phe Gln Ile Leu Ile Asp Gly Glu Ala Val Lys Asn Gly Thr
225                 230                 235                 240

Leu Leu Glu Asp Phe Ser Pro Ala Val Asn Pro Gln Lys Glu Ile Asp
                245                 250                 255

Asp Pro Glu Asp Lys Pro Lys Asp Trp Val Asp Glu Thr Arg Ile
            260                 265                 270

Pro Asp Pro Thr Ala Thr Lys Pro Asp Asp Trp Asp Glu Asp Ala Pro
            275                 280                 285

Tyr Glu Ile Ile Asp Thr Glu Ala Thr Lys Pro Asp Asp Trp Leu Asp
            290                 295                 300

Ser Glu Pro Asp Ser Ile Pro Asp Pro Glu Ala Gln Lys Pro Glu Asp
305                 310                 315                 320

Trp Asp Asp Glu Glu Asp Gly Asp Trp Ala Ala Pro Thr Ile Pro Asn
                325                 330                 335

Pro Lys Cys Ser Glu Val Ser Gly Cys Gly Lys Trp Glu Ala Pro Met
            340                 345                 350

Lys Lys Asn Pro Asp Tyr Lys Gly Lys Trp Thr Pro Pro Met Ile Asp
            355                 360                 365

Asn Pro Ala Tyr Lys Gly Pro Trp Thr Pro Arg Lys Ile Pro Asn Pro
            370                 375                 380

Asn Tyr Phe Glu Asp Lys Thr Pro Ala Asn Phe Glu Pro Met Gly Ala
385                 390                 395                 400

Ile Gly Phe Glu Ile Trp Thr Met Gln Asn Asp Ile Leu Phe Asn Asn
                405                 410                 415

Ile Tyr Ile Gly His Ser Ile Glu Asp Ala Gln Lys Leu Lys Ser Glu
            420                 425                 430

Thr Trp Asp Ile Lys His Pro Ile Glu Val Ala Glu Glu Ala Thr
            435                 440                 445

Arg Pro Lys Asp Asp Glu Lys Asp Ser Ser Phe Val Ser Phe Lys Glu
450                 455                 460

Ala Pro Val Gln Phe Val Arg Glu Lys Ile Asn Leu Phe Ile Ser Ile
465                 470                 475                 480

Ala Arg Lys Asp Pro Val Gln Ala Ala Lys Ser Val Pro Glu Val Ala
                485                 490                 495

Gly Gly Leu Gly Ala Leu Val Ile Thr Leu Ala Leu Ile Ile Val Gly
            500                 505                 510

Ala Ile Gly Leu Ser Ser Pro Ala Pro Ala Pro Ala Val Ala Lys Lys
            515                 520                 525

Val Asp Gly Lys Glu Lys Asp Gly Ala Ser Lys Glu Lys Ala Ala Glu
            530                 535                 540

Ala Val Ser Thr Thr Ala Asp Asn Val Lys Gly Ala Ala Thr Arg Arg
545                 550                 555                 560

Ser Gly Lys Ala Asn Asn Glu
            565

<210> SEQ ID NO 91
<211> LENGTH: 561
```

<212> TYPE: PRT
<213> ORGANISM: Coccidioides immitis

<400> SEQUENCE: 91

Met Arg Leu Asn Ala Ar

```
Gly Phe Glu Ile Trp Thr Met Gln Asn Asp Ile Leu Phe Asp Asn Ile
                405                 410                 415

Tyr Ile Gly His Ser Ile Glu Asp Ala Lys Lys Leu Lys Ala Glu Thr
            420                 425                 430

Phe Asp Ile Lys His Pro Ile Glu Val Ala Glu Glu Ala Ala Lys
        435                 440                 445

Pro Lys Asp Glu Pro Ser Thr Asp Ser Gly Leu Asn Phe Lys Asp Asp
    450                 455                 460

Pro Val Lys Tyr Ile Arg Ser Lys Val Asp Gln Phe Ile Leu Met Ala
465                 470                 475                 480

Lys Asp Asn Pro Val Glu Ala Val Lys Ala Val Pro Glu Val Ala Gly
                485                 490                 495

Gly Leu Ala Ala Leu Leu Ile Thr Leu Ile Leu Val Val Phe Gly Ala
                500                 505                 510

Ile Gly Leu Ser Ser Pro Ala Pro Ala Pro Lys Lys Asp Ala Gly
            515                 520                 525

Lys Gly Lys Glu Lys Ala Lys Glu Lys Ala Ala Glu Ala Val Ser Thr
    530                 535                 540

Gly Ala Glu Asn Val Lys Ala Gly Ala Thr Lys Arg Ser Lys Ser Ser
545                 550                 555                 560

Glu

<210> SEQ ID NO 92
<211> LENGTH: 598
<212> TYPE: PRT
<213> ORGANISM: Histoplasma capsulatum of strains G186AR

<400> SEQUENCE: 92

Met Ile Pro Ala Ser Asp Ile Ala Gln Arg Ile Glu Ile Trp Gln Ile
1               5                   10                  15

Asp Ser Gly Ser Lys Leu Gln Leu Ala Thr Thr Leu Ser Asn Trp Arg
            20                  25                  30

Pro Ser Val Thr Met Arg Leu Asn Ala Ser Leu Ala Ser Leu Ile Leu
        35                  40                  45

Ser Ser Val Ala Leu Ile Gly Asn Val Arg Ala Glu Glu Glu Val Lys
    50                  55                  60

Gly Asp Ala Pro Ser Pro Ser Ser Ala Ile Glu Lys Pro Thr Phe Thr
65                  70                  75                  80

Pro Thr Thr Leu Lys Ala Pro Phe Leu Glu Gln Phe Thr Asp Asp Trp
                85                  90                  95

Glu Thr Arg Trp Thr Pro Ser His Ala Lys Lys Glu Asp Ser Ser Ser
            100                 105                 110

Asp Glu Asp Trp Ala Tyr Ile Gly Thr Trp Ala Val Glu Glu Pro His
        115                 120                 125

Val Leu Asn Gly Met Val Gly Asp Lys Gly Leu Val Val Lys Asn Pro
    130                 135                 140

Ala Ala His His Ala Ile Ser Ala Lys Phe Pro Lys Lys Ile Asp Asn
145                 150                 155                 160

Lys Gly Lys Thr Leu Val Val Gln Tyr Glu Val Lys Leu Gln Asn Ser
                165                 170                 175

Leu Val Cys Gly Gly Ala Tyr Met Lys Leu Leu Gln Asp Asn Lys Lys
            180                 185                 190

Leu His Ala Glu Glu Phe Ser Asn Ala Ser Pro Tyr Val Ile Met Phe
        195                 200                 205
```

Gly Pro Asp Lys Cys Gly Val Thr Asn Lys Val His Phe Ile Phe Arg
210                 215                 220

His Lys Asn Pro Lys Thr Gly Glu Tyr Glu Lys His Met Asn Ala
225                 230                 235                 240

Ala Pro Ala Ala Lys Ile Asn Lys Leu Ser Thr Leu Tyr Thr Leu Ile
                245                 250                 255

Val Lys Pro Asp Gln Ser Phe Gln Ile Arg Ile Asp Gly Lys Ala Val
            260                 265                 270

Lys Asn Gly Thr Leu Leu Glu Asp Phe Ser Pro Ala Val Asn Pro Pro
            275                 280                 285

Lys Glu Ile Asp Asp Pro Glu Asp Lys Pro Glu Asp Trp Val Asp
290                 295                 300

Glu Ala Arg Ile Ala Asp Pro Asp Ala Thr Lys Pro Glu Asp Trp Asp
305                 310                 315                 320

Glu Asp Ala Pro Tyr Glu Ile Val Asp Ala Asp Ala Val Gln Pro Glu
                325                 330                 335

Asp Trp Leu Ile Asp Glu Pro Thr Ser Ile Pro Asp Pro Glu Ala Glu
            340                 345                 350

Lys Pro Glu Asp Trp Asp Asp Glu Glu Asp Gly Asp Trp Thr Pro Pro
            355                 360                 365

Thr Ile Pro Asn Pro Lys Cys Ser Glu Val Ser Gly Cys Gly Lys Trp
370                 375                 380

Gln Gln Pro Met Lys Lys Asn Pro Asp Tyr Lys Gly Lys Trp Val Ala
385                 390                 395                 400

Pro Met Ile Asp Asn Pro Ala Tyr Lys Gly Pro Trp Ala Pro Arg Lys
                405                 410                 415

Ile Pro Asn Pro Asp Tyr Phe Glu Asp Lys Thr Pro Ala Asn Phe Glu
            420                 425                 430

Pro Met Gly Ala Ile Gly Phe Glu Ile Trp Thr Met Gln Ser Asp Ile
            435                 440                 445

Leu Phe Asn Asn Ile Tyr Ile Gly His Ser Ile Glu Asp Ala Glu Lys
450                 455                 460

Leu Lys Ala Glu Thr Trp Asp Leu Lys His Pro Val Glu Val Ala Glu
465                 470                 475                 480

Glu Glu Ala Ser Arg Pro Lys Asp Glu Glu Lys Glu Ala Gly Thr Ser
                485                 490                 495

Phe Lys Glu Asp Pro Val Gln Tyr Ile Arg Lys Ile Asp Leu Phe
            500                 505                 510

Ile Ser Leu Ala Leu Glu Asn Pro Val Glu Ala Val Lys Thr Val Pro
            515                 520                 525

Glu Val Ala Gly Gly Leu Gly Ala Leu Leu Val Thr Leu Ile Leu Ile
530                 535                 540

Ile Val Ser Gly Ile Ser Leu Gly Ser Ser Ser Ser Pro Ala Pro Lys
545                 550                 555                 560

Lys Gln Ala Glu Lys Gly Lys Glu Lys Lys Ala Ser Ala Ser Glu
            565                 570                 575

Ala Val Ser Thr Gly Ala Asp Asn Val Lys Gly Gly Ala Lys Lys Arg
            580                 585                 590

Ser Thr Lys Thr Ser Glu
            595

<210> SEQ ID NO 93
<211> LENGTH: 562

<212> TYPE: PRT
<213> ORGANISM: Aspergillus flavus

<400> SEQUENCE: 93

```
Met Arg Phe Asn Ala Ala Val Ala Ser Ala Leu Val Ser Ser Ala Thr
1               5                   10                  15

Leu Met Gly Tyr Ala His Ala Glu Glu Ala Glu Lys Asn Pro Asp Ala
            20                  25                  30

Thr Ser Val Val Glu Lys Pro Thr Phe Thr Pro Thr Thr Leu Lys Ala
        35                  40                  45

Pro Phe Leu Glu Gln Phe Thr Asp Asp Trp Glu Ser Arg Trp Thr Pro
50                  55                  60

Ser His Ala Lys Lys Asp Asp Ser Gln Thr Glu Glu Asp Trp Ala Tyr
65                  70                  75                  80

Val Gly Glu Trp Ser Val Glu Glu Pro Thr Val Phe Lys Gly Ile Asp
                85                  90                  95

Gly Asp Lys Gly Leu Val Val Lys Asn Pro Ala Ala His His Ala Ile
            100                 105                 110

Ser Ala Lys Phe Pro Lys Lys Ile Asp Asn Lys Gly Lys Thr Leu Val
        115                 120                 125

Val Gln Tyr Glu Val Lys Pro Gln Asn Ser Leu Val Cys Gly Gly Ala
    130                 135                 140

Tyr Leu Lys Leu Leu Gln Glu Asn Lys Lys Leu His Ala Glu Glu Phe
145                 150                 155                 160

Ser Asn Ala Thr Pro Tyr Val Ile Met Phe Gly Pro Asp Lys Cys Gly
                165                 170                 175

Ala Thr Asn Lys Val His Phe Ile Phe Arg His Lys Asn Pro Lys Thr
            180                 185                 190

Gly Glu Tyr Glu Glu Lys His Leu Lys Ala Pro Pro Ala Ala Arg Thr
        195                 200                 205

Asn Lys Val Thr Ser Leu Tyr Thr Leu Ile Val Arg Pro Asp Gln Ser
    210                 215                 220

Phe Gln Ile Leu Ile Asp Gly Glu Ala Val Lys Asn Gly Thr Leu Leu
225                 230                 235                 240

Glu Asp Phe Asn Pro Val Asn Pro Glu Lys Glu Ile Asp Pro
                245                 250                 255

Lys Asp Lys Lys Pro Asp Asp Trp Val Asp Val Lys Ile Pro Asp
            260                 265                 270

Pro Glu Ala Thr Lys Pro Glu Asp Trp Asp Glu Glu Ala Pro Tyr Glu
        275                 280                 285

Ile Val Asp Glu Glu Ala Thr Lys Pro Glu Asp Trp Leu Glu Glu Glu
    290                 295                 300

Pro Thr Ser Ile Pro Pro Glu Ala Glu Lys Pro Glu Asp Trp Asp
305                 310                 315                 320

Asp Glu Glu Asp Gly Asp Trp Ile Pro Pro Thr Val Pro Asn Pro Lys
                325                 330                 335

Cys Asn Asp Val Ser Gly Cys Gly Pro Trp Ser Ala Pro Met Lys Lys
            340                 345                 350

Asn Pro Ala Tyr Lys Gly Lys Trp Thr Ala Pro Met Ile Asp Asn Pro
        355                 360                 365

Ala Tyr Lys Gly Pro Trp Ser Pro Arg Lys Ile Ala Asn Pro Ala Tyr
    370                 375                 380

Phe Glu Asp Lys Thr Pro Ser Asn Phe Glu Pro Met Gly Ala Ile Gly
385                 390                 395                 400
```

```
Phe Glu Ile Trp Thr Met Gln Asn Asp Ile Leu Phe Asp Asn Ile Tyr
                405                 410                 415

Ile Gly His Ser Pro Glu Asp Ala Glu Gln Leu Arg Lys Glu Thr Phe
            420                 425                 430

Asp Val Lys His Pro Val Glu Val Ala Glu Glu Ala Ser Lys Pro
        435                 440                 445

Lys Lys Glu Glu Thr Ala Pro Ala Thr Ser Val Ser Phe Gln Glu Asp
    450                 455                 460

Pro Ile Thr Phe Val Arg Glu Lys Val Asp His Phe Val Gly Leu Ala
465                 470                 475                 480

Lys Gln Asp Pro Val Asn Ala Val Lys Gln Ala Pro Glu Val Ala Gly
                485                 490                 495

Thr Leu Gly Ala Leu Val Leu Ser Met Val Leu Ile Ile Val Gly Ala
            500                 505                 510

Ile Lys Ala Ser Ser Pro Ala Pro Ala Pro Val Lys Lys Gly Lys Glu
        515                 520                 525

Ala Ala Gly Ala Ala Lys Glu Lys Val Ser Glu Ala Val Ser Ser Ser
    530                 535                 540

Ala Asp Thr Gly Lys Gly Gly Ala Ser Lys Arg Thr Thr Arg Ser Ser
545                 550                 555                 560

Ala Gln

<210> SEQ ID NO 94
<211> LENGTH: 581
<212> TYPE: PRT
<213> ORGANISM: Candida albicans

<400> SEQUENCE: 94

Met Lys Tyr Ala Leu Val Leu Leu Leu Ser Leu Val Asn Ala Leu Lys
1               5                   10                  15

Tyr Val Pro Phe Asp Lys Thr Gln Leu Asp Pro Ser Ser Val Phe Glu
            20                  25                  30

Gln Phe Asp Tyr Pro Ser Leu Asn Ser Ser Pro Trp Gln Val Ser Thr
        35                  40                  45

Ala Lys Lys Phe Asp Glu Gly Arg Asp Glu Ile Val Arg Tyr Ser Gly
    50                  55                  60

Glu Trp Lys Ile Glu Ser Ser Thr Ser Lys Tyr Pro Gly Leu Glu Gly
65                  70                  75                  80

Asp Leu Gly Leu Val Met Lys Ser Arg Ala Ser His Tyr Ala Ile Ser
                85                  90                  95

Tyr Lys Leu Pro His Glu Val Thr Asn Thr Asn Pro Asn Asn Asn Lys
            100                 105                 110

Thr Gln Asp Leu Val Leu Gln Tyr Glu Val Lys Leu Gln Gln Gly Leu
        115                 120                 125

Thr Cys Gly Gly Ala Tyr Ile Lys Leu Leu Asp Ser Ser Pro Ser Gly
    130                 135                 140

Tyr Lys Phe Phe Asn Ser Glu Thr Pro Tyr Gln Ile Met Phe Gly Pro
145                 150                 155                 160

Asp Val Cys Gly Ser Glu Asn Lys Ile His Phe Ile Ile Arg Lys Lys
                165                 170                 175

Leu Pro Asn Gly Ala Ile Glu Glu Lys His Leu Lys His Lys Pro Met
            180                 185                 190

Ala Arg Thr Asn Glu Leu Thr Asn Leu Tyr Thr Leu Ile Ile Lys Ser
        195                 200                 205
```

```
Asn Gln Asp Phe Glu Ile Arg Val Asn Gly Gln Val Ala Lys Ala Gly
    210                 215                 220
Asn Leu Tyr Lys Asn Gln Lys Leu Phe Asn Pro Phe Glu Pro Pro
225                 230                 235                 240
Lys Glu Ile Pro Asp Val Asp Asp Lys Lys Pro Asp Asp Trp Asp Asp
                245                 250                 255
Arg Ala Tyr Ile Pro Asp Pro Asn Val Glu Lys Pro Glu Asp Tyr Glu
                260                 265                 270
Leu Lys His Glu Tyr Pro Gln Ile Arg Asp Pro Asn Ala Val Lys Pro
            275                 280                 285
Asp Glu Trp Asp Glu Ser Ala Pro Arg Tyr Ile Pro Asp Pro Asp Ala
        290                 295                 300
Val Lys Pro Lys Asp Trp Asn Asp Ala Glu Lys Gln Trp Glu Pro Pro
305                 310                 315                 320
Leu Ile Val Asn Pro Lys Cys Ala Thr Gly Cys Gly Pro Trp Glu Ala
                325                 330                 335
Pro Leu Ile Pro Asn His Asp Tyr Ile Gly Pro Trp Phe Pro Pro Asp
                340                 345                 350
Ile Lys Asn Pro Asn Tyr Asn Gly Ile Trp Thr Pro Arg Leu Ile Pro
            355                 360                 365
Asn Pro Tyr Tyr Tyr Gln Val Lys Thr Pro Gly Lys Leu Asp Lys Pro
        370                 375                 380
Ile Gly Gly Ile Gly Phe Glu Leu Trp Ser Ile Glu Ser Asp Ile Leu
385                 390                 395                 400
Phe Asp Asn Ile Tyr Leu Gly Asn Ser Ile Ala Glu Ala Glu Leu Ile
                405                 410                 415
Gly Asn Thr Thr Phe Lys Ile Lys Tyr Glu Leu Glu Ala Asp Gln Arg
            420                 425                 430
Arg Glu Asn Lys Pro Arg Val Lys Asn Glu Pro Val Ala Pro Pro Arg
        435                 440                 445
Asn Phe Glu Asp Ile Ile Arg Asp Asp Ser Ile Ser Thr Phe Gln Gln
    450                 455                 460
Phe Leu Ile Phe Ile Lys Leu Phe Trp Leu Lys Gln Tyr Val Gln Leu
465                 470                 475                 480
Lys Asp Phe Tyr Phe Glu Leu Thr Leu Asp Pro Ile Gly Leu Ile Met
                485                 490                 495
Ala Asn Pro Leu Lys Thr Leu Leu Tyr Ala Phe Leu Phe Leu Phe Ser
                500                 505                 510
Phe Thr Ile Phe Phe Gly Phe Ala Ser Thr Ile Met Phe Leu Leu Gln
            515                 520                 525
Gly Gly Glu Ala Phe Gly Ser Ser Ser Ile Thr Thr Thr Thr
        530                 535                 540
Thr Asp Ser Asn Arg Lys Asn Val Leu Thr Ala Glu Glu Ile Glu Met
545                 550                 555                 560
Pro Ser Asn His Val Gln Lys Ile Glu Ile Leu Asp Glu Gln Ile His
                565                 570                 575
Val Arg Gln Arg Lys
            580

<210> SEQ ID NO 95
<211> LENGTH: 554
<212> TYPE: PRT
<213> ORGANISM: Cryptococcus gattii
```

<400> SEQUENCE: 95

Met Arg Pro Gln Asn Val Ala Gly Val Ala Gly Thr Gly Ala Leu Ile
1               5                   10                  15

Met Ala Ala Gly Ala Leu Ala Asp Arg Ala Val Phe His Pro Thr Ser
            20                  25                  30

Leu Thr Ala Pro Phe Ile Glu Gln Phe Leu Glu Ser Ile Pro Glu Ser
        35                  40                  45

Arg Trp Thr Val Ser Arg Ala Thr Lys Gln Thr Pro Val Gly Asp Glu
    50                  55                  60

Ile Phe Ser Tyr Val Gly Gln Trp Glu Ile Glu Pro Asp Val Tyr
65                  70                  75                  80

Pro Gly Ile Ser Gly Asp Lys Gly Leu Val Leu Lys Thr Lys Ala Ala
                85                  90                  95

His His Ala Ile Ser Thr Leu Phe Asp Glu Pro Ile Asp Pro Lys Gly
            100                 105                 110

Lys Ser Leu Val Val Gln Tyr Glu Val Lys Leu Gln Lys Gly Leu Glu
        115                 120                 125

Cys Gly Gly Ala Tyr Ile Lys Leu Leu Thr Asp Gln Gln Asp Glu Gly
    130                 135                 140

Leu Arg Ala Gly Glu Asp Tyr Thr Asp Lys Thr Pro Phe Thr Ile Met
145                 150                 155                 160

Phe Gly Pro Asp Lys Cys Gly Ser Thr Asn Lys Val His Phe Ile Phe
                165                 170                 175

Arg His Lys Asn Pro Leu Thr Gly Glu Trp Glu Glu Lys His Leu Lys
            180                 185                 190

Asn Pro Pro Ala Pro Lys Ile Thr Lys Thr Thr Ala Leu Tyr Thr Leu
        195                 200                 205

Ile Thr Lys Thr Ser Pro Asp Gln Thr Phe Glu Ile Leu Ile Asn Asp
    210                 215                 220

Glu Ser Val Arg Lys Gly Ser Leu Leu Glu Asp Phe Asp Pro Pro Val
225                 230                 235                 240

Asn Pro Pro Lys Glu Ile Asp Asp Pro Glu Asp Phe Lys Pro Glu Thr
                245                 250                 255

Trp Val Asp Glu Ala Glu Ile Asp Asp Val Thr Ala Thr Lys Pro Asp
            260                 265                 270

Asp Trp Asp Glu Asp Ala Pro Ile Met Ile Thr Asp Thr Ser Ala Val
        275                 280                 285

Lys Pro Glu Asp Trp Leu Glu Glu Pro Gly Thr Ile Pro Asp Pro
    290                 295                 300

Glu Ala Glu Lys Pro Glu Glu Trp Asp Asp Glu Glu Asp Gly Asp Trp
305                 310                 315                 320

Ile Pro Pro Met Val Pro Asn Pro Lys Cys Glu Asp Val Ser Gly Cys
                325                 330                 335

Gly Pro Trp Thr Ala Pro Lys Val Arg Asn Pro Ala Tyr Lys Gly Lys
            340                 345                 350

Trp Thr Ile Pro Lys Ile Pro Asn Pro Asp Tyr Lys Gly Pro Trp Ala
        355                 360                 365

Pro Arg Lys Ile Ala Asn Pro Ala Phe Phe Glu Asp Leu His Pro Ser
    370                 375                 380

Asp Phe Thr Lys Ile Gly Gly Val Gly Ile Glu Leu Trp Thr Met Thr
385                 390                 395                 400

Glu Asp Ile Leu Phe Asp Asn Leu Tyr Ile Gly His Asp Ala Ala Gln
                405                 410                 415

-continued

```
Ala Lys Lys Phe Ala Glu Glu Thr Tyr His Val Lys Lys Pro Ile Glu
            420                 425                 430

Lys Glu Ala Glu Gly Ser Asn Glu Asp Glu Leu Glu Glu Pro Ser Ser
        435                 440                 445

Leu Ile Asp Lys Val Gln Leu Lys Val Tyr Glu Phe Leu His Leu Ala
    450                 455                 460

Thr Phe Asp Ile Ser Gln Ala Val Lys Gln Met Pro Glu Val Ala Ala
465                 470                 475                 480

Gly Leu Ala Ala Ala Val Phe Thr Leu Leu Gly Met Leu Leu Ala Leu
            485                 490                 495

Phe Gly Phe Ile Gly Ser Ala Pro Thr Lys Val Lys Gln Thr Ser Val
            500                 505                 510

Lys Thr Lys Ser Val Ala Pro Val Ala Pro Ala Gly Glu Glu Glu Lys
            515                 520                 525

Lys Ala Leu Asp Gln Ala Gly Val Glu Val Pro Ala Val Glu Gly Ser
            530                 535                 540

Lys Lys Arg Val Thr Arg Ser Thr Lys Glu
545                 550
```

METHOD OF TREATING FUNGAL INFECTION

CROSS-REFERENCE TO RELATED APPLICATION(S)

This application is a continuation of U.S. patent application Ser. No. 14/203,898, filed Mar. 11, 2014, which claims the benefit of U.S. Provisional Patent Application Ser. No. 61/777,842 filed on Mar. 12, 2013, each of which is incorporated by reference herein.

STATEMENT REGARDING FEDERALLY SPONSORED RESEARCH OR DEVELOPMENT

This invention was made with government support under A1035681, A1040996 and A1093553 awarded by the National Institutes of Health. The government has certain rights in the invention.

BACKGROUND

The incidence of fungal infections and mycoses has increased significantly in the past two decades, mainly due to the growing number of individuals who have reduced immunological function (immuno-compromised patients), such as cancer patients, patients who have undergone organ transplantation, patients with AIDS, patients undergoing hemodialysis, critically ill patients, patients after major surgery, patients with catheters, patients suffering from severe trauma or burns, patients having debilitative metabolic illnesses such as diabetes mellitus, persons whose blood is exposed to environmental microbes such as individuals having indwelling intravenous tubes, and even in some elderly individuals. Fungal infections are often also attributed to the frequent use of cytotoxic and/or antibacterial drugs, which alter the normal bacterial flora. Fungi include moulds, yeasts and higher fungi. All fungi are eukaryotic and have sterols but not peptidoglycan in their cell membrane. They are chemoheterotrophs (requiring organic nutrition) and most are aerobic. Many fungi are also saprophytes (living off dead organic matter) in soil and water and acquire their food by absorption. Characteristically fungi also produce sexual and asexual spores. There are over 100,000 species recognized, with 100 infectious members for humans.

Human fungal infections are uncommon in generally healthy persons, being confined to conditions such as *Candidiasis* (thrush) and dermatophyte skin infections such as athlete's foot. Nevertheless, yeast and other fungi infections are one of the human ailments which still present a formidable challenge to modern medicine. In an immuno-compromised host, a variety of normally mild or nonpathogenic fungi can cause potentially fatal infections. Furthermore, the relative ease with which human can now travel around the world provides the means for unusual fungal infections to be imported from place to place. Therefore, wild and resistant strains of fungi are considered to be one of the most threatening and frequent cause of death mainly in hospitalized persons and immuno-compromised patients.

The identity of conserved antigens among pathogenic fungi is poorly understood. This is especially true for immunologically significant antigens that may serve as immunogens to vaccinate against infection. There are currently no commercial vaccines against fungi despite the growing problem of fungal infections. A vaccine against pathogenic fungi, especially one that protects against multiple fungal pathogens, would be of enormous clinical benefit, and of commercial interest.

An improved vaccine and a method of vaccination against fungi are needed in the art. Specifically, a vaccine antigenic to multiple fungi, e.g., multiple dimorphic fungi, and a method of using such vaccine are needed in the art.

There is currently no way to identify CD4 T cells in mammalian blood or tissue, and thus to determine an individuals profile of CD4 T cell based immune resistance or susceptibility. Therefore, needed in the art are compositions and methods for evaluating immunization status of a patient by identifying and evaluating CD4 T cells in the patient.

SUMMARY OF THE INVENTION

In one aspect, the present invention relates to a vaccine to immunize a patient against fungi, wherein the vaccine comprises a Calnexin fragment. The vaccine additionally comprises at least one of a stabilizer, a buffer, or an adjuvant. In one embodiment of the vaccine, the Calnexin fragment is either a full-length native version or a functionally equivalent version of full-length Calnexin. In one embodiment of the vaccine, the Calnexin fragment comprises or consists of at least the 13 amino acid sequence LVVKNPAAHHAIS (SEQ ID NO:1). In another embodiment, the Calnexin fragment comprises or consists of a sequence selected from the group consisting of SEQ ID NOs:2-9, 11, 13-14, and 20-24. In yet another embodiment, the Calnexin fragment comprises or consists of a sequence selected from a group consisting of SEQ ID NOs:2, 6, 11, 12, 17, and 29. In one embodiment, the Calnexin fragment comprises a sequence selected from a group consisting of SEQ ID NOs:2-29. In another embodiment, the suitable calnexin fragment may comprise or consist of a sequence selected from a group consisting of the sequences presented in FIG. 7. Specifically, the group may consist of those sequences highlighted in FIG. 7.

In another aspect, the present invention relates to a method of protecting a patient from fungal infection comprising of the steps of obtaining the vaccine as disclosed, wherein the vaccine comprises a Calnexin fragment and providing a therapeutically effective amount of the vaccine to a subject, wherein the subject is protected from fungal infection. In one embodiment of the method, the fungi are either dimorphic fungi or non-dimorphic fungi, and the dimorphic fungi are selected from a group consisting of *Histoplasma, Coccidiodes, Paracoccidiodes, Penicillium, Blastomyces*, and *Sporothrix*, and the non-dimorphic fungi are selected from a group consisting of *Aspergillus, Pneumocystis, Magnaportha, Exophiala, Neuroaspora, Cryptococcus, Schizophyllum*, and *Candida*.

In one embodiment of the vaccine, the Calnexin fragment comprises or consists of at least the 13 amino acid sequence LVVKNPAAHHAIS (SEQ ID NO:1). In another embodiment, the Calnexin fragment comprises or consists of a sequence selected from the group consisting of SEQ ID NOs:2-9, 11, 13-14, and 20-24. In yet another embodiment, the Calnexin fragment comprises or consists of a sequence selected from a group consisting of SEQ ID NOs:2, 6, 11, 12, 17, and 29. In one embodiment, the Calnexin fragment comprises a sequence selected from a group consisting of SEQ ID NOs:2-29. In another embodiment, the suitable calnexin fragment may comprise or consist of a sequence selected from a group consisting of the sequences presented in FIG. 7. Specifically, the group may consist of those sequences highlighted in FIG. 7.

BRIEF DESCRIPTION OF THE DRAWINGS

The patent or application file contains at least one drawing in color. Copies of this patent or patent application publication with color drawings will be provided by the Office upon request and payment of the necessary fee.

FIG. 1A: Flow diagram that illustrates the generation of eluate #1 from the BAD1 vaccine strain #55. FIG. 1B: Silver nitrate stain of PAGE of B. dermatitidis Ags CW/M and Eluate #1 (left to right). FIG. 1C: Gel free separation of Eluate #1 into fractions by Mr. FIG. 1D: Stimulation of 1807 TCR Tg cells in vitro by gel free fractions from panel C, as measured by IFN-γ response. The arrow in fraction 7 indicates the material that was subjected to MS/MS. FIG. 1E: The identification of Calnexin by MS/MS. This figure shows data collected for one Calnexin-derived peptide, as an example. The top set of paired traces are a comparison of the HPLC separation of the non-stimulatory control fraction (upper) and the stimulatory fraction #7 (lower). The peak present in fraction #7 is not represented in the control. MS analysis of this peak (bottom set of paired traces) identified it as the peptide: LQNSLNCGGAYMK [728.34Da; +2H], and this mass is significantly better represented in the stimulatory fraction #7 (lower) compared to the non-stimulatory control (upper).

FIG. 2A: Induction of E. coli transformed with pET28c-Calnexin plasmid produces recombinant Calnexin (63 kD). FIG. 2B: Recombinant Calnexin stimulates 1807 T cells to produce IFN-□ in vitro. FIG. 2C: Recombinant Calnexin activates (CD44) and induces proliferation (CFSE) of adoptively transferred 1807 cells in vivo.

FIGS. 3A, 3B, and 3C are a set of graphs showing identification of Calnexin's 1807 TCR epitope. FIG. 3A: In vitro activation of 1807 T cells by Calnexin peptide 1. $10^5$ BMDC were loaded with various concentrations of antigens or peptides shown and then co-cultured with $3 \times 10^5$ CD4+ purified 1807 T cells. Three days later, T-cells were analyzed for activation by flow cytometry. FIG. 3B: Naïve 1807 T cells were co-cultured as in Panel A, and cell culture supernatants analyzed for IFN-γ by ELISA. FIG. 3C: In vivo activation of 1807 T cells by Calnexin peptide 1.

FIGS. 4A, 4B, and 4C are a set of graphs of experimental observations showing that Calnexin is present on the yeast surface. FIG. 4A: Western-blot of the water-soluble extract. FIG. 4B and FIG. 4C: Surface staining of vaccine and challenge yeast.

FIG. 5A: Mice received adoptive transfer of $10^6$ 1807 T cells before vaccination, and were challenged with $2 \times 10^4$ B. dermatitidis yeast. 4 d after infection, lungs were collected and 1807 T cells analyzed for cytokine products by FACS (FIG. 5A) and lung CFU (FIG. 5B).

FIG. 6 is a set of graphs of Calnexin's protein sequence alignment among different strains, showing that Calnexin is highly conserved in dimorphic fungi. The deduced Calnexin protein sequences of B. dermatitidis strain 26199 (B.d. 26199; SEQ ID NO:35), H. capsulatum strain G217B (H.c. G217B; SEQ ID NO:88), C. posadasii strain C735 (C.p. C735; SEQ ID NO:89) and P. brasiliensis strain PB01 (P.b. Pb01; SEQ ID NO:90) were aligned using ClustalW software. Regions of identity (in at least three of the four species) are indicated in grey and boxed with a black border. Two different MHC class II peptide-binding prediction algorithms were use to analyze the Calnexin sequence of B. dermatitidis and the highest-ranking predictions are indicated on the sequence (Methods). The IEDB (red) boxes represent the regions where multiple overlapping peptides have been predicted. The six regions predicted to bind with an $IC_{50}$ value less that 500 nM are labeled -A through -E, based on lowest to highest value. The Marc Jenkins algorithm predicts nine amino-acid MHCII-binding peptides. Ten predicted binding nanomers are shown, with two amino acids added to each end. These 13-mers were synthesized to test epitope-specific 1807 T-cell activation (see the Example and FIGS. 3A, 3B, and 3C). The peptides are labeled 1 through 10, based on the highest-to-lowest strength of the predicted binding.

FIG. 7 is a diagram showing an analysis of the predicted peptides that are suitable to work with the known epitope binding domain of several Human HLA DRB1 alleles (SEQ ID NOs:37-87). The diagram is produced by using the publicly available ProPred software (www.imtech.res.in/raghava/propred). In the output, the Blastomyces Calnexin sequence is shown on a separate line for each of 51 DRB1alleles, and peptides that are predicted to fit in the MHCII groove of that allele are indicated in blue, with red used to indicate a so-called anchor amino acid that would be at position one of the 9 amino acid core sequence. A peptide of interest is "promiscuous" if it is predicted to interact with many different human MHCII molecules. Since the human HLA locus is so polymorphic, a good vaccine for humans will have to have epitopes that are promiscuous, and can work with many different HLA MHC molecules in order to stimulate an immune response. The webarchive shows that Blastomyces Calnexin does, indeed, have several peptide sequences (blue) that are predicted to fit into the MHC groove for presentation to T-Cells. Of particular interest is that there is a predicted epitope for the sequence of Peptide1 (which was predicted for B6 mouse HLA interaction, and has been experimentally shown to do so with 1807 cells) at position 103 to 115. There are several other promiscuous epitopes throughout the Calnexin sequence as predicted by the ProPred software.

FIG. 8 is a list showing the protein sequences of Blastomyces Calnexin of strains ATCC 18188 (SEQ ID NO:36) and ATCC 26199(SEQ ID NO:35; EQL28292.1; GI:531977705). The sequences are deduced from genomic sequences. (www.ncbi.nlm.nih.gov/protein/327357651; Protein database Accession number: EGE86508; Broad Institute predicted Gene name: BDDG_09453).

FIG. 9 is a diagram showing the comparison analysis of Calnexin among dimorphic fungi, e.g., Blastomyces, Histoplasma, Coccidioides and Paracoccidioides and other, more distantly related fungi, e.g., Aspergillus, Candida and Cryptococcus.

FIG. 10 is a diagram showing the formatted alignment and the comparison analysis of Calnexin among dimorphic fungi, e.g., Blastomyces, Histoplasma, Coccidioides and Paracoccidioides and other, more distantly related fungi, e.g., Aspergillus, Candida and Cryptococcus. B.d. 26199: SEQ ID NO:35. P.b. Pb01: SEQ ID NO:90. C.i. RS: SEQ ID NO:91. H.c. G186AR: SEQ ID NO:92. A. flavus: SEQ ID NO:93; C.a. 5314: SEQ ID NO:94. C. neoform.: SEQ ID NO:95.

DETAILED DESCRIPTION OF THE INVENTION

Figure 1A:
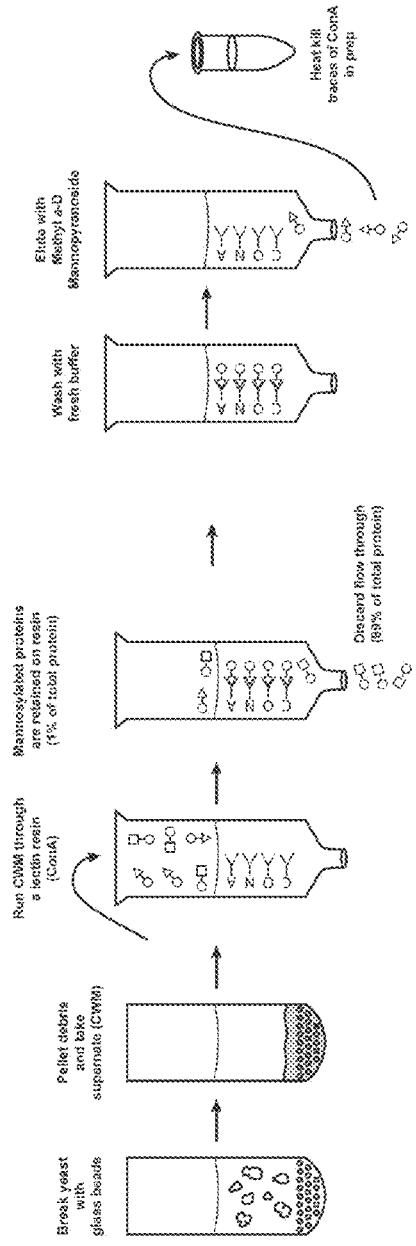
FIGS. 1A, 1B, 1C, 1D, and 1E are a set of graphs showing identity of shared fungal antigen (Ag).

As used herein, the term "patient" refers to a human or non-human mammalian patient in need of vaccination. The vaccines of the present invention may be intended for use by any species, including, for example, human, feline, canine, equine, porcine, bovine, ovine. Preferably, the vaccines of the present invention may be intended for use by human.

The term "fungi" or "funguses", as used herein, refers to a member of a large group of eukaryotic organisms that may include microorganisms, e.g., yeasts and molds. These organisms may be classified as a kingdom of fungi, which is separate from plants, animals, and bacteria. One major difference between fungi and the others is that fungal cells have cell walls that contain chitin, unlike the cell walls of plants, which contain cellulose.

These and other differences show that the fungi form a single group of related organisms, named the *Eumycota* (true fungi or *Eumycetes*), that share a common ancestor (a *monophyletic* group). This fungal group may be distinct from the structurally similar *myxomycetes* (slime molds) and oomycetes (water molds). Genetic studies have shown that fungi are more closely related to animals than to plants. In the present invention, the terms "fungi", "funguses", or "fungal" may refer to fungi which may cause infection in humans and animals.

In the embodiments of the present invention, fungi may include dimorphic fungi and non-dimorphic fungi.

The term "dimorphic fungi", as used herein, refers to fungi which may exist as mold/hyphal/filamentous form or as yeast. An example is *Penicillium marneffei*. At room temperature, it may grow as a mold. At body temperature, it may grow as a yeast. The exception to these conditions are *Candida* spp. *Candida* grows as a mold at body temperatures and as a yeast at room temperatures. Several species of dimorphic fungi may be potential pathogens, including *Coccidioides immitis, Paracoccidioides brasiliensis, Candida albicans, Ustilago maydis, Blastomyces dermatitidis, Histoplasma capsulatum*, and *Sporothrix schenckii*.

The term "Calnexin", as used herein, refers to a 67 kDa integral protein of the endoplasmic reticulum (ER) (Williams D. B., 2006; Myhill N., Lynes E. M., et al., 2008).

Calnexin may appear variously as a 90 kDa, 80 kDa or 75 kDa band on western blotting depending on the source of the antibody. Calnexin may consist of a large (50 kDa) N-terminal calcium-binding lumenal domain, a single transmembrane helix and a short (90 residues), acidic cytoplasmic tail. Calnexin may be one of the chaperone molecules, which may be characterized by their main function of assisting protein folding and quality control, ensuring that only properly folded and assembled proteins proceed further along the secretory pathway.

The function of Calnexin may include retaining unfolded or unassembled N-linked glycoproteins in the ER. Antibodies against Calnexin may be used as markers for the ER in immmunofluorescence experiments. Calnexin may bind only those N-glycoproteins that have GlcNAc2Man9Glc1 oligosaccharides. Oligosaccharides with three sequential glucose residues may be added to asparagine residues of the nascent proteins in the ER. The monoglucosylated oligosaccharides that are recognized by Calnexin result from the trimming of two glucose residues by the sequential action of two glucosidases, I and II. Glucosidase II may also remove the third and last glucose residue. ATP and calcium ions may be two of the cofactors involved in substrate binding for Calnexin.

Calnexin may also function as a chaperone for the folding of MHC class I alpha chain in the membrane of the ER. After folding is completed Calnexin is replaced by calreticulin, which assists in further assembly of MHC class I.

The term "Calnexin fragment", as used herein, refers to at least one portion or domain of the full-length version of wild-type Calnexin, or at least one portion or domain of the modified version or recombinant Calnexin. A Calnexin fragment may retain at least 90% activity of the wild-type version of Calnexin. A preferable fragment is at least 13 amino acids.

The term "functionally equivalent", as used herein, refers to a Calnexin fragment or a modified version of wild-type Calnexin that retains at least 90% activity of the wild-type version of Calnexin. In one embodiment, one may wish to use only selected domains of the native Calnexin protein.

The term "activity", as used herein, refers to antigenic reactivity of Calnexin fragments against fungi, as demonstrated below in the examples.

The term "therapeutically effective amount", as used herein, refers to an amount of an antigen or vaccine that would induce an immune response in a subject receiving the antigen or vaccine which is adequate to prevent signs or symptoms of disease, including adverse health effects or complications thereof, caused by infection with a pathogen, such as a virus or a bacterium. Humoral immunity or cell mediated immunity or both humoral and cell mediated immunity may be induced. The immunogenic response of an animal to a vaccine may be evaluated, e.g., indirectly through measurement of antibody titers, lymphocyte proliferation assays, or directly through monitoring signs and symptoms after challenge with wild-type strain. The protective immunity conferred by a vaccine may be evaluated by measuring, e.g., reduction in clinical signs such as mortality, morbidity, temperature number, overall physical condition, and overall health and performance of the subject. The amount of a vaccine that is therapeutically effective may vary depending on the particular virus used, or the condition of the subject, and may be determined by a physician.

The term "protected", as used herein, refers to immunization of a patient against a disease. The immunization may be caused by administering a vaccine comprising an antigen. Specifically, in the present invention, the immunized patient is protected from fungal infection.

The term "vaccine", as used herein, refers to a composition that includes an antigen, as defined herein. Vaccine may also include a biological preparation that improves immunity to a particular disease. A vaccine may typically contain an agent that resembles a disease-causing microorganism, and the agent may often be made from weakened or killed forms of the microbe, its toxins or one of its surface proteins. The agent may stimulate the body's immune system to recognize the agent as foreign, destroy it, and "remember" it, so that the immune system can more easily recognize and destroy any of these microorganisms that it later encounters. Vaccines may be prophylactic, e.g., to prevent or ameliorate the effects of a future infection by any natural or "wild" pathogen, or therapeutic, e.g., to treat the disease. Administration of the vaccine to a subject results in an immune response, generally against one or more specific diseases. The amount of a vaccine that is therapeutically effective may vary depending on the particular virus used, or the condition of the patient, and may be determined by a physician. The vaccine may be introduced directly into the subject by the subcutaneous, oral, oronasal, or intranasal routes of administration.

The term "administration", as used herein, refers to the introduction of a substance, such as a vaccine, into a subject's body through or by way of a route that does not include the digestive tract. The administration, e.g., parenteral administration, may include subcutaneous administration, intramuscular administration, transcutaneous administration, intradermal administration, intraperitoneal administration, intraocular administration, intranasal administration and intravenous administration.

The vaccine or the composition according to the invention may be administered to an individual according to methods known in the art. Such methods comprise application e.g. parenterally, such as through all routes of injection into or through the skin: e.g. intramuscular, intravenous, intraperitoneal, intradermal, mucosal, submucosal, or subcutaneous. Also, the vaccine may be applied by topical application as a drop, spray, gel or ointment to the mucosal epithelium of the eye, nose, mouth, anus, or vagina, or onto the epidermis of the outer skin at any part of the body. Other possible routes of application are by spray, aerosol, or powder application through inhalation via the respiratory tract. In this last case the particle size that is used will determine how deep the particles will penetrate into the respiratory tract. Alternatively, application may be via the alimentary route, by combining with the food, feed or drinking water e.g. as a powder, a liquid, or tablet, or by administration directly into the mouth as a: liquid, a gel, a tablet, or a capsule, or to the anus as a suppository. The term "animal-based protein", as used herein, refers to proteins that are sourced from ruminant milk, and other sources, for example the muscle meat, of an animal, particularly a mammal. Suitable animal-based proteins may include, but are not limited to, digested protein extracts such as N-Z-Amine®, N-Z-Amine AS® and N-Z-Amine YT® (Sheffield Products Co., Norwich, N.Y.), which are casein enzymatic hydrolysates of bovine milk.

The term "vegetable-based protein", as used herein, refers to proteins from vegetables. A vegetable-based protein may include, without limitation, soy protein, wheat protein, corn gluten, rice protein and hemp protein, among others. Preferred vegetable based proteins in the present invention are soy proteins and corn gluten. Corn gluten is a mixture of various corn-derived proteins. The soy proteins can include 100% soy protein (available as VegeFuel® by Twinlab), textured soy protein, and soybean enzymatic digest. Textured soy protein is a soy protein that is made from defatted soy flour that is compressed and processed into granules or chunks. Soybean enzymatic digest describes soybean peptones that result from the partial hydrolysis of soybean proteins.

As used herein, the term "major histocompatibility complex" or "MHC" refers to a set of cell surface molecules encoded by a large gene family in all vertebrates. MHC molecules may mediate interactions of leukocytes, also called white blood cells (WBCs), which are immune cells, with other leukocytes or body cells. MHC determines compatibility of donors for organ transplant as well as one's susceptibility to an autoimmune disease via cross-reacting immunization. In humans, MHC is also called human leukocyte antigen (HLA).

Protein molecules—either of the host's own phenotype or of other biologic entities—are continually synthesized and degraded in a cell. Occurring on the cell surface, each MHC molecule displays a molecular fraction, called epitope, of a protein. The presented antigen can be either self or nonself.

The MHC gene family may be divided into three subgroups: class I, class II and class III. Diversity of antigen presentation, mediated by MHC classes I and II, may be attained in at least three ways: (1) an organism's MHC repertoire is polygenic (via multiple, interacting genes); (2) MHC expression is codominant (from both sets of inherited alleles); (3) MHC gene variants are highly polymorphic (diversely varying from organism to organism within a species).

Of the three MHC classes identified, human attention commonly focuses on classes I and II. By interacting with CD4 molecules on surfaces of helper T cells, MHC class II mediates establishment of specific immunity (also called acquired immunity or adaptive immunity).

The present invention is generally applied to humans. In certain embodiments, non-human mammals, such as rats, may also be used for the purpose of demonstration. One may use the present invention for veterinary purpose. For example, one may wish to treat commercially important farm animals, such as cows, horses, pigs, rabbits, goats, and sheep. One may also wish to treat companion animals, such as cats and dogs.

Vaccines of the Present Invention

In one embodiment, the present invention relates to a vaccine against fungi comprising a Calnexin fragment. In one embodiment, the vaccine comprising a Calnexin fragment may be applicable to any fungi. In another embodiment, the vaccine comprising a Calnexin fragment may be applicable to any dimorphic fungi. In another embodiment, the vaccine comprising a Calnexin fragment may be applicable to a dimorphic fungus selected from a group consisting of *Histoplasma, Coccidiodes, Paracoccidiodes, Penicillium, Blastomyces*, and *Sporothrix*.

In another embodiment, the vaccine comprising a Calnexin fragment may be applicable to any non-dimorphic fungi. In another embodiment, the vaccine comprising a Calnexin fragment may be applicable to a non-dimorphic fungus selected from a group consisting of *Aspergillus, Pneumocystis, Magnaportha, Exophiala, Neuroaspora, Cryptococcus, Schizophyllum*, and *Candida*.

In one embodiment of the present invention, the Calnexin fragment is part of a full-length native version or a functionally equivalent version of full-length Calnexin. The Calnexin fragment may be produced and isolated from any fungi, e.g., those as discussed above and below. In one specific embodiment, the Calnexin fragment may be produced from any dimorphic fungi, e.g., those as discussed above. In yet another embodiment, the Calnexin fragment may be produce and isolated from any non-dimorphic fungi, e.g., those as discussed above. Further, the Calnexin fragment may also be produced from any other non-fungi sources. For example, the Calnexin fragment may be produced from bacteria and the as-produced Calnexin fragment may not be glycosylated. Thus, the as-produced Calnexin fragment may need to be glycosylated before it can be used as a vaccine.

In one specific embodiment, the Calnexin fragment of the present invention comprises or consists of the 13 amino acid sequence LVVKNPAAHHAIS (SEQ ID NO:1). Table 1 shows a comparison of a Calnexin fragment of Calnexin peptide 1, the 13 amino acid sequence among fungi species and Homo sapiens (Calmegin). As shown in Table 1, to be a suitable vaccine, the Calnexin fragment, comprising the completely conserved 13 amino acid sequence LVVKNPAAHHAIS (SEQ ID NO:1), may be produced from fungi species. The Calnexin fragment, comprising the completely conserved 13 amino acid sequence LVVKNPAAHHAIS (SEQ ID NO:1), may be produced from *Blastomyces dermatitidis* of strains 26199 (SEQ ID NO:2), 18808 (SEQ ID NO:3), Er-3 (SEQ ID NO:4), 14081 (SEQ ID NO:5);

9

*Histoplasma capsulatum* of strains G186AR (SEQ ID NO:6), Nam1 (SEQ ID NO:7), H88 (SEQ ID NO:8), and H143 (SEQ ID NO:9), *Aspergillus* sp.1 of strains group.1, *A. flavus* (SEQ ID NO:17), and group.1, *A. oryzae* (SEQ ID NO:18), *A. terreus* (SEQ ID NO:19), and *Magnaporthe oryzae*_70-15 (SEQ ID NO:26). In another preferred embodiment, the Calnexin fragment of the present invention comprises one or more of peptide 2, peptide 3, peptide 4, peptide 5, peptide 6, peptide 7, peptide 7, peptide 8, peptide 9, and peptide 10 as shown in FIG. 6. In another embodiment, the Calnexin fragment of the present invention consists of peptide 2, peptide 3, peptide 4, peptide 5, peptide 6, peptide 7, peptide 7, peptide 8, peptide 9, and peptide 10 as shown in FIG. 6.

embodiment, the suitable Calnexin fragment may comprise LVVKNAAAHHAIS (SEQ ID NOs:13 and 14) from *Coccidioides posadasii* of strains C35 Δ SOWgp and Silveira, respectively. In another specific embodiment, the suitable Calnexin fragment may comprise LVLKNPAAHHAIS(SEQ ID NO:15) from *Penicillium marneffei*. In another specific embodiment, the suitable Calnexin fragment may comprise LVVKNAAAHHAIS(SEQ ID NO:16) from *Penicillium chrysogenum*. In yet another specific embodiment, the suitable Calnexin fragment may comprise LVVKNVAAHHAIS from *Aspergillus* sp.2 of strains group.2, *A. nidulans* (SEQ ID NO:20), group.2, *A. kawachii* (SEQ ID NO:21), group.2, *A. niger* (SEQ ID NO:22), group.2, *A. fumagatus* 293 (SEQ ID NO:23), or group.2, *A. clavatus* (SEQ ID NO:24). In yet

TABLE 1

Calnexin peptide #1, 13 amino acid sequence

| Genus species_strain | | | | | | | | | | | | | | 1807 reactive |
|---|---|---|---|---|---|---|---|---|---|---|---|---|---|---|
| *Blastomyces dermatitidis* (SEQ ID NOs: 2-5)[a] | L | V | V | K | N | P | A | A | H | H | A | I | S | + |
| *Histoplasma capsulatum* (SEQ ID NOs: 6-9)[b] | — | — | — | — | — | — | — | — | — | — | — | — | — | + |
| *Paracoccidioides brasiliensis*_Pb18 (SEQ ID NO: 10) | — | — | I | — | — | A | — | — | — | — | — | — | — | |
| *Paracoccidioides lutzii*_Pb01 (SEQ ID NO: 11) | — | — | I | — | — | A | — | — | — | — | — | — | — | + |
| *Coccidioides immitis*._RS (SEQ ID NO: 12) | — | — | — | — | — | A | — | — | — | — | — | — | — | |
| *Coccidioides posadasii* (SEQ ID NOs: 13-14)[c] | — | — | — | — | — | A | — | — | — | — | — | — | — | + |
| *Penicillium marneffei* (SEQ ID NO: 15) | — | L | — | — | — | — | — | — | — | — | — | — | — | |
| *Penicillium chrysogenum* (SEQ ID NO: 16) | — | — | — | — | — | A | — | — | — | — | — | — | — | |
| *Aspergillus* sp.1. (SEQ ID NOs: 17-19)[d] | — | — | — | — | — | — | — | — | — | — | — | — | — | |
| *Aspergillus* sp.2 (SEQ ID NOs: 20-24)[e] | — | — | — | — | — | — | V | — | — | — | — | — | — | + |
| *Pneumocystis carinii*_Rat Form 1 (SEQ ID NO: 25) | — | — | L | — | — | E | — | — | — | — | — | — | — | − |
| *Magnaporthe oryzae*_70-15 (SEQ ID NO: 26) | — | — | — | — | — | — | — | — | — | — | — | — | — | |
| *Exophiala dermatitidis*_NIH/UT8656 (SEQ ID NO: 27) | — | — | — | — | — | A | — | — | — | — | — | — | — | |
| *Neurospora crassa*_OR74A (SEQ ID NO: 28) | — | — | — | — | — | A | — | — | — | — | — | — | — | |
| *Cryptococcus neoformans* (SEQ ID NO: 29) | — | — | L | — | T | K | — | — | — | — | — | — | — | |
| *Schizophyllum commune*_H4-8 (SEQ ID NO: 30) | — | — | A | — | T | K | — | — | — | — | — | — | — | |
| *Candida albicans*_5314 (SEQ ID NO: 31) | — | — | M | — | S | R | — | S | — | Y | — | — | — | − |
| *Homo sapiens* (Calmegin) (SEQ ID NO: 32) | — | — | L | — | S | R | — | K | — | — | — | — | — | |
| *Homo sapiens* (Calnexin) (SEQ ID NO: 33) | — | — | L | M | S | R | — | K | — | — | — | — | — | |
| *Geomyces destructans* (SEQ ID NO: 34)[f] | — | — | — | — | — | A | — | — | — | — | — | — | — | |

[a]*B. dermatitidis* strains: 26199, 18808, Er-3, 14081
[b]*H. capsulatum* strains: G186AR, Nam1, H88, H143
[c]*C. posadasii* strains: C35 Δ SOWgp, Silveira
[d]*Aspergillus* species group.1: *A. flavus, A. oryzae, A. terreus*
[e]*Aspergillus* species group 2: *A. nidulans, A. kawachii, A. niger, A. fumagatus* 293, *A. clavatus*
[f]*Geomyces destructans* now called *Pseudogymnoascus destructans*

In another embodiment of the present invention, a suitable Calnexin fragment, comprising 13 amino acid sequence of LVVKNPAAHHAIS (SEQ ID NO:1), may have at least one modified amino acid sequence among the 13 amino acid sequence. In one specific embodiment, the suitable Calnexin fragment may comprise LVVKNAAAHHAIS(SEQ ID NO:12) from *Coccidioides immitis*._RS. In another specific another specific embodiment, the suitable Calnexin fragment may comprise LVVKNAAAHHAIS from *Exophiala dermatitidis*_NIH/UT8656 (SEQ ID NO:27). In yet another specific embodiment, the suitable Calnexin fragment may comprise LVVKNAAAHHAIS from *Neuroaspora crassa*_OR74A (SEQ ID NO:28). In another embodiment, the suitable Calnexin fragment may comprise LVVK- NAAAHHAIS from *Geomyces destructans*, which are now called *Pseudogymnoascus destructans* (SEQ ID NO:34).

In another embodiment of the present invention, a suitable Calnexin fragment, comprising the 13 amino acid sequence of LVVKNPAAHHAIS (SEQ ID NO:1), may have at least two changed amino acid sequences among the 13 amino acid sequence. In one specific embodiment, the suitable Calnexin fragment may comprise LVIKNAAAHHAIS from *Paracoccidioides brasiliensis_Pb*18 (SEQ ID NO:10). In another specific embodiment, the suitable Calnexin fragment may comprise LVIKNAAAHHAIS from *Paracoccidioides lutzii_Pb*01 (SEQ ID NO:11).

In another embodiment of the present invention, a suitable Calnexin fragment, comprising the 13 amino acid sequence of LVVKNPAAHHAIS (SEQ ID NO:1), may have at least three changed amino acid sequences among the 13 amino acid sequence. In one specific embodiment, the suitable Calnexin fragment may comprise LVLKTKAAHHAIS from *Cryptococcus neoformans* (SEQ ID NO:29). In another specific embodiment, the suitable Calnexin fragment may comprise LVAKTKAAHHAIS from *Schizophyllum commune_H*4-8 (SEQ ID NO:30).

In another embodiment of the present invention, a suitable Calnexin fragment, comprising 13 amino acid sequence of LVVKNPAAHHAIS (SEQ ID NO:1), may have more than three changed amino acid sequences among the 13 amino acid sequence.

In one preferred embodiment, a suitable Calnexin fragment may comprise a sequence selected from the group consisting of SEQ ID NOs:2-11, 13-14, and 20-24.

In another preferred embodiment, a suitable Calnexin fragment may comprise a sequence selected from the group consisting of SEQ ID NOs:2, 6, 11, 12, 17, and 29.

In one embodiment, Applicants found or envisioned that the Calnexin fragment comprising LVLKNEAAHHAIS (SEQ ID NO:25) from *Pneumocystis carinii_Rat Form* 1, the Calnexin fragment comprising LVMKSRASHYAIS (SEQ ID NO:31) from *Candida albicans_*5314, and the Calnexin fragment comprising LVLKSRAKHHAIS (SEQ ID NO:32) from *Homo sapiens* (Calmegin) were not reactive with the 1807 cells. Thus, the Calnexin fragments from these species may not be suitable for a vaccine of the present invention.

In another embodiment, a suitable Calnexin fragment in the vaccine of the present invention may comprise a full-length native version of a Calnexin. In one specific embodiment, the full length native version of a Calnexin may comprise a sequence from *Blastomyces dermatitidis* of strains 26199 (SEQ ID NO:35) or 18188 (SEQ ID NO:36). In another embodiment, a suitable Calnexin fragment in the vaccine of the present invention may comprise a functionally equivalent version of full-length wild-type Calnexin.

Applicants envision that many peptide sequences of Calnexin fragments would be suitable vaccines for human in the present invention. FIGS. 7A, 7B, 7C, 7D, 7E, and 7F show predicted peptide sequences of Calnexin fragments for 51 Human HLA DRB1 alleles, where the predicted peptide sequences of Calnexin fragments would fit in the known epitope binding domain of all the 51 Human HLA DRB1 alleles. In one embodiment, a suitable Calnexin fragment for human vaccination may comprise a sequence selected from a group consisting of each of the 51 amino acid sequences shown in FFigure 7. In another embodiment, a suitable Calnexin fragment for human vaccination may comprise a sequence selected from a group consisting of each of the 51 amino acid sequences at least having the highlighted amino acid sequences as shown in FIG. 7.

In one embodiment, a suitable calnexin fragment for human vaccination may comprise a sequence selected from a group consisting of at least one of the highlighted amino acid sequences as shown in FIG. 7. In one embodiment, a suitable calnexin fragment for human vaccination may comprise a sequence selected from a group consisting of at least two of the highlighted amino acid sequences as shown in FIG. 7. Applicants envision that the amino acid sequences highlighted in blue color can likely bind (based on motifs) to human HLA class II molecules and thus may be antigens for stimulating human CD4 T cells and eliciting calnexin antigen-dependent cellular immunity to fungi. In one embodiment, the suitable calnexin fragment may comprise or consist of a sequence selected from a group consisting of the sequences presented in FIG. 7. Specifically, the group may consist of those sequences highlighted in FIG. 7.

In another embodiment, the present invention relates to a method of vaccination for protecting a patient from fungal infections. The method of vaccination in the present invention may generally be applicable to any fungi comprising any dimorphic or non-dimorphic fungi. In a preferred embodiment, the method of vaccination may be used to protect a patient from the infections of dimorphic fungi. In one specific embodiment, the method of vaccination may be applicable to a dimorphic fungus selected from a group consisting of *Histoplasma, Coccidiodes, Paracoccidioides, Penicillium, Blastomyces*, and *Sporothrix*. In another embodiment, the method of vaccination may be applicable to a non-dimorphic fungus selected from a group consisting of *Aspergillus, Pneumocystis, Magnaportha, Exophiala, Neuroaspora, Cryptococcus, Schizophyllum*, and *Candida*.

A Calnexin fragment suitable for a vaccine in the present invention may be in any form as discussed above. In one embodiment, a vaccine of a Calnexin fragment may be expressed in commercially available sources, e.g., *E. coli*. The vaccine of a Calnexin fragment may be then isolated and purified from the sources. The protein expression, isolation, and purifications are well known to a person having ordinary skill in the art. The Example demonstrated methods of expression, isolation, and purifications of a Calnexin fragment according to one embodiment of the present invention.

A vaccine comprising a Calnexin fragment may also comprise other suitable ingredients. In one embodiment, a vaccine may also comprise a carrier molecule as a stabilizer component. As the types of vaccines enclosed in the present invention may be rapidly degraded once injected into the body, the vaccine may be bound to a carrier molecule for stabilizing the vaccine during delivery and administration. A suitable carrier or stabilizer may comprise fusion proteins, polymers, liposome, micro or nanoparticles, or any other pharmaceutically acceptable carriers. A suitable carrier or stabilizer molecule may comprise a tertiary amine N-oxide, e.g., trimethylamine-N-oxide, a sugar, e.g., trehalose, a poly(ethylene glycol) (PEG), an animal-based protein, e.g., digested protein extracts such as N-Z-Amine®, N-Z-Amine AS® and N-Z-Amine YT® (Sheffield Products Co., Norwich, N.Y.), a vegetable-based protein, e.g., soy protein, wheat protein, corn gluten, rice protein and hemp protein, and any other suitable carrier molecules.

Suitable Carrier Or Vehicle

Suitable agents may include a suitable carrier or vehicle for delivery. As used herein, the term "carrier" refers to a pharmaceutically acceptable solid or liquid filler, diluent or encapsulating material. A water-containing liquid carrier can contain pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, wetting agents or other biocompatible materials. A tabulation of ingredients listed by the above categories, may be found in the *U.S. Pharmacopeia National Formulary,* 1857-1859, (1990).

Some examples of the materials which can serve as pharmaceutically acceptable carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen free water; isotonic saline; Ringer's solution, ethyl alcohol and phosphate buffer solutions, as well as other non toxic compatible substances used in pharmaceutical formulations. Wetting agents, emulsifiers and lubricants such as sodium lauryl sulfate and magnesium stearate, as well as coloring agents, release agents, coating agents, sweetening, flavoring and perfuming agents, preservatives and antioxidants can also be present in the compositions, according to the desires of the formulator.

Examples of pharmaceutically acceptable antioxidants include water soluble antioxidants such as ascorbic acid, cysteine hydrochloride, sodium bisulfite, sodium metabisulfite, sodium sulfite and the like; oil-soluble antioxidants such as ascorbyl palmitate, butylated hydroxyanisole (BHA), butylated hydroxytoluene (BHT), lecithin, propyl gallate, alpha-tocopherol and the like; and metal-chelating agents such as citric acid, ethylenediamine tetraacetic acid (EDTA), sorbitol, tartaric acid, phosphoric acid and the like.

Stabilization Agent

In another configuration, the present formulation may also comprise other suitable agents that stabilize the formulations. For example, an approach for stabilizing solid protein formulations of the invention is to increase the physical stability of purified, e.g., lyophilized, protein. This will inhibit aggregation via hydrophobic interactions as well as via covalent pathways that may increase as proteins unfold. Stabilizing formulations in this context may often include polymer-based formulations, for example a biodegradable hydrogel formulation/delivery system. The critical role of water in protein structure, function, and stability is well known. Typically, proteins are relatively stable in the solid state with bulk water removed. However, solid therapeutic protein formulations may become hydrated upon storage at elevated humidities or during delivery from a sustained release composition or device. The stability of proteins generally drops with increasing hydration. Water may also play a significant role in solid protein aggregation, for example, by increasing protein flexibility resulting in enhanced accessibility of reactive groups, by providing a mobile phase for reactants, and by serving as a reactant in several deleterious processes such as beta-elimination and hydrolysis.

An effective method for stabilizing peptides and proteins against solid-state aggregation for delivery may be to control the water content in a solid formulation and maintain the water activity in the formulation at optimal levels. This level depends on the nature of the protein, but in general, proteins maintained below their "monolayer" water coverage will exhibit superior solid-state stability.

A variety of additives, diluents, bases and delivery vehicles may be provided within the invention that effectively control water content to enhance protein stability. These reagents and carrier materials effective as anti-aggregation agents in this sense may include, for example, polymers of various functionalities, such as polyethylene glycol, dextran, diethylaminoethyl dextran, and carboxymethyl cellulose, which significantly increase the stability and reduce the solid-phase aggregation of peptides and proteins admixed therewith or linked thereto. In some instances, the activity or physical stability of proteins may also be enhanced by various additives to aqueous solutions of the peptide or protein drugs. For example, additives, such as polyols (including sugars), amino acids, proteins such as collagen and gelatin, and various salts may be used.

Certain additives, in particular sugars and other polyols, may also impart significant physical stability to dry, e.g., lyophilized proteins. These additives may also be used within the invention to protect the proteins against aggregation not only during lyophilization but also during storage in the dry state. For example sucrose and Ficoll 70 (a polymer with sucrose units) exhibit significant protection against peptide or protein aggregation during solid-phase incubation under various conditions. These additives may also enhance the stability of solid proteins embedded within polymer matrices.

Yet additional additives, for example sucrose, stabilize proteins against solid-state aggregation in humid atmospheres at elevated temperatures, as may occur in certain sustained-release formulations of the invention. Proteins such as gelatin and collagen also serve as stabilizing or bulking agents to reduce denaturation and aggregation of unstable proteins in this context. These additives can be incorporated into polymeric melt processes and compositions within the invention. For example, polypeptide microparticles can be prepared by simply lyophilizing or spray drying a solution containing various stabilizing additives described above. Sustained release of unaggregated peptides and proteins can thereby be obtained over an extended period of time.

Various additional preparative components and methods, as well as specific formulation additives, are provided herein which yield formulations for mucosal delivery of aggregation-prone peptides and proteins, wherein the peptide or protein is stabilized in a substantially pure, unaggregated form using a solubilization agent. A range of components and additives are contemplated for use within these methods and formulations. Exemplary of these solubilization agents are cyclodextrins (CDs), which selectively bind hydrophobic side chains of polypeptides. These CDs have been found to bind to hydrophobic patches of proteins in a manner that significantly inhibits aggregation. This inhibition is selective with respect to both the CD and the protein involved. Such selective inhibition of protein aggregation may provide additional advantages within the intranasal delivery methods and compositions of the invention.

Additional agents for use in this context include CD dimers, trimers and tetramers with varying geometries controlled by the linkers that specifically block aggregation of peptides and protein. Yet solubilization agents and methods for incorporation within the invention involve the use of peptides and peptide mimetics to selectively block protein-protein interactions. In one aspect, the specific binding of hydrophobic side chains reported for CD multimers may be extended to proteins via the use of peptides and peptide mimetics that similarly block protein aggregation. A wide range of suitable methods and anti-aggregation agents may be available for incorporation within the compositions and procedures of the invention.

Stabilizing Delivery Vehicle, Carrier, Support Or Complex-Forming Species

In another embodiment, the present formulation may also comprise other suitable agents such as a stabilizing delivery vehicle, carrier, support or complex-forming species. The coordinate administration methods and combinatorial formulations of the instant invention may optionally incorporate effective lipid or fatty acid based carriers, processing agents, or delivery vehicles, to provide improved formulations for delivery of Calnexin or functionally equivalent fragment proteins, analogs and mimetics, and other biologically active agents. For example, a variety of formulations and methods are provided for delivery which comprise one or more of these active agents, such as a peptide or protein, admixed or encapsulated by, or coordinately administered with, a liposome, mixed micellar carrier, or emulsion, to enhance chemical and physical stability and increase the half-life of the biologically active agents (e.g., by reducing susceptibility to proteolysis, chemical modification and/or denaturation) upon mucosal delivery.

Within certain aspects of the invention, specialized delivery systems for biologically active agents may comprise small lipid vesicles known as liposomes or micelles. These are typically made from natural, biodegradable, non-toxic, and non-immunogenic lipid molecules, and can efficiently entrap or bind drug molecules, including peptides and proteins, into, or onto, their membranes. The attractiveness of liposomes as a peptide and protein delivery system within the invention is increased by the fact that the encapsulated proteins can remain in their preferred aqueous environment within the vesicles, while the liposomal membrane protects them against proteolysis and other destabilizing factors. Even though not all liposome preparation methods known are feasible in the encapsulation of peptides and proteins due to their unique physical and chemical properties, several methods allow the encapsulation of these macromolecules without substantial deactivation.

Additional delivery vehicles carrier, support or complex-forming species for use within the invention may include long and medium chain fatty acids, as well as surfactant mixed micelles with fatty acids. Most naturally occurring lipids in the form of esters have important implications with regard to their own transport across mucosal surfaces. Free fatty acids and their monoglycerides which have polar groups attached have been demonstrated in the form of mixed micelles to act on the intestinal barrier as penetration enhancers. This discovery of barrier modifying function of free fatty acids (carboxylic acids with a chain length varying from 12 to 20 carbon atoms) and their polar derivatives has stimulated extensive research on the application of these agents as mucosal absorption enhancers.

For use within the methods of the invention, long chain fatty acids, especially fusogenic lipids (unsaturated fatty acids and monoglycerides such as oleic acid, linoleic acid, linoleic acid, monoolein, etc.) provide useful carriers to enhance delivery of Calnexin or a functionally equivalent fragment, and other biologically active agents disclosed herein. Medium chain fatty acids (C6 to C12) and monoglycerides have also been shown to have enhancing activity in intestinal drug absorption and can be adapted for use within the mucosal delivery formulations and methods of the invention. In addition, sodium salts of medium and long chain fatty acids are effective delivery vehicles and absorption-enhancing agents for mucosal delivery of biologically active agents within the invention. Thus, fatty acids can be employed in soluble forms of sodium salts or by the addition of non-toxic surfactants, e.g., polyoxyethylated hydrogenated castor oil, sodium taurocholate, etc. Other fatty acid and mixed micellar preparations that are useful within the invention include, but are not limited to, Na caprylate (C8), Na caprate (010), Na laurate (C12) or Na oleate (C18), optionally combined with bile salts, such as glycocholate and taurocholate.

The vaccine of the present invention may advantageously include a pharmaceutically acceptable excipient such as a suitable adjuvant. Suitable adjuvants include an aluminium salt such as aluminium hydroxide gel (alum) or aluminium phosphate (as described in WO93/24148), but may also be a salt of calcium, iron or zinc, or may be an insoluble suspension of acylated tyrosine, or acylated sugars, cationically or anionically derivatised polysaccharides, or polyphosphazenes. The suitable adjuvants may also comprise mannose-containing, carbohydrate based adjuvants such as fungal mannans.

The vaccine formulation may additionally include a biologically acceptable buffer to maintain a pH close to neutral (7.0-7.3). Such buffers preferably used are typically phosphates, carboxylates, and bicarbonates. More preferred buffering agents are sodium phosphate, potassium phosphate, sodium citrate, calcium lactate, sodium succinate, sodium glutamate, sodium bicarbonate, and potassium bicarbonate. The buffer may comprise about 0.0001-5% (w/v) of the vaccine formulation, more preferably about 0.001-1% (w/v). The buffer(s) may be added as part of the stabilizer component during the preparation thereof, if desired. Other excipients, if desired, may be included as part of the final vaccine formulation.

The remainder of the vaccine formulation may be an acceptable diluent, to 100%, including water. The vaccine formulation may also be formulated as part of a water-in-oil, or oil-in-water emulsion.

Also provided as part of the invention is a method of preparation of the vaccine formulation herein described. Preparation of the vaccine formulation preferably takes place in two phases. The first phase typically involves the preparation of the stabilizer component. The first phase may typically involve the preparation of the stabilizer component. The stabilizer component may comprise any suitable components as discussed above. For example, a vegetable-based protein stock solution may be prepared by dissolving the vegetable-based protein in a diluent. The preferred diluent may be water, preferably distilled and/or purified so as to remove trace impurities (such as that sold as purified Super Q®). In a separate vessel an animal-based protein may be dissolved in a diluent, additionally with the sugar component and buffer additives. Preferably, an equal volume of the vegetable-based protein stock solution is added to the animal-based protein solution. It is desirable that after HCl/KOH adjustment to achieve a pH of approximately 7.2±0.1, the stabilizer component may be sterilized via autoclave. The stabilizer solution may be refrigerated for an extended period prior to introduction of the Calnexin fragment.

The second phase of preparation of the vaccine formulation may include introduction of the Calnexin fragment with the stabilizer component, thereby yielding the vaccine formulation. Preferably, the Calnexin fragment may be diluted with a buffer solution prior to its introduction to the stabilizer component.

Once this vaccine formulation solution has been achieved, the formulation may be separated into vials or other suitable containers. The vaccine formulation herein described may then be packaged in individual or multi-dose ampoules, or be subsequently lyophilized (freeze-dried) before packaging in individual or multi-dose ampoules. The vaccine formulation herein contemplated also includes the lyophilized version. The lyophilized vaccine formulation may be stored for extended periods of time without loss of viability at ambient temperatures. The lyophilized vaccine may be reconstituted by the end user, and administered to a patient.

The vaccine of the present invention may be either in a solid form or in a liquid form. Preferably, the vaccine of the present invention may be in a liquid form. The liquid form of the vaccine may have a concentration of 50-4,000 nanomolar (nM), preferably between 50-150 nM. In some embodiments, the concentration will be between 1-50,000 nM.

To vaccinate a patient, a therapeutically effective amount of vaccine comprising Calnexin fragments may be administered to a patient. The therapeutically effective amount of vaccine may typically be one or more doses, preferably in the range of about 0.01-10 mL, most preferably 0.1-1 mL, containing 20-200 micrograms, most preferably 1-50 micrograms of vaccine formulation/dose. The therapeutically effective amount may also depend on the vaccination species. For example, for smaller animals such as mice, a preferred dosage may be about 0.01-1 mL of a 1-50 microgram solution of antigen. For a human patient, a preferred dosage may be about 0.1-1 mL of a 1-50 microgram solution of antigen. The therapeutically effective amount may also depend on other conditions including characteristics of the patient (age, body weight, gender, health condition, etc.), the species of fungi, and others.

A vaccine of the present invention may be administered by using any suitable means as disclosed above. Preferably, a vaccine of the present invention may be administered by intranasal delivery or intramuscular administration, e.g., needle injection.

After vaccination using a vaccine of the present invention, a patient may be immunized from at least one of fungi. In one specific embodiment, a patient after vaccination may be immunized from at least one of dimorphic fungi. In one preferred embodiment, a patient after vaccination may be immunized from multiple dimorphic fungi of *Histoplasma, Coccidiodes, Paracoccidiodes, Penicillium, Blastomyces*, and *Sporothrix*.

In one embodiment, the present invention relates to a therapeutic device for vaccination a patient against fungal infection. In one embodiment, the therapeutic device may comprise any suitable devices charged with a preparation of Calnexin or a functionally equivalent fragment. In another embodiment, the therapeutic device may comprise any suitable devices charged with a preparation of Calnexin or a functionally equivalent fragment and at least one additional active compound.

The instant invention may also include kits, packages and multicontainer units containing the above described pharmaceutical compositions, active ingredients, and/or means for administering the same for use in the prevention and treatment of diseases and other conditions in mammalian subjects. Briefly, these kits include a container or formulation that contains Calnexin or a functionally equivalent fragment, and/or other biologically active agents in combination with mucosal delivery enhancing agents disclosed herein formulated in a pharmaceutical preparation for delivery.

Methods for Determining the Immunization Status of a Patient

In one aspect, the present application discloses diagnostic methods for determining immunization status of a patient. Applicants envision that the present methods would be used to access the status of receipt in a tissue transplantation procedure.

In one embodiment, the present application discloses proteins or peptides and methods of using such proteins or peptides to evaluate the immunization status of a patient. In one embodiment, proteins or peptides may be used to detect endogenous calnexin specific CD4 T cells. As discussed above, Applicants identified calnexin as a major shared antigen that is recognized by T cells that mediate protection against pathogenic fungi that are members of the broad fungal taxonomic group called Ascomycetes.

In one embodiment, the family of Ascomycetes may comprise *Blastomyces dermatitidis, Histoplasma capsulatum, Aspergillus fumigatus, Fonsecea pedrosoi*, and *Geomyces destructans* (the latter is the "white nose fungus", which is decimating bat populations in North America), to name a few.

In one preferred embodiment, the proteins or peptides may comprise peptide-MHCII tetramers (pMHC tetramers). Calnexin peptide #1 specific T cells recognize many of these fungi and confer protection against them. As used herein, calnexin peptide #1 specific T cells refers to the T cells that are directed against the calnexin peptide number 1 (that is, residues 103-115 of the calnexin protein; SEQ ID NOs:1-34). The examples of calnexin peptide #1 are shown in the Table 1.

Helper T cells play an essential role in protecting the host from infection and cancer. Each helper T cell expresses a unique receptor (TCR), which via the aid of the CD4 coreceptor is capable of binding to a specific foreign peptide embedded in a Major Histocompatibility Complex II (MHCII) molecule on the surface of another host cell—the so-called antigen-presenting cell. Recognition of the relevant peptide:MHCII ligand causes a helper T cell to produce various lymphokines that help B cells produce antibodies and enhance the microbicidal activities of phagocytes and cytotoxic lymphocytes. Therefore, the pMHC tetramers may be used to track the emergence and persistence of these T cells after exposure to the fungus in question.

In one embodiment, the fungus in question may include any fungi as discussed above and any others appreciated by one person having ordinary skill in the art.

The pMHCII tetramers may be produced from suitable methods. For example, the pMHCII tetramers may be synthesized by using the method described previously (www.jenkinslab.umn.edu/Jenkins_Lab/Protocols_files/New%20tetramer%20production%20052 212.pdf). In one preferred embodiment, the pMHCII tetramers may comprise at least one fluorescent label. For example, the design of the tetramer may incorporate Fos-Jun leucine zipper motifs to force dimerize the coexpressed MHCII α and β chains (Teyton,et. al., *J. Exp. Med.* 183:2087), and the *E.coli* BirA signal sequence (Schatz, et. al., *Protein Science* 8:921) on the a chain to allow for site-specific biotinylation. The resulting biotinylated peptide:MHCII (pMHCII) heterodimers may be tetramerized with fluorochrome-labeled streptavidin.

In one embodiment, the present proteins or peptides such as the pMHC tetramers may be used to identify "endogenous" calnexin peptide #1 specific T cells that reside in the body of a patient before infection.

In one embodiment, the present proteins or peptides such as the pMHC tetramers may be used to quantify "endogenous" calnexin peptide #1 specific T cells that reside in the body of a patient before infection.

In one embodiment, the present proteins or peptides such as the pMHC tetramers may be used to monitor the response of calnexin peptide #1 specific T cells.

In one embodiment, the present proteins or peptides such as the pMHC tetramers may be used to monitor expansion and characteristics of the calnexin peptide #1 specific T cells after infection and vaccination.

In one embodiment, the present application discloses compositions to identify and track calnexin peptide specific T cells in a patient. In one embodiment, the compositions may comprise proteins or peptides. Specifically, the suitable proteins or peptides may comprise pMHC tetramers.

A composition comprising pMHC tetramers may also comprise other suitable ingredients. In one embodiment, the composition may also comprise a carrier molecule as a stabilizer component. As the types of proteins or peptides enclosed in the present invention may be rapidly degraded once injected into the body, the proteins or peptides may be bound to a carrier molecule for stabilizing the proteins or peptides during delivery and administration. A suitable carrier or stabilizer may comprise fusion proteins, polymers, liposome, micro or nanoparticles, or any other pharmaceutically acceptable carriers. A suitable carrier or stabilizer molecule may comprise a tertiary amine N-oxide, e.g., trimethylamine-N-oxide, a sugar, e.g., trehalose, a poly (ethylene glycol) (PEG), an animal-based protein, e.g., digested protein extracts such as N-Z- Amine®, N-Z-Amine AS® and N-Z-Amine YT® (Sheffield Products Co., Norwich, N.Y.), a vegetable-based protein, e.g., soy protein, wheat protein, corn gluten, rice protein and hemp protein, and any other suitable carrier molecules. The composition may also comprise any suitable carrier or vehicle, such as those as discussed above. The composition may also comprise other stabilization agents, such as those as discussed above.

In one embodiment, the composition may also comprise suitable stabilizing delivery vehicle, carrier, support or complex-forming species, such as those as discussed above. For example, the composition may additionally comprise at least one of a stabilizer, a buffer, or an adjuvant.

In one embodiment, the present application discloses methods for evaluating the immunization status of a patient.

In one specific embodiment, the present methods for evaluating the immunization status of a patient may be accomplished by detecting and evaluating "endogenous" calnexin peptide #1 specific T cells in a patient.

In one embodiment, a method for evaluating the immunization status of a patient against a fungus comprises the steps of 1) obtaining pMHC tetramers; 2) exposing a sample of a patient to a suitable amount of pMHC tetramers; 3) identifying helper T cells such as "endogenous" calnexin peptide #1 specific T cells in the patient's sample; 4) quantifying helper T cells such as "endogenous" calnexin peptide #1 specific T cells in the patient's sample; and 5) monitoring the response, expansion and characteristics of helper T cells such as calnexin peptide #1 specific T cells the after infection and vaccination, wherein the immunization status of a patient against the fungus is obtained by comparing the quantity, expansion and characteristics of the helper T cells before and after infection and vaccination.

In one specific embodiment, the suitable sample is a fresh blood sample from a patient.

In one embodiment, the peptide-MHCII tetramers comprise at least one fluorescent label. The fluorescent peptide-MHCII tetramers may bind to helper T cells such as "endogenous" calnexin peptide #1 specific T cells. One may identify the help T cells through a fluorescence detection technique.

In one embodiment, the method may be applied to evaluate the immunization status against any fungi such as dimorphic fungi or non-dimorphic fungi. In one embodiment, the method may be applied to evaluate the immunization status against a dimorphic fungus selected from a group consisting of *Histoplasma, Coccidiodes, Paracoccidiodes, Penicillium, Blastomyces*, and *Sporothrix*.

In another embodiment, the method may be applied to evaluate the immunization status against a fungus selected from a group consisting of *Blastomyces dermatitidis, Histoplasma capsulatum, Aspergillus fumigatus, Fonsecea pedrosoi*, and *Geomyces destructans*.

In one aspect, the present application discloses a kit for evaluating the immunization status of a patient against a fungus. The kit may comprise (1) a container or formulation wherein the container or formulation comprises peptide-MHCII tetramers, (2) means for exposing peptide-MHCII tetramers to a sample of a patient, and (3) means for detecting helper T cells in the patient's sample, wherein the peptide-MHCII tetramers are binding to the helper T cells.

In one embodiment, the sample is a fresh blood sample of a patient.

In one embodiment, the peptide-MHCII tetramers may be either a powder or a solution. In one specific embodiment, the means for delivering peptide-MHCII tetramers is selected from a group consisting of subcutaneous administration, intramuscular administration, transcutaneous administration, intradermal administration, intraperitoneal administration, intraocular administration, intranasal administration and intravenous administration.

In another embodiment, the kit may be used to evaluating the immunization status of a patient against a fungus selected from a group consisting of *Blastomyces dermatitidis, Histoplasma capsulatum, Aspergillus fumigatus, Fonsecea pedrosoi*, and *Geomyces destructans*.

In another embodiment, the kit may be used to evaluating the immunization status of a patient against a fungus selected from a group consisting of *Blastomyces dermatitidis, Histoplasma capsulatum, Aspergillus fumigatus, Fonsecea pedrosoi*, and *Geomyces destructans*.

In one embodiment, the peptide-MHCII tetramers may comprise at least one fluorescent label. In one specific embodiment, the means of detection may be a fluorescence technique.

EXAMPLES

Methods

Fungi.

Strains used were ATCC 26199 (Harvey, Schmid, et al., 1978), a wild-type strain of *Blastomyces dermatitidis*, and the isogenic, attenuated mutant lacking BAD1, designated strain #55 (Brandhorst, Wuthrich, et al., 1999), as well as *Histoplasma capsulatum* strain G217B, *Coccidiodes posadasii* (isolate C735) and *Candida albicans* strain #5314 (Wuthrich, Hung, et al., 2011). *B. dermatitidis* was grown as yeast on Middlebrook 7H10 agar with oleic acid-albumin complex (Sigma) at 39° C. H. capsulatum was grown as yeast at 37° C. and 5% $CO_2$ on brain-heart infusion agar (BHI) slants. *C. albicans* was grown on YPD plates. The saprobic phase of *C. posadasii* (isolate C735) was grown on GYE medium (1% glucose, 0.5% yeast extract, 1.5% agar) at 30° C. for 3 to 4 weeks to generate a confluent layer of arthroconidia (spores) on the agar surface. Formalin killed spherules (FKS) of *C. posadasii* were generated as described (Levine, Cobb, et al., 1960; Levine, Kong, et al., 1965.).

Mouse Strains.

Inbred C57BL/6 mice were obtained from Jackson laboratory, Bar Harbor, Me. *Blastomyces*-specific TCR Tg 1807 mice bred to B6.PL (Thyl.1$^+$) mice to obtain Thyl.1$^+$ 1807 cells were described elsewhere (Wuthrich, Ersland, et al., 2012). Mice were 7-8 weeks old at the time of these experiments. Mice were housed and cared for as per guidelines of the University of Wisconsin Animal Care Committee, who approved this work.

Generation of Eluate #1.

Cell wall membrane (CW/M) antigen (Ag) was extracted from BAD1 vaccine yeast (Brandhorst, Wuthrich, et al., 1999) as previously described (Wuthrich, Filutowicz, et al., 2000). Briefly, yeast were broken open with glass beads, debris pelleted, and the aqueous supernatant harvested. CW/M Ag was diluted to a protein concentration of 1.5 mg/ml in binding buffer containing 20 mM Tris, pH7.6, 0.3 mM NaCl, 1 mM $MnCl_2$, 1 mM $MgCl_2$, 1 mM $CaCl_2$ and centrifuged to remove insoluble complexes. To enrich the mannosylated proteins in the CW/M Ag preparation we used a Con A column (FIGS. 1A, 1B, 1C, 1D, and 1E). To prepare the column, we washed 0.75 ml Con A-Sepharose resin with 5 ml of binding buffer at least three times, each time the resin was pelleted by centrifugation at 1,000×g for 3 min. After equilibration of the resin with an equal volume of binding buffer, the CW/M Ag extract was allowed to bind for 60 to 120 min under agitation at 4° C. The resin was then centrifuged at 1,000×g for 3 min, and washed twice for 10 min with 15 ml of binding buffer containing 0.1% Tween 20. After a final wash with detergent free binding buffer, the bound fraction was eluted by incubating it for 10 min in 5 ml 20 mM Tris-HCL buffer pH 7.6 containing 500 mM □-D-methylmannopyranoside and 0.3 M NaCl. After pelleting the resin at 2,000×g for 3 min, the supernatant was saved as eluate #1 and aliquoted for subsequent use. To inactivate Con A that might have leached from the resin, eluate #1 aliquots were heat treated for 15 min at 85° C.

Enrichment of the Shared Ag by Gel-Free Separation and Identification by Mass Spec Analysis.

Eluate #1 was applied to a Gel-free 8100 fractionation system (Protein Discovery, Knoxville, Tenn.), and separated on a 10% Tris-Acetate cartridge. Fractions were collected that corresponded to separately eluted MW markers. These fractions were surveyed for protein content by PAGE analysis and silver stain. The fractions that activated 1807 T cells (quantified by production of INF-□) were concentrated by FASP for MS analysis (below).

Filter Aided Sample Preparation [FASP] Method.

FASP sample preparation (Universal sample preparation method for proteome analysis (Wsniewski, Zougman, et al., 2009) and mass spectrometric analysis was done at the Mass Spectrometry Facility at the Biotechnology Center, University of Wisconsin-Madison. In short, samples were bound to 10 kDa MW cut-off Microcon filters (Millipore Corp., Bedford Mass.) and washed twice with 500 μL of 25 mM $NH_4HCO_3$ (pH8.5). Sample was denatured for 2 min in 100 μL of 8M Urea/50 mM $NH_4HCO_3$ (pH8.5) then spun 6 min at 14,000×g. Disulfides were reduced at 37° C. in 100 μl of 6.4M Urea/40 mM $NH_4HCO_3$ (pH8.5)/5 mM DTT for 45 min then spun 2 min at 14,000×g. Cys alkylation was performed at room temperature in the dark for 15 min in 100 μl of 6.4M Urea/40 mM $NH_4HCO_3$ (pH8.5)/11 mM IAA then spun 2 min at 14,000×g and washed once with 100 μL of 8M Urea/50 mM $NH_4HCO_3$ (pH8.5) and once with 25 mM $NH_4HCO_3$ (pH8.5). Digestion with 200 ng trypsin (Promega Corporation, Madison Wis.) was performed in 50 μl of 1M Urea/20 mM $NH_4HCO_3$ (pH8.5)/5% ACN overnight at 37° C. Peptides were spun through the membrane and washed through with 50 μl of 25 mM $NH_4HCO_3$ (pH8.5), 5 min at 14,000×g. Eluted peptide solution was acidified with 2.5% TFA [Trifluoroacetic Acid] to 0.3% final and C18 solid phase extracted with OMIX SPE tips (Agilent Technologies, Santa Clara, Calif.). Peptides were eluted off the C18 column with 20 ul of acetonitrile/$H_2O$/TFA (60%:40%:0.1%) into 1.5 mL Protein LoBind tube (Eppendorf) dried in the SpeedVac to ~2 μl, diluted to 18 μl with 0.05% TFA and 8 μl loaded for nanoLC-MS/MS analysis.

NanoLC-MS/MS.

Peptides were analyzed by nanoLC-MS/MS using the Agilent 1100 nanoflow system (Agilent Technologies) connected to a hybrid linear ion trap-orbitrap mass spectrometer (LTQ-Orbitrap XL, Thermo Fisher Scientific) equipped with a nanoelectrospray ion source. HPLC was performed using an in-house fabricated 15-cm C18 column packed with MAGIC C18AQ 3 μm particles (MICHROM Bioresources Inc., Auburn, Calif.). Solvents were 0.1% formic acid in water (solvent A) and 0.1% formic acid, 95% acetonitrile in water (solvent B). The gradient consisted of 20 min loading and desalting at 1% solvent B, an increase to 40% B over 195 min, to 60% B over 20 min, and to 100% B over 5 min.

MS survey scans from m/z 300 to 2000 were collected in centroid mode at a resolving power of 100,000. Dynamic exclusion was employed to increase dynamic range and maximize peptide identifications, excluding precursors up to 0.55 m/z below and 1.05 m/z above previously selected precursors (40 sec expiration). Data was referenced against *B. dermatitidis* amino acid sequence database (19,126 protein entries) using in-house Mascot search engine 2.2.07 (Matrix Science, London, UK). Peptide mass tolerance was set at 20 ppm and fragment mass at 0.6 Da. Quantification was done with Scaffold software (version 3.6.3, Proteome Software Inc., Portland, Oreg.). Protein identifications were reported above 95.0% probability within 0.9% False Discovery Rate and comprising at least 2 identified peptides. Probabilities were assigned by the Protein Prophet algorithm (Nesvizhskii, Keller, et al., 2003).

Generation and Purification of Recombinant Calnexin.

*Paracoccidiodes brasiliensis* Calnexin was amplified from the pGEM-Calnexin plasmid (dos Santos Feitosa, de Almeida Soares, et al., 2007), generously provided by Jose Daniel Lopes, using oligonucleotides designed to omit the stop codon and add NheI and SalI restriction sites to the 5' and 3' ends, respectively. The resulting 1.7 kb fragment was ligated into the pET28c vector digested with NheI and XhoI, in frame with a C-terminal 6xHis tag. The pET28c-Calnexin construct was transformed into BL21(DE3) *E. coli* for expression of recombinant Calnexin. Calnexin-expressing *E. coli* was grown at 37° C. in LB medium supplemented with 50 ug/ml kanamycin to an OD600 of ~0.9, at which point isopropyl-β-D-1-thiogalactopyranoside (IPTG) was added to a final concentration of 0.2 mM. Cells were induced for 24 hours at 15° C. Cells were harvested and resuspended in lysis buffer (50 mM Tris-HCl (pH 7.5), 200 mM NaCl, 0.1% Triton X-100, 5 mM DTT, and 0.1 mg/ml lysozyme supplemented with complete EDTA-free Protease Inhibitor Cocktail Tablet (Roche)), followed by sonication and centrifugation. Calnexin was purified from the supernatant using a Ni-NTA column (Qiagen) and the wash and elution buffers were used according to manufacturer instructions for purification under native conditions. Calnexin eluate was then dialyzed into 1xPBS using 3,500 MWCO dialysis tubing (Pierce).

Generation of Anti-Calnexin Polyclonal Antibody and Staining of Yeast.

Mice were vaccinated with 200 pg recombinant Calnexin (rCalnexin) thrice. For the first immunization, the protein was emulsified in CFA, the following two boosters were formulated in IFA (Wuthrich, Filutowicz, et al., 2000). Two weeks after the last boost, mice were bled and the serum harvested. Oligospecific anti-Calnexin antibodies were purified from the serum using affinity-purification. Briefly, >200 µg purified recombinant Calnexin was run on an SDS-10% polyacrylamide gel at 20 mAmp for one hour, transferred to PVDF membrane (Millipore), and stained in Ponceau S. The band corresponding to Calnexin was excised from the membrane and probed overnight at 4° C. with anti-Calnexin mouse serum diluted 1:2 in PBS. After washing once in PBS+0.1% Tween 20 and three times in PBS, the anti-Calnexin antibodies were eluted from the membrane in 100 mM glycine (pH 2.6). Following neutralization with 100 mM Tris-HCl (pH 8), the purified antibody was functionally verified by spectrophotometric analysis and Western blot.

For staining yeast, B. dermatitidis strain #55 was grown in liquid HMM for three days at 37° C., passed back to an OD600 of 0.8 and grown for an additional two days. Aliquots of $10^6$ yeast were washed in PBS, resuspended in 90 pl PBS +10 pl anti-Calnexin antibody, and incubated at 4° C. for one hour. Cells were washed in PBS, and then incubated at room temperature for 40 minutes with rhodamine red-conjugated goat anti-mouse (Molecular Probes) diluted 1:100 in PBS containing 0.5% BSA and 2 mM EDTA. After washing in PBS, the yeast were fixed in 2% PFA, pelleted, and resuspended in PBS. Fluorescent microscopy was carried out on an Olympus BX60 using mirror cube U-MWIG, with images taken under a 40× objective using QCapture Pro software.

Comparison of Calnexin Sequence Among Different Fungi and Prediction of its Class II Epitopes.

To determine the degree of conservation of the Calnexin protein among the systemic dimorphic fungi, the deduced Calnexin protein sequences of B. dermatitidis strain 26199, H. capsulatum strain G217B, C. posadasii strain C735 and P. brasiliensis strain PB01 were aligned using ClustalW (Thompson, Higgins, et al., 1994) in the MacVector software package (v. 12.5.1; MacVector Inc., Carey, N.C.). To aid in determining possible epitopes within the Calnexin protein sequence, two different algorithms were used to predict binding peptides for the mouse C57/B6 MHC-class-II-allele, H2-IAb. In the first algorithm the Calnexin protein sequence of B. dermatitidis was analyzed using the Immune Epitope Database (IEDB) Analysis Resource (tools.immuneepitope.org/main/html/tcell_tools.html). The output of this software designates each peptide and its $IC_{50}$ value. Several peptides, with nine amino-acid-core sequences that had $IC_{50}$ values less than 500 nM (considered strong to moderate binding affinity) were predicted, and clustered into six regions of extended peptides within the B. dermatitidis Calnexin protein sequence (FIG. 6). A second algorithm developed in the Laboratory of Marc Jenkins, University of Minnesota, which is based only on peptides that have been eluted from affinity purified H2-IAb molecules and sequenced by mass spec (Mark Jenkins, personal communication), generated ten strong-binding nanomers, with greater than 5 standard deviations above random peptides. The peptides were named Peptide 1 through Peptides 10, based on the strength of predicted binding to H2-IAb (FIG. 6).

The ten predicted nanomers were synthesized as 13aa peptide—harboring an additional two flanking amino acids at each end—by GeneScript USA Inc. (Piscataway, N.J.; www.genscript.com) and used to test epitope-specific 1807 T-cell activation.

Stimulation of 1807 T Cells in vitro.

To test the antigenic properties of the Calnexin protein and peptides we loaded bone marrow derived dendritic cells (BMDC) with the respective antigens and cultured them with naïve 1807 T cells to assess T-cell activation and cytokine production. After three days of co-culture, the cell culture supernatants were harvested and analyzed for cytokines by ELISA and 1807 T cells stained for the activation markers CD44 and CD62L (Wuthrich, Ersland, et al., 2012). In some experiments, the Blastomyces CW/M-reactive T-cell clone #5, whose TCR was cloned to generate 1807 transgenic mice (Wuthrich, Filutowicz, et al., 2007), was used as a reporter T-cell to identify the presence of the antigen. Cell-culture supernatants were generated in 96-well plates in 0.2 ml containing $1×10^5$ BMDC, 0.05 to 10 µg/ml of CW/M antigen (Wuthrich, Filutowicz, et al., 2000), 0.05 to 50 µg/ml Calnexin and Drk1 (as a negative control) (Nemecek, Wuthrich, et al., 2006) and 0.001 to 100 µM Calnexin peptides #1-10 (FIG. 6). Supernatants were collected after 72 hours of co-culture. IFN-γ and IL-17A were measured by ELISA (R&D System, Minneapolis, Minn.) according to manufacturer specifications (detection limits were 0.05 ng/ml).

Generation of a Water-Soluble Extract from Vaccine Yeast.

Yeast surface proteins were extracted three times with three yeast-pellet volumes of water by agitating the yeast for one hour at 4° C. The yeast were separated from the supernatant by centrifugation and filtration through a 0.2 µm filter. The water soluble-extract was concentrated by a Centricon column with a 30 kD cutoff.

Vaccination and Infection.

Mice were vaccinated as described (Wuthrich, Filutowicz, et al., 2000), twice, two weeks apart, subcutaneously (s.c.) with 20 to 200 pg recombinant Calnexin emulsified in complete Freund's adjuvant or with $10^8$ heat killed C. albicans yeast and mineral oil. Mice were infected intratracheally (i.t.) with $2×10^3$ or $2×10^4$ wild-type yeast of B. dermatitidis strain 26199, $2×10^5$ H. capsulatum G217B, $2×10^5$ FKS or 60 spores of the virulent C. posadasii isolate C735 (Wuthrich, Filutowicz, et al., 2000; Wsniewski, Zougman, et al., 2009; Nesvizhskii, Keller, et al., 2003; (dos Santos Feitosa, de Almeida Soares, et al., 2007; Thompson, Higgins, et al., 1994; Wuthrich, Filutowicz, et al., 2007; Nemecek, Wuthrich, et al., 2006; Wuthrich, Gern, et al., 2011). To assess the infiltration of primed CD4 T cells into the lungs, challenged mice were analyzed at day 4 post-infection. To analyze the extent of lung infection, homogenized lungs were plated and yeast colony forming units (CFU) enumerated on BHI agar (Difco, Detroit, Mich.), sheep-blood containing Mycosel plates, or GYE plates containing 50 µg/ml of chloramphenicol (Wuthrich, Gem, et al., 2011).

Adoptive Transfer of 1807 Cells and Experimental Challenge.

To assess the T helper cytokine phenotype of Calnexin-specific $CD4^+$ T cells after vaccination with Calnexin and various adjuvants, we transferred $10^6$ naïve 1807 Tg cells into C57BL/6 wild-type mice before vaccination. On the same day, recipients were vaccinated, boosted two weeks later and challenged two weeks after the boost.

Intracellular Cytokine Stain.

Lung cells were harvested at day 4 post-infection. Cells ($0.5\times10^6$ cells/ml) were stimulated for 4 hours with anti-CD3 (clone 145-2C11; 0.1 µg/mL) and anti-CD28 (clone 37.51; 1 µg/mL) in the presence of Golgi-Stop (BD Biosciences). Stimulation with fungal ligands yielded comparable cytokine production by transgenic T-cells compared to CD3/CD28 stimulation (data not shown). After cells were washed and stained for surface CD4 and CD8 using anti-CD4 PerCp, anti-CD8 PeCy7, and anti-CD44-FITC mAbs (Pharmingen), they were fixed and permeabilized in Cytofix/Cytoperm at 4° C. overnight. Permeabilized cells were stained with anti-IL-17A PE and anti-IFN-☐☐☐Alexa 700 (clone XMG1.2) conjugated mAbs (Pharmingen) in FACS buffer for 30 min at 4° C., washed, and analyzed by FACS. Cells were gated on CD4 and cytokine expression in each gate analyzed. The number of cytokine positive CD4+ T cells per lung was calculated by multiplying the percent of cytokine-producing cells by the number of CD4+ cells in the lung.

Cytokine Protein Measurements of in vivo Primed T Cells.

Cell-culture supernatants were generated in 24-well plates in 1 mL containing $5\times10^6$ splenocytes and lymph node cells and various concentrations of *Blastomyces* CW/M antigen (Wuthrich, Filutowicz, et al., 2000), rCalnexin, Drk1, and Calnexin peptides. Supernatant was collected after 72 hours of co-culture. IFN-γ and IL-17A were measured by ELISA as above.

Statistical Analysis.

The number and percentage of activated, proliferating or cytokine producing T-cells and differences in number of CFU were analyzed using the Wlcoxon rank test for non-parametric data (Fisher and vanBelle, 1993) or the T-test when data were normally distributed. A P value of <0.05 is considered statistically significant.

Results

Steps Used to Identify Calnexin as the Shared Antigen (Ag).

Figure 1B:
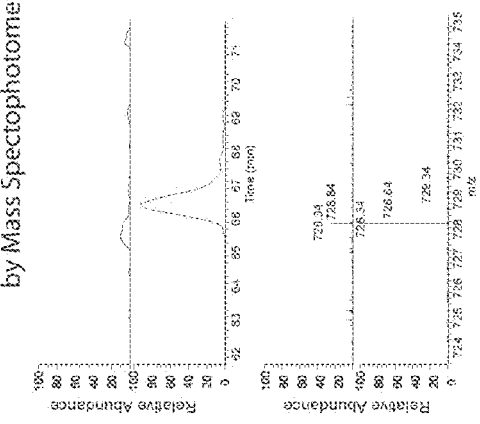
Figure 1C:
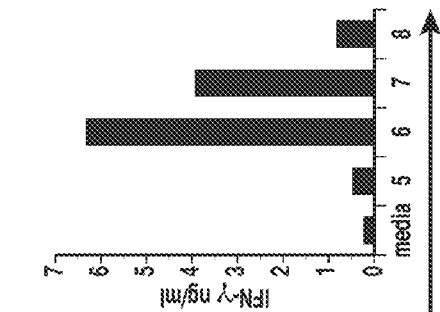
Figure 1D:
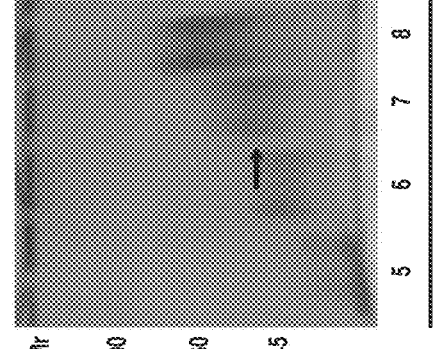
Figure 1E:
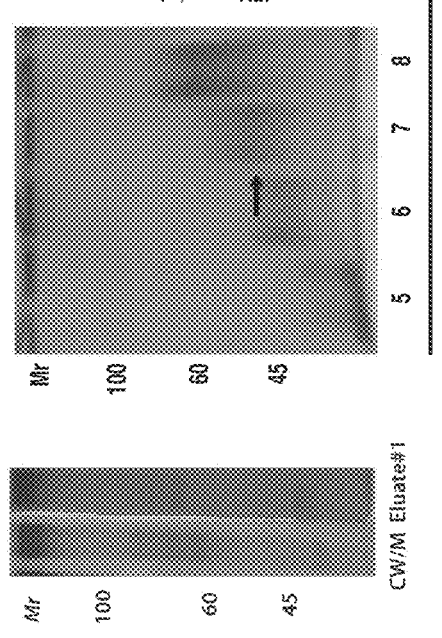

1807 TCR Tg cells recognize a protective antigen that is shared among systemic dimorphic fungi (Wuthrich, Hung, et al., 2011; Wuthrich, Ersland, et al., 2012). To identify the shared antigen, we prepared a cell wall membrane (CW/M) extract from *B. dermatitidis* vaccine yeast as previously described (Wuthrich, Filutowicz, et al., 2000). After running CW/M through a Con A column that retains mannosylated proteins, we collected Eluate 1, which contained 1% of the protein present in the starting material (FIG. 1A). Traces of active Con A released from the column into Eluate #1 were heated to destroy its mitogenic activity (not shown). Eluate #1 (FIG. 1B) was further fractioned in a gel free system to separate individual constituents by size (FIG. 1C). Fractions 6 and 7 stimulated 1807 T cells to produce IFN-☐, whereas medium alone as a control, and fractions 5 and 8 did not (FIG. 1D). To identify the T cell reactive Ag, we subjected fraction 7 to mass spec analysis. Proteins were identified by cross-referencing the mass of detected peptides against a database of the *B. dermatitidis* proteome. Proteins present in non-stimulatory fractions and proteins diverging from the mass parameters of the gel-free fraction were discounted. This technique yielded a roster of five protein candidates potentially representing the shared antigen. Calnexin was one of these five proteins.

Proof Positive that Calnexin is the Shared Antigen

Figure 2A:
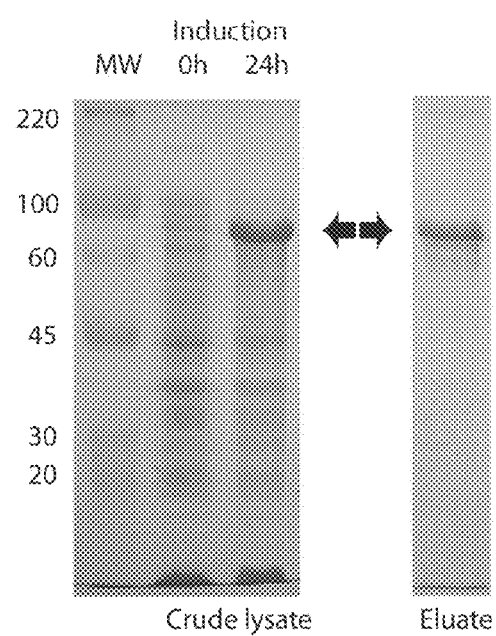
FIGS. 2A, 2B, and 2C are a set of graphs showing experimental evidence proving that Calnexin is the shared antigen (Ag).
Figure 2B:
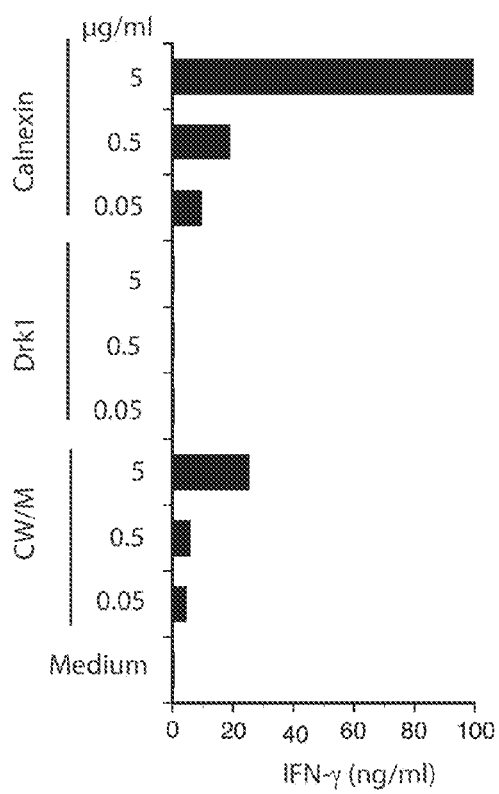

To investigate whether Calnexin is the shared Ag that stimulates 1807 T cells, we cloned the gene into the plasmid pET28c and used IPTG to induce gene expression in transfected *E. coli*. 24 h later, the crude lysate from *E. coli* harbored an additional prominent band that migrated between 60-70 kD, which corresponds with the predicted molecular weight of 63 kD for recombinant Calnexin (rCalnexin) (FIG. 2A). We purified the recombinant protein over a Ni-NTA column (FIG. 2A) and used the eluate to stimulate 1807 cells in an in vitro co-culture system with BMDC. In response to rCalnexin, 1807 T cells produced IFN-☐ in a dose-dependent manner. The response to rCalnexin exceeded the response to CW/M extract, which also harbors Calnexin, but at a lower concentration (FIG. 2B). In contrast, recombinant Drk1—a hybrid histidine kinase of *B. dermatitidis* (Nemecek, Wuthrich, et al., 2006) expressed and purified from *E. coli* as a control—did not induce IFN-☐ production by 1807 T cells. Thus, rCalnexin (not LPS from *E. coli*) induced cytokine production by 1807 T cells specifically and in a dose-dependent manner.

Figure 2C:
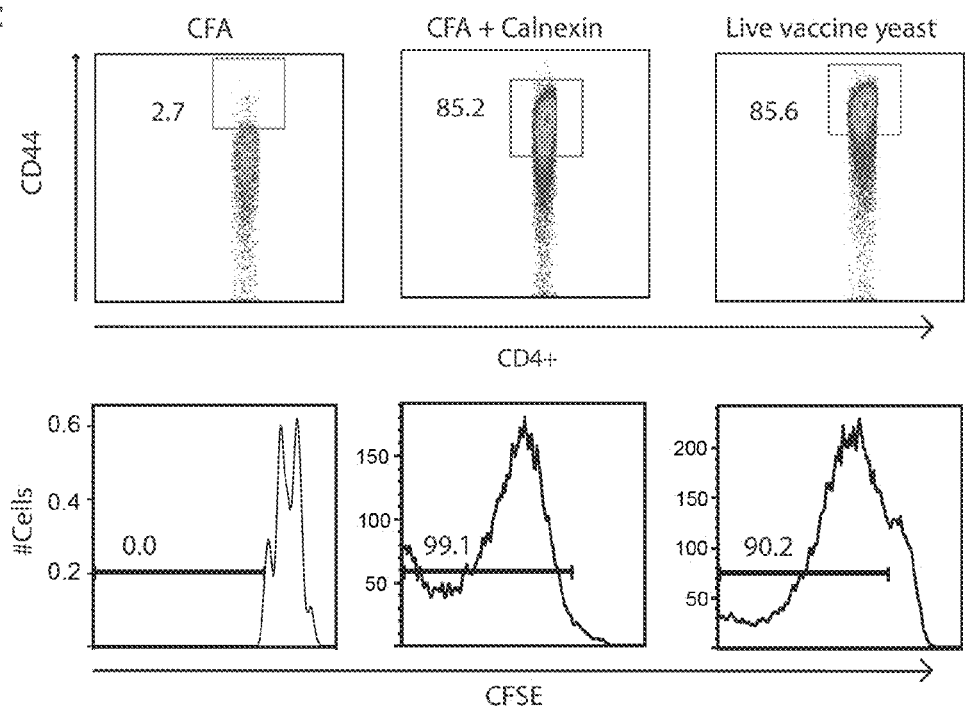

To investigate whether rCalnexin induces activation and proliferation of 1807 cells in vivo, we adoptively transferred 1807 Tg T cells into naïve wild-type recipient mice prior to vaccination. Similar to live *B. dermatitidis* vaccine yeast, rCalnexin emulsified in complete Freund's adjuvant activated and stimulated proliferation of >85% of the transferred 1807 cells (FIG. 2C), whereas adjuvant alone did not. These results identify Calnexin as the shared Ag that is recognized by 1807 TCR Tg T cells, which confer resistance to multiple systemic dimorphic fungi (Wuthrich, Hung, et al., 2011; Wuthrich, Ersland, et al., 2012).

Identification of Calnexin's Peptide Epitope

To identify the 1807 T cell reactive peptide epitope, we first aligned the amino acid sequence of the fungal species that we have reported stimulate 1807 T cells in vivo (Wuthrich, Hung, et al., 2011), including *B. dermatitidis, H. capsulatum, C. posadasii* and *P. brasiliensis*. We investigated regions of sequence conservation that might represent the shared epitope for the 1807 T-cell receptor. We found that Calnexin is highly conserved across the entire Calnexin sequence among this group of dimorphic fungi (FIG. 6). Thus, the identification of highly conserved areas of the protein was not a sufficient measure to hone in on the 1807 epitope-containing sequence. To narrow the focus of possible peptides to test for 1807 reactivity, we subjected *Blastomyces* Calnexin to two class II I-Ab restricted-epitope prediction algorithms (FIG. 6). The IEBD algorithm predicted six regions of overlapping peptides with binding affinities values ($IC_{50}$) less than 500 nM. In a second analysis, an algorithm developed in Marc Jenkins' laboratory (unpublished data) refined the above analysis, and predicted ten strong H2-IAb epitopes in *B.dermatitidis* Calnexin (FIG. 6). We chemically synthesized peptides of thirteen amino acids in length, representing these ten predicted epitopes (named Peptide 1 though Peptide 10), and tested them to determine the cognate epitope for the 1807 T-cell receptor.

To test whether the synthetic peptides activate naïve 1807 T cells in vitro, we loaded BMDC with individual peptides and co-cultured them with 1807 cells. Peptide #1 strongly activated naïve 1807 T cells as measured by their reduced expression of CD62L (FIG. 3A) and increased expression of CD44 (data not shown). In contrast, an irrelevant control OT2 peptide, and all other synthetic Calnexin peptides did not activate 1807 cells. Peptide 1 also stimulated the production of IFN-☐ by 1807 cells in a dose dependent manner (FIG. 3B). As little as 1 to 10 nM of peptide 1 stimulated as much IFN-☐ as 10 µg/ml of CW/M Ag, which has been shown to induce substantial amounts of the cytokine (data not shown). Neither Calnexin Peptide 5, nor the other synthesized Calnexin peptides, induced the production of IFN-☐ by 1807 cells.

Evidence that Calnexin is Displayed on the Yeast Surface

Among fungal pathogens, most of the virulence factors and antigenic proteins are secreted or associated with the cell wall or surface. Despite the fact that Calnexin is a molecular chaperone and folding sensor that regulates the transport of proteins from the ER to the Golgi apparatus, (Ellgaard and Helenius, 2003) vaccination with *B. dermatitidis* yeast efficiently stimulates 1807 T cell responses in vivo. Thus, we wondered how presumably intracellular Calnexin is accessed by antigen-presenting cells and displayed to T cells. To address this conundrum, we sought to investigate whether Calnexin is instead present on the yeast surface. During our search for the shared Ag, we found that a water-soluble extract of surface proteins from the vaccine yeast activated 1807 T cells (data not shown). Western-blot analysis of the water-soluble extract detected a doublet that migrated on SDS-PAGE at the same position as rCalnexin produced by *E. coli* (FIG. 4A). To investigate whether vaccine yeast harbor Calnexin on their surface, we stained yeast in vitro at 37° C. and yeast harvested from the site of vaccination (subcutaneous tissue) with polyclonal anti-Calnexin antibodies. Both in vitro and in vivo grown vaccine yeast stained positively with the anti-Calnexin serum (FIGS. 4B and 4C). The virulent parental strain 26199 that is used for the pulmonary challenge of mice also harbored Calnexin on the yeast surface when harvested and stained at day 4 post-infection (FIG. 4C). These results indicate that Calnexin is present on the surface of vaccine and challenge yeast.

Functional Relevance of Calnexin and Peptide T Cell Responses.

Figure 5A:
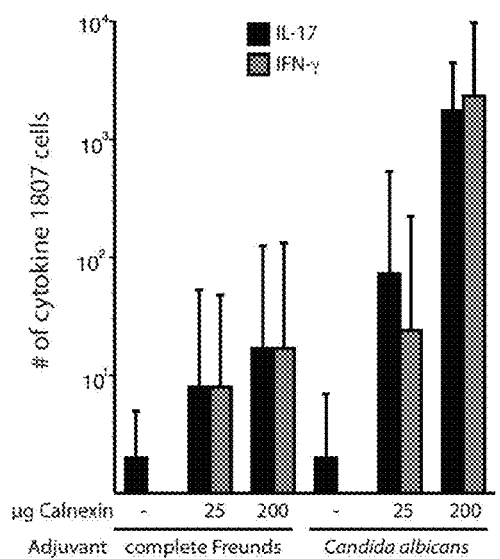
FIGS. 5A and 5B are a set of graphs of experimental observations showing response to Calnexin.
Figure 5B:
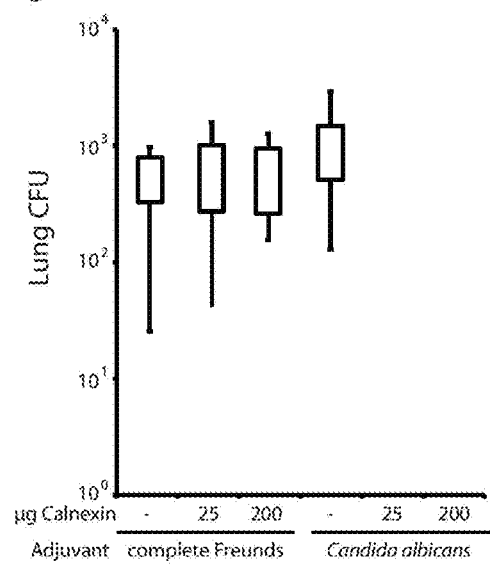

To determine whether vaccination with Calnexin induces protective immunity against lethal *B. dermatitidis* infection, we immunized mice with soluble recombinant protein plus either complete Freund's adjuvant (CFA) or heat killed *C. albicans* yeast (contains fungal PAMPs) to polarize naïve T cells into Th1 cells or Th17, respectively (LeibundGut-Landmann, Gross, et al., 2007). To evaluate whether these vaccine formulations efficiently stimulate the generation and recruitment of Th17 and Th1 cells to the lung upon recall, we adoptively transferred naïve 1807 T cells into mice prior to vaccination and determined the number of cytokine producing 1807 T cells at day 4 post-infection. Mice vaccinated with Calnexin recruited Th17 and Th1 cells into the lung in a dose and Ag-specific manner. The antigen formulation prepared with heat killed *C. albicans* yeast expanded more 1807 T cells than that prepared with CFA (FIG. 5A). Most strikingly, mice that were vaccinated with rCalnexin and *C. albicans* yeast as the adjuvant completely cleared lung infection by day 4 post-infection, whereas mice vaccinated with either *Candida* adjuvant alone or Calnexin and CFA together did not (FIG. 5B). These data indicate that recombinant Calnexin protein has the capacity to protect vaccinated mice against lethal pulmonary infection when Ag-specific T cells have been primed in sufficient numbers.

Peptide Prediction Of Calnexin Fragments To Human.

Applicants performed an analysis of the predicted peptides that could work with the known epitope binding domain of several Human HLA DRB1 alleles, using the publicly available ProPred software (www.imtech.res.in/raghava/propred/). The results were shown in FIG. 7. In the output, the Blasto Calnexin sequence was shown on a separate line for each of 51 DRB1 alleles, and peptides that are predicted to fit in the MHCII groove of that allele were indicated in blue, with red used to indicate a so-called anchor amino acid that would be at position one of the 9 amino acid core sequence. A peptide of interest is "promiscuous" if it is predicted to interact with many different human MHCII molecules. Since the human HLA locus is so polymorphic, a good vaccine for humans will have to have epitopes that are promiscuous, and can work with many different HLA MHC molecules in order to stimulate an immune response. The results in FIG. 7 show that Blasto Calnexin does, indeed, have several peptide sequences (blue) that are predicted to fit into the MHC groove for presentation to T-Cells. Of particular interest is that there is a predicted epitope for the sequence of Peptidel (which was predicted for B6 mouse HLA interaction, and has been experimentally shown to do so with 1807 cells) at position 103 to 115. There were several other promiscuous epitopes throughout the Calnexin sequence as predicted by the ProPred software.

Peptide MHCII Tetramers To Detect Endogenous Calnexin Specific Cd4 T Cells

Applicants have taken advantage of the discovery of calnexin as a major shared antigen that is recognized by T cells that mediate protection against pathogenic fungi that are members of the broad fungal taxonomic group called Ascomycetes. Having already discovered that calnexin peptide #1 specific T cells recognize many of these fungi and confer protection against them, Applicants created an immunological tool—peptide-MHCII tetramers (pMHC tetramers)—to track the emergence and persistence of these T cells after exposure to the fungus in question. The synthesis of pMHCII tetramers has been previously described. The present application discloses methods of creating reagents to identify and track calnexin peptide specific T cells.

Applicants have now used the tetramers to find and quantify "endogenous" calnexin peptide #1 specific T cells that reside in the body before infection, and then to monitor their response, expansion and characteristics after infection and vaccination. Applicants initiated this work by studying mice before and after infection with *Blastomyces dermatitidis* or after vaccination with calnexin recombinant protein or attenuated *B. dermatitidis*. Applicants envision that the process of the experiments may be extended to other fungi that are members of the family of ascomycetes. Other fungi may include *Histoplasma capsulatum, Aspergillus fumigatus, Fonsecea pedrosoi*, and *Geomyces destructans* (the latter is the "white nose fungus", which is decimating bat populations in North America), to name a few. Applicant's results suggest that infection with these fungi activates and expands endogenous calnexin peptide #1 specific T cells.

The tetramers that we are developing pave the way toward a clinical application. Individuals with cancer or other disorders who are to receive bone marrow or stem cell transplants may be at risk for opportunistic fungal infection with *Asperillus* species. These infections may carry high morbidity and mortality rates that reach 80-90%. It would be clinically advantageous to use the tetramer to screen and discern whether a bone marrow or stem cell donor has evidence of strong immunity against *Aspergillus* as a way of planning the clinical management of the recipient. For example, the tetramers in the present application may be used to, 1) gauge the risk of *Aspergillus* infection in the transplanted recipient (who will receive the immune or non-immune cells); 2) to plan anti-fungal prophylaxis strategies for the at-risk recipient, or 3) plan vaccination of the donor (pre- transplant) to induce calnexin or peptide #1 antigen-specific T cells.

REFERENCES

1. Harvey, R. P., Schmid, E. S., Carrington, C. C., and Stevens, D. A. 1978. Mouse model of pulmonary blastomycosis: utility, simplicity, and quantitative parameters. *American Review of Respiratory Disease* 117:695-703.
2. Brandhorst, T. T., Wüthrich, M., Warner, T., and Klein, B. 1999. Targeted gene disruption reveals an adhesin indispensable for pathogenicity of Blastomyces dermatitidis. *J Exp Med* 189:1207-1216.
3. Wüthrich, M., Hung, C. Y., Gem, B. H., Pick-Jacobs, J. C., Galles, K. J., Filutowicz, H. I., Cole, G. T., and Klein, B. S. 2011. A TCR Transgenic Mouse Reactive with Multiple Systemic Dimorphic Fungi. *J Immunol* 187:1421-1431.
4. Levine, H. B., Cobb, J. M., and Smith, C. E. 1960. Immunity to coccidioi-domycosis induced in mice by purified spherule, arthrospore, and mycelial vaccines. *Trans N Y Acad Sci* 22:436-449.
5. Levine, H. B., Kong, Y. C., and Smith, C. 1965. Immunization of Mice to Coccidioides Immitis: Dose, Regimen and Spherulation Stage of Killed Spherule Vaccines. *J Immunol* 94:132-142.
6. Wüthrich, M., Ersland, K., Sullivan, T., Galles, K., and Klein, B. S. 2012. Fungi subvert vaccine T cell priming at the respiratory mucosa by preventing chemokine-induced influx of inflammatory monocytes. *Immunity* 36:680-692.
7. Wüthrich, M., Filutowicz, H. I., and Klein, B. S. 2000. Mutation of the WI-1 gene yields an attenuated Blastomyces dermatitidis strain that induces host resistance. *J Clin Invest* 106:1381-1389.
8. Wisniewski, J. R., Zougman, A., Nagaraj, N., and Mann, M. 2009. Universal sample preparation method for proteome analysis. *Nat Methods* 6:359-362.
9. Nesvizhskii, A.I., Keller, A., Kolker, E., and Aebersold, R. 2003. A statistical model for identifying proteins by tandem mass spectrometry. *Anal Chem* 75:4646-4658.
10. dos Santos Feitosa, L., de Almeida Soares, C. M., Dos Santos, M. R., Bailao, A. M., Xander, P., Mortara, R. A., and Lopes, J. D. 2007. Cloning, characterization and expression of a calnexin homologue from the pathogenic fungus Paracoccidioides brasiliensis. *Yeast* 24:79-87.
11. Thompson, J. D., Higgins, D. G., and Gibson, T. J. 1994. CLUSTAL W: improving the sensitivity of progressive multiple sequence alignment through sequence weighting, position-specific gap penalties and weight matrix choice. *Nucleic Acids Res* 22:4673-4680.
12. Wüthrich, M., Filutowicz, H. I., Allen, H. L., Deepe, G. S., and Klein, B. S. 2007. V{beta}1+J{beta}1.1+/V{alpha}2+J{alpha}49+CD4+ T Cells Mediate Resistance against Infection with Blastomyces dermatitidis. *Infect Immun* 75:193-200.
13. Nemecek, J. C., Wüthrich, M., and Klein, B. S. 2006. Global control of dimorphism and virulence in fungi. *Science* 312:583-588.
14. Wüthrich, M., Gem, B., Hung, C. Y., Ersland, K., Rocco, N., Pick-Jacobs, J., Galles, K., Filutowicz, H., Warner, T., Evans, M., et al. 2011. Vaccine-induced protection against 3 systemic mycoses endemic to North America requires Th17 cells in mice. *J Clin Invest* 121:554-568.
15. Wüthrich, M., Gem, B., Hung, C. Y., Ersland, K., Rocco, N., Pick-Jacobs, J., Galles, K., Filutowicz, H., Warner, T., Evans, M., et al. 2011. Vaccine-induced protection against 3 systemic mycoses endemic to North America requires Th17 cells in mice. *J Clin Invest*.
16. Fisher, L. D., and van Belle, G. 1993. Biostatistics: A Methodology for the Health Sciences. John Wiley & Sons, N.Y.: 611-613.
17. Ellgaard, L., and Helenius, A. 2003. Quality control in the endoplasmic reticulum. *Nat Rev Mol Cell Biol* 4:181-191.
18. LeibundGut-Landmann, S., Gross, O., Robinson, M. J., Osorio, F., Slack, E. C., Tsoni, S. V., Schweighoffer, E., Tybulewicz, V., Brown, G. D., Ruland, J., et al. 2007. Syk- and CARD9-dependent coupling of innate immunity to the induction of T helper cells that produce interleukin 17. *Nat Immunol* 8:630-638.
19. Myhill Nathan, Lynes Emily M., Nanji Jalal A., Blagoveshchenskaya Anastassia D., Fei Hao, Simmen Katia Carmine, Cooper Timothy J., Thomas Gary, Simmen Thomas, The Subcellular Distribution of Calnexin Is Mediated by PACS-2. *Molecular Biology of the Cell* 2008, 19, 2777-2788.
20. Williams David B. Beyond lectins: the calnexin/calreticulin chaperone system of the endoplasmic reticulum. *Journal of Cell Science,* 2006, 119, 615-623

---

We claim:

1. A vaccine to immunize a patient against fungi, wherein the vaccine comprises a therapeutically effective amount of an immunogenic Calnexin peptide consisting of a sequence of 13 amino acids with 1, 2, or 3 amino acid substitutions relative to SEQ ID NO:1 and at least one of a stabilizer, a buffer, or a therapeutically effective amount of an adjuvant.

2. The vaccine of claim 1, wherein the Calnexin peptide consists of a sequence selected from the group consisting of SEQ ID NOs: 10, 12, 15, 20, 25, 29, and 30.

3. A method of protecting a patient subject from fungal infection comprising administering a therapeutically effective amount of the vaccine of claim 1 to the subject, wherein the subject is protected from fungal infection.

4. The method of claim 3, wherein the fungi are either dimorphic fungi or non-dimorphic fungi.

5. The method of claim 4, wherein the dimorphic fungi are selected from a group consisting of *Histoplasma, Coccidiodes, Paracoccidiodes, Penicillium, Blastomyces*, and *Sporothrix*.

6. The method of claim 4, wherein the non-dimorphic fungi are selected from a group consisting of *Aspergillus, Pneumocystis, Magnaportha, Exophiala, Neuroaspora, Cryptococcus, Schizophyllum*, and *Candida*.

7. The method of claim 3, wherein the Calnexin peptide of the vaccine is expressed and isolated from *E. Coli*.

8. A vaccine to immunize a patient against a fungi comprising recombinant full-length Calnexin having a sequence selected from the group consisting of SEQ ID NO:35 and SEQ ID NO:36 and at least one of a stabilizer, a buffer, or a therapeutically effective amount of an adjuvant.

9. The vaccine of claim 8, wherein the recombinant full-length Calnexin is not glycosylated.

10. The vaccine of claim 1, wherein the vaccine additionally comprises complete Freund's adjuvant and heat killed *C. albicans*.

11. A method of protecting a patient from fungal infection comprising administering a therapeutically effective amount of the vaccine of claim 8 to a subject, wherein the subject is protected from fungal infection.

12. The method of claim 11, wherein the fungi are either dimorphic fungi or non-dimorphic fungi.

13. The method of claim 12, wherein the dimorphic fungi are selected from a group consisting of *Histoplasma, Coccidiodes, Paracoccidiodes, Penicillium, Blastomyces*, and *Sporothrix*.

14. The method of claim 12, wherein the non-dimorphic fungi are selected from a group consisting of *Aspergillus, Pneumocystis, Magnaportha, Exophiala, Neuroaspora, Cryptococcus, Schizophyllum*, and *Candida*.

15. The method of claim 11, wherein the recombinant full length Calnexin of the vaccine is expressed and isolated from *E. Coli*.

\* \* \* \* \*

UNITED STATES PATENT AND TRADEMARK OFFICE
CERTIFICATE OF CORRECTION

PATENT NO. : 10,806,776 B2
APPLICATION NO. : 15/969169
DATED : October 20, 2020
INVENTOR(S) : Bruce Steven Klein et al.

It is certified that error appears in the above-identified patent and that said Letters Patent is hereby corrected as shown below:

In the Specification

Column 3, Line 36, "IFN-" should be --IFN-γ--.

Column 4, Line 41, "Peptidel" should be --Peptide1--.

Column 4, Line 50, "Gl" should be --GI--.

Column 11, Line 63, "FFigure" should be --Figure--.

Column 16, Line 8, "(010)" should be --(C10)--.

Column 21, Line 38, "-D" should be --α-D--.

Column 21, Line 55, "Wsniewski" should be --Wisniewski--.

Column 25, Line 13, "anti-IFN- Alexa" should be --anti- IFN-γ-Alexa--.

Column 25, Line 32, "Wlcoxon" should be --Wilcoxon--.

Column 25, Line 52, "IFN-" should be --IFN-γ--.

Column 26, Line 7, "IFN-" should be --IFN-γ--.

Column 26, Line 13, "IFN-" should be --IFN-γ--.

Column 26, Line 64, "IFN-" should be --IFN-γ--.

Column 26, Line 66, "IFN-" should be --IFN-γ--.

Signed and Sealed this
Fifteenth Day of December, 2020

Andrei Iancu
*Director of the United States Patent and Trademark Office*

CERTIFICATE OF CORRECTION (continued)
U.S. Pat. No. 10,806,776 B2

Column 27, Line 3, "IFN-" should be --IFN-γ--.

Column 28, Line 13, "Peptidel" should be --Peptide1--.

In the Claims

Column 249, Claim 3, Line 37, "a patient subject" should be --a subject--.